US007229813B2

(12) United States Patent
Hosted et al.

(10) Patent No.: US 7,229,813 B2
(45) Date of Patent: Jun. 12, 2007

(54) EVERNINOMICIN BIOSYNTHETIC PROTEINS

(75) Inventors: Thomas J. Hosted, Summit, NJ (US); Tim X. Wang, Roselle Park, NJ (US); Ann C. Horan, Summit, NJ (US)

(73) Assignee: Schering Corporation, Kenilworth, NJ (US)

( * ) Notice: Subject to any disclaimer, the term of this patent is extended or adjusted under 35 U.S.C. 154(b) by 207 days.

(21) Appl. No.: 11/021,825

(22) Filed: Dec. 23, 2004

(65) Prior Publication Data

US 2005/0233414 A1    Oct. 20, 2005

Related U.S. Application Data

(62) Division of application No. 09/758,759, filed on Jan. 11, 2001, now Pat. No. 6,861,513.

(60) Provisional application No. 60/175,751, filed on Jan. 12, 2000.

(51) Int. Cl.
| | |
|---|---|
| C12N 9/10 | (2006.01) |
| C12N 15/74 | (2006.01) |
| C12N 15/64 | (2006.01) |
| C12N 1/20 | (2006.01) |
| C12N 1/00 | (2006.01) |
| C12P 21/06 | (2006.01) |
| C07H 21/04 | (2006.01) |

(52) U.S. Cl. ............ 435/193; 435/69.1; 435/91.4; 435/252.3; 435/254.11; 435/471; 536/23.1; 536/23.2

(58) Field of Classification Search .............. None
See application file for complete search history.

(56) References Cited

U.S. PATENT DOCUMENTS

| 5,190,870 A | 3/1993 | Lipscomb et al. ............ 435/155 |
| 5,190,871 A | 3/1993 | Cox et al. .................... 435/477 |
| 5,741,675 A | 4/1998 | Friedmann et al. .......... 435/691 |
| 6,833,135 B1 * | 12/2004 | Frazao Moniz Pereira et al. ........................ 424/248.1 |

FOREIGN PATENT DOCUMENTS

| EP | 350341 B1 | 5/1995 |
| JP | 3139284 | 6/1991 |
| WO | WO 93/07904 | 4/1993 |
| WO | WO 93/13663 | 7/1993 |
| WO | WO 95/16046 | 6/1995 |
| WO | WO 97/13777 | 4/1997 |

OTHER PUBLICATIONS

Altreuter and Clark, 1999, Curr. Op. Biotech. 10:130.
Baltz and Hosted, 1996, TIBTECH 14:245.
Baltz et al., 1998, Trends Microbiol. 2:76-83.
Baltz, 1990, Curr. Op. Biotech. 1:12-20.
Bao et al., 1999, J. Bacteriol 181:4690-5.
Bao W, et al., 1999, *Biochemistry.* 38: 9752-9757.
Beck et al., 1990, European Journal of Biochemistry 192:487-498.
Becker A, etal., 1993, *Mol Gen Genet.* 241: 367-379.
Brautaset T, et al., 2000, *Chem Biol.* 7: 395-403.
Buttner et al., 1990, J. Bacteriol. 172:3367-78.
Cheng-Cai, 1996, Molecular Microbiology 20:9-15.
Cundliffe, 1989, Annual Review of Microbiology 43:207-33.
Distler J, et al., 1987, *Nucleic Acids Res.* 15: 8041-8056.
Donadio et al., 1993, Proc. Natl. Acad. Sci. U.S.A. 90:7119-23.
Fath et al., 1993, Microbial Reviews 57:995-1017.
Faust B, D Hoffmeister, et al., 2000, *Microbiology.* 146: 147-154.
Fernandez et al., 1996, Molecular and General Genetics 251:692-698.
Fernandez et al., 1998, Journal of Bacteriology 18:4929-4937.
Flett F, et al., 1997, *FEMS Microbiol Lett.* 155: 223-229.
Foster DR, 1999, *Pharmacotherapy.* 19: 1111-1117.
Gaisser et al., 1997, Journal of Bacteriology 179:6271-6278.
Ganguly AK, et al., 1975, *J Am Chem Soc.* 97: 1982-1985.
Ganguly AK, et al., 1979, *J Antibiot* (Tokyo). 32: 1213-1216.
Garbe TR, et al., 1994, *Microbiology.* 140: 133-138.
Guilfoile et al., 1991, Proc. Natl. Acad. Sci. USA 88:8553-8557.
Hanlon et al., 1997, Molecular Microbiology 23:459-71.
Hopwood, et al., 1990, Annual Review of Microbiology 24:37-66.
Hosted and Baltz, 1997, J. Bacteriol. 179:180-6.
Hung-wen et al., 1994, Annual Review of Microbiology 48:223-56.
Hutchinson CR, et al., 1993, *Antonie Van Leeuwenhoek.* 64: 165-176.
Hutchinson et al., 1995, Annual Review of Microbiology 49:201-238.
Ikeda H, 1999, et al., *Proc Natl Acad Sci U S A.* 96: 9509-9514.
Johnson et al., 1998, Current Opinion Chem. Biol. 5:642-9.
Kim et al., 1995, J. Bacteriol. 77:1202.
Lichenstein HS, et al., 1990, *Gene.* 88: 81-86.
Liu and Thorson, 1994, Annu. Rev. Microbiol. 48:223.

(Continued)

*Primary Examiner*—Sheridan Swope
*Assistant Examiner*—Ganapathirama Raghu

(57) ABSTRACT

This invention is directed to nucleic acids which encode the proteins that direct the synthesis of the orthosomycin everninomicin and to use of the nucleic acids and proteins to produce compounds exhibiting antibiotic activity based on the everninomycin structure. The DNA sequence for the gene clusters responsible for encoding everninomicin biosynthetic genes, which provide the machinery for producing everninomicin, are provided. Thus, this invention provides the nucleic acid sequences needed to synthesize novel everninomicin-related compounds based on everninomicin, arising from modifications of the DNA sequence designed to change glycosyl and modified orsellinic acid groups contained in everninomicin. A *Micromonospora* site-specific integrase gene is also provided, which can be incorporated in a vector for integration into any actinomycete, and, particularly into *Monospora*. Thus, the invention further provides methods for introducing heterologous genes into an actinomycete chromosome using this particular vector.

6 Claims, 128 Drawing Sheets

OTHER PUBLICATIONS

Figure 1:
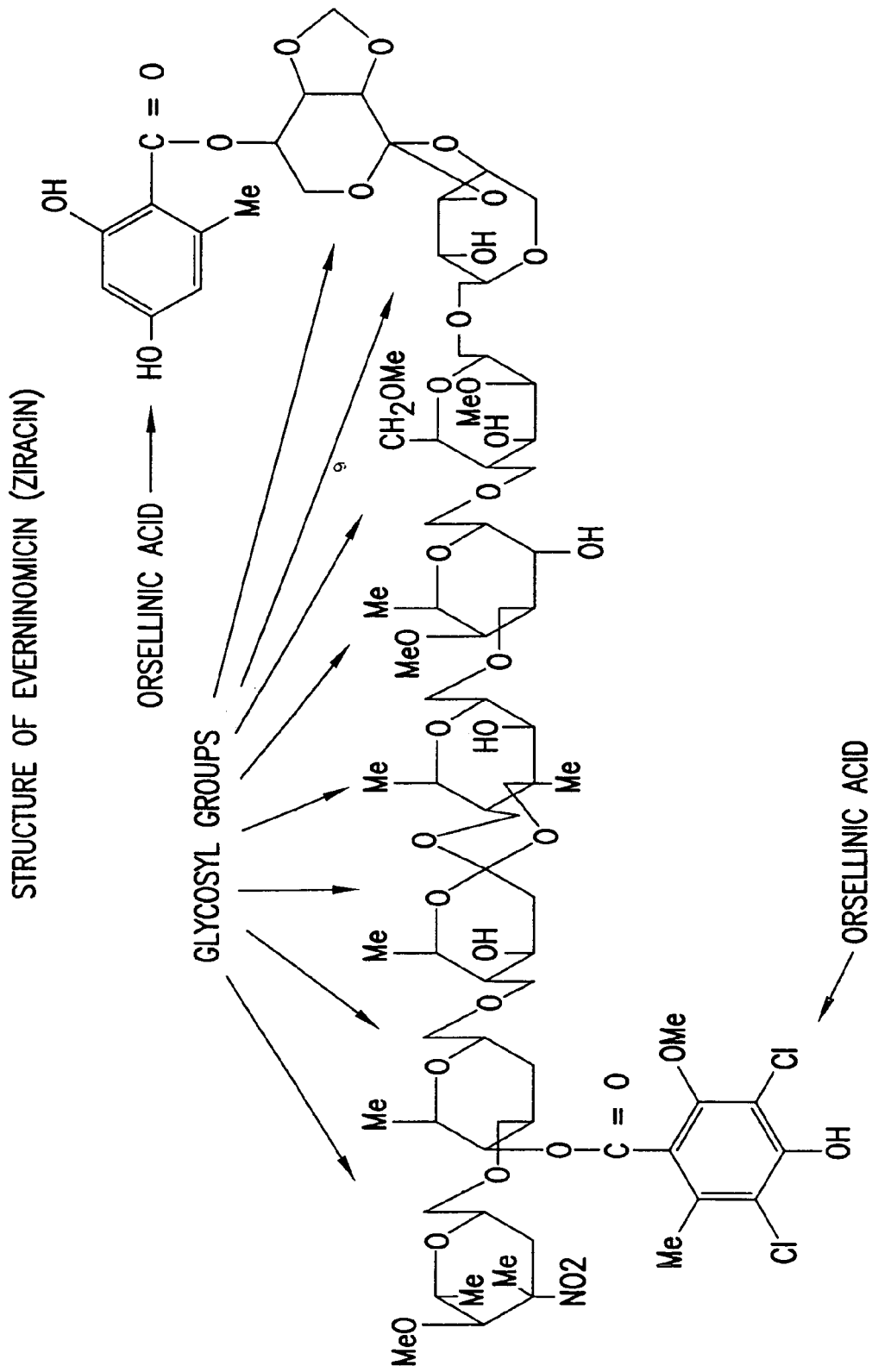

Liu W, et al., 2000., *Antimicrob Agents Chemother.* 44: 382-392.
Madduri et al., 1998, Nature Biotechnology, 16:69-74.
McNicholas et al., Abstract C-846, ICAAC, San Francisco, CA, 1999.
McNicholas PM, 2000, *Antimicrob Agents Chemother.* 44: 1121-1126.
Merson-Davies LA, et al., 1994, *Mol. Microbiol.* 13: 349-355.
Mertz JL, et al., 1986, *J Antibiot* (Tokyo). 39: 877-887.
Ninet L, F Benazet, et al., 1974, *Experientia.* 30: 1270-1272.
Oh and Chater, 1997, J. Bacteriol. 179:122-7.
Olano et al., 1998, Molecular Gen. Genetics 3:299-308.
Paget E, et al., 1996, *J Bacteriol.* 178: 6357-6360.
Piepersberg W., et al., 1994, *Crit Rev Biotechnol.* 14: 251-285.
Pissowotzki K, et al., 1991, *Mol Gen Genet.* 231: 113-123.
Puar MS, et al., 1998, *J Antibiot* (Tokyo). 51: 221-224.
Rao et al., 1987, Methods in Enzymology 153:166-198.
Reynolds, Proc. Natl. Acad. Sci. USA, 1998, 95:112744.
Rodriguez E, et al., 1999, *Microbiology.* 145: 3109-3119.
Saitou N, et al., 1987, *Mol Biol Evol.* 4: 406-425.
Smith et al., 1997, FEMS Microbiol. Lett. 155:223-9.
Solenberg et al., Chem Biol, 1997, 4:195-202.
Strohl et al., 1991, J. Industr. Microbiol. 7:163.
Stutzman-Engwall KJ, et al., 1992, *J Bacteriol.* 174: 144-154.
Summers et al., 1997, Microbiology 143:3251-3262).
Tang L, et al., 1994, Ann. N Y Acad. Sci. 721:105-16.
Trefzer A., et al., 1999, *Nat Prod Rep.* 16: 283-299.
Ueda et al., 1996, Gene 169:91-95.
van Wageningen AM, et al., 1998, *Chem Biol.* 5: 155-162.
Weinstein MJ, 1965, *Antimicrob Agents Chemother.* 5: 821-827.
Wilson et al., 1998, Gene 214:95-100.
Wohlleben et al., 1994, Acta Microbiol. Immunol. Hung 41:381-9.
Wolk CP, 1991, *Proc. Natl. Acad. Sci.* 88: 5355-5359.
Wright F, et al., 1992, *Gene.* 113: 55-65.
Ylihonko et al., 1996, Microbiology 142:1965.
Zhang et al., 1998, Molecular and General Genetics 258:26-33.
Adrian PV, et al., 2000, *Antimicrob Agents Chemother.* 44: 732-738.
Decker, H., (1996), FEMS Microbiology Letters 141:195-201.
Bechthold, A., (1999), Biorganic Chemistry, Diederichsen U. et al. Wiley-VCH Verlag GMBH, Weinheim, Germany, p. 313-321.
Malpartida, F., (1987), Nature, 325:818-821.
Koch, C., (1996), International Journal of Systematic Bacteriology, 46(2):383-387.
International Search Report for International Patent Application No. PCT/US01/01187; Date of Completion: Aug. 7, 2001.

\* cited by examiner pSPRH830b *E.coli*-MICROMONOSPORA SHUTTLE VECTOR pSPRH830b – pSPRH826b BACKBONE

| FUNCTION | SOURCE |
|---|---|
| – AMPICILLIN RESISTANCE | (pUC18) |
| – MULTIPLE CLONING SITE | (pUC18) |
| – pUC18 ORIGIN | (pUC18) |
| – HYGROMYCIN RESISTANCE | (p16R1) |
| oriT (ORIGIN OF TRANSFER) | (pRL1058) |
| pIJ702 ORIGIN OF REPLICATION | (pIJ702) | pSPRH840 INTEGRATING VECTOR pSPRH840 – pSPRH826b BACKBONE, pMLP1 *xis*, *int* attP INSERT

| pSPRH840 CONJUGATED FROM E.coli INTO | HmR TRANSFORMANTS OBTAINED |
|---|---|
| M. CARBONACEA | + |
| M. ROSARIA | − |
| M. HALOPHITICA | + |

FIG. 7B(1)

```
1391 ACGGTGTGGATCGAGAAGAACGGGCCCGTCTACGGCATTCGGGACCTCGTTCGGCGTAAAAAGGTCACCATTCAGACGGGTTATCCGACGAAGACCAGCGGCGAAGAATGCGATGG
   1▷  V  W  I  E  K  N  G  P  V  Y  R  I  R  D  L  V  R  G  K  K  V  T  I  Q  T  G  Y  P  P  T  K  T  S  A  K  N  A  M

1506 TGCAGTTCCGTGCCGAGCAGTTGCAGGGCAACGGCTCTCATGCCGGCGGGCGTCAGATTACCCTCGCGGATTTCGTTGGCGAGTGGATGCCGAGCTACGAAAAGACGCTGAAACCG
  38▷ V  Q  F  R  A  E  Q  L  Q  G  N  A  L  M  P  R  G  G  Q  I  T  L  A  D  F  V  G  E  W  M  P  S  Y  E  K  T  L  K  P

1622 ACCGCCGTGAACTCGGAGGGCAACGGACGCAACCACTCTGCCATATCGGCCATCTCCTGACGAGCTTGACGAGTCACCCAGAGTGGGTCAACGACCTGGA
  77▷ T  A  V  N  S  E  G  N  R  I  R  N  H  L  L  P  I  L  G  H  L  T  L  D  E  L  D  G  Q  V  T  Q  Q  W  V  N  D  L  E

1738 GGCCGGGCGTCGGCCGTGGCCGGAGTCCACCGGGAGCTGCTGCAGCGGATCAGCAACTGCCACGGCCTCCTGCACGATCTGCCGCGGCGGATCGCG
 115▷ A  G  V  G  P  W  P  E  S  T  R  G  R  R  K  P  L  A  A  K  T  I  S  N  C  H  G  L  L  H  T  I  C  G  A  A  I  A

1854 CGAAACGGATCAGGCTCAACCCGTGCTCTTGACGATGCTGCCCCGGCGAAGAGATGAAGTTCCTGAGCGACCCGGAGATCGGTCGCTTATCACGGCGCTTCTGCCG
 154▷ A  K  R  I  R  L  N  P  C  S  S  T  M  L  P  R  R  E  P  K  E  M  K  F  L  S  D  P  E  I  G  R  L  I  T  A  L  P  P

1970 CACTGGCGACCTCCAGGAGCTGCTTGTCTTCCAGTCCCTGAGGTGGGAGGCGATCGGCCTGCGCTGGGGTGAGGCAATCGGCCTGCGCGCCGAAGGGCGACGTCAGTTCACCGAAAGTCGCTCTACTGCTTACGCCAC
 193▷ H  W  R  P  L  V  M  L  L  V  A  T  G  L  R  W  G  E  A  I  G  L  R  A  G  R  V  D  L  L  A  A  R  P  R  L  T  V  V

2086 CGAGCAGCTCCAGGAGCTGGCCCAGAGAGCTGTCTTCCAGTGCAGTTCACCCGCGAAGGGCCGGCAATTCCGGCGGATCTGGGTCAAGGCGTGCCGAGGAAGCCGGGCTTCCG
 231▷ E  Q  L  Q  E  L  A  S  T  G  E  L  V  F  Q  S  P  K  T  A  K  G  R  R  T  V  S  F  T  T  K  V  A  L  L  L  T  P

2202 TCATCGCCGGAAAGAAAGTGACGAGGTCGTGTTCACCGCGCCGAAAGGCGGATGGTAAGGACGGCAATTTCGGCGGATCTGGGTCAAGGCGTGCCGAGGAAGCCGGGCTTCCG
 270▷ L  I  A  G  K  K  S  D  E  V  V  F  T  A  P  K  G  G  M  V  R  T  R  N  F  R  R  I  W  V  K  A  C  E  E  A  G  L  P

2318 GGCTTACGGCATTCACGATCTGCGCCACACTCACGGCGCACTCCGATTCTGCCGGCGTCCGATCCCGCCGCTCGGTCACTGGTCGGTCACGGATCT
 309▷ G  L  R  I  H  D  L  R  H  T  H  A  A  I  L  I  S  A  G  R  P  L  S  A  I  S  R  R  L  G  H  S  S  I  A  V  T  D  L
```

FIG. 7B(2)

FIG. 7B(3)

3812  CGAGTCCCTCAGGGGCGCAGCTCGGCGACCGCCCGTCGCCGACGGTGCCCCTGCCCACCCGTACTCCTGGCTCAGCCGGAGTCTCGCTGGGCAGCAGCCCGCCTGGGCAGCCCCGCCAGGCGTACGTGCCG

3928  TCCTGGATGCCGGGGCGCGCAGCAGCGCGGCCAGCTGGAGGGGCGGCCGCCAGCTGGAGGGGCGGCCAGCTGGAGGGGCGGCCAGCTGCCGGGCAGGAGTGCGGGCTGATCACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACACAGGCCGGGAGTGCGGGCACGTTCGCCCGGCGCAA

FIG. 7B(4)

Analysis of M. Carbonacea and M. Halophytica pSPRH840 insertion site AttB/AttP region Alignment of pMLP1 attP region with religation clone edge sequence

| | |
|---|---|
| M. Halophytica PstI relig-9 | TGATCAACTCTAGGGGAGGGGTAGGGGAATCCACTCCGGAGACGCCCGGAGCAATCCGGA 60 |
| M. Carb PstI relig-1 | TGATCAACTCTAGGGGAGGGGTAGGGGAAT-CNCTCCGGAGACGCCCGGAGCAATCCGGA 59 |
| M. carb PstI relig-4 | TGATCAACTCTAGGGGAGGGGTAGGGGAATCCACTCCGGAGACGCCCGGAGCAATCCGGA 60 |
| pMLP1.intTGA.att region | TGATCAACTCTAGGGGAGGGGTAGGGGAATCCACTCCGGAGACGCCCGGAGCAATCCGGA 60 |

Consensus TGATCAACTCTAGGGGAGGGGTAGGGGAATCCNCTCCGGAGACGCCCGGAGCAATCCGGA 60

| | |
|---|---|
| M. Halophytica PstI relig-9 | GCATGACGGAGCAACCAGAGGTCAGGTGGCCTGTGTTGACCCCTGACCAGGGCCCCGGTA 120 |
| M. Carb PstI relig-1 | GCATGACGGAGCAACCAGCAGGTCAGGTGGCCTGTGTTGACCCCTGACCAGGGCCCCGGTA 119 |
| M. carb PstI relig-4 | GCATGACGGAGCAACCAGCAGGTCAGGTGGCCTGTGTTGACCCCTGACCAGGGCCCCGGTA 120 |
| pMLP1.intTGA.att region | GCATGACGGAGCAACCAGCAGGTCAGGTGGCCTGTGTTGACCCCTGACCAGGGCCCCGGTA 120 |

Consensus GCATGACGGAGCAACCAGCAGGTCAGGTGGCCTGTTGACCCCCTGACCAGGGCCCCGGTA 120

FIG.9A(1)

```
M. Halophytica PstI relig-9    CGGGTTCAATTCCCATCAGTCACCCCAGGTAAGACCCAGGTCAGGGCCGGTTCTCACC-G 179
M. Carb PstI relig-1           CGGGTTCAATTCCCATCAGTCACCC---GT-ACACGAAGGCCCCTCCAC-TCGGAGGGG 174
M. carb PstI relig-4           CGGGTTCAATTCCCATCAGTCACCC---GT-ACACGAAGGCCCCCTCCAC-TCGGAGGGG 175
pMLP1.intTGA.att region        CGGGTTCAATTCCCATCAGTCACCC---G--GCAAGTGGATCTACTCCACAGCAGATCAG 175

Consensus                      CGGGTTCAATTCCCATCAGTCACCCQAGGTARSAMSHRGRYCHVSKCCRSWKCDSABSRG 180

M. Halophytica PstI relig-9    GCCCT-GACGCATTTTCAGGGG------------ 200
M. Carb PstI relig-1           GCCTTCGGCGT-TCCTGAGGGTTCGCG-- 200
M. carb PstI relig-4           GCCTTCGGCGT-TCCTGAGGGTTCGC-- 200
pMLP1.intTGA.att region        GCCCCCCTCCG----AAGAGGGGCCTGAT 200

Consensus                      GCCYCKVCGYATYHWSAGGGKKCSYGAT 209
```

FIG.9A(2)

pMLP1 attP region

```
  1 TGATCAACTCTAGGGGAGGGGTAGGGGAATCCACTCCGGAGAGCGCCCGGAGCAATCGGAGCATGACGGAGCAACCAGCAGGTCAGGTGGCCT

94 GTTGACCCCTGACCAGGCCCCGGTACGGGTTCAATTCCCATCAGTCACCCGGCAAGTGGATCTACTCCACAGCAGATC

174 AGGCCCCTCCGAAGAGGGGCCTGATGCGTCATAGGGGACAGGTAGGGGAACTCAA
```

Insertion juncture

FIG.9B

```
   1 GGTACCCGACCGTGTCCCGGAACAACGAGTCGAGATACGGCGAGAGGAACACCCCGGGTAGTCCGGGTAGACGGTGGGCGAAGGCGTAC
  93 GCGCCTTCGACGGTCAGCGGGCGGGGCGGGGACAGGCGGGTCAGCTCGTACGCTGTACGGATCACTGTCCGCCAGCC
       <  .  S  T  V  H  V  R  P  V  Y  L  I  W  Q  G  G  A
 184 CGGCGGGAACTCCTGCTCCTTCGCCATGATCTCGTCGGGCGTTGGTTCCAGGCGGTCAGCGCGTAGTCGCGGAAGAGCAGCGCGTTCCACGCGTGAACGCGTC
      <R  R  F  E  Q  E  K  A  M  I  E  D  A  H  N  W  A  F  L  L  A  Y  D  V  A  D  P  T  F  A  D
 276 CGGGGTGCGCAGGGATGTGCGTGGCGGGGGTGAGCCCGGTCCTGCCGGCGGTCGTGTCGCACACCCAGGAGACCAGGTCCGGACCGA
      <P  T  R  V  P  I  H  T  G  P  T  L  R  G  Q  K  A  P  T  T  D  C  V  W  S  V  L  D  P  G  I
 368 TGCCGCAGAAGTTCGTCACGGTTGCCGTCTTCGCCGCCCTTGAGCGAGTTCAGCAGGCG
      <  G  C  F  N  T  V  T  A  S  K  A  T  A  G  Y  A  V  V  R  K  G  E  A  K  L  S  N  L  L  A
 460 AGCAGGTCGGTGCGATGCCCTGCCGACGTGTCGGCCCGGGAACCTGTCGGGTGCGGTCCTCTCGCGATCAG
      <L  D  T  R  I  G  E  V  D  A  A  F  R  D  L  R  S  R  D  A  V  G  R  A  D  E  E  G  I  L
 552 CCGCGGCCACCCGCTCGGCGAAGCCGAAGCGGGCCTGCAGCGCGGCCGCCTGACGCGTCCCCACCGTGCACCGGAAGGCGTTCCAGTCGA
      <A  A  V  R  E  A  P  Q  R  A  G  A  R  A  I  T  Y  R  V  E  G  G  H  V  P  L  R  E  V  D  V
 664 CGAGCGCGAAGCCGAAGCCCTCGAGTGCGCCGAGGACGCGGGTCCTCGAAGACGAAGAGAAATGCTCGTAGATCTGGTCGAAGGACGTC
      <L  A  F  G  F  R  A  A  L  A  Q  V  S  R  A  S  F  F  F  H  E  D  Y  I  Q  D  F  S  T
 736 TTGTCCAGGATGTCCCCGAGTACGGCCTGGCCGCGGGCGGGCGTCCTGACCCGGACCCGTCCGCTGCCAGCAGCGGTCAACGCGTCCCTGACCGGTCCCGAAGA
      <K  D  L  I  D  G  L  Y  P  D  E  F  V  F  V  G  D  P  A  L  L  A  D  V  G  R  L  I  S  D  L
 828 GTAGGGGATGTGGCAGATGTGTTGGCCGCGAAGATCACATCGGCGGGCGGTGCTCGATCCCGGACTCCTCGAAGA
      <Y  P  I  H  C  I  T  N  A  A  F  I  V  D  A  P  G  D  T  E  R  V  R  R  A  T  S  E  E  F  F
 920 ACTCGGTCGACCACCGCCACCTGCGACGCCCACCGTGCCGAAGCTCCCGGTGGCCTTGGCCTTCGTCCTCCAGCCGGTCCTCGCCGCCGGT
      <E  T  V  V  R  V  G  H  G  R  A  V  D  A  V  G  G  S  P  E  F  G  L  H  R  V  G  A  E  H
1012 ACGGTACGCAGCATCACCCGTTGCACCCGATCTCCACCGAACGGGTCCGGCCTTCGTCCTCCAGCAGGTGCCGCGCCGGT
      <V  T  R  L  M  V  G  D  N  C  G  I  E  V  V  F  P  D  P  G  T  A  E  H  E  L  L  H  R  A  T
```

FIG.11A(1)

```
1104 GTCGGGGAAGTGCTTCTGCATCACGGAGGAGCCCGACGAGTGGTACGGGTAGTCCTGGTGGAACATCTCCTCCCGGGGCACCTCCTCCATGA
     <D  A  F  H  K  Q  M  V  S  S  G  S  S  H  Y  P  Y  D  Q  H  F  M  E  E  R  P  V  E  E  M  L

1196 GCTGCACCATCGTGCAGCCCGGCAGACCCCACCGGCCAGTGGAAGAAGAACTCGTCCGCGAGCTGGTCCTCGTGAGGAACCGGTCGGAG
     <  Q  V  M  T  C  G  A  C  V  G  V  A  L  H  F  F  E  D  A  L  Q  D  E  T  L  F  R  D  S

1288 AGCGGCTGCCGACCCAGGTCGAGGAACTGGGCGGTGGTGCCGCCACACGTGCCGGCCAGTGCCGCCGGGGCGTGCCGTCGGCTGAATCGGT
     <L  P  Q  R  G  L  D  L  F  Q  A  T  T  G  C  A  R  C  T  G  R  R  P  T  G  D  A  S  D  T

1380 CATCGGCATTCCTCCAGGCAGGCCGGATACCCCTGCCTCAGCGAGCGCCGCGAGCAGTGTCAACGACGTCTCCTTGTCGGGATGGGTCGTCCAGCTCTCGGC
     <  M

1469 TGCGGCGTGCCGGCGACTCAGAGCGCCGCGAGCACGTCGCGTGGTGGGAGGGAGCCGGTCTGGTAGCCGAGCTTGGCGAAGCCGGTCATGGT
     <  .  L  A  A  L  V  D  R  L  A  D  I  V  R  D  Q  T  E  P  P  L  S  P

1560 TACATGGGGGAGGGAGAAGATCTCGCCGGCCAACCGTTCCGTGGTGGGAGGGAGCCGGTCTGGTAGCCGAGCTTGGCGAAGCCGGTCATGGT
     <Y  M  P  L  S  F  I  E  G  A  L  R  E  T  T  P  L  S  G  T  Q  Y  G  L  K  A  F  G  T  M  T

1652 GTGCACCGGCCAGGGGTAGCTCGATGTTGAGGCGCGATGTCCCGCGCCCAACTGTTCGAGGATGCGGTCGCGGGGTGGCGGACCACGT
     <H  V  P  W  P  Y  S  I  N  L  A  I  D  R  A  A  L  Q  E  L  I  R  D  R  A  P  H  R  V  V  Y

1744 AGACGTACCAGAGACGTGTTCGTTGTCGGTCCGTCACCGGCAGGTCAGGCGACCTGGTCGGCGATGTCGGCCAGGCCCTCTGCTAGCGC
     <  V  Y  W  H  E  N  D  T  A  T  V  P  L  T  L  G  V  Q  D  A  I  D  A  L  G  E  E  Y  R

1836 CGGGCCACGGCGTGCCGGCGACTCAGAGCGCCGCGAGCACGTCGCGTGGTGAGCCGGCACAGCTTGCGCGTCAGCAGGATCTCGGCCTGCACCTCGTCGAGGCGGCAGTT
     <R  A  V  A  R  R  G  A  I  Y  D  D  L  R  C  L  K  R  R  L  I  E  A  Q  V  E  D  L  R  C  N

1928 CGCGCCGCCGGCGTCTCGACGATCGATGCCATGCGTCGTTCCATGCCGTAGTAGCCGTGATCAGCCGCTCGTCGATCACGGCGTCCGGGTGA
     <H  G  P  T  E  V  V  Y  V  Q  E  M  G  Y  Y  R  L  R  E  D  I  V  A  D  A  T  V

2020 GTGCCCCGGCGTCTCGACGATCGATGCCATGCGTCGTTCCATGCCGTAGTAGCCGTGATCAGCCGCTCGTCGATCACGGCGTCCGGGTGA
     <H  G  P  T  E  V  V  Y  V  Q  E  M  G  Y  Y  R  L  R  E  D  I  V  A  D  A  T  V

2112 CCACGCCGCCGGCGACTGCGCCGTCGCGCAGTCGCGCATCCGGCGTCCCGGGCCGTGTTCCCGGAGGACCTTGAGGCGTGTCAGCAGCGGCCACCGGTGTTCCCGGAGGACCTTGAGGCGTGTCAGCACCGGGTCGCCAGCGTCCG
     <V  G  G  G  D  G  Y  A  G  L  V  K  T  P  Y  F  S  F  A  A  A  D  G  M  T  G  A  L  R  G

<G  R  R  A  G  H  S  Q  A  C  D  E  L  V  K  L  G  H  E  R  A  V  R  L  V  P  D  M  D  V  C
```

FIG.11A(2)

```
2204 CTGGCCGTAGAGGTGCACCGGCAGCAGGCCCTTCGTCGTCCGGGGGGTGACCGGCTCGGCCAGCAGTCGGTGTCCATCAGGTAGTCGTCGGCGC
     < Q  G  Y  L  H  V  P  L  L  A  K  T  R  P  T  V  A  E  A  L  L  E  T  D  M  L  Y  D  D  A  R
2296 GGACGTCCACGAAGACCGGCGTCGCCGACCGTCGATGGCGAGACCGTCGGCCGTGTTGGAGACGGTGATGACTCGTGCCC
     < V  D  V  F  V  P  T  A  G  V  A  D  I  A  L  V  T  P  A  A  T  N  S  V  T  I  V  E  D  G
2388 GGCCCGACGTCGAGCGCCTGAAGTGCGACCTTGATGCCGAGCTTGATGCCGTTGTGCCGCATGTCGGCATGTGTGATAGGCGGGCGAA
     < P  G  V  D  L  A  Q  L  A  L  K  I  A  N  T  G  N  D  V  T  C  H  P  M  D  H  Y  A  A  F
2480 CTCCTGCTCGAAGCCGCGCACGCTCGCGCCAGGATGAGGTTCCCGGACTGAAGACCGTCTGCACGGCGTCGAGGAGGTCGTCCGTTCCT
     < E  Q  E  F  G  R  V  S  A  G  L  I  L  N  G  S  E  F  V  T  Q  V  A  D  L  L  D  D  R  E  K
2572 TCTCGTACTCCGGCAGGTAGCCCACACTCGGATGGTCATCTTCGCCCTTCTACGGCGAGGTCCGGGAGCGGCGCACGCTCAT
     <             E  Y  E  P  L  Y  G  W  V  R  I  T  M   <-   A  S  T  R  S  R  L  A  R  V  S  M
2661 GTAGTCGTTGTCCGGCTGAGTCCAAGTGCTCAGGTAGTGCTCACGTAGGGCTGCATGAACCCGGCC
     < Y  D  N  D  R  D  L  G  L  A  Q  G  S  L  Y  D  V  A  D  V  Y  S  Y  P  Q  M  F  G  G  A  R
2753 GCACGTCCGATAGAGCCGGGAGAGTGGGCCGCCGAGGGTCATCATCGGAACGGGTCTTCGCCGTTCGTCCACCGCCGGGGCC
     < D  A  N  T  L  A  A  G  V  T  T  R  L  A  Y  L  R  T  D  L  G  A  V  L  A  R  A  G  A  R  P
2845 AGCTCGTTGACGGTCATCTTCGCGGTCATTCTGAAACGGGTGTGCGTAGAGCGCGGCCGATGCCGATGTCGAGCATGGTGATCGAGCTG
     <L  E  N  V  T  M  K  A  Y  Q  F  P  T  M  R  R  G  R  E  D  P  D  G  S  L  D  V  S  A  A
2937 GTCGGGCGTTGGTCAACGCCGCAGGTAGATGCCAGCCGCGCTAGATGCCGGCGATGCCGGCGTAGATGCCGAGCATGGTGATGAGCATGTG
     < D  A  N  T  L  A  A  G  V  T  T  R  L  A  Y  L  R  T  D  L  G  A  V  L  A  R  A  G  A  R  P
3029 GCTCGCCGCCGCCGGCCAGCAGCGACACGGCCGTCCCGCCGACCCGGCTCCAGCAGCCTCGTCGGCCCGGACCTGTCGGCACCGGTCGAAGAC
     < E  G  G  R  G  A  C  F  G  V  A  I  D  R  A  A  Q  A  I  G  A  Y  I  G  L  M  T  I  S  S
3121 ACCGGTCAGGCTCTGCCCGGCCAGCGACGGCCGCCGAGGCGTCCCGGGCGTCTTCGGCGTCCTGGAGGACGCCCGGGTCCGGTCGAAGAC
     <V  T  Q  G  A  L  V  V  A  D  R  R  A  G  V  P  G  R  E  L  L  E  D  A  R  V  P  C  R  D  F  V
```

FIG.11A(3)

```
3213 CACCTCCAGGCGTCCCGAGGCACGCATTCCCAGGCCGTGTCCAGTTGTCCAGCACCGTGAGCCCGGGGCGTCGCGGTGCACGACCGGCACGG
     < V E L T G S A R M G L G D W N D L V T L G P A D R H V V P V A

3305 CGAGGAACACCGAGCGTCGTCGCGCCGTCGTGGGCGCTGCGATGCGTGCACGAAGAAGTGGGTCGCAGCAGCACCTTGCGGCCC
     < L F V S G D D D R R Q A H V F F H T A I P A M S V L V K R G

3397 GACAGCAGCGAGGCCAGCCAGCCGTGGACAGCCGTCGGAATGCAGCCGTGGATGACCATCGCCGCGGGCGTCTTGAGCGCGCGCCGCGCCTC
     < S L L W G G A G D S H L E T V V G P A D K L A G C V A A E G E

3489 CGCCATGCCCGGAGCCGCAGCCGCTCCGCATCGCGCGTCGCATGCTCGCCACTGTGTAGGTGAGGGTGAGCCCCGGTGAGCT
     < A M A R L L R E A M A R V P P T G H Q W E Y T L T L G R S L Q

3581 GCACGTGCCAGGCCAGCGACGCGGTGCACGCCCTGGACGCCGTCGGCCCAGCGCCATCAGCGCGGTCGTACAGCCGGGTCAACCCCAGGCCG
     < V H W A L A T S A D E A L R M L A T A V D Y L R T L G L G

3673 CCCAGCTCGGGCGGGAACGGTGGGCGCCCATCAACCCGAGCTTCGCGAACTGCTCGAACCGCCTCCACGGGAAGGTGCCGGTCGGTCCGGTG
     < G L E A P V T A G M L G L K A F Q E F A E V P F T G T R D R D

3765 GGCGGCCTCCGCACTGATTCTCGGGATCAAGCAGGTGCAAGCCAGGGCCGTTGAGCGCGGTGAGCGGCGCGGAAGATCCGCCG
     < A A E A S I R P I V G A L L D V V T R G A P T L P A R L D A A

3857 CCACCCCATCTCTCCTCGGTCAGATTAGACATCGCCCTGTCCGAACCTGTCGCTATCAGGGTGCGCGGGATCACC
     < V

3947 AATTGCTGGCTGTGATTGTCCACGGAGTCTCGACAGGGGATACCCAGAATAGGCGGCAACCCTGTGCGGAAACCCTGTGCCGGAGT
     > V K I L F I A G P T K S S L F G L A P L A I A A R M

4039 TCGCCAAGTCTAGTTGGATCACTCGAGCTTCCCCGCAGAAGCCGTTGAACCATGGGCCAGCGGTTGACGTCGTATATTCGGCCGACACG
     > S G H E V V M A S T Q E V V P A T M S V G L P A F F L A A L T

4131 TGCGGAGGACTCGTGAAGATACTGTTCATCGCCGCCAAGAGTCCAGCCTATTCGGCCTGGCCACTGGCAATCGCCGCCCGGATG
     > V K I L F I A G P T K S S L F G L A P L A I A A R M

4221 AGCGGGCACGAGGTCGTGATGGCTTCCACGCAGGAGTCGTACCGGACGATGTCCGGCGCTTCCGCTGCCGGCTTCCGGTCCGGGCTGAC
     > S G H E V V M A S T Q E V V P A T M S V G L P A F F L A A L T

4313 CCTCGCCGAGCTCATGACCACCGACCGGGCCGGGGCGATCCGCTGCGCCGAGGACGCCGCCTTCGTCCCCTTCGTCGGCCGGATGT
     > L A E L M T T D R A G D P L R I P A E D A A F V P F V G R M
```

FIG. 11A(4)

```
4405  TCGGCCGGGCTGCCGCTGGAGATCAGCCTGGATCCGCTGCGCGATCTGGTCGGCGGGTGGCGGCCCGACCTGATCGTCGGCGGCCCGCACGCCTAC
     >F  G  R  L  A  A  I  S  L  D  P  L  R  D  L  V  G  G  W  R  P  D  L  I  V  G  G  P  H  A  Y

4497  GCCGGCCCGATCCTGGCCACCGAACTTGGGGTGCCCTGCTGCCTCGGCCGGCACTTGCTCACCGGTGGACCGGTCAACCCGGTGGACCGGGAGGGCACCCATCCGGG
     >A  A  P  I  L  A  T  E  L  G  V  P  C  V  R  H  L  L  T  G  N  P  V  D  R  E  G  T  H  P  G

4589  GGTCGACGAGGAGCTGCGCCCGGAGCTGGCCGCGCTGGGCCTGGCCCAGGTGCCGCCGTTCCACCTGGCCCTGGACATCTTCCCGGCCAGCA
     >  V  D  E  E  L  R  P  E  L  A  A  L  G  L  A  Q  V  P  P  F  H  L  A  L  D  I  F  P  A  S

4681  CCCGGATCGACGACGTCCCCGGCCAGCCGGTCGCGACCGTCGCGCTCGGGATTCGACCAACAGCAGCCGGTGGCGCCGTGGATGCTC
     >T  R  I  D  D  V  P  P  A  Q  P  V  R  P  L  R  W  I  P  T  N  Q  Q  P  V  A  P  W  M  L

4773  TCGCGCGGGCCGCGTCGCGAGGTCCTGGTCACCGGCCAGTCTGGTCACCACCAACTTCGACTTCCTCCACGACTTCCTGCACGGCCTGGCCGGCACTGGCCGGCAC
     >  S  R  G  P  R  R  R  V  L  V  T  A  G  S  L  V  T  T  T  H  N  F  D  F  L  H  G  L  A  G  T

4865  CCTGGCCGAGCAGGACGTCGAGGTCGTGGTCGCCGAGCTGTGCCCCACTGTGACCTGATCGTGCCCCACTGTGACCGCGCTGAACGCGGGGGGTG
     >  L  A  E  Q  D  V  E  V  V  V  A  A  P  E  V  G  R  A  L  H  D  V  P  G  V  R  H  A  G

4957  GGCTCCCCGCTGGACGTGGTGCTGCCCCACTGTGACCTGATCGTGCACCACCACTCCGGCACGATGACCGCGCTGACCGCTGAACGCGGGGGGTG
     >W  L  P  L  D  V  V  L  P  H  C  D  L  I  V  H  H  S  G  T  M  T  A  L  T  A  L  N  A  G  V

5049  CCCCAGCTGATCGTGCCGCAGGAGAGCCGGTTCATCGAGTGGGCGCAACCTGTCGACCTGGGCGTGGCGCAGACCCTCGCGCGGCGA
     >  P  Q  L  I  V  P  Q  E  S  R  F  I  E  W  A  R  N  L  S  T  L  G  V  A  Q  T  L  A  P  G  E

5141  GGACACGCCGGAGGCCGTGGGCAAGGTCGCCCGCCTGCTGCTGGAGGATCCGGTCCACGGCCACCAGGCGCCGGATCGCCGGGAGATCG
     >  D  T  P  E  A  V  G  K  V  A  R  L  L  L  E  D  P  V  H  A  T  S  A  A  A  I  A  R  E  I

5233  CCGAGATGCCGGCCCCACGGAGGTCGTGGGCCAGCTCACCGAGTTCGCGACGCGGGGCCTGACATGCGCGTCCTCGTGACCGGCGGAGCC
     >A  E  M  P  G  P  T  E  V  V  G  Q  L  T  E  F  A  T  R  G  L  T  C  A  S  S  .
                                                                                  >  V  T  G  G  A

5324  GGGTTCATCGGCTCCACCTCACGCTGCTCGAACGCGGCAGCGTCACGGTGCTCGACGACCTGTCCACCGGGCGCCCGAGCC
     >  G  F  I  G  S  H  L  T  D  A  L  L  E  R  G  D  S  V  T  V  L  D  D  L  S  T  G  R  P  E  R

5416  GCTGCCCGCCGGGGTGCCGCTGCACCACGGGTCGATCACCGACCGGGCCGGGTTGACCGGTTGACCCGGAGCAGTGTCGCCGAGGTCATCT
     >  L  P  A  G  V  P  L  H  H  G  S  I  T  D  R  A  G  L  T  R  L  A  E  Q  C  R  P  E  V  I
```

FIG.11A(5)

```
5508 GCCACCTGGCCGCCCAGGCGGACGTGCGCAACTCGGTGGCCGACGCCACCTCGGACACCGGGGTCAACGTGGTCGGCACGGTCAACGTCCTG
     >C  H  L  A  A  Q  A  D  V  R  N  S  V  A  D  A  T  S  D  T  G  V  N  V  V  G  T  V  N  V  L
5600 GAGGCGCGCGCCCGGGCCATCGACGCGCGGGTCGTCTTCGCCTCCAGCGGCGGCGCCCTCTACGGGGAGGTCGACGAGCTGCCCTCCCCCGAGGA
     >E  A  A  R  A  I  D  A  R  V  V  F  A  S  S  G  G  A  L  Y  G  E  V  D  E  L  P  S  P  E  D
5692 CGTCCGGCCGGCCCCGTACGGGGCGGCCAAGTACTGCGCGGAGCAGTACCTGGCGCTCTACAACCGGCTCTACGGCTCGACCC
     >  V  R  P  A  P  Y  G  A  A  K  Y  C  A  E  Q  Y  L  A  L  Y  N  R  L  Y  G  S  T
5784 ACGGGGCGCTGCGGCTCGGCAACGTGTACGGGCCGCGGCAGGACCCCACCGGCGAGGCCGGGGTCGTCTCGATCTTCTGCGGCTGCCTGGTG
     >H  A  A  L  R  L  G  N  V  Y  G  P  R  Q  D  P  T  G  E  A  G  V  V  S  I  F  C  G  C  L  V
5876 GCCGGGCGCCGGCCGACGGTGTTCGGCGACGGCGAGCAGACCCGGGACTACATCTACGTGGCCGACGTGGTGGAGGCGTTCCTGCTCGCGGT
     >A  G  R  R  P  T  V  F  G  D  G  E  Q  T  R  D  Y  I  Y  V  A  D  V  V  E  A  F  L  L  A  V
5968 CGGGCACGGTGGCCCCGGCCTGTGGAACATCGGCACCGGGACCTCCACCAGCATCCGCAAACTGCTGGACCTGGTCGGCCGCACCGCGGGC
     >  G  H  G  G  P  G  L  W  N  I  G  T  G  T  S  T  S  I  R  K  L  L  D  L  V  G  R  T  A  G
6060 GCGTCCCGGACCCCGCTTCGAGCCCCCGCGCCTCGGCGAGCTGAAGCACTCCGCGCTGGAGGTGACCCGCGCGGCGCGGGAGCTGCGCTGG
     >R  V  P  D  P  R  F  E  P  P  R  L  G  E  L  K  H  S  A  L  E  V  T  R  A  A  R  E  L  R  W
6152 GCGGCCCGGAACGAGGCTCGCCGACGGCATCGCGAAGGTCTACAAGTGGGTCGAGGCGGACGAACCGGTCCGGGGGGAGCGGGAGCGA
     >  A  A  R  T  R  L  A  D  G  I  A  K  V  V  Y  K  W  V  E  A  D  E  P  V  R  G  E  R  .
                                                                                    >M  T  R
6242 AGGGGTCAACGCGGGTTAGGGTGCGGCCACCATCACGGTCGGCCACCGAGATCCGTTGGCTGGACCGCGCGCTCGGCTCGCTGCTCGCC
     >E  G  S  T  P  P  V  R  V  A  T  I  T  V  G  T  N  E  I  R  W  L  D  R  A  L  G  S  L  L  A
6334 AGCGACACGACGGGCTTCGAGCTGACCGTCTTCTACGTGGTCGACAACCGCTCGGCCGACGGCAGCGTGGCGCACGTCATGTCGGCGTTCCCGG
     >S  D  T  T  G  F  E  L  T  V  F  Y  V  D  N  A  S  A  D  G  S  V  A  H  V  M  S  A  F  P  G
6426 CGTCCGGGTCATCCGCGAAACCCCGAATCTCGGCTTCACCGGCGAACAACGTCGGCATGCGGGCGGCCCTGGCGCGGGGCTTCGACCACA
     >  V  R  I  R  N  P  R  N  L  G  F  T  G  A  N  N  V  G  M  R  A  A  L  A  R  G  F  D  H
6518 TCTTCCTGGTCAACCCGGACACCTGGACACCGCCCGGCCTGGTCCGCGGCCTGGTCGAGTTCGCGCAGCGGTGGCCGCAGTACGGCGTCATC
     >I  F  L  V  N  P  D  T  W  T  P  P  G  L  V  R  G  L  V  E  F  A  Q  R  W  P  Q  Y  G  V  I
```

FIG.11A(6)

FIG.11A(7)

```
7713 TGCTTCGGCCTGGCAGCGCCGGTGCGGCACCGGCTGGAACTGGGCACCGGCGCCCAGTCGCGGCCCGTACGACCTCCAGTACATCGGCAGCAA
     > C F G L A A P V R H P L E L G T G A Q S R P Y D L Q Y I G S N
7805 CTGGTGGCGGTGGGAGCCGATGACCGAGATGGTCGAGGCGGCGGCGGCCCGCCCGCTGCGCCGGCTGCGGGTGTGCGGACGCTGGT
     > W W R W E P M T E M V E A A A A R P L R R L R V C G R W
7897 GGGACGGCGGCAGTTGCGCGGGCTTGCGAGGAGGACGACGCTCAGCGAGCCGGGCTGGCGTCGAGGCGTGCAGGTGCATCCGCCGTG
     > W D G G S C A G F E E A T L S E P G W L R A R G V E V H P P V
7989 CCGTTCGGCCACGTGGTCGAGCAGATGGGCCGGTCCCTGATCTCGCTGTCCCGGTGCTGGTCGTGGCGGCCTGTTGACCCC
     > P F G H V V E Q M G R S L I S P V L V R P L V T S T G L L T P
8081 CCGGATGTTCGAGACGCTGGCCTCGGGCAGCCTGCCGGTGCTGCCGGTGGCCGCGAAGTTCCTCGCGCCGGTGTACGGCGACGAGGCGGAAC
     > R M F E T L A S G S L P V L P V A A K F L A P V Y G D E A E
8173 ACCTGATGCTCGGCGACGACCCGGCCGGTACCCTCTCGCGTCTGCGGCTGAGCGCTGCGGAGCACGAACGTTACGGACGACTGGTCGGTGAGATTCAGGAC
     > H L M L G D D P A G T L S R L S A E H E R Y G R L V G E I Q D
8265 CGGCTCCGGCGAGTACCCTCGAGTACCCGAGCTGCTGGCCTGAGGAATGAGGAGCAGATGACCCCCTG
     > R L R V E Y G Y P R V L R D L L D L L A .
                                                  > M T P L
8354 CGGATCGCGATGGTCAACATACCGTTCCGGTTGCCGAGCGACGAGCCAGTGGATCACGCGGTCCCGCGCAGGGTACGGCGGGATCCAGTG
     > R I A M V N I P F R L P S D E R Q W I T V P P Q G Y G G I Q W
8446 GATCGTGGCCAACAAGATCAAGGGCCTGCTCGAACTCGGGCACGAGGTGTTCCTGCTCGGCGCAGTCGGCGTACGCATCCACGCC
     > I V A N K I K G L L E L G H E V F L L G A P G S P R T H P R
8538 TGACCGTGGTGCCGGGGGAGCCCGAGGACATCCGGGCATGGTTGAAGTCCGGTGACGTGTCAACGACTACAGCTGCGGCAAG
     > L T V V P A G E P E D I R A W L K S A P V D V V N D Y S C G K
8630 GTGGTCGTCGAGATCGAGCTGCCCCGGGGTCGGCCTGGTGGCCTCGCCAACATGACCACCCGCCCGTCTATCCGGCCTGCTGTACGC
     > V D P I E L P P G V G L V A S H H M T T R P S Y P A G C V Y A
8722 CTCGAAGGCGCAGCGGGAGCAGTGCGGCGGCGCGGACGCCCCGGTCATCCCGATCGGGGTGGACGACCCGTCCCTCTACCGCCCCGGACC
     > S K A Q R E Q C G G A D A P V I P I G V D D P S L Y R P G D
```

FIG.11A(8)

```
8814 GCAAGGACGACTTCCTGCTCTTCATGGGCCGGATCTCCCCGTTCAAGGGCGCGCTGGAGGCGGCCGCGTTCGCCCGGGCCGCGGGCCGG
    >R  K  D  D  F  L  L  F  M  G  R  I  S  P  F  K  G  A  L  E  A  A  A  F  A  R  A  A  G  R  R
8906 CTACTGATGGCCGGTCCGGCCTGGGAGCCGGAGTACCTCGACCGGATCATGGGCGACCAGTACCTCACCCTCGTCGGCGAGGTGGG
    >L  L  M  A  G  P  A  W  E  P  E  Y  L  D  R  I  M  G  E  Y  G  D  H  V  T  L  V  G  E  V  G
8998 GGGTCAGGAGAACGTATGGACCTGCTCGCCACGGCCTGCTCTCCCAGCCGGTGCCGGCCGGTGGGGCGGCACGTGGTGCG
    >  G  Q  E  R  M  D  L  L  A  T  A  A  A  I  L  V  L  S  Q  P  V  P  G  P  W  G  G  T  W  C
9090 AGCCGGGTGCGACCGTGGTGTCCGAGGCGGCCAGCGGCACCCCGGTGGTCGGCACGAGCAACGGCTGCCTGGCGGAGATCGTGCCGGCC
    >E  P  G  A  T  V  V  S  E  A  A  S  G  T  P  V  V  G  T  S  N  G  C  L  A  E  I  V  P  A
9182 GTCGGGCGAGGTGGTGGGCTTCGGCACGGGCTTTGACGAGGGGAGCCCGGCGCAGGCGCGTCTGCCCGTGCCGCGTCCCAGGCGCGGAA
    >V  G  E  V  V  G  F  G  T  G  F  D  E  R  E  A  R  A  V  L  S  R  L  P  S  P  A  Q  A  R  K
9274 GGCCGCGATCCGGTGCTGGGGGCACGTGGGAGATCGCCCGACGTAGGGGGCGTCGACCCGGTGTCGGCGGTCCGACACCGGCGCGCCCG
    >  A  A  I  R  C  W  G  H  V  E  I  A  R  R  Y  E  A  V  Y  R  D  V  L  A  G  A  R  W  S  .
9365 GCCGGCCCGGGCTACCGGCGGCTCCGGGTCTCGCGGGGTCTCGGGGTCTGCAGCCAGGTCGGCCTCATGAACACCAGGACGTACGCGCGG
    <  S  R  D  H  L  W  P  R  P  E  P  D  T  V  E  V  P  Q  S  M  F  V  L  V  Y  A  R
9548 CGCGGCTGGTCCGTCTCGTTCGGGCCGGCGTAGTGCGGGCACGAAGTCGTGCATGACCGCCTGCCCGGCCGCGGGCCAGGCGACGCT
    <R  P  Q  D  T  E  N  P  G  A  Y  H  P  A  R  F  D  H  M  V  A  E  G  P  R  L  P  C  A  V  S
9640 GTCCGTGTCGTCGACCTCGTCCGTCATCAGACCTTCGATGGTCGTCGTTGATGTGAGCACCCCGGTGCGGGAGCACCCCGGTGCAGGC
    <D  T  D  D  V  E  D  T  M  L  G  E  I  R  D  D  H  N  I  H  H  P  L  V  G  G  R  H  L  G
9732 CCGGCAGGTACTGCAGGGACACCAGCCGCTGCCTCGTCGAGGAGATGCTCAGGATGCTCGAGGCCGTAGCAGCCGGGTCCATG
    <  P  L  Y  Q  L  C  G  S  S  V  T  A  E  D  L  P  T  W  I  S  L  G  R  R  S  W  R  P  D  M
9824 TACGCCTCGTCCTGGTGCCACGAGTGGGTGCCGCTTGAGGATCGCGTAGAAGTGCAGTTCGTCCTCCTCGGGGAT
    <Y  A  E  D  Q  H  W  P  T  P  A  G  Y  R  P  P  K  L  I  A  H  G  Y  F  D  L  E  D  E  P  I
9916 GTCGAGGAAAGCGAGGCGACATGCCCGGCATGCCGTCCTCCACCAACTCCGGCAGGTATTTCTCCGGCCGACGATCTGCG
    <D  L  F  A  S  I  A  R  C  R  A  F  H  A  T  E  V  L  E  P  L  Y  K  E  P  R  V  I  Q  P
```

FIG.11A(9)

10008 GGAGACGGGCAGGCGGCGTCGTCGCCACGGGCCGGGCGATCGACCGGGATGTCCGGTAGTCGCCGGTGTCGGGCGACGCGTGATCGGGCGAAGAGCCGGTCG
      < L R A P A A D D G R G A I D R Y D G T D P S A H D A F L R D

10100 TAGGCGGCCCGGGAGCCAGGCGACCTCGGCGTCGTTGCGGAGCCATCGCGAAGCCATCGCGCCGGTAAGCCTCCAGCCGACGGTC
      < Y A A R L W A V E A D D A L Q P L T V F G D R R Y A E L R R D

10192 GACGACCTCCGCACCAACAGTCCCACGGCCATTTGACCACCTCTCGGAATAGCCTGTCCGGAATAAACCATACGTAGGAACAGGCG
      < V V E A G V T G V A M

10282 GCGATACCGCTCCCGAGCGGGAAATAGGGATTCGACTAGTATTCGGTCCGCTGCCAGAACGGCACGCGCTCGATTGTCCATTCAT

10374 CCCCGTGCGAGACTCGCTCGCCTCGATGTCCTCGATGTCGTGGGGGTTTGGGATGACAGGGCACAGCGCCGTCGCGCTGCGGACGTCGGCGGGGT
      > M T G H S A V A L D V G G V

10465 CGTCTACTACGACGAGCCGTTCGAGCTGGCCTCCAGGACACCTTCGACACCGCCTCCAGGACCCGACCGCTCGACCCGACCCGACTCGGAGGCGCGCTGAGCTGG
      > V Y Y D E P F E L A W L Q D T F D R L Q A T D P T L D L R A

10557 TTCTGGAGCACGTCGAGCGGTTCTACCACTACGGCGAGGGCGACCCAACCGGCTGCTCCACTCGGAGGCGCGCTGAGCTGG
      > F L E H V E R F Y H Y G E G D P T G R T W L H S E A A L S W

10649 TCGCGGGTCCGGCAGTCCTGGGGCGAGCTGGCCCAGGAGATTCCCGGTGCCGTTCGCGGTGCCAGGGAACTGGCCAGGGAACTACCGTCGT
      > S R V R Q S W G E L A Q E I P G A V R A V T R L A R E L P V V

10741 GATCGTCGCCAACCAGCCCCCGAGTGCGCGGACGTACTGGCCGCCCAGGTCTGCCGGGAGGTGCTGCTGGACTCCCTCG
      > I V A N Q P P E C A D V L A R W Q V S Q V C R E V L L D S L

10833 TCGGGGTGGCCAAGCCGGACCCGGCCCTGCTCGGGCTCGGTTGCCGGTGCCGGTACCGGCCGCCGAGTTGCTGGTGGTGGGCAACCGG
      > V G V A K P D D P A L L G L A L R R L A I P P A E L L V V G N R

10925 ACGGATCACGACGTCCTGCCCGGCCTCTACACGGAGCTGAGGGCGTTCCGCACCGGCGTCACCGGTACCCGCCGCGCCGGGTCCA
      > T D H D V L P A L G L G C P V A F V L P D D A Y R R P P G V H

11017 TCCGGACCTGGTCCGGGTCTACACGGAGCTGAGGGCGTTCCGCACCGGCGTCACCGGTACCCGCCGCGCCGGGTCCA

11109 CGGCCCTGCCGACTCTCCCCGACGAGTGCCACCCCGGTTCGAAGCCGAGGACGACTTTGACGAAGGAGTGCAGTGCGACGCC
      > A A L A D S P L T S A T P R S N A G T G G L .

FIG. 11A(10)

11200 CCGCAGCGGTGGTCGGCGCGCCACCGGCTTCATGGCTCACGCCTCTGTCTCCCGCTGGCCTGAGGCGGGCATCCGGTGGCGCGCTTCAGCCG
11291 TGCCGCCCACCCGTCGTCGACGGCCCGCCGGGCCTCGACGGCGCCAGGTCGTCTACTTCCTCGCGCCGGCTGAGCCCGGCGC
11383 TGGCGGAGCAGCAACGGGAACGCGAGTTGTTGCTGACGTCGTCTAAGTGCGTGCTGGACCACCGGCCGGTG
11475 TTCGTCCTGGCCAGTCTCGGGCGGTGTACAGGAGCGTGCGCCACCAGGGCTGCGGAGCGGTGTGTGACCGGCTGAGCAGGTC
11567 CGGCCGGGCAGGCGAAGCTGGCGACCCCGGGTACGTCGGGAGAACAGGAGCTGGTGGTCGACGCGGTGGTGACCGGCGATCCG
11659 CGGGGCAGGCGGCCGACCCCGGGTACGTCGGGACTACGTGCTGGTGCTCGTCACACTGGCTGTCTGTCACGCGGAGGTCATGAGAGCGCAGAGCCACGATCCGGCGATCCG
11751 GCCGTGGTGCGGGACTACGTGCTGGCCCTCGGGCTCGTGAACGTCGTCGGCCACGTCGTGAACGTCGTCGGGCCTCGTGAACGTCGTCGGCCACGATGTCCAGACGATGTCCAGACGATGTCCAGACGATGTCTGAGCTGGAGG
11843 GCCCACGTCGTGAACGGTCTCGGGCCTCGTGAACGTCGTCGGCCACGATGTCTGAGCTGGAGG
11935 TCATCCGGACGTCCCGGCAGTTCGACCAGTTCGCCAGTGCTGTGGGAGGCCGTCTGCTCACCGGCGGGCGGTTCCCCGGCCCGACCGTCAGCCGGC
12027 AGCCTCCCGACGGCGTCCGCAGCGTCCGCAGCGTCCGCCAGTGCTGTGGGAGGCCGTCTGCTCACCGGCGGGCGGTTCCCCGGCCCGACCGTCAGCCGGC

> S L P D G V R Q C W E A V L T R A G G P G G S P A R P S A R
< . G P junction marker 12118 TCGGGAGAGCGTCTCGGGGGCGAGCCGGGATTCCGGGGGCGGACCGTGGTGCCGTTCGTGCCCTTCGCAGCAGTTCGTGCTCAACCCGGCTGCTCAACCCGGCGGCGTCGCCGGTGTAGCC >L G R A S R G R E P P Q P F R G R T V P V P F L A Q A G P C L V P S G
<E P S R R P P P F R R L R A R R L L R H S L G A A T A A T Y G 12210 GAGGGCCAGTGCTGGCAGGGCGAGCCGGCCCTGGCCCTGCGCTCCGAGCCGGCCACCCGCCATCCTTGGCCAGGCCGGTCGGCCGATGTCATGGGTGACC > E G Q W Q G E P G F R G R T V P V P F L A Q A G P C L V P S G
< L A L P L A L R S E P A T R H R D W E K R L G A R A Q N R G A 12302 CCTCGCACCGCCGCCCCTGCCACGTACGCCCAGCAGGTACCCGGGGGCAGGGTACCGGGGGTCAGCGGGTCGATGTCATGGGTGACC > L A P P L P V R P P Q Q V P G G Q P A R V D V M G D
< E C R G Q W Y A R R L L Y R P T L R G P D I D H T V

12382 GCGTGGTCCGGGAGCAGTTGCTCGCGGGCGGCCTGCATGGCGCTGATGAAGGAGGTGTCCTCC

>R V V R E Q L L A G G L H G A D E G G V L
<A H D P L L Q E R A G A A K M A S I F S T D E

FIG.11A(11)

```
12451 CCTGACTGGGAGGTTGCCCCCGGTACGGGCTGAGGGCCAGGTCGAAATCCAACCCGTGGGCGTGCGCGAAC
     >P .
     <G  S  Q  L  N  G  G  T  R  S  L  A  L  D  F  D  L  G  H  A  H  A  F
12520 GCGGAGTCCACCCCCATGCACGCGCCCCAGATCTTGATGTTCCCTGGTCACGTGCCAGCCAGGTGGAACTGGCCGGA
     <A  S  D  V  G  M  C  A  G  W  I  K  I  N  G  Q  D  R  H  W  G  V  L  H  F  Q  G  S
                                    junction marker
12603 GGTGACGTACCACGGCAGAGACGCAGCGCGGGGCGGGCCAGCCACGTGCCGACCACGTGCGCGCCGTCGCGGACCGGTCGA
     <T  V  T  Y  H  G  R  D  T  Q  R  R  G  R  P  A  T  C  R  P  T  A  R  G  R  P  V  R
12695 CGGCAGGGCGTCGAGCCGTCACGTCGTGACGAACATCAGATGGTGGTGCGGGCCAGCGAGCGGGAGCATCGCGTTGCGGAGGCCGACAGG
     <R  Q  G  V  E  P  S  R  R  D  E  H  Q  M  V  V  R  A  S  E  R  E  H  R  V  A  E  A  D  R
     <T  V  Y  W  P  L  R  L  A  P  R  A  L  R  T  G  V  V  H  A  G  D  R  L  S  K  R  V  A  D  V
12787 CCATTGGTGGCACCGAGGATGCGCATGGCCATGGGCCCTCCCGGCCGACCTCCTCGGCGACCTCCGGCCTGCGACGGGCCGGTCCAG
     < A  A  D  L  R  V  D  D  D  V  F  M  L  H  H  H  P  W  R  A  L  M  A  N  R  S  A  S  L
12879 CAGGACGTAGTACTCGCCGGAGAGCTGGGCATTGTGCCGGAACCATGAGGCGTTCCTGACGTGTTCTCCACCGGAACGCAGATCGCCACCA
     <G  N  T  A  G  L  I  R  M  T  G  G  A  A  R  V  E  E  A  E  A  T  V  P  R  D  L
12971 CCATCGGGTTGGTCGGACGGATCGCGTGTTGTTCGGCAATGTCCTCCCTGCACATGAGCGTTGTGGGGCGGCGGGGAGA
     <L  V  Y  Y  E  D  G  S  L  Q  A  M  N  H  A  L  H  K  R  V  N  E  V  R  F  A  C  I  A  V  V
     < M  P  H  D  S  P  D  R  S  V  V  S  A  N  N  P  M
13061 GGCGGCCCACGCGGATCGCGCTCCGGCACCGCTGCCGCCACCGGACAGGTGGGCGACCAGCGGCGGGCCGTCCGG
13153 TGAGCGGCCGGGCGGAGCTCAGGCGCCGCCCTTGCTGCTGCTCCCGACGGTGCCCCGCGAGGATGCCCATCGCGTACGCCTT
13245 CGCGATCAGGGCGCGGCCGGTTGGGCACTCGCGCAGGTTCTGCAACAGCTTGCTGACGTTGGTGCTGACGGCTTGAGGTGGTAGACCTTGT
13337 TGGCGATATGCACCGTCGTTGGCTCGTGATCTGTTGCCCAGAGCTTTCGATGATGCGGGCGCCAGTGAGACGGTCCGGTGACGAGTTGTGCTTCCGCT
13429 CCTTGATTGTGATGACCGTCAGCGACGTCAGGCGGAAAGGCCTGCGGCTTGGGCTCTGTCGGCAGCTGTCTCAGTGTGGGGCGATGCCCCCGGCACG
13521 GGAAGACCGTCAGCGCGGAAAGGCCTGCGGCTTGGGCTCTGTCGGCACATGACGAGGCGATTAGTTACGGAAAGTGACAATCGGCTGGCC
13613 TAGCCCGCCTGACGGCCTGTCGATGACATCACTGGCCAACATCGGCGAAATGAAACCGGATTCGAGCGATAGTTACGGAAAGTGACAATCGGCTGGCC
13705 GAAGCCCTTGCTACTGTCGATCAGCGTCAGGCGGAAAGGCCTGCGGCTTGGGCTCTGTCGGCACCTGAGCGATTACGGAAAGTGACAATCGGCTGGCC
13797 CTGTCGCTCGCGCTGAACTCACCAACTCGCCAAATGCGGCCGCTAGCGGGCCGGGCCACTGCGGAGCGTCCACCCCCGAGGATATCGCCAGGCTTCCATG
```

FIG. 11A(12)

FIG. 11A(13)

```
15176 AACACGGGCGGCCAGCGCGGCGGGCTCCAGGGTGGCGACGTCGCCGGTACGGCAGCCCGCCGACGGGACGCGGCGGGCCAA
      <F V A A L A A P E L T A V D L A R A R Y P L G A S P V R R A L

15268 CACGAGGACGTCGTCGACGGCCAAGCGCGGCGGCTCACGTCACGAAGCCCGTACCACGACGACCAGGCCGCCGCGC
      <V L V D D G R A A L A A S V H R G V F G T G G V V V R R A G

15360 CCATCCGTACCTCCTGGGATCAGTCTCGTGCGCCGGCGTCCAGGCGACGCCCGGCACCCCTGACAGGTCACGGGGGCGCAACAC
      <M       <. D R A G A A D L R G G P G Q C T V P A R L V

15449 CCTGGCCCGGTCGCGAACCTCTGCGCAGCCGGACCCGGCGCGGATCGCGTCACCTCCTCCGCGGCTGACGGCGGTGACGCGCGGA
      <R A R D R V E D L L R A R A R I A T V E E A P Q G A T V A R V

15541 CGAACTCTCGCATCGTGTTGACGAACTGGTCTCCGGCCGGAAGGTCAGTCCCGCGTCTCGCCGTCTCGTCTTCACCACCGGGTGC
      <F E R M T N V F Q D E A P F T L E R T E D Q R E V R V P H

15633 CAGGCCCGGTGCTGGGGTGTACGCCCGGTCGACGACGATCCGGCTTCCCCAGAGACTGGTACTCGCACCGGTAGGAGTGCTGAAACC
      <W A P P P T Y A R D V V I R G A S G W L Q Y E C R Y S H E F G

15725 GAAGGCGATCTGTGCGCCCGTCCGGCTACACACAGCGGGAAACGTCCACGCGGATCGGGGTTCCTCCGGAGGGTGG
      <F A I Q A T R G D P T C L L A A G S V D V G R D P D E R L T A

15817 CCGCCACCACCTCCGGCTCCTCCGGCAGGAAGAACCCGAAGAGCGGGGATCTCAGCTCGCCGATCTCGCCGGTCCACCCGCCTCG
      <A V V E P E E P L F F R A A G L P Y V G L D L L A G G G L E

15909 GGTCGGTAACGGATGTGCCCGCAGGCAGCGGAAACCCGAAGAGACGGGAGACCATCCGCAGCTCGCCGATCTCGCCGGTCGCCGACCAT
      <P R Y R I D G A P L P P F G F V G S V M R L E G I E G A A V M

16001 CCGGCCGACGAAGTGGTGCACCCCATGTCGACACGTGTTCATCAACGAGCCCACGGCCTGGGTCAGCACCGCCG
      <R R V F H H V G H R L F T L N D M L V L G R S R A Q T L V A A

16093 CGGTGTCGACCGAAGTGGTGCTCCACCAGCCGTCGATCCAGGCCGGCAGGGCCGTTCGATCTCGAGGCCAAGTGTGGTGCAGCCGG
      <T D V L R T T L P K E V L V H K G A A L A R E I W T H H L G

16185 GTCGGCAGCGGAATGTAGACGGCATCGATGTCCGGGCGGTGCTAGCCCTCGGGCGGCGACACCGAACTCCGGCGAA
      <T P L P I Y V A D I D D P R D L V S Q Y G E A A A C G F E A A F
```

FIG. 11A(14)

FIG.11A(15)

```
17379 GCCACGGTGCACCCGGGTGTAGTTGCTCCGGGTGGCCTGCACCGTCGGCGAGAGCTGCATGACGTTGATGTTGCCGGGCTCCACCTTGGCCT
       <G  R  H  V  R  T  Y  N  S  R  T  A  Q  V  T  P  S  L  Q  M  V  N  I  N  G  P  E  V  K  A  Q
17471 GGAGCAGGCAGTACGGTGTCCCGTGACGAGACCTTGACGGAGCATGCCGAGGATGCCGATCTCGGTTGATGATCGGCTGGTGCCATTCG
       <L  L  C  Y  P  T  G  D  V  V  K  V  L  M  G  L  I  E  P  Q  N  I  I  P  Q  H  W  E
17563 CGCACCGCGCGTAGGTGGTCTGGACGTGCAGCCCCTCGATCACGAAGAACCGGCTGCCTCGTGCCGGAGGTTGCCGGTCACCGGGTCGAA
       <R  V  A  G  Y  T  T  Q  V  H  L  G  E  I  V  F  F  R  G  S  E  H  G  L  N  G  T  V  P  D  F
17655 CGCCCACCCGGCAGCCGGTTCCAGCGACGCGGTCCAGCGGTCAGTAGGTCGACCGGGTCCGCTCGGCGAACCAGGAGGAAGTCCGGCC
       <A  W  G  P  L  R  D  L  P  V  R  D  V  E  C  Y  T  S  R  T  R  E  A  F  W  S  L  F  D  P  R
17747 GGAACCCCTCGGCGTGAACGACGCCAGCGAGCCGTGCTCCGGGCCCGTGCGGGCCGGGGAAGGCGTGGGAAGACCCGTCCGTGTCCGCCAA
       <V  G  E  A  H  L  A  S  W  S  G  G  D  V  P  G  P  R  H  P  G  A  D  R  T  L  L  P  G  D
17839 GCGCGGACCTTCGGGCGACGAGTCGCTCACCACAGCTCGGCCAGTTCGGGCGGAAAGGCGTGGGAAGACCCGTCCGTGTCCGCCAA
       <A  R  V  K  P  D  P  S  S  D  S  V
                                          <-  W  L  E  A  L  E  A  S  F  A  H  S  S  G  D  T  D  A  L
17930 CAGGGCGCAGATCGCTGTCGACCATCATGGCGACCATCTCCTCGAAGGAGAACGGAGGGTTTCCAGCCGAGCCGCTTCGTCGGAT
       <L  R  L  D  S  D  V  M  M  A  V  M  E  E  F  S  V  S  P  K  W  G  L  R  Q  R  A  K  T  P  D
18022 CCGGCGAGCAGCAGTCGACCTCGACCTCGTCCACCACAGTCGTTGAGGCCACGTTGAGGCGCAGTTGAGGCCCACGTTGAGGCGAAGGCC
       <A  C  L  L  E  V  E  A  P  R  I  L  S  E  D  V  V  H  D  R  W  N  L  G  V  H  A  F  A
18114 GCCTCGACCAGTCGCGGAGCGTGTCGTGACCGTAGTCGTCCGGGCCAGCATCAGGACCATGCCCCG
       <A  E  V  L  E  R  V  S  H  T  V  G  T  G  L  V  Y  D  E  P  E  D  Q  A  L  M  L  V  M  G  R
18206 CACGTAGTCGCCCGCGAAGCCCAGTCCCGCTCCGGCGAATGCAGCTGCAGCTTCACCGCCGCCACGC
       <V  Y  D  G  A  F  G  W  D  R  E  A  S  L  N  G  L  R  L  S  S  R  I  G  L  K  V  A  A  V  G
18298 CCAGGCAGGACACCTTGCCGGGTGACGAACTCGGGAACCACCGGCGTGATTCGTTGAACAGAATGCCGATACACGGCTACGAC
       <L  S  V  K  R  T  V  F  E  P  G  R  V  P  S  E  H  N  F  L  I  G  S  V  A  Y  M  G  Y  S
18390 TCACGGTAGTTCTGCACCATGTAATGCCACGCCTTGGCCGCGAACGCCTTGGCCGCGAACGGGTGAACGGGGTCAGTCATTCTGGACGGG
       <E  R  Y  N  Q  V  M  Y  H  G  F  A  K  A  A  G  Y  P  S  R  P  H  F  P  P  T  L  E  N  Q  V  P

FIG. 11A(16)
```

```
18482  CTCCCGCACCTTGCCGAACATCTCCGACGAAGAGCGCCTGATAAAAGGCGGGCTGACCGGCTGCGGGATCCGACAGGCCCCCA
         < E  R  V  K  G  F  M  E  S  S  A  Q  Y  F  R  P  Q  G  A  A  P  S  R  S  D  S  L  G  G  V
18574  CGATCCGCAAGGCTTCGAGCATGGAGAGCAGCGCACACCCATGCCGGTGACCTCGTGGTGACTGGACTGTTGATCGCCGCTGCCCCACGACGTACGAC
         < I  R  L  A  E  L  M  R  L  V  G  M  G  T  V  E  A  T  T  T  S  Q  R  W  S  V  P  V  Y  S
18666  AGCGCGCTGGAGGTTGTAGACCTCGTCCGGCGCGTTCGATCGCGCTGTCTGATCGAAGGTGCGCTGATCAGGTT
         < L  A  G  L  N  Y  V  E  D  P  A  A  R  E  I  A  A  V  L  S  T  Q  D  L  L  D  G  S  I  L  K
18758  GACCGCTGGATCAGGTTGCCGAACGGCTGCGGGACCGGTCTGCCGCCGACGCGGCGTCGCCGTATCCGGACTGAAGCAGGT
         < V  A  P  D  P  Q  R  L  S  R  V  S  P  A  T  Q  G  R  V  L  G  F  V  E  Y  G  S  Q  L  L  H
18850  GCTCCGCGAGATACGTGCCGTCCTGGCCGGTAATTCCAGTGATCAGCCGGTGTCAGGGTAGTCTCCAGCCGTGAAGCCACCTGGCC
         < E  A  L  Y  T  G  D  Q  G  T  I  G  T  I  L  A  R  R  T  L  T  T  E  L  R  S  A  V
18941  GAGGCGTGACCTCGCGCTGGACGATGGCGGACCAAAGATCCGCCGTTCGAAATGGGTCGGATCTCCCGCTCAGGTACGCGAATCT
19033  CCAAGCGGATTCAGCGACCGACCCGGCGACCAATATAGGAGGTTACTACGAGGTCTCCACGCTCTTCGGGGACACCTTCGTCGCCGAGCCGGATGCGACCGGCA
19125  GGATCGCCCCGTTCGCCGGACGCTTCCACGGAGCTCTTCGGGATGTCGTCGCCGAGCTCCACCGGAGGCCGGGTTCACGAAGGGCCAACTTCCGGTGAACTGCTTGACTCC
19217  ACCGTTTGTCCCCCTAACGTCGGCCCGCTCGCGAGCCGGCCCGAGCGGCCACGTGCCGCGCCATGGTCGCGTTGGTCGCGGTGATGAT
         > M  V  A  L  V  A  V  M  I
19309  GGCTCATGTCGCAGGGCACGCGCGGAGTTGGGCGCTCGAGTTGGGGCCTCAGCACGCTCTCCT
        > M  V  A  L  V  A  V  M  I
19400  CCCGATGGTGCTGGCCACCCTCGACAACACCATCATCGGCACTGCCCTGCCGACCGTCGTCGGCGAGCTCGGCGGGCTCAGCACCCTGTCG
         > P  M  V  L  A  T  L  D  N  T  I  I  G  T  A  L  P  T  V  V  G  E  L  G  G  L  S  T  L  S
19492  GGGTGATCACCTCGTACACGCTGGCCACGGCCGCAGCGTCTCGGGGCAAGCTCGCCGACATGTACGGCGGCAAGGTGGTCTTCGTG
         > W  V  I  T  S  Y  T  L  A  T  A  A  S  T  P  V  W  G  K  L  A  D  M  Y  G  G  K  V  V  F  V
19584  GCCACGCTGGTCGTGTTCCTGGCCGGGTCTCTGCTGTCCGGCATGGCGCAGAGCATCACCCAGCTGACCGTCTTCCGGGCCGTGCACGGGCT
         > A  T  L  V  V  F  L  A  G  S  L  L  S  G  M  A  Q  S  I  T  Q  L  T  V  F  R  A  V  H  G  L
19676  CGGCGCGGGGCGGCCTGATGGTCTGCGCCTTCGCCATCATGGTGGAGGTTCTGGCCCCTGACCTGCCCAAGTACCAGGGCATCATGTCGG
         > G  A  G  G  L  M  V  C  A  F  A  I  M  V  E  V  L  A  G  P  D  L  P  K  Y  Q  G  I  M  S
```

FIG.11A(17)

```
19768 CGACCATGGGCCTGACCATGGTGGCGGGCCCGCTCGTCGGCGGCCTGATCACCGATGAGCTCGGCTGGTGCTTCTACATCAACCTG
     >A  T  M  G  L  T  M  V  A  G  P  L  V  G  G  L  I  T  D  E  L  G  W  C  F  Y  I  N  L
19860 CCGATCGGGGCGGTCGCGCTGCTCATCGTGGTGCTGATGATGCACCTGCCGCGCCACACCAAGGCCCGGATCGATTACGCGGGTGCTGC
     >P  I  G  A  V  A  L  L  I  V  V  L  M  M  H  L  P  R  R  H  T  K  A  R  I  D  Y  A  G  A  A
19952 CCTGCTCACCGTGGTCAGTTCGTGCGTGCTGGTGACCGCATCACTTACCCTGGGCGTCTCCAGATGATCCTGGGGCTGG
     >L  L  T  V  V  S  S  C  V  L  V  T  T  W  G  G  I  T  Y  P  W  A  S  P  M  I  L  G  L
20044 TCGCGCTCGGGGTGCTGACCTGCGCGCTCTTCGTGGTGGTCGAGCGACGGGTGGCCGAGCCGTTGGTGCCCCTGGCCCATGTTCCGCAGCCTG
     >V  A  L  G  V  L  T  C  A  L  F  V  V  V  E  R  R  V  A  E  P  L  V  P  L  A  M  F  R  S  L
20136 AACTTCACCCTGAGCACCCTCATCGCCTTCCTGGTCGGCTTCGCCCTCATCGCGGGCCTGACCTTCCTGGCCCTGTTCCAGCAGGCGGTGCA
     >N  F  T  L  S  T  L  I  A  F  L  V  G  F  A  L  I  A  G  L  T  F  L  A  L  F  Q  Q  A  V  Q
20228 GGGTGCCTCCGCGTCCGACTCCGGCCTGCTGCTGCCCCTGCTGCTGTCCATGGCGGTCAACGTGGTCGGGGGTCGCCTGATGAGCG
     >G  A  S  A  S  D  S  G  L  L  L  P  L  L  L  S  M  A  A  V  N  V  V  G  G  R  L  M  S
20320 GCGGGCGGTTCCTACCGGCTGCTGATGCTCGCGGGTGCCGCGCCCTGATGACCCTGAGCCTGCTCTTCGCCCTGATGGACGTGGGCACCAGC
     >G  G  R  S  Y  R  L  L  M  L  A  G  A  A  L  M  T  L  S  L  L  F  A  L  M  D  V  G  T  S
20412 CGGACGTGACCTGCTTCCGCACGTCCACGCTCTTCCGCACCATCGGTGGGGCGGTCGGCGCCAGCGCCACGGTCTCGTGTTCT
     >R  T  V  T  A  I  P  M  V  G  F  G  A  G  L  G  L  L  M  Q  T  S  L  M  V  A  L  S  S  V  E
20504 GATGAGGAACCTGGGCGTCGCCGCCTCCACGTCGACGCTGTTCCGCACCATCGGTGGGGCGGTCGGCGCCAGCGCCACGGTCTCGTGTTCT
     >M  R  N  L  G  V  A  A  S  T  S  T  L  F  R  T  I  G  A  V  G  A  S  A  T  V  S  L  F
20596 CCGTGCGGGTGCAGTCGCAGTCGGCCGTGCTGGCCGATCGGGGTGGCGATGCCGATGTCCACTTCATGACGGTGCTGGGCCTTCCTGATGATGA
     >S  V  R  V  Q  S  A  L  A  D  R  G  V  A  D  L  L  G  H  S  A  R  L  D  A  A  G  L
20688 GCCCAACTCCCCCGCTGCAGTCCGCCCGTCCACTTCATGCACGTCGCGGGTGGCACCGTGACGTCGGCACCCGTTGACGTCGGCACGCGCTGGCGC
     >A  Q  L  P  R  A  V  R  V  H  F  M  H  A  V  A  S  G  T  R  W  A  F  L  M  T  V  L  A  G  L
20780 GATCTGCGTCGCGGGCGGCGTGGTTCCTGCGCGGGTCACCCCGCTCACCAGCGCCCCGGTGGCCGAACCGGCACGCGACGTCGCCGCGC
     >I  C  V  A  A  A  W  F  L  R  R  V  T  P  L  T  S  A  P  V  A  P  E  P  A  R  D  V  A  A
```

FIG.11A(18)

```
20872 CCGCCGCCAGCAGGGGCGGCGCCGAACTACTAGCCGGATTTCCTCGTCGACGGTAGAGCTGAATTCACCGGCGACCTAACA
      >P  A  A  S  S  G  R  A  P  N  Y  .
20963 TTCTTTCGCGATCCGGAATCCGTCCATTCCCCTGTCTGGGATGGTCGACGGCCCGGTGCCGAGCGGACAGACAGATTCTCGGAT
20055 TGGAGCTCGATGTCCAGCAAGATCCTAGTCATCGGTCGGAGGTCCGGCCATCACCGGCGCTCCCGATCGGGACTCGTGTCG
      >M  S  S  K  I  L  V  I  G  G  P  A  G  S  T  A  A  L  L  A  R  S  G  L  S
21145 GTGACGCTCCTGGAAAAGGAGACGTTCCCGCGATACCACATCGGCGAGTCGATCGCCTCGTGCCGCACCATCGTCGATTTCGTGGGCGC
      >V  T  L  L  E  K  E  T  F  P  R  Y  H  I  G  E  S  I  A  S  S  C  R  T  I  V  D  F  V  G  A
21237 TCTCGACGAGGTCGACTCGGGGTACCCGCAGAAGAACGGGTCCTGCGCTGGGGCAACGAGGACTGGGCCATCGACTGGGCCAAGA
      >L  D  E  V  D  S  R  G  Y  P  Q  K  N  G  N  V  L  L  R  W  G  N  E  D  W  A  I  D  W  A  K
21329 TCTTCGGTCCGGGCGTGCGCTCCTGGCAGGTCGACGACTTCGACGGCGACCAGTCCTGCTCAACAACGCCGGCAAGCAGGGCGCCAAGATC
      >I  F  G  P  G  V  R  S  W  Q  V  D  R  D  D  F  D  H  V  L  L  N  N  A  G  K  Q  G  A  K  I
21421 ATCCAGGGCGCGCCGCTGTCCAAGCGGGTGTTGTTCGACGGGGAGCGGGCCGAGTGGTTCGACCCCGAGTCGGGTGAGGTCCGCAC
      >I  Q  G  A  A  V  K  R  V  L  F  D  G  E  R  A  T  A  A  E  W  F  D  P  E  S  G  E  V  R  T
21513 CATCGATTTCGACTACGTTGGTCGACGCATCTGGGGCTACTGGCAGGGCGGCTCCTGCTCCAGCACTTCAAGCACCGGCCCACCGAGACGTTCA
      >I  D  F  D  Y  V  V  D  A  S  G  R  A  G  L  I  P  S  Q  H  F  K  H  R  R  P  T  E  T  F
21605 AGAACGTGGCCATCTGGGGCTACTGGCAGGGCGGCTCCCTGCTCCCGAACGTCATCTCCGCGGATCAACGTGTCATCTCCGCGCCGACGGC
      >K  N  V  A  I  W  G  Y  W  Q  G  G  S  L  L  P  N  S  P  S  G  G  I  N  V  I  S  A  P  D  G
21697 TGGTACTGGGTCATTCCGCTGCGCGGCGACCGGTACAGCATCGGTTTCGTGTGCCACCAGAGCCGCTTCCTGGAGCGGCGCAAGGAGCACGC
      >W  Y  W  V  I  P  L  R  G  D  R  Y  S  I  G  F  V  C  H  Q  S  R  F  L  E  R  R  K  E  H  A
21789 CTCGCTGGAGGACATGCTCGCCGCACTGGTACAGGAGTCCCCGACGGTACGGGGACTGACCGCCAACGGGACGTACCAGCCGGGCGTGCGGG
      >S  L  E  D  M  L  A  A  L  V  Q  E  S  P  T  V  R  G  L  T  A  N  G  T  Y  Q  P  G  V  R
21881 TGGAGCAGGACTTCTCGTACATCTCCGACAGCTTCTGCGGCCCGGGCTACTTCGCCGCGGGCGACTCCGCCTGCTTCCTGGACCCACTGCTG
      >V  E  Q  D  F  S  Y  I  S  D  S  F  C  G  P  G  Y  F  A  A  G  D  S  A  C  F  L  D  P  L  L
```

FIG.11A(19)

```
21973 TCCACCGGGGTGTGCACCTCGCCCTCTACAGGGGCATGCTGGCCTCGGCGTCCATCCTGGCCACCATCCACGGTGACGTCACCGAGGAGGAGGC
      > S T G V H L A L Y S G M L A S A S I L A T I H G D V T E E E A
22065 GCGGGCGGTTCTACGAGTCCCTCTACCGCAACGCGCTGTTCACCCTCGTCGCGGGCGTCTACCAGCAGCCGGCAGGCCAAGAGGG
      > R A F Y E S L Y R N A Y Q R L F T L V A G V Y Q Q Q A G K R
22157 CATACTTCGGCCTCGCCGACGCGCTGGTGCACGACAGCGGCGAACCGAGTACGAGAAGGTAGACGGGGCCGGCCCTTCGCCAGCTCGTC
      > A Y F G L A D A L V H D S G E P E Y E K V D G A R A F A Q L V
22249 GCCGGCCTCGCCGACCTGGACGACGCGGCGGAGGGACACGCCGGAGCACAGCCGGAGCCCGGACGAGGACAACTCCGTCCGGCA
      > A G L A D L D D A A E G R H D S T A A A P A E Q D N S V R Q
22341 GCTCTTCCTGGCCGCCGAGGAGGCCCGCCGGATGGCCGACGCGCGCACCCCGTCAGCGCCCGTCAGCGAGGCGCCAAGCTCGACAGCC
      > L F L A A E E A R R M A D A R T P S A P V S E A P G K L D S
22433 ACGAGCAGTCTGCTGGCCAACCGGCCTCTACCTGGTCACCACCCCGCGCCTCGGCATCCGCCGAAGCCAAGCCGGACACGCAGGCGGCG
      > H D L F D S A T G L Y L V T T P R L G I R R A K P A D T Q A A
22525 GCAGAGCAGTCTGCTGGCCAACCTCTCACCCCTCGTCGACCCTCGGGGACTTCCACCGACCAAGGCTCACCTCTCCCGTGCTGAACAGACGACA
      > A E Q S A .
22616 GCATCCGGTGCCGGGCTGAGCAGGGCTGGCCGCCGGATCTCAGCGCCGACCGCACCGTCATGTCCTCAGACGACGCACCGGC
22708 GTTGCTGGCCCTCGGCAGCGTGGCCGCCCGGGCCAACCCGCACGCGCACGCCCATCGGCGCAGGTGCAGATCCTG
                                                > M S R S L R R D A Q A A P A
22798 GTCGCCCGCCAACCCGCACGCCATCCCGGTCTCCGACCCGGCATGCGCCGGTTCCTTGCTCGGCCCGACGCCGCGTGCGGATCACCTA
      > S P A N P H A G H A A P V P S R V S T T T V A V T P F T E P
22890 TGCCCGTCCCCCGCGACGTCTCCGACCCGGCATGCGCCGGTTCCTTGCTCGGCCCGACGCCGCGTGCGGATCACCTA
      > M P V P P R L T P V S R R D G I D V Y E I P I R P A Q V Q I L
22982 CCCGGGCCTGCTCACCCCGGCCTACACCGCCGGTTCCTTCGTCGGCCCGACGATCGCCAGGACCGGGCCGCGTGCGGATCACCTA
      > P G L L T P A Y T Y A G S F V G P T I R A R T G R P V R I T Y
23074 CACCAACGGGCTCGACACCCACGCCAACGTCCACCTGCACGGCGGGCACGTGCCGGCCACGAGCGACGGTCACCGATGGACCTGATCCCGC
      > T N G L D T H A N V H L H G G H V P A T S D G H P M D L I P
```

FIG.11A(20)

```
23166 CGGGGCGGCTCGAAGGTCTACGACTACCCGAACCTTCAGCGGGGCGGCGACGCTCTGGTACCACGACCACACCCAGCCTACGAGGCCGACCAC
      >P  G  G  S  K  V  Y  D  Y  P  N  L  Q  R  G  A  T  L  W  Y  H  D  H  T  H  A  Y  E  A  D  H

23258 GTCTACCGCGGACTGCACGGCTTCTATCTGATCGACGACCCGGCCGAGCATCACCTGCGCCTGCCCGCCGAGTACGACGTGCCGATCAT
      >V  Y  R  G  L  H  G  F  Y  L  I  D  D  P  A  E  H  H  L  R  L  P  A  G  K  Y  D  V  P  I  M

23350 GCTGCGCAACGCCCAGTTCGACGACTCCGGCGCGCTGGTCTTCGGCCACCCGGACGACCGGGTCACCATCCTGGCGAACGGCAAGGCCAGC
      >L  R  N  A  Q  F  D  D  S  G  A  L  V  F  G  H  P  D  D  R  V  T  I  L  A  N  G  K  A  Q

23442 CCTACTTCGAGGTGGCCCCGCGCAGGTACCGGTTCCGCCTGCTCAACGCGGCGCTGAAGCACGTCTTCCGGCTCAACCTGGGCGGCGAACCG
      >P  Y  F  E  V  A  P  R  R  Y  R  F  R  L  L  N  A  A  L  K  H  V  F  R  L  N  L  G  G  E  P

23534 CTCACCCGCATCGCCACGGACGGCGGGCTGCTGCCCGCCACCAGCCACACCGAGCTGGCGCTCTCCTCCGGGGAGCGGGTCGAGATTGT
      >L  T  R  I  A  T  D  G  G  L  L  P  A  P  T  S  H  T  E  L  A  L  S  S  G  E  R  V  E  I  V

23626 GATCGACTTCGCCGAGCACGCCAGGCGGCCGGTCACCTGCGCGGTGCCGCCGCGATCCTGCGCTTCGACGTGTCGTCCCGGCGG
      >  I  D  F  A  E  H  A  G  G  G  P  V  L  Y  D  G  D  N  P  I  L  R  F  D  V  S  S  R  A

23718 TCACCGACCCCAGCCGGGTGCCGGTCACCCTGCGCGCCCTGCCCCCGATGGGCACGCCGGTCGAGCGCACCGTGTCGATGAGCTTCGAC
      >V  T  D  P  S  R  V  P  V  T  L  R  A  L  P  P  M  G  T  P  T  V  E  R  T  V  S  M  S  F  D

23810 ATGTCGGCCCGGCCCCCGATCGCCCTCATGGACGGCAAACGTCCCCCTTCGACGGCAAGCCGTTCGACGATCCGTTGCGGGAGGACCAGAT
      >M  S  A  R  P  P  I  A  L  M  D  G  K  P  F  D  P  F  F  D  H  P  F  H  L  V  T  F  R  V  L  G  R  D

23902 CTGGAACGTGGTCAACGCGGATACCGATCCGTTCCCCTTCGACCATCCGTTCCACCTGGTGACGTTCCGGGTGCTCGGCCGCGACG
      >W  N  V  V  N  A  D  T  D  P  F  P  F  D  H  P  F  H  L  V  T  F  R  V  L  G  R  D

23994 GCGGGCCGCCCCGCCGGAGGACGCGGGCCTCAAGGACACCGTCGTGGTCTCGCCCAAGGGGTCTGTCAAGATCCAGGTCACCTTCGCCACG
      >G  G  P  P  A  P  E  D  A  G  L  K  D  T  V  V  S  P  K  G  S  V  K  I  Q  V  T  F  A  T

24086 CCGTACCTCGGGCAGTACGTCTACCACTGCCACTACCTGGAGCACTCGTCGCTGGGGATGATGGCCCAGCTGGAGGTTGTGCCCTGAGGGC
      >P  Y  L  G  Q  Y  V  Y  H  C  H  Y  L  E  H  S  S  L  G  M  M  A  Q  L  E  V  V  P  .

24177 TCAGCCGTGCAGGTCGACGATCGAGGGGTGGCGCCCACCCCGAACGCGTCGCCGTCGACCAGGGTGGCCGGGGCGGCGCGGGGGCCAGG
      < .  G  H  L  D  V  I  S  P  H  A  G  F  L  S  V  P  R  V  D  G  V  G  F  G  A  A  R  A  L
```

FIG.11A(21)

```
24268  TCGGCCTGGTCGGGGAACTCGTGCAGCAGTACCGCGCCCGCCGTCGACCGTCACCCGGCGCAGCTCCGCGAAGAGGCGGCCGGAATC
       <D  A  Q  D  A  F  E  H  L  L  L  V  A  R  G  G  D  V  T  V  R  R  L  E  A  F  L  R  G  S  D
24360  ACCGGCGAGCACGCCCCGCGCCTGCCACCTGGCGGATTGCTGACCACCCGGTCCACCCGGTCCGACCGGCAATCGTC
       <D  R  G  A  L  V  G  R  A  Q  V  Q  R  D  W  P  P  N  S  V  V  R  D  V  R  G  T  R  L  P  L  R  G
24452  CGGCGTCGGGCGACCGGCAGGTGACGGTGAGTTGGCGACGGCCGAGTCTCCGGGTCGTGTCCGAGCCG
       <  A  D  A  V  A  W  T  V  R  A  G  S  A  A  S  N  A  V  A  A  G  V  T  E  P  D  H  D  S  G
24544  AACAGCACCGCCCCCGGTGCCAGCCCGGTGCCTGCCTCCACGGGGATCGTGCCGCAGCACGGATCGGCCACCAGCATCCCGGGGCGGAT
       <F  L  V  A  G  P  A  L  G  A  A  E  V  P  I  T  G  T  G  C  C  P  D  A  V  L  M  G  P  R  I
24636  GCCGGGCCAGCCAGGCCAGGCCAGCCCGGGCGGCCAGCCCGGGCGAGCGCTTGTAGGCCCGGTGCAGCGGCCGGT
       <G  A  L  W  A  L  A  A  A  L  P  P  H  L  T  G  P  T  S  S  R  K  Y  A  R  R  H  L  P  R  D
24728  CGGCCACCCGTACCGCCAGCGTGCCTGGGCCCTGACCGGTGAGGTCTCGATGTCCTCGATGTCGTAGTTGCGGCGGCCGAGGAAGGA
       <  A  V  R  V  A  L  T  A  Q  T  G  E  V  T  V  R  L  S  L  G  G  E  P  P  A  E  G  G  R  R
24820  GAGTGGTAGCGCAACCCGAGCGCGGCAACGCGCCGGGCACGCGCGGGCACGCGCCGGCAGCGCCCGGCCAGCC
       <S  H  Y  R  L  G  L  A  A  V  A  H  R  G  V  A  D  E  I  D  Y  R  N  Y  N  R  R  G  L  F  S
24912  GGCGGCGACGTCCACGGTCGCGCCGGTCCGCCTTGGTGTCCGCCGCCTTGGTGGAGAACAGGTCGTCGTCGAGGTACGCAGATCCAGC
       <  A  A  V  D  V  T  A  P  R  G  P  V  G  C  A  A  R  A  P  L  V  A  P  L  A  A  A  R  A  L  R
25004  GGGTGAAGGCCGGCAGGTCCGCCTTGGTGGCGGAGAACCACCTCGCGGTGCGGCCCCGCGCTCCTCGATCTCCTGGGC
       <  T  F  A  A  L  D  A  K  T  H  G  V  G  D  A  V  L  F  L  D  D  V  T  R  L  D  L
25096  AGGCGCGGCTCCGGCTCCGCCTGGCGGCGGAGAACCTCGCGGTGCGGCGCCACCGTGAAGCGCACCGTCCGCCATGAAGGCGCACCGTCCGCCATGAAGGCGCACGCCGA
       <L  R  P  E  A  S  A  A  S  F  W  V  E  R  H  R  H  E  V  R  G  L  G  R  E  E  I  E  Q  A
25188  GGCCACCTCCTCCCAGCCTCGCGGAGCTCCGGCGTCCGGACGTCCGGACGCCGACCGCGACCGACCGCGACGCGCCGA
       <  A  V  E  E  L  G  R  L  T  R  A  M
25278  GTGCCGGGCGTCCGGAAGACTAGGTGAACCTCTATAGGAATTCGGTGCCCCTTCATAGGGTCCGAAAGGGGTAATGGAACCGTCCGGCACCGGA
25370  CCGGACCCGCCAAGACTAGGTGAACCTCTATAGGAATTCGGTGCCCCTTCATAGGGTCCGAAAGGGGTAATGGAACCGTCCGGCACCGGA
```

FIG.11A(22)

```
25462  CGGCTCGTTTCTTCCCCAATTCCGTCCGTCCGACCTGAGCCGTCGCAGGAAGGCGAGGCCGAGTCGAGCAGTCGATCGGTCGATG
                                                                                        > M

25553  CCGCACGGGCCCGTGCGCAGGATTGCGCAGTGCTGTATACACCGGATCTGTTCATCGGCCCGTTCGGCCTTCGTCCCGCCGAC
        > P H G P V R R N R G D C A V R T P D L F I G A V G A F V P P T

25645  GGTGAGGCGTGGAGTGGGCGAGATGGGCTGCTCTTTACTCCCGAGAGCTGGAGCTGGGGGCGGCACGGCCATCGCCGGCGACC
        > V S V E W A I D R G L Y S R E Q V E L H E L A G T A I A G D

25737  TGCCCCGGCCGGAGATGGGCTGCGGCCCAACAGGCGGTCAAGCGCTGGGGCGGTCCGCCAGGAGTTCGACCTGCTGCTCTACGCC
        >L P A P E M A L R A A Q Q A V K R W G G S P T E F D L L L Y A

25829  AGCACCTGGCACCAGGGGCCCGACGGCTGGCCGCCGCACTCCTCCAGGCGCCTGGTCGGCGGCGACCTGCTGGCGTTGGAGATCCG
        > S T W H Q G P D G W P P H S Y L Q R H L V G G D L L A L E I R

25921  GCAGGGCTGCAACGGGATGTTCAGCGCGTTCGAGCTGGCCGCCAGCCACCTGCAGGCGGTACCCGAGCGCACCAGCGCCCTGCTGGTCGCCG
        > Q G C N G M F S A F E L A A S H L Q A V P E R T S A L L V A

26013  CCGACAACTACGGCACCCGATGGTCGACCCCGATGGTGGATCGGTGCCGGATGCCAGCGCCCTCATCCTCACCAAG
        >A D N Y G T P M V D R W R M G P G F I G G D A G S A L I L T K

26105  CGACCCGGCTTCGCGCGCCTCCGGTCGCACCAAGTGCACTGCCAGCGGCGACGAGCGCCTGCACCGCGGCGACGAGCCGCTGTTCCCCC
        > R P G F A R L R S V C T K S V P E A E R L H R G D E P L F P P

26197  GAGCGTCCTGACGGGCACGGAGAATGAGGAGGTCGGTGGGCGCGCCCTGGCCGAAGCCGAGGAGATCGAGGTCGGCGACCTCGGCCAGGTGCGCCTTCATGAACTTT
        > S V L T G R E L N F T A R I D Q Q F A A R S P A S I A M A D

26289  TCGGCGACCACACATCGAGGAGGTCGTGGGCCGCGCCCTGGCCAACTGGGGCCTGCCCATGAGCCGGTCCACCTTCGACTTCGGCCGGATCGGGCACTG
        >V G D H I E E V V G R A L A E A E I E V G D L A R V A F M N F

26381  TCCCGGGAGATCATGAGCAGCAGCCCCTTGCTGGCCCTGGAACACCTGGCTCGGCGGACGGGCCTGGGCCCGGGGGACACCTGCTCACCCTGGGCACCGCC
        > S R E I M E Q R C L A N W G L P M S R S T F D F G R R I G H C

26473  CGGGGCGAGCGACCCCTTGCTGGCCCTGGCCCTGGAACACCTGGCTCGGCGGACGGGCCTGGGCCCGGGGGACACCTGCTCACCCTGGGCACCGCC
        > G A S D P L L A L E H L A R T G G L G P G D H L L T L G T A
```

FIG.11A(23)

```
26565 CGGGGCGTGGTGGTGTCGTGCGCGATCGTCCAGGTTGATCGAGTCGCCGACGTGGCGGAGTCGCCGAGACCTGCGGGCGGCCCGCCCA
      >P  G  V  V  V  S  C  A  I  V  Q  V  I  E  S  P  T  W  R  E  .
26656 GCCCAGCAAACCGACAGCAGGGGATGATTGTGGAAGCAGAGAAGGACCGGTTGCGTCCGGTCCGAGGCGGTCGCGGTGGTGGGGA
      >V  E  A  E  K  D  R  L  R  P  V  A  S  E  A  V  V  G
26746 TCGGCTGCCGGTTCCCGGGCGACGTCAACTCGCCCGAGTTCTGGGACCTTCTGGGCAGGAACACCGGCAACTTCCTGGCCGACATCTC
      >I  G  C  R  F  P  G  D  V  N  S  P  D  E  F  W  D  L  L  T  G  R  N  T  G  T  V  P  E
26838 GAGCGCTGGAGCGCGGTACCGCGACCTGGGTCCGAGTCCGGCGTTCGAGTCCGCGCTCCGGTCGGCCGAGCTGATGGACCGACTGCTCATGCTGGAGGTGACCTGGCAGG
      >E  R  W  S  A  Y  R  D  L  G  P  A  F  E  S  A  L  R  S  A  T  R  A  G  N  F  L  A  D  I  S
26930 CGGCTTCGACGCGGACTTCTTCGGCATCTCCCGCGAGGCCGAGCTGATGGACCCGCAGCAGCGTCTCATGCTGGAGGTGACCTGGCAGG
      >G  F  D  A  D  F  F  G  I  S  P  R  E  A  E  L  M  D  P  Q  Q  R  L  M  L  E  V  T  W  Q
27022 CGCTGGAGGACGACCCGGGATCCCGCCGCACCCTGGCCGGCACGGACGTCGGCGTCTTCGCCGGCGTGTGCACCTACGACTACGGCGGCCAC
      >A  L  E  D  A  G  I  P  P  R  T  L  A  G  T  D  V  G  V  F  A  G  V  C  T  Y  D  Y  G  G  H
27114 CAGTTGGAAGACCTGCCGAGCCTGTCGATCGACACCGCCTGCTCGGCGTTGCACCTGGTCGCCCTGCACCTCGCCGCAGAGCCTGGGCGAGAGCA
      >Q  L  E  D  L  P  H  I  D  T  A  C  S  A  S  L  V  A  L  H  L  A  A  Q  S  L  R  L  G  E  S
27206 GCGCGGGCCGAGCCTGAGCATCGATACCGCGGGTCAACCTGCTCGTCGTCCGGCAGTGCAGGGTCGTCGGCGAGGGGTGCCGGTCCTCAAGCTGCTCTCCGACGCGCAGCGGGA
      >R  G  P  S  L  S  I  D  T  A  C  S  A  S  L  V  A  L  H  L  A  A  Q  S  L  R  L  G  E  S
27298 CGCTGGCCCTCGCCGGCGGGGTGCTGGCCGGCGGCGGTCTGCTGGGTCGGCCGGCAGCGGTTGCCGGCAGGCGAGCTTCGGCGAGCGACGGCGAGGCGGAGACGGCCGACGGCGCGGGAGCGCTGGCCCCGGACGGGCGC
      >T  L  A  L  A  G  G  V  N  L  I  V  T  P  G  Q  S  I  T  L  G  S  A  G  A  L  A  P  D  G  R
27390 CGCTGGCCACCGACGGCTACGGGCGCGAGGGCGGCGTCAACCAGGACGGCCGTAACGGGATCATGGCACCGTGCGGCCAGGCCCAGG
      >S  K  S  F  D  A  T  A  D  G  Y  G  R  G  E  G  C  G  V  L  V  L  K  L  L  S  D  A  Q  R  D
27482 CGGGGACCGGGTGCTGGCCGTGCTGCGCGGTTCGGCCGTCAACCAGGACGGCCGTAACGGGATCATGGCACCGTGCGGCCAGGCCCAGG
      >G  D  R  V  L  A  V  L  R  G  S  A  V  N  Q  D  G  R  T  N  G  I  M  A  P  C  G  Q  A  Q
27574 AGCACGTGATGGTCCGCGCCCTGCGCTCCGCGGCATCGAGGCGAGGGTCCGACTACATCGAGGCGCACGGCACCGGCACCCCGCTCGGT
      >E  H  V  M  V  R  A  L  R  S  A  G  I  E  A  G  S  V  D  Y  I  E  A  H  G  T  G  T  P  L  G
```

FIG.11A(24)

```
27666 GACCCGATGGAGGCCGCGGCGATCGGCTCGGTCTACGGGCAGGACAGGCCCGACGACGAGCCCTGCCTGATCGGTTCGGTCAAGTCCAACAT
      >D P M E A A A I G S V Y G Q D R P D D E P C L I G S V K S N I
27758 CGGCCACCTGGAGGGCGCGGCCGGCGTCGCAGGCGTCATCAAGGCGGTTCTGGCTCTGAACCTGGCCGAGGTGCCCGCCACCCTGCTGGTCA
      >G H L E G A A G V A G V I K A V L A L N R A E V P A T L L V
27850 CCGAGGTCAACCCGGACATCGAGTGGAAGCGGCTGCGCCTGGTCACCCGCAACCAGCCCTGGCCCGACCGGCCCGGGCCGCGCCGC
      >T E V N P D I E W K R L R L V T R N Q P W P D R P G P R R
27942 GCCGGAGTCTCCGGCTTCGGCTACGGCGGCACCGTTGCCGTTGCTGGAACAGGCCCCCGTTGTTGAACAGGCCCCGGTGGCTGAGCCGGCCCTGGCGCT
      >A G V S G F G Y G G T V A H V L E Q A P P V A A E P A P A L
28034 GACCGGGGAGACCCTGTTCCCGATCTCCGCGGGCTCGGCGCACTCCCTTCGCGAGCGGGCCCGCCTGGCCGGGATCGTCCCGGATGTCG
      >T G E T L F P I S A G S A H S L R E R A R A L A G I V P D V
28126 ACCTGGCCGCGCTCGGCCACACCCTGGCGCGTCGGCGGTTCGCACCTGACCCACCGGGCGGTTGCCGTCGCGGGACGACCTGGTC
      >D L A A L G H T L A R R S H L T H R A V A V A A G R D D L V
28218 GCGGGCGTTCGGCGGCGTGCTCGCGGACGACCGGCCCCACGACCGGCCGGTGCGGACCGGGTCGCCGGTGGCCGAGCCGCGCACCGTGTGGGTGTT
      >A A F A A L A D D R P H D R P V R T G S P V A E P P R T V W V F
28310 CTCCGGGCACGGCAGTGGCAGGTCGGGATGGGGCGAGAACTGCTGGCGGCCTTCGCGACGCCTTCGACGAGAGGCCATCGACGAGA
      >S G H G S Q W T G M G R E L L A T E P A F A D A I D R I E Q
28402 TCTTCCTCGACGAGATCGGTTTCTCACCCGCCAGGCAGATCCTCGACGGCGACTACGAGGCCGTGGACCGCACAATGATCTTCGCG
      >I F L D E I G F S P R Q A I L D G D Y E A V D R T Q T M I F A
28494 ATGCAGCTCGGCCTGGCCGAGATGTGGCGAGCGGGAGGGCGAGGGCTCGGTCGGAGAGATCGCCGCGGCGGT
      >M Q L G L A E M W R A R G V E P D A V I G H S V G E I A A A V
28586 GACGCCGGCATCCGGCTGCCGTGCCGGAGGTCGCCGAGGTGCCGGCCAGGGCGCGATGG
      >T A G I L T V A D G A R L I C R S L L R E V A G Q G A M
28678 CCCTGGTGACGCTGCCCTTCGAGGAGGTCGCCGCCCGTCTGGCGCCGATCGCTCCCCTCGTCGACC
      >A L V T L P F E E V A A R L A G R V D V V A A I A S S P S S T
```

FIG.11A(25)

```
28770 GTGGTCTCCGGGGACCCGGCCGCGCTGGACGCGCTGGTCGCCGAGTGGACCGAGGAGGGCCTGGGCGTACGCCGGGTGCGCCTCCGACGTGGC
     >V  V  S  G  D  P  A  A  L  D  A  L  V  A  E  W  T  E  E  G  L  G  V  R  R  V  A  S  D  V  A

28862 CTTCCACAGCCCGCACATGGATCCGCTGCTCGACCGGCTGCGCGCCGCCGTCGACTTCACCGCCCGCGCACCCCGGGTGCCGATCTACAGCA
     > F  H  S  P  H  M  D  P  L  L  D  R  L  R  A  A  V  D  F  T  A  R  A  P  R  V  P  I  Y  S

28954 CGGGGCTGGCCGACCCGCGTCTCCGACGGCGAGTACTGGGCCGCGAATCTGCGCAACCCGGTGCGCCTGGCCGCAGCGGTG
     >T  A  L  A  D  P  R  A  P  I  T  A  D  G  E  Y  W  A  A  N  L  R  N  P  V  R  L  A  A  A  V

29046 GCCGCCGCCGTCTCCGACGGACACGGGCCTTCATCGAGGTCTCCCCGCACCCGGTGACCACCGTGATCCAGACGCTGGCCGGAAG
     > A  A  V  S  D  G  H  R  A  F  I  E  V  S  P  H  P  V  T  H  S  I  H  E  T  L  A  G  S

29138 CCTCGACGACGAGGTCTTCGTCGGGCCGGTGCATCCGTCCGGGCCGCTGGTCACCCTGCCCGGCTACCCTGGCTACCCCGGAGTCACTGGCAC
     > L  D  D  E  V  F  V  G  G  T  L  R  R  D  T  P  E  A  Q  A  F  L  S  S  L  G  A  A  H  C

29230 ACGGGCTCGCGGTCGACTGGGGCCGGGTCCACCCGTCGGGGCCCACGGCCCAGGCCAGCAACCGTGCGGGGCAGCGACGT
     >H  G  V  A  V  D  W  G  R  V  H  P  S  G  P  L  V  T  L  P  G  Y  P  W  R  H  R  S  H  W  H

29322 TGGCCGACGGGAGACGCGGCCACGACCCGGCCAGCCACACCCTGCTCGGGGCAGCGGTGGACAACGGTGGCCGGCAGCGACGT
     > W  P  T  P  A  A  A  T  G  R  G  H  D  P  A  S  H  T  L  L  G  A  V  D  N  V  A  G  S  D  V

29414 GCGGGTGTGGCGGACCACTCGACGACGCCGCCAGCCGTACCGGGCAGCAGCCCTCAACGGCGTGGAGATCGTTCCGGCCGTGC
     > R  V  W  R  T  A  L  D  D  A  S  R  P  Y  P  G  S  H  A  L  N  G  V  E  I  V  P  A  A  V

29506 TGGTGGAGACCCTCATGGCTGCCGCGGCGCCGGGGCGGGACGGGCGGCCGCTGCTGACCGGCCTTGTCGATGCCGGTACCCGCTGATGACGCCCGGG
     >L  V  E  T  L  M  A  A  A  G  R  G  D  G  R  P  L  L  T  G  L  S  M  R  Y  P  L  M  T  A  G

29598 CTGCACGAGGTCCAGGTGGTGCGGGACGGTGCCGAGGTGCGCCTGGCGTCCCGTTCCGTCGACGCGGAGGCCGACCCGAGCCGGGACTGGCT
     > L  H  E  V  Q  V  V  R  D  G  A  E  V  R  L  A  S  R  S  V  D  A  E  A  D  P  S  R  D  W  L

29690 GATCCACACCGACGCCACGGTGGCCGACGCGACCGTGCTCGCCGCGGTGCTCGCCGCGGTGTTGGCCGACCGATGGAACCGG
     > I  H  T  D  A  T  V  A  D  A  D  A  T  V  L  A  A  R  A  L  A  D  P  D  D  H  R  M  E  P

29782 GCGACCCGGGGCTCCATCCACCGCCGCCTCGCCGAGGTCGGGGTGCCGTCGACGGGCTTCGACTGGTCGGTGGAGGAGCTGCTCTCCGGGTAC
     >G  D  P  G  S  I  H  R  R  L  A  E  V  G  V  P  S  T  G  F  D  W  S  V  E  E  L  L  S  G  Y
```

FIG. 11A(26)

```
29874  GGCGTGCTCCGCGCGGGTGCGCTCGGCCGACTCGTCGTCCACCTGGGCGCTGGAGACGCCGTCATGTCGGTGCCCGCCGTCTTCCC
       >  G   V   L   R   A   R   V   R   S   A   D   S   S   T   W   A   P   V   L   D   A   V   M   S   V   A   P   A   V   F   P
29966  CGGGCGTGCCGCAGCTACGCCATGGTGTATGTCGACGAGGTGCTGCTCACCGGCGAGCCACCGGAGGTGACGCTGATCGAGGTGCCCTCG
       >  G   V   P   Q   L   R   M   V   V   Y   V   D   E   V   L   L   T   G   E   P   P   E   V   T   L   I   E   V   A   L
30058  ACCCAGACCGGCCCGACGCGAACGCGTGGTCGGCAGGACAGTTCCGGCGAGGTGGAGGAGGCGGTCTCTTCGGCCGTGTCCGACGAGAACTGCACGAGCG
       >  D   P   D   R   P   D   T   A   N   A   L   V   A   D   A   Q   G   R   V   V   A   S   L   P   G   L   R   Y   P   V   I
30150  GACCAGCCGGTCGCCCCGGCGCAGGACAGTTCCGGCGAGGTGGAGGAGGCGGTCTCTTCGGCCGTGTCCGACGAGGAACTGCACGAGCG
       >  D   Q   P   V   A   P   A   Q   D   S   S   G   E   V   E   E   A   V   S   F   A   G   L   S   D   E   E   L   H   E   R
30242  GGTGTTCGACGAGGTGCGCCGGCAGATCGCCGGAGAGATGCGACTGGACGACGATCTCCCGCGACCGTCTTCTGGCCGAGCAGGGCC
       >  V   F   D   E   V   R   R   Q   I   A   G   E   M   R   L   D   A   D   D   L   H   P   R   R   P   L   A   E   Q   G
30334  TCGACTCGGTGATGACGGTGGTGATCCGGCGCCTGGAGAAGCGCACCGGGAGTGAGAGGATCCGGCAGGAGTCTGTTCGTTCCGCA
       >L  D   S   V   M   T   V   V   I   R   R   L   E   K   R   T   G   R   S   L   S   P   T   V   F   W   Q   R   P   T
30426  GTCGCCGGCCATCGCCGACCATCTCGTCGAGCTGCTGTCCACCCCTCAGGAGTGGCGGGTCCACTCCAGGTGGCG
       >  V   A   A   I   A   D   H   L   V   E   L   L   S   T   P   Q   E   .       G   P   R   Q   D   V   A   P   T   A   A   W   E   L   H   R
30517  CGGGCCCCTCCCGCTGCCAGGGTCTCCTCGGCGTCTGTTGTTCAGGTGGGGGCTCAGCCGCCAGCATGACGCAGCCGCCCATGACCGAGGTGACGACGCGA
       <                                           G   P   R   Q   D   V   A   P   T   A   A   W   E   L   H   R
30608  GCTCTCCCGCCAGGGTCTCCTCGGCGTCTGTTGTTCAGGTGGGGGCTCAGCCGCCAGCATGACGCAGCCGCCCATGACCGAGGTGACGACGCGA
       <  S   E   R   L   T   E   E   A   N   Q   E   V   R   R   M   A   V   R   L   M   P   P   A   M   V   S   T   V   V   A   V
30700  CCAGCACCACGATGGTGTATGAGGCGGTGTTCAGCGTGTTCAGCGAGCCCATCGACGATGATCTCCACGGCACCGGCGTTG
       <  L   V   V   I   T   Y   S   A   T   N   L   V   G   L   R   L   G   V   M   A   I   I   E   V   A   G   R   A   N
30792  AGCCCGAGGGGCAGGGCTCGGCGGCTGGCGGCCCCGGGGAGTGGCACAGCCAGAGGGCTCTGCGGGCGGCTGGGCTGTACTTGCCGCGTACGGCGGCGAG
       <  L   G   A   G   L   A   V   G   E   W   H   S   Q   R   A   L   R   A   G   L   Y   A   G   T   Y   K   G   L   V   A   L
30884  CGCCAGGATCACCCCGGGCGGGCAGGTCGAGCCCGACGCTCTCCGGGTCGGCGAGGGCGAGAGCCGCGGAGGGGAAGATCGGGG
       <  A   L   I   V   A   G   A   A   L   V   E   P   D   A   L   A   R   L   D   V   R   L   G   A   S   A   L   F   I   P   A
```

FIG. 11A(27)

```
30976 CGAGCACGGACAGCACCGTGCGCAGCGGTGCCAGCGGCTCCCGTTGCCGGAAGGCCGATCAGGACACCGCCACCAGCGCG
      < L  V  S  L  V  V  T  R  L  P  A  L  R  A  P  E  G  N  G  P  L  G  I  L  V  G  A  V  L  A
31068 CCGAAGATCGCCTCCAGGCCCAGCGCGTGCGCCCCGCCGAAGGCACGGCACGATCACCGGCGACGGCTGGCGGCCCGCGTCGGG
      < G  F  I  A  E  L  G  L  A  H  A  G  A  A  F  A  L  V  I  V  V  A  V  A  S  A  A  G  G  D  P
31160 CTGGGCGTTCGCCCAGCCATGGCGCGCCGGGTCACCGGCCGGGCCAAGGAGGTAGGCCACGAGGTAAAGCAGGGCGG
      < Q  A  N  A  W  R  M  A  R  R  T  V  P  R  G  V  L  V  A  V  A  L  Y  A  V  L  Y  L  L  A  T
31252 TCACCACCTGCCTGGGCGGGTGAGGGTGCTCACCGCCACCGGCAACCAGGCCGCAGCGTCCTCCAGCGACGCCGCA
      < V  V  Q  G  A  T  L  T  S  V  A  V  S  S  I  L  S  L  L  F  W  A  A  A  D  E  L  S  A  A
31344 GCCAGGATGATCTGCCCCACGTGCGGTGCAGCAGGCGCATGTCGGTGAGCGTCTTCGCGGATCACCGGCCTGACCGGCCATGCCCAC
      < A  L  I  I  Q  G  V  D  R  H  L  L  R  M  D  T  L  T  K  A  I  V  P  V  A  S  V  A  M  A  V
31436 GCCGACGAACAGCGCGAAGACAGTCCGCTCCTGCCGCTCTGCCGGGCCAGCGCCGGGCAGGTCCAGGTGCAGACCGCGGCCACGGCGACC
      < G  V  F  L  A  F  V  T  R  E  Q  G  A  A  L  L  A  A  P  A  L  L  G  A  A  I  G  L  G  L  P
31528 GCACCGGAGGCGCGCCGAGGCCGATGGCGTCGAGCAGGATGGCTGCGTGCAGCAGCCACCGTCCGATGTCGGGTGCCAG
      < V  A  L  G  G  V  A  V  A  G  I  T  G  A  R  R  V  L  R  L  D  L  H  L  G  A  V  A  V
31620 AGCAGTACGACGCCGAGGGGCCGGTGACCAGCAGCAGCCCGGTTGGCCTGGTCGCGGCAGGCCGAAGCGTTGCGCCACCGTCGTCCCAGGA
      < L  L  V  V  G  F  Q  G  I  A  D  L  L  H  V  Q  D  P  D  A  P  L  L  W  R  G  I  D  P  A  L
31712 GGCCCCCCAGCACCGAGGGCCGGGGCCTGGTTGTGGGCACCCTGGAGGAACAGCAGTAGCTGGTGGAGCCGGGGCACCGGGCCACGATCA
      < A  G  L  V  S  P  G  L  L  V  G  T  L  L  E  G  V  V  A  P  L  G  F  R  Q  A  V  R  G  L  V
31804 CGACGGCGAGCAGCAGCAGGCCCACCTGGAGCAGGAACAGCAGGCCCCCGGCGGATCTCGGGGCCAGGTCACCGGGTCGGCCGAGT
      < V  A  L  L  L  L  L  G  V  Q  L  L  F  L  L  L  Q  H  S  G  L  P  P  V
31894 CGGTCGTTGTTCCTTTCGTCTCTGACGCCCGGGCCCAGGTCGGGCGGCCCAGCCCGGTGTCAGGCCGCGATCTCGGGCCAGTCCAACCGGGCCACCAATCGATGAGGAGGTCAGCTCCCGGTG
      <                                                                                   A  A  I  E  P  P  L  D  V  P  D  A  S  N
31985 TCATGAAGGTCCGCAGGGCCGGGGCTTCTCCAGCGGCCGGGGTCGGGGGACCAGGTCGGGCGGGCTCGATCGACGCTCCGGGTG
      <                                   M  F  T  R  L  A  R  L  D  A  A  P  K  E  W  G  L  G  A  C  W  D  I  L  S  T  L  E  G  T
```

FIG. 11A(28)

```
32077 GCCCGAACCTTGTCCTCTCGGGCAGGCTGAGCACCGACATCTCGGCCGCCACTGCACCACGTTGGCCAGTTCCACGTCGAGCCCTCGGC
       < A  R  V  K  D  E  E  P  L  S  L  V  S  M  E  A  P  W  Q  V  V  N  A  L  D  V  D  L  G  E  A
32169 CCGGGCGAACTCCAGCAGGTCGCGCAGCCCCAGACGTTGTCCGCTGGGGTGCCACTGGAGCCAGAGGTTGACCTCGAGCGGGCCCGGC
       < R  A  F  E  L  L  D  R  L  G  W  V  N  D  R  Q  P  A  V  Q  L  W  L  N  V  E  S  R  A  R  R
32261 GGACGTTCGCGATGAAGGTCTCCCACTTGCGCCCTGCGACACCTCGAACACCTCGCGCTAGCGCGTCGCGAGGAGGCGATGCCGATG
       < V  N  A  I  F  T  E  W  K  A  G  Q  R  I  R  E  F  V  E  G  Y  G  D  C  S  A  G  I  G  I
32353 CTCTTGAAGTGCCGGAACCGGTTCGAAGACTCCGGAACACCGACTCCGGCAACACCGGTTGAGGTTGTAGACACGGTGTTCGCCGGTTACCCGT
       < S  K  F  H  R  F  R  D  F  V  S  E  P  L  V  T  L  N  S  N  Y  V  V  D  V  N  G  A  N  G  T
32445 CTCCACCAGCAGGTCGAGCAGGGCGAAGTGCCGGAAGTACAGCCGGAAGTACACCGGCGAAGTACACCGGCGACTCCTTGGCGCCCCAGCCGGTTCT
       < E  V  L  L  D  L  L  A  F  H  G  P  Q  M  F  P  E  G  G  A  F  Y  L  R  R  I  L  H  A  N  E
32537 CGGCAGGGTCTGCCACAGCATCACGGCCACCAGGTTGCAGGGTTGCCAACGCAGGTGATGCCAACGAAGTCCTGACGGTGCCGTC
       < R  L  T  Q  W  L  E  D  D  D  R  Y  A  D  I  V  A  S  S  W  A  P  R  K  K  A  G  W  G  S
32629 CTGACCCGGGTACGCCATGGTGCCAGCCCCGGTAGGAGCAGGTTGCAGGTTGCCGAACGATGTCCGGAACCTGGTTGATCTCCTGCCGAAGCGGCGTGGTCCT
       < S  V  P  Y  A  C  M  V  C  R  L  N  C  T  N  G  F  R  I  D  L  F  F  P  F  D  E  V  T  G  D
32721 GGGCGGCGGTGTAGCAGTAGGAGCAGGGCGTCCAGCCAGCCTGTCGCCGGGTTGTCCGGACCATGTGGGCGTGTTGAAGGCGTC
       < P  A  T  R  A  A  L  R  D  P  D  A  I  D  R  F  R  Q  N  I  E  Q  R  Y  S  L  A  G  H  D  E
32813 CGGGGTGGTAGCAGTAGGAGCAGGGCGTCCAGCCAGCCTGTCGCCGGGTTGTCCGGACCATGTGGGCGTGTTGAAGGCGTC
       < R  H  Y  C  Y  S  C  A  D  V  R  E  G  A  L  M  A  L  R  T  R  R  M
32904 CGCCAGGCCCATCACCCGGCTAGCGGGGTTGTCGCCGGGAGCGGACGCGTCGTCGTTGAGCAGGAACTCCGGCT
       < G  V  T  E  V  R  P  L  P  F  F  I  L  R  T  G  S  A  L  M  E  A  E  R  A  V  I  E  D  R  F  H
32996 CCTCCTCGTCTACAGCTTGTGTGGTACATCGAGTCGTCACGCCGTAGACACCGTCGATGACGCGAGAGATGGATC
33088 CAGGGCAGCACGCACATGTCCGGGACCGGCTTCCGGGTCAGTCATGAAAGTTGATCACCTCGGTGGTGGGGGTGTCATCCCGGTCG
33179 GCCGACCCGTCTCGACCCGGGCAGCGGAAAGATCAACCGGGTGCCAGCATCTCCGCCTCCCGGGGCGACGATCTGTCCGGAAGT
                                                                                       < .  G  P  R
```

FIG.11A(29)

FIG.11A(30)

```
34375 CACACACCCGGCAGGTGGTCCGCTCGACCACCTCCGACGCCAACTCCTCGCCGGCCGCCAACTGGCTCAGTCCTCCTCGT
      < C  V  R  C  T  T  R  E  V  V                                          < .  T  R  R  T
34464 CTCGTGCCGGTGTGCGGGGACCAGGCGCCCGTCGTGCGGTTTGCTGGCGACCAGCAGGATGTCCAGATAGAAGGGCTGGTCGGGCCCTCGC
      < E  H  R  H  A  P  G  P  A  G  D  H  P  K  S  A  V  L  L  I  D  L  Y  F  P  Q  D  P  G  E  S
34556 TGCGGGCCGAGATGCCGGAACGCCCGGTTCGAGGTACTCGTCGAGGCCCGGTCCACCAGCCGGTCCAGCCGGTCCACAGCGCGCAGGGCCAGA
      < R  G  L  H  R  G  A  R  D  L  Y  E  D  L  A  R  P  R  L  R  D  V  L  W  L  A  R  L  A  L
34648 CCCACCGGGCCGCCAGGCGTCAGCCGTGCTCGCGGGCCGTACCAGCAGCAGCAACAGGCGCGGCGGCCCGCAGGTCAGCTTGACGGT
      < G  V  P  G  G  S  P  W  G  H  E  R  G  Y  W  E  L  L  L  L  L  G  R  P  G  C  T  L  K  V  T
34740 GCGGTCGACGGTGAAGCCGGCCACTCGGCCTGGCGGGCCCAGCCGTCCACCGCCACAGGTCCTCGGCGCGTGCTCCTCCACA
      < R  D  V  T  F  G  A  W  E  A  Q  R  A  L  G  D  A  T  W  R  W  L  D  Q  G  G  H  E  E  W  V
34832 CCCCGTGGGTGGGAGAGCACCAGCCGGCCGCCGACGTCCCGTCGAACGTCCCGTCCGGACCAGGTCCGGTCCCGAGTACGCCTCCCGCAGGTACGCCTCCCGAGACGTGTTCGAGC
      < G  H  T  S  L  V  L  R  G  G  P  R  L  L  R  Y  A  E  R  L  Y  A  D  A  D  S  V  H  E  L
34924 ACCTGGGTGGAGAGCACCCGTCGAACGTCCCGTCGGACTTCCGGAGGGCGTGGTCGGCCGGCAGGGACTCACC
      < V  Q  T  S  L  V  G  D  F  T  G  D  P  V  P  C  R  G  D  R  D  L  A  H  D  A  P  L  S  E  G
35016 GCCCGGGATGTCGGCGGTCTGCAACTCGGCGGTCGCGCCAGGCTCGCCGCAGGTCCAGGAAGTGGGCGTAGTCGAGCCAGACTCCCGTGG
      < G  P  I  D  A  T  Q  L  E  A  S  R  F  L  G  R  Y  P  S  T  G  A  G  Y  D  L  W  V  G  T  A
35108 CGTCCGGGACCGGCTCCCCAGCGGCGTCGCCAGGTCGAGGAAGTGGGGTATGCCGAGGCTCGATCCGCTCCCGGAAC
      < D  R  V  A  E  A  L  A  D  R  L  D  L  F  H  A  Y  A  W  D  G  P  R  P  E  I  R  E  R  F
35200 CGTTCGGCCATCACCTCGTCCAGGACGGCCGGTGGGGCGGTCAGCAGGGACCAAGCCCGGTACGGCGGCGCAGC
      < R  E  A  M
35290 AGGGTCGAAGGGCTGCTCGCCGGCGTACCCATGGTGGTCGGCTCCCAGGCCTCCGGCAGGCCCTCCCAGGCCGCCAGCGACGCGGGGCCG
      < .  W  R  W  Y  E  E  H  P  Y  R  M  T  T  P  E  P  L  G  E  W  R  R  L  S  A  A  P  R
35381 GTACTCGAAGGGCTGCTCGCCGGGCGTGCTCCGGGTGCTGCCGCCAGGAGAGCAGCACTCTGCTTGAGCCCGATGTACT
      < Y  E  F  P  Q  E  G  A  H  E  P  A  A  R  R  Q  A  L  C  S  L  L  V  Q  Q  K  L  G  I  Y  E
```

FIG.11A(31)

FIG. 11A(32)

```
36576  TGACCAGGTCGATCCGGGGTCACCGGGGAGCACGTCGTCGACCGTGTCGACCGTCTCGACCGTCTCGTCCGGCGGTCG
           < V L D I R R D G P L V D D L R V T D V T L E R L T E D P R D
36668  TAGGGACGCCGGCAGCCCGTCGTAGCCGGGTTGGACGACCACGTGCTGCCCGGCCGGTGCGCTGCGGCGGCCGGCCAC
           <Y P R R R L G S Y G P N S V V H V F S D R G T R E A A A A V
36760  CACCGTCACGCGCGGCCGGGAAGTCCCGGCGCAGCCCTCGGCGTACGACGGCAGCCGCCTCGGCGGCCACGCCGACCGCA
           < V T V G P F D R R L G E A Y S P L A E V A V H R G R P A V R L
36852  GCAGGTGACGCAGGATGTCGCCGGCGGCGATGTCGCCGGTGTTCGCCGATCTGCTCGATCAGCGCCACGGTGAGC
           < L H R L I D G A G A G I D V T N A D P E C I Q E I L A V T L
36944  TGGTCGTACCAGTCGTTCATCGACAGTCGTTCCTCGTCCGGTCGCGGAAAGCTCAGTGGACATCGTCACGCTCCTCGGCACGCC
           <. H V D D R E E T R C A
           <Q D Y W D N M
37035  GGTCCGGCCCGGAGCCGGCGACCGCCGGGGCGGTACGACCGCCAGGAGTTCCAGCTCGATCTCGGACAGCTCCAGGCCGGCGGCG
           <P G A G S G V A P A T R V L L E L E R L E I E S L E L G A A R
37127  GACGGTCTCCTCGACGACTCCGGGCCGGGGTGGTGCAGGCCCAGTGCGCCAGTGCCACCTGCG
           <V N E E V V G P S Q A G F V P V V G A P H H L A W A L A V Q A
37219  CGACGGTGTGCCAGTGCTCGGCCGCCACGCTCGGGCGGCGAGGCCGTAGTCCTCACCCCGGAAGGCGTGCGAG
           < V T H G R E A A F A A L G D V V D L L Q A Y D E G R F A H S
37311  TAGGCCCGCCAGTCCTCGGCGAACTGCGCCTGGTCGCGGTGCCGTGAGCAGCCCGTCGAGCCGCCAGCACCCC
           <Y A R W D E P A F A Q D R H L A G T L L G H A L A S G G L V G
37403  GACGCCGCTCCTGCAGCAGCAGCACCTCTCGGCCACCACGTTGAACGGTTGAAGCAGGTTCGAGCAGTCCAGCAGCCCGG
           <V G A E Q C R P L V E K E A G R D L L N F P V Q V V D L L G T
37495  TCGGCACCACGTCTCGCCAGTCGGCATGCCGAAGGCGACATGCCGGCCCTCGCGCACAGCGTCCTCGTGCCAGCACCTCG
           < P V L E A L D G A T V N A F G V H R A L G E R V F G A L V E
37587  GCGGTCTCCGCAGGGACGGAGCCAGTCGGTCGGGCACGTGCCGAGTCGCCAGCAGGCTGGCCAGCAG
           <A T E A L P V T P D D P W H V S Y V D V H D T G L Q R L S A L L
```

FIG.11A(33)

```
37679 CTCGTCCCGGAGGAACGCGGGTCGCTGTTACGCACGTCCGTCGTTGTGCGTCGCACGCGGGGCCGGGTCTCCAGCC
       < E D R L F A P D S N R V T R G P P D L K H R R V G P R T E L G
37771 CGCCGGCCGTGGCGATCACGATCTGTCCCGGTGCGCGGGCAACAGGTCGGCGGCCAAGGGCCGCTCGGCGGCCGCCGCG
       < G A T A I V I E D R H A P L L D A L G R A L A A E A A G G G
37863 TACGCCCGGGAGGTGTCGAAAAAGGGTCACGCCCAGGTCGAGAGCCCGGCTCGAAGGCCCCGCTGTTCGATCGCCGGCCACTGGCC
       < Y A R S T D F L T V G L D F A R R V A Q A G P E I R R G W Q G
37955 GCCGAGCGCCCAGGTGCCCAGGACGCCGAGACCGGACCAGCGATGCAGCGCGTCGCGCGTGCTGCCCGCGTCCGCCGGTG
       < G L A W T G L G L A S V L P G R E G I C R Q R V
38046 CCCCACCCACGCCCGTCGGCCGGCCGTCACGCGTCCGGCGCGATGCCGGTCATCAACTCCACGCCCTTGAACTCCACGGGG
       <             • A A P E G D S R L T L F V V G D H N I M K
38137 TGTCGGTGACCGGCTCAGCCCGGCCTCGGCGTAGGTGGAAAGCCGCGGGTAGGTCGGAGCAGAAGTCCAGGAAGTTGAAGCAGAACAGCCCGCGGG
       < D T V P T L G A E A A I G T M L E V G H W N L F G K F E V P
38229 TTCGCGGTCGCGGTACGCGCTCGGCGGTGTGGAAGACCGGCGTAGGTCGCGGAGGTCCAGGAAGTTGTGCGGAGAAGTTCAGGAAGCAGTTGAAGACGTTGGATGAACACGTTCAGGGAGGAGAACCCGGCGTCGAACG
       < N A D R Y R E A Y T H F F G R T N D G L D L F N F C F L G G P
38321 CCGCAGGATCCGCGGATCTGACGGAAGTCGTTCTCCAGGAAGTGTTGGTGGTAGGAGACGTTCTCCCGGCCCTTCGCAGGTGGCGCGCCTTGTCGAGG
       < R L I R R I Q R F Y L F V E F V N L H I F V N L S F G A D F A
38413 CGGCGGGTCGGCAGCTTCTCCAGGAAGTCCCGGCCGAGAGCACGGCCCATGATGCCCTGCCGCTGCCGATCTCGAAGAT
       < A T P L K E L F D N E I H H Y S V N E R G E C T A R A K D L
38505 AAGGATCGGGCTGACGTCGGCGCAGACCTCCCTCCCCGAGCTGCTCGACGGTCGACAGGCGCTCCGAGGTACTCCTCGCGGGTGGTAGCCGG
       < F S R S V D A C L V A R V R D A L G A A M
38597 CTCCGATTCGGGCGAGCCCGAGCTGCTCGACGTGTCCCGAGACGTAGTTGAGGTCCGAGACGCCCGGGGGGGGGTCC
38689 CGAGCTGCATCTGCATCTCCCGCGTCCACTCCGAGACCTCGTTCATCGGTCGCGCTCTGTCGGGACTCTGCGCGGCCAACTGGGCGGGCTGCG
38781 TGCGCGGCGGGGCGGGGCGGGCGAACGCGGGACGCGTCGGCTCCTCAGCGGGCTCAGCGGGTGTCGGCGCCGGGCCAGCGGGCAGGAG
38873 GAAAACTGGGCGGGCGGGGCGGGCGAACGCGGGACGCGTCAGCGGGCGAACTCGGCGACGCTCGGGGCGAACTGGGCGGGCGGGGGGGGGGGCAGGAG
       < P R R A F E A V D E P S L A G T D A L R A L L
```

FIG.11A(34)

```
38964 TTCGGCCACCTGAGACGGCGTCGGCCCGGTGGTCGACGGACTCCCGCTGGCCGCCGCCACCCGGAATCGGTGGTCGTAGAGACGGAGC
       < E  A  V  Q  V  A  T  P  G  T  T  V  S  E  R  M  R  Q  A  A  V  R  F  R  H  D  Y  L  V  S  G
39056 CGAGGGCCTCGTCGACCTCCTCGCGGGAGACGCCTTCAGGCCGGGCAGGCTCTTCGTCGCGGGTCGAGCCCGCCGCCCGTAGATCAGG
       < L  A  E  D  V  E  E  R  S  A  K  L  G  P  L  T  K  T  A  G  Q  P  D  L  R  R  G  Y  I  L
39148 GCGTCGTAGTTGAGGCCAGGACAACTGCGCACGACACGGACCCCATGGCGAGCCCGTTCATGTAGCAGTTGGCGTGGTGCACCAGCAAGTC
       < A  D  Y  N  L  A  L  S  L  Q  P  V  G  M  A  L  G  N  M  Y  C  N  A  S  G  H  H  V  L  L  D
39240 GCAGTCGGGGAGGATGAGCTCCAGCAGGGGGTCCAGCACCCCGACGTTGCTGAGCACCCTCCACCTCGGAGGAGGCGG
       < C  D  P  L  I  L  E  L  P  C  N  S  L  V  R  V  N  P  P  L  A  G  L  G  E  V  E  S  S  A  A
39332 CGGTGATCACGACCTCCACGCAGACCCGCTTGCCCCGCAGCAGCCAGGGGTCCACGTCCTGGGAGCCGTTGTAGGGCTGGTAGCGGAT
       < T  I  V  V  E  V  G  R  Q  A  A  A  D  V  A  H  R  L  A  P  V  Q  A  G  F  V  G  T  A  S
39424 TTGCCCCACACCACGCAGACCCGCTCGCCCATCGGCGCGTCGCCCATCGGCGATCTGGTGCCGGTCTCCACTCGACGC
       < N  G  W  V  V  C  V  R  K  G  R  R  P  G  L  L  W  P  D  V  D  Q  S  G  N  Y  P  Q  Y  R  I
39516 CGGGATCGCCAGCGCGTCGCCCATCGGCGGGATCGCGACGGTCGCCAGTCGCCTCCAGCTCGAGCCGATGAACCGGGCGAGAAGTAG
       < P  I  R  L  A  D  G  M  P  P  I  A  V  D  P  S  P  D  I  A  Y  R  I  Q  H  R  S  W  E  V  G
39608 CGTACTTGCCGAACTCGGTGCCGATCGGGTCGCCGGAGACCAGGTCGAGACCCGGGCTCGGTCTCGAGGCTGTGCCGATGGTCCGGTA
       < Y  K  R  F  E  T  V  P  D  G  S  V  L  D  L  G  P  E  T  E  I  T  G  I  F  G  P  S  F  Y
39700 ACGCTGGGGATGTGGTGCAGCTCGGCAGCCAGGGAGCGCGCCCTCCACGGCCATGATGTCGTTGGACCACCAGGTTCGGCGGTAGGGCGGGCGTA
       < V  S  P  I  H  H  L  E  A  V  L  A  G  E  V  A  M  I  D  H  V  V  L  D  P  R  Y  H  A  A  Y
39792 GTCGACCGCGTTGTCGTAGCTCGGACGCGCTGCGCTTCCAGTAGTCGGACCAGGTCGGTGTCGAAGTCGGCGAGCGAGT
       < D  V  A  N  D  Y  S  R  Q  V  A  T  V  T  R  K  W  Y  D  A  L  L  D  T  D  F  D  A  L  S  D
39884 CCATCGGCCGCCCGTGAAGGGGTTCAACGCAGGTTGCTCCACATGTGCTGCGGGTGTAGAGGCCTGACGTAGAAGCCTAGAGCCCAGCCGG
       < M  P  R  G  T  F  P  N  L  P  L  P  Q  E  V  M  H  Q  P  T  Y  L  A  Q  V  Y  F  G  L  R
39976 GCGCTCTCCATCATGTCGGGTCCGTCGAGCAGGCATGGGCATCATGCGCCGCGGGACCTGGGACGGCGGCGAACAGGCGAC
       < A  S  E  M  M  D  P  G  D  L  V  S  V  P  M  M  G  A  A  A  V  G  R  V  Q  S  P  S  C  A  V
```

FIG.11A(35)

FIG. 11A(36)

```
41168 AGATTCCCGCCGGACGCCCGCGATGTCCTTCAGCAGGTCCACGGCTTCCACGCACGTGGTAGAGCAGGCCCGCAGAGACGGGCTGAAC
      < I  G  A  A  V  G  A  I  D  K  L  L  T  W  P  E  R  V  H  Y  L  L  G  A  C  L  V  A  D  F
41260 TCGGCCCAGCTCGGTGAAGTCGGCTCCACGTCGGCGACGCGCAGCTCCACGTTGGTGATGCCGTTGACCTCCATCACCAGTCCGCGCG
      <E  G  L  E  T  F  D  I  R  E  V  D  A  V  R  L  E  V  N  T  I  G  N  V  E  M  V  L  E  A  R
41352 GCGCAGGTTCTCCGGACGGCCCTCGCCAGGGCAAGCACCGTCGTGCCGGGTGCCGGGCGAAGGCAAGCGTGTCCGCGCAGTGCGCCGA
      <R  L  N  E  P  R  G  E  L  A  L  V  T  T  G  P  H  R  A  L  A  L  T  D  A  G  E  L  A  G  L
41444 GTTCGAGGATCCGCCGCGTCGGGAAACGCACCGAAGAACTTCGCGGTCGGCCCGGGACTGGCTCAGCAGATAACCGTGCTGCTGGGAG
      < E  L  I  R  R  A  D  P  F  A  G  F  F  K  A  A  R  D  A  P  S  Q  S  L  L  Y  G  H  Q  S
41536 CCCTCGGCGTAACGCACTCCGTCGTCGAATCCATTCACCCACGGCTCGAGCCTCGAGGCCTTTCGTTGACCAGCCG
      <G  E  A  Y  R  V  G  D  H  E  F  G  N  V                    <  ·  R  S  A  T  S  L  R  E  N  V  L  R
41627 GATCAAAGCCTAGCGGATGCCATTGCGGTTGCCGACTAGTGTTTCATCATATTCAGGCGGCTTCCGCCGAGTTCCGGCCGTCCACCTGGCGGTGC
                                 <  ·  R  S  A  T  S  L  R  E  N  V  L  R
41718 GGGCCCATTCCGGAATCCGTCCCCGCGGAATCTCGATATCGAAGGACGACTGGAGTTCCGGCCCAGTCGGGCGTTCCGCCCACCTGGCGGTGC
      < A  W  E  P  I  R  D  G  G  I  E  I  D  F  S  S  Q  L  E  A  P  G  A  D  A  A  W  R  A  T  R
41810 GGGCCAGTCCCTCGGCGGGGTGTCCTTCCAGTCCGGCGAAGACCGATCGGCCAGTCCTGCGGTCGGTGTACGGCGGTTCGCACTCGTCC
      < A  L  G  E  A  L  P  T  D  T  W  D  G  F  V  S  R  A  L  E  T  A  T  Y  A  T  R  V  E  D
41902 CGGCGACGCAGGTCGGCGATCGACGCCAGCGGCACGCGCGGGCCGCCACGGGCCTACCGGCTCGCAGCACGTGTTGGTGCTGACGA
      <R  S  P  L  H  A  I  P  H  E  P  V  G  A  A  S  R  V  A  Q  A  L  E  L  V  T  N  T  S  S  S
41994 GCCCACGTTGAATGCCGCCCCCACGCGCTCGGTCTCGGCGGTCCTGACCACGTTCACCACGACGTACAGTGAACGCGCGGA
      <G  V  N  F  A  R  G  W  A  A  E  T  E  A  A  R  S  V  V  N  V  V  D  G  V  Y  T  F  A  R  V
42086 CCTGGCGCCGCGCCGTCGCCGTACACGGTGATCGGCCTCGCCAGGATCTGGTTGAAGAAGATGGCGACGCGTTGCGGTACGGGTCCGCATG
      < Q  G  G  D  G  Y  V  T  I  P  E  G  R  L  I  Q  N  F  F  I  A  V  A  N  R  Y  P  D  R  M
42178 TTCTGCCACTCGCGCTCGAGACGTTGTGCATGGGAAGGGCAGCCCTGGTCGAAGGGTGAAGGGCAGCCCCTGGTCCGCATCGTCACCTCCAGTCGCGCTCGACCAG
      <N  Q  W  E  G  Y  V  N  H  M  R  F  A  T  F  P  L  G  Q  T  R  M  T  V  E  L  E  R  E  V  L
```

FIG.11A(37)

```
42270 GTACTTGGCCAGGCCGTAGCTGTCCGCGGGGACGGGGAGGACGACTCGGCGTCTCGCCGTGGCCGTCTCGCCGTAGACCGCCCACGGAGGAGG
       Y  K  A  L  G  Y  S  D  A  P  V  P  V  V  S  E  R  M  P  T  E  G  H  G  Y  V  A  V  S  S  A
42362 CGAAACAGAAGAACCGACGCACGCGGTACGCCGGTGATCAGATTTATGCCCATCACATTGGTGCCGTAGTTGAGCTGCTTCACC
       F  C  F  F  R  V  G  T  R  L  S  A  N  I  L  N  I  S  G  M  V  N  T  G  Y  N  L  Q  K  V
42454 GAATGGCTGATCGCCTCCGCGCGGAAGGCGACCAGGTCCAGAAGTGGAAGACCCGCTGAATCGGTTCTCGGCGAACAGTGAATGACGAAGTCCACGTC
       S  H  S  I  A  E  A  A  F  A  A  F  H  F  V  R  E  F  R  N  E  A  F  L  S  D  V  F  D  V  D
42546 GGTCACCGAACCGACGGCCAGGTCCACCGGGCCGGAACCGCTGCCGGTGCCGTGAGGTCGTCCAGAACGGTGACCGTGCCAT
       T  V  S  G  V  A  L  D  V  G  A  P  V  R  Q  R  S  G  G  S  L  D  D  L  V  T  V  R  H  G  N
42638 TCCTGACCAATGACTCCACCAGGTGCGAGCGGGGCGATCTGCGGCGGCCCTTCGTCGGCGAACACCGACCCCCGAGAGAAAGTTCGCCTCAGGGCAC
       R  V  L  S  E  V  L  H  S  G  I  F  G  A  G  G  T  V  L  C  R  V  M
                                                                        <  ·  P  V
42728 GATCCGGCGAAAGGGTTGACGGAGCGGGCGGGCGGCCGCAGGCCGGTCGGCGGAAGG
                                                                     ·  P  V
42819 CGGCGACCGGTCGGCCTGCTTCTTCAGGCCTCCCACCAGTCCCGGTGCGTCCGGTACCAGTCGATCGTCTCGGCCAGGCCGTCGGCGAAGG
       P  S  R  D  A  Q  K  K  L  P  E  W  D  R  H  T  R  Y  W  D  I  T  E  A  L  G  D  A  F  A
42911 CGACCTCGGGCCGGTAGCGCGGCGCTCGAGCGCCGCAGTTCGCGTCGAGTAGCGGGTCGTGTGGCCCTTGCGTCCGGCACCCGCTCGACC
       V  E  P  R  Y  G  L  A  R  L  K  A  D  T  L  S  Y  R  R  D  H  G  K  R  D  P  V  R  E  V
43003 CGGTCCCACCGGGTCCCCAAGGCGTCCAGCAGCGCCGCCGGTCAGCTCCATGTTGGACAGTCCAGTGGCCGATGTGGTAGACCTCGCC
       R  D  W  G  A  G  L  A  D  L  L  R  G  T  L  E  M  N  S  L  E  A  T  G  A  I  H  Y  V  E  G
43095 GGGGACACCGGTCGACGCGGGTCCCGGGGTCTGGATGCCGGGCAGTGGTCCGTCACGTGGATCCAGTCAGTGGCGGACGTTCCCGCCGTCGGCGGCGACGCG
       P  V  G  R  D  V  V  T  Q  I  G  R  C  H  D  T  V  H  I  W  D  R  V  N  G  G  D  G  Y  L  P
43187 GCACCCCGTCGCCGAGCCGGCCGGGCGGGGTGCGGGGCGTAGGCGGCCAGGGCGATCAGGTCGGGACCTTCCCGCCCCCCTTCGTTGTGCCGACCGGGTG
       V  R  R  G  N  L  L  E  T  V  F  L  P  I  L  K  E  P  F  Q  Y  P  G  Y  N  N  G  C  R  T
43279 AGGCAGACCGGCAGCCGGAGTTCGGCGCCAG
       L  C  V  P  L  G  H  T  R  A  Y  A  L  A  I  L  D  G  G  A  K  A  A  A  Y  P  S  N  P  A  L
```

FIG.11A(38)

```
43371 GGGGGTGTCTCGGCCAGGAACCCTCGTCGATGCTGCCGTAGACCTCGGTGGAGACCCCGGCGACCACCCGGGCGACCCGGGTCGAGAC
       < P T D E A W S G E D I S G Y V E D T S V Q V V R A V G A D L C

43463 ACGCCTGCATGAGCGTCTGGACGCCCTGCACGTTGGTGCGGACGAACTCGCGCAGTCGGCGATGGACCGGTGCGACTCGGACGCGGCG
       < A Q M L T Q V G Q V N T R V F E A S D A I S R D V H S E A A

43555 AAGTTGACCACCACGTCGTGCCGGACGCAGCAGTCGGCCGCGTACGTCAGTTGCCCGGCACCCGGGCTGCGCGTGTAGGCACGGTGGCCA
       < F N V V D H G P L V E A L L A T D C V D G Q V F T I R D Q V

43647 CGGTTCGAGGTTGGCGAGGTTGCCGCGTACGTCAGCTTGTCCAGCACGCTGACCACCGCCGGGCCTGCGCGTGTGGGGTAGGCACGGTGGCCA
       < P E L N A L N G A Y T L K D L V T V R A Q A T D P Y A G T A L

43739 GGTCGCGGACGTACTGCGAGCCGATGAAACCGGTCGGTCCGGTGACCAGGACGACGCATCAGACCCCACCTTCGCTGTGAT
       < D R V Y Q S G I F G A G G T V L V R R M

< V G V R V E S H D

43828 CGCCGAGGACGAACCGGTGCGTCTTGGGCACCCGGGGACCCGCCTCCCGGCCGATCATCGAGAACTCGATGCCGATG
       < G L V F R H T K P V R P G P V V R A E R G I M S F E I R G I

43920 CCCTCGATGTAGGCACGCGCAGCAGCGATGAGCTGCTCGATCTCCAGCAGGTGCAGTCGCAGTCGATCGAGGTGTACGGGCCGAG
       < G E I Y A G R L V I S H E I E T E L L T C D C D I S T Y P G L

44012 GTAGGAGTTGCGGATGATCGAGCCGGTCGACCTTGCCCTCGACGTGCCGAGGACGAACCGGTTCATCTCCAGCATGTCGGCG
       < Y S N R I I S G A G V V V P G V I R S G S V D A G A S I V V P

44104 GGCCGATCAGTTCGGTGCGGTCCTTGCCTCCAGTAGCCGGTGATCATGGGAGTCGATCATCCACTGCACCGGTCGGTGATCTC
       < G I L E T R D D V K G E V L P E V S G L V F R N M E L M D A

44916 AGGTTGCCGGTGTCCTTGCCCAGTAGCCTGCTTCAGCTCGGCGATCATCGGCCACCGGGCTGAAGAGCTGAGACCCGGTCGGTGATCTC
       < L N G T D K W Y G T I M T S D V R H G R D I M M Q V A D T I E

44288 CAGCTCGTTGCGCCAGGACGCTTCAGCTCGGCGACTTCCTCCTCACCCGCCGTCGCGATCACCCGGCCAGGGCCAGGTCGCTCT
       < L E N R W S P K L E A V A D H V V P S F V V G V L A L D S K

44380 TGGGGTGCTCGGGCTTCTCCTCCACCCGATCTCCGGCGGACCCGCCATCTCGGCGACGCGAAGGCGTGCGGGTCGGCGACCCGGGTC
       < P H E P K E E V G I V R G D A G M E A V G F A H P D A V R T
```

FIG.11A(39)

```
44472  AGCATGATCTGCGCGTGCGGTGCGCTTCTGCCGAAGCGCTCGACGATGTCCTTGATCCCGCGAGATGAAGTTGTCGCCGAGGTACATGAG
       < L  M  I  Q  A  H  P  R  E  Q  R  F  R  E  V  I  D  K  I  G  G  V  I  F  N  D  G  L  Y  M  V
44564  GAAGTCGTCGTCGCCGAGGTAGTCGGCCGAGAGATGAGCACGGCGTGCGCCAGCCGCGTTCGGGGAGCCTTGCGGAAGGTAGTCACCTGGAGGC
       < F  D  D  D  G  L  Y  D  R  S  I  L  V  A  H  A  L  G  R  P  A  E  Q  P  L  Y  T  V  Q  L  G
44656  CGAACTGGGAACCATCGCCGACCACGGCTGAATTTCGGGGCTGCTGCCGACGATGCCCACCTCCTCGATACCGCCCTCACGAATA
       < F  Q  S  G  D  G  V  R  Q  I  E  P  A  T  S  G  V  V  I  G  V  E  E  I  G  G  E  R  I
44748  GCCTCGAGCCCGTAGAACAGCACGGCTTGTTGGCCACGGGAATGAGTTGTTTGGCGGACGTGTGGGTGATCGGACGCAATCTGATCCCAC
       < A  E  L  G  Y  F  L  V  P  K  N  A  V  P  I  L  Q  K  A  S  T  H  T  I  P  R  L  R  S  G  V
44840  CCCTCCCGCCAGGACCAGCGCCTTCACGAACGCCCTCGAAAAGGATGGGACCGAGACGGGTGCTGGTTCACGAGCACTCCAGGGGTCACGG
       < G  G  A  L  V  L  A  K  V
44931  TGGACTGGGCTCTTCGTGAACGTACCGAAGGATCACTCGATTCCCTACTTATGGGCCACGAGGTGTGATCGGTACGCGCAGGCCTGGCC
                                                                            <·  A  D
45022  CCGCCATTTCCGCAAACGGGGCCTGCCGCCGGCCAGTTCGAGACGCGGCCAGGCCGTGCACGGGTGTCCGGCGGGCTGGCC
       < A  M  E  A  F  P  P  R  A  P  G  G  G  V  L  E  L  V  A  A  L  G  H  V  T  D  P  P  S  A
45114  GGCAGCAGCAGGGTCTGCAGGCCGGTACACGCGGCGTCGCCACCATCAGCGCCGTCGCTGGGGAGAAGACGTAGGGCGTCCGCCATCC
       < P  L  L  L  T  Q  L  G  A  Y  V  A  G  G  D  A  L  T  D  G  V  M  L  A  R  E  P  A  V  K  L
45206  CTCGTCGCAGGCGGTGCGGAAGATCCGGGATCGGGCTTGACCGCCCCACCTCGTGGGAGAAGACGTAGGCGTCCGCCATCC
       < E  D  C  A  T  R  F  I  R  P  D  P  K  V  A  G  V  E  H  S  F  V  Y  A  D  V  L  E  A  M  G
45298  CGTACGCCGTCGCGGTAGGGCAGCAGGTGGGCGGCCTCGGCGAGGCCGGGATGGGGCAGGTCGACGGTGGA
       < Y  A  A  F  T  P  R  L  D  W  A  I  N  S  V  V  A  T  G  C  G  R  R  L  E  A  L  V  P
45390  GCGGCGTCGCGGTAGGGCAGCAGCCGGTCGTCGAAACAGCCGGTCGTAGAGACCGGCCTCGGCGAGGCCGGGATGGGGCAGGTCGACGGTGGA
       < A  A  D  R  Y  P  L  W  G  D  T  R  F  L  R  D  Y  L  A  E  A  L  G  P  H  P  L  D  V  T  S
45482  GAGCGCCCACGCGTGCGCTAGGCGGGGCGAGCCCGGCGTACACCTCGGCGAGCCCGGCGAGCCCGGCGACGGCGTGCGGCT
       < L  G  V  Y  Y  A  S  R  H  T  E  P  S  L  D  R  R  A  Y  V  E  A  L  G  P  P  V  A  H  P  E
```

FIG. 11A(40)

```
45574  CCGGGCCCGCGGGACGGCCGGCCGCCCAGCAGCAACCGGTTCAGGGCCTCCTGCTGCGCCGGGTCGAGCTGGACGCCGACGGTGGCCGCCGCC
        < P  G  G  P  R  G  A  A  L  L  G  T  L  A  E  Q  Q  A  P  F  L  Q  V  G  V  T  A  A  A
45666  GCCCGCAGCCAACGCTGCGGCCAGTTCCACGGCGAACAGCGTGCCGGAGAAGTCGAAGACAGGAGGCGTCGATCGGACGGTCGACGGGCAGGGGGTCGT
        <A  R  L  W  R  Q  P  L  E  V  A  F  L  T  G  S  F  D  F  L  V  A  D  I  P  R  P  L  P  T  T
45758  CATCGCTCTCCTCGGTGCGCTCAGGGCGGCCGGTCAGCCAGCCGGATCGGACCGGATGTCCATCATGGAGGAATGCGCCGGGTCG
        < M
45848  GGCGCGCCCCGCCATGGCCGCCGGTCCGGACGACGACAGGCATTTTCGGTACTCTTGCCTTCTAGGCGGATTTCTTCAAAGATGGCTGTCAATTC
                                                    > V  T  R  T  R  T  A  L  R  R  L  L  A  G  L  A  S  L  A  T  A  A
45940  TTCAGGCGATCCTGGAGGCATCCGTGACGATCCGGTACCCGCAACCCCCGCATCGAACGTGTCCACTACCAGGATCGATCAACTGGACGA
        > A  T  L  V  A  T  A  G  P  A  A  A  T  T  P  G  I  D  V  S  H  Y  Q  G  S  I  N  W  T
46030  CGGTGACCCTCGTCGCCAACGGGGCATCCAGTTCGGTTCATCAAGGCCACCCCGGAGGTACAAGGACCACATCTCCGGCCAACTTCAACGCCAACTACGTCAAC
        > A  T  L  V  A  T  A  G  P  A  A  A  T  T  P  G  I  D  V  S  H  Y  Q  G  S  I  N  W  T
46122  GGTTCCGCAACGGGGCATCCAGTTCGGTTCATCAAGGCCACCGAGGGTACCACTCTCCGGCCGAACATCTCCGGCCAACTTCAACGCCAACTACGTCAAC
        > S  V  R  N  A  G  I  Q  F  A  F  I  K  A  T  E  G  T  S  Y  K  D  P  N  F  N  A  N  Y  V  N
46214  TCCTACAACGCCGGAGTGATCCGGGGAGCTTACCACTTCGCCCGGCCGAACATCTCCGGCGCCACCCAGGCCAACGTGCTACGGCCTCA
        > S  Y  N  A  G  V  I  R  G  A  Y  H  F  A  R  P  N  I  S  S  G  A  T  Q  A  N  Y  L  A  S  N
46306  CGGGCGGGCCTGGTCGGCGGATGCAGTGCGGACAGTCGGATCCAGGACTTCCTGAACACGTACAAGGCCCGGCTACGGGTCATCTACACCACCAGAGC
        > G  G  A  W  S  A  D  S  R  T  L  P  A  A  L  D  V  E  A  N  P  Y  S  G  G  T  C  Y  G  L
46398  GCACGTCGGATCGGAGCTGCACCGGGATGCAGTAGCTGGATCCAGGACTTCCTGAACACGTACAAGGCCCGGCTACGGGTCATCTACACCACCAGAGC
        > S  T  S  G  M  R  S  W  I  Q  D  F  L  N  T  Y  K  A  R  T  G  R  Y  A  V  I  Y  T  T  S
46490  TGGTGGAACCAGTGCACCGGCTTCGGTCTGGAGAGCTTCTGGCAGTACACGGCCTCCGGCAGTACACCGGGATCAGCGGCAACGTCGACCGCAACAACTGGAACG
        > W  N  Q  C  T  G  S  W  T  G  P  W  A  N  H  P  L  W  L  A  R  W  S  S  T  P  G  T  L  P
46582  GGCCGGGCTGCGTTCGGTCTGGAGAGCTTCTGGCAGTACACGGCCTCCGGCAGTACACCGGGATCAGCGGCAACGTCGACCGCAACAACTGGAACG
        > A  G  A  S  V  W  S  F  W  Q  Y  T  A  S  G  S  V  S  G  I  S  G  N  V  D  R  N  N  W  N
46674  GCGACCGCACCCGCCTGATCGCCCTGGCGAACAACACCTGACCCGAACGGCAGGCAGCAGGAACCCGAATCGCGACCGT
        > G  D  R  T  R  L  I  A  L  A  N  N  T  ·
```

FIG. 11A(41)

```
46765  ACGGTCGGGGCCGGTCCGGCTGCCGCTGCCCCAGCCCGTCACCCGGCCCGGGCCGCCGCGGCATCCGGTCCTGCCGGCCCGGGGTGGCC
46857  CGCCGTGCCATCCGCCAGGCGGCCACGCCTGCGACGGCCACGACACAGCGCGAACAGCGCGAACACCGGAAGACCCGCTGACCAG
46949  CAGCAGCACCACGTCGCTGCCAAGGCGGACGAGCATCCACAGTGCCAGCCCGGGTCTGCCTGGTGTCCCATGTCGCACCTCCTCG
47041  CATCGTCCGGGATCAGATACCCCGTTCGACGCAAGTACATGCGAATCGACATCCGGCTTCAGCGGCCGAGTCGGC
47133  AATGGAGCCCCGGCCCCGGGCGCTCAGTGACCTCGGCTTGAAGCTCGGTCGAAGTCGGCCAGCGCGCCAGT
                <  .  D  V  R  D  P  K  F  G  K  A  I  R  D  F  D  A  L  R  A  Q  W  D
47224  CCTTGTTCGCCACCTCCCACCGGAGGGCGTACCCCGGTTGCTGCGTGACGAAGCCCGGTTGCGGACGTGGATCCGAGTGCCGTCCCGG
              <  K  N  A  V  E  W  R  L  A  Y  G  R  N  S  A  T  V  F  G  R  N  R  V  H  I  R  T  G  D  R
47316  TTCTCAACCACTCCAGTCCGCGCACGTCTTGTAGTAGTCGCAGCGCGTTGACGTAGTTCTTCCGGGC
              <  N  E  L  W  E  D  A  C  T  K  Y  Y  D  C  R  K  I  S  L  Y  Q  Y  G  N  V  Y  N  K  R  A
47408  CGGTTCCTTCTCTTCAGTGGCGTCGGCGTCGCCCCTGCCGGCGTCGCCACTGCCTGGTCCACTGACCAGCTCGCGCTCGTCGA
              <  P  E  K  E  K  W  D  A  Y  A  D  G  E  P  T  S  T  W  Q  V  L  L  E  G  V  G  D  R  E  D  F
47500  AGACGATCGTGTTCGCCCCAGCCTGGGTCCCACGGAGACTGGCAGAGGGACAGCGAGAAGCCCGGGGTCTTGTGCAGGAGCCAACCC
              <  V  I  T  N  Q  G  V  S  R  R  V  W  G  K  P  L  S  F  G  A  P  D  K  H  L  L  W  G
47592  TCGGGCAGGGCGTTCGGGTCGACGCCGTTCCACGGAGCGTCCAGGACGGTCGGTGCGTGCTGGTCGCCGGCCGACGGCGT
              <  E  P  L  A  N  P  D  V  S  P  S  A  S  P  T  P  S  P  P  A  A  S  S  T  A  P  A  A  S  P  T
47684  CGGGGTCGACAGGGCCTGCGGGTCGCCGGGGAGGGGCCGCCGGGCCGCCGAGCAGCGGCCACCGCGCCAGCAGGCCGA
              <  P  T  S  V  G  A  Q  P  D  G  G  P  G  P  D  D  D  G  S  R  G  L  L  P  V  A  A  L  L  G  I
47776  TCAGCAGCACCACCGCCGAGGCCGGACGAGCGTCGGCCCGACGTTCGTGCCCCGGCCTTCGGCCCGGCCGTCGAC
              <  L  L  V  A  V  L  A  G  V  L  L  G  R  R  R  E  P  K  T  G  G  V  V  T  A  R  G  T  S
47868  GAGAGTGCCGGCGGGAGGGCGAGCGGCCGACGTCCGGCGGGCGAGCTCGCGGGGCTCGGGGGCCGGGGCGGGG
              <  S  L  A  P  G  S  A  A  P  L  V  S  T  P  A  A  E  E  R  P  A  V  A  P  E  R  A  P  A  P  P
47960  CGAAACGGGCACAGCCCGCCGCGGATCGTGTCGACCCGGGTGTCGTCGGCGTGTCGTCGGCGCCCGTCGGCCCTT
              <  S  V  P  V  A  A  G  P  D  V  R  T  D  D  A  R  T  D  D  A  R  G  A  A  P  A  G  D  A  G  E
```

FIG. 11A(42)

```
48052  CGTCCCCAGCCTCGGGCCCGGCGGCCGGTCCGCCTCACTCCCTCCGGGCTGCCGCAGCCTCGTCGGCGCTGGTCGCGGCGTCG
         < D  G  A  E  A  A  R  D  A  P  P  G  D  S  G  G  A  P  T  G  A  A  E  D  A  S  T  A  A  D
48144  GGGGCGGGGATCTTCGCGGTGGAGGCCGCCGAAGTCGGTGACCTTCGCGGCGTCGGCGCTCGGCGCTCGGCAGGTCGAC
         < P  A  P  I  K  A  T  P  D  A  A  Q  P  G  F  D  T  V  K  A  T  P  D  A  D  A  S  P  L  D  V
48236  CATCGGGCTCGGCGCGACGGCGTCGGGGACCCGCCGGCGACCGCGCCGCCACGCCGCCGCCACCGGCGGCAA
         < M  A  T  P  A  A  D  V  G  A  P  V  K  A  T  A  D  G  G  G  V  G  A  A  A  A  G  G  A  A  L
48328  GACCACCTTCCGGGGTACGCGGTGCGGTGGGGCCCGGTGCTGTTCGGCGGGCGCGTTGCGGGCCACCACCGGCGGTCGC
         < G  G  E  P  T  R  P  A  P  P  A  A  P  R  G  T  R  Q  E  A  P  R  P  A  P  V  V  P  P  R
48420  GGCTCGCGGCCACCTCGGCCCGTTCGGCGGCCGGTCGATCCGGCGGTCGGCGGCGGTTCTTGGCGGCGACGGAGGAGCCG
         < P  E  R  P  G  N  P  G  P  R  R  V  G  D  L  L  S  I  T  K  A  R  R  G  A  A  R  R  L  L  R
48512  CTCGGCCACCTCGGTGGCCGCCGATCCGCAGGAGGCCGCCGAGGTCGGGCGAACGGCCGTTGCCCTCCACCGCGTTCGCG
         < E  A  V  E  A  D  I  R  E  A  P  D  K  R  L  L  G  N  L  V  P  K  L  P  G  A  N  R  P  P  P
48604  GCATCGGCTCGGTGGCCAGCCGCGCCAGGGTCGGCCGGGCCCGCCGGTCGCGGGGAGCCCAGCCCAGGCCACCATTCCGGT
         < M  P  E  T  A  L  A  A  L  T  A  I  A  S  P  R  A  F  P  S  K  G  E  V  A  A  Y  L  T  A
48696  CCCCAGGACCAGACCAGAGGTCCGGCTCACGGTCGGGCGGGGATGGTGCCAGGCCGGCCGAAATCGGTTCAGCGCCGTCG
         < G  L  S  W  L  D  A  E  P  G  A  T  G  D  R  A  R  E  P  A  I  Y  A  P  S  G  L  V  M  G  T
48788  CCGGCGTCACGTTCGGGTCGCCGGTGATGTGCCAGGCCGGCCTTGTCGAGCGCCGTCGGCAGCAGCACGTTGCCCGGCT
         < R  T  V  N  P  D  G  P  I  T  A  L  G  F  D  T  L  V  V  R  G  D  T  G  L  L  V  N  G  P  K
48880  TGATGTGCCGGTGCATGACGCCGGCCTTGTGCGCCTTGAAGAGGCCGATCTCGACGCGCCAGCGTCGCCGGCGACACC
         < I  D  R  H  M  V  G  A  K  H  A  A  K  L  A  G  L  V  G  L  G  I  E  V  A  K  A  P  S  V
48972  GGCCCGTCTCCCCGGAGAGTGTCCTGAAGGACTTCGAGCGCCACTACTCCATGACGCCGTCGCCGTCGAACGTGTCGAA
         < P  G  D  E  A  L  T  D  Q  L  S  K  S  A  V  Y  E  M  V  I  W  P  D  G  D  T  R  L  V  D  F
49064  GATGCGGACCACGTTGACGTTGGTTGAGTCGACGGCGATGGCGCGGAGCGGTTCCCGGCTCCTCCGGGGTGA
         < I  R  V  V  N  V  H  N  L  R  A  I  A  R  A  E  R  L  S  R  E  R  M  E  R  E  E  P  T  L
```

FIG. 11A(43)

```
49156 GGCTGGGGGCGGGGACCAGTTCCTTGATCGCCACATCCCGGTGCAGCACCTGTCGCGCGCCTTCCATACCGACCCATGCCACCCTGACC
        < S  P  P  P  V  L  E  K  I  A  V  D  R  H  L  V  E  D  R  A  K  W  V  R  G  M
49247 GAGCGGCGAAATCAGCCGGTACCCGGTCGGCAACGAGTTGGGGAAGCGCGTTGACATCGGTGGAGACGGTACCCGGCGGCGGCCGCCAC
49339 ACCGCCGGCACACGGCCACTGTGCCGAGGAACTGGCCGCGGCGAAGGTCAAGTTCGCGACGCGTACGCTGGCGGTCATGTCTGCCGACATCCGGGTGACCC
49431 GGGGCGGTTCCGACCGCCGGAGGAACTGGCCGCCGGGACTGGCCGCGGTGCTCGCGCCCGGAGCTGGGCGCTCCGGTCTGCCCGTGACGCAC
49523 TCGGCCTGGGCACGGCAGCAGCGGTCGGCCAGTGTGGCCAGTGTGGGCCGCGCCGAGGGCGGTGGCGGGGAGGAACACCGTTAACCTCACTCAGGGA
49615 TGCCAGCATGTGCCGTGACGGATAGGGAGGGGTCGATGATTCCCGAGGCGGAGGTCGAGCGGCTACGGCAGCATCGAGGCCGAC
49707 GACGATGCCGTGACGGATAGGGAGGGGTCGATGATTCCCGAGGCGGAGGTCGAGCGGAACTACGACCACGCATCTGTGTACATAGGGACGACATGAA
49799 ATCCGCCAGATGCGCGAGTTCGCCGACAAACTCCGCCGAACGGCCTTCGTCGAACTGGTGCAGTTCGCACACGGGGATCGCCGAGCAGTAGCCGACTCCGACCAGCAGCCGACGCCTTCTCCGCGCT
49891 GGCACAGATCCCCAACCGCCACCGGCCACCGGCCACCGGCCACCGGCCACCGGGCACCGGGCACCGAGCAGTAGCCGACTCCGACCAGCAGCCGACGCCTTCTCCGCGCT
49983 TCTGGTCCGTCGGTGGGGCCGGGGCAGGGCGCCCTCGCCAACTGATGATGAGGGCAGGGCCGCGGCGGACGTCGCGGCCTCACCGGCTGATGGACCTGCTGAG
50075 CGCGTCTCCGATGGAGCGGGGCCGGGGCAGGGCGCCCTCGCCAACTGATGATGAGCGCGGCGGACGTCGCGGCCTCACCGGCTGATGGACCTGCTGAG
50167 CGGCGGGCCGGGCGGGTGGTGCTGCCATGAGAGGACCGCGGGCGGCGGGCACTGGAAGCGCAGGTCGCCGGCCACCTCGGCGCAGGCCACC
50259 CATGTGGGGCGTGCATCCAGGAGCGGCGGCATCCAGGAGCGGCGCAAGCGGGCACCGGAGCGTGGCCAACGCGCCCGGGACCGGGTACGGGAGCTGCTCGGGCGAACTGGAC
50351 TGGGCCGCCTCAAGGAGTACCGGCTCAAGGAGTACCGCAACGCCGGACCGGGCGAACCGGACCGGCCTACCGGCCTACCTCGGGCGAACTGGAC
50443 GACCTGATCGACAAGGTGCAACGCTACACGACGAGTACGTGGAGAAACTCAGCGACGCGGATCAGCAGGCGCTGA
50535 CACCGAACTCAAGCCGGCTGCCGACAGGCCGGTGACTGCGCCAACTGGAACGACTCAACGCCCAGGACGACTACCGGCGAAGGCGCTGA
50627 TGGGCAGCCAACAGGCCGGCTGCCGACAGGCCGGTGACTGCGCCAACTGGAACGACTCAACGCCCAGGACGACTACCGGCGAAGGCGCTGA
50719 GAACTCCAACAGGCCTTGCCGGCTGCCGACAGGCCGGTGACTGCGCCAACTGGAACGACTCAACGCCCAGGACGACTACCGGCGAAGGCGCTGA
50811 AGGCACGCCTCCGTCATCCGCCCGTATTACCAGTCCCAACCATTAGGCCTTCAATTCCTCAAGCGCTCAGCAAGCCACGCACGCCCTG
50903 TTCCTGTCCAGAGCACGCACCCCAAACAGGTCCGTGTACTACTGGGGAATCGGGACGCGGGAAAACACCACTTGCCACCTCGCATTTCTCCGGC
50995 ACCGGCCACCCAGTGACGTAACATCCAACCCGGAGGAGGTGCTGGCCCTACCCTCCGCCACCTGCCACTGCCCCCACTGGACGAGG

51087 CAGCACAACCGGCCAGTAGGAAACCAGCCCTGTCTTCACGACCATTCTTGCCAGGCGGCCTGATCGGCGGCGGGGCCCGGCGA
51179 TGGGGATTAATCAACCCCTTGGCAATACTCCTCCGGAAGGATCAACCCAATTGGAGGGGTGATCGGGGGCGGTGGGGCTGGAACCTCACCA
                                                                            junction marker
```

FIG. 11A(44)

```
51271 ACCGGGCGCTGCAGGCACTCGCCCGGGCTGGGACGTGGTCCCCACTTTAACCTGACCCCTGGGCGCTCCGAATGGGCACCGCAAGGCGT
51363 CGTAAACACCTTAGGTCTGAATGGTGAGCCGTCACGCTCATCCCACCGGAGCAAGGCGATACTGACGGCGTACTGGGATCCGACCATC
51455 CATGGGCAACCAGCAGGCGAGGGGCGGTTCCTCCAGTAGTCCCAGGGACCAATCGACCCGAGGGACCAGGGCCAGTATTGGCTTCGACCGG
51547 TGAAAACGCTCCTCCAGCGGGGCGCTACCTTCACCTTGCATCAGCGTACGCCCGAGCGCCGTGCCGTGCGA
                                                             > V R A
51637 GTCCTGAAACCGATGGTGCCTTGCGAATACGGGCTGGCACCTTAACTACTGAAGGCGGGAGGCTCAGAAGCTGTCACTGGGA
     >S  P  E  T  D  G  A  L  R  I  R  A  D  Q  W  H  L  N  Y  L  K  A  A  E  A  Q  K  L  S  L  G
51729 GAAGGGGTTGTAGTAGCGGTCCCGGATACTGGCGTTGATCCACACCCGGTTGATGACTGTTCAGCGCAATCTAATCAAAGGATTGACATCATTCCCGG
     > E  G  V  V  A  V  P  D  T  G  V  D  P  H  P  D  L  Q  R  N  L  I  K  G  I  D  I  I  P  G
51821 GGGCAATGGAGATGGCCAGAAAGATCGCAACAGTCACGGCAACATGGCTACGGACAGGGCCAGAGGGCAGAGGCGGCCT
     >  G  N  G  D  G  Q  K  D  R  N  S  H  G  T  S  M  A  G  L  I  A  A  H  G  Q  G  Q  S  G  A
51913 TAGGCATAGCACCCAGAGCACCAAGATCATGCCAATCCTGTCTTCCGGTGATGCAGACGCTTGGCTGCGGGTATAGAA
     >L  G  I  A  P  R  A  K  I  M  P  I  L  S  S  A  S  N  N  L  G  D  A  D  G  L  A  A  G  I  E
52005 TTTGCAATCTCGCATGGGGCGGATGTCATCAATGTCTCCAGCGGCGGCGCCAGCGTTGACTCCATCAAGGCAATCAGAGAGGCGGTCGC
     > F  A  I  S  H  G  A  D  V  I  N  V  S  S  G  G  A  S  V  R  L  I  K  A  I  R  E  A  V  A
52097 CGCAGACATTGTAGTTGTCGCAGCGGGCAATGACAGTCCCGAAGACATTGGCTATCCAGCCAGCGAGGAAGGAGTCGTCGCAGTTG
     >  A  D  I  V  V  V  A  A  A  G  N  S  P  E  D  M  T  I  G  Y  P  A  S  E  E  G  V  V  A  V
52189 GCGGAATTGATCGACAGGGAGAGCATGCTTCAGTTTCTGCTGTCGGAAGTTGACTTAGTCGACACCGGCAGTCGACATCTACAGCACC
     >G  G  I  D  R  Q  G  E  H  A  S  V  S  V  V  G  P  E  V  D  L  V  A  P  A  V  D  I  Y  S  T
52281 AGTTACGACGGGAAGTACTCCAAAGGCACCGGTCGTCCAGTAGTCGTCGATAGTGCCAGCGATAGTCGATAGTCGATCGAAGTTTCC
     > S  Y  D  G  K  Y  S  K  G  T  S  S  A  T  A  I  V  A  G  A  A  A  L  V  R  S  K  F  P
52373 CGACCTGCCCGCCTCGGAGTTGTGCCGCGCTTACGGACGGAGGTCGTTAGCCGCTTGACCCCGGTCCACCCCGGTCACCGACCCGCACGGGCG
     > D  L  P  A  S  E  V  V  H  R  L  T  A  T  A  I  D  K  G  P  P  G  H  D  D  Q  Y  G  Y  G
52465 TTATCGACCTGGTTGCCGCGCTTACGGCAGGAGTCGTTACGGCACAGAGACTACCCCGGTCGGGCGACGTGCCCGACGTGCCTGGGTCGACC
     >V  I  D  L  V  A  A  L  T  A  D  V  P  P  V  G  F  E  S  A  T  A  D  V  P  D  V  P  G  S  T
```

FIG.11A(45)

FIG.11A(46)

```
53659 GCCGCGGCTGCCGCCGGAGGCGAGGATGCAGGTGGCCCCGGAGCAAGCCGCGGTTCCTCACCCGGTTGATCGGGGCGCGGCGGGC
      > A A L P A E A R M Q V A P E Q A A F L T F L T R L I G A R R A
53751 GGTGGAGGTGGGCACCTTCACCGGGCTGTCCTCCCTGGCGATCGCGCGGCTGGCCGAGGGCGGGCGGTTGACCTGCTTCGACATCTCGG
      > V E V G T F T G L S S L A I A R L A E G G R L T C F D I S
53843 AGGAGTACACGGGCGTCGCGGGGCGTACTGGGCGGGTGGCCGTAGCCGATCAGATCGACCTGCGCTACGGCCCGGCGGGAGACACGCTG
      > E E Y T G V A R R Y W A R A G V A D Q I D L R Y G P A G D T L
53935 CGCGGGGTTGCCGTACGAACGGCACCTGGACTTCGCGTTCATCGACGCGGACAAGGTCGGCTACCCGGTCTACTGGGCGGAGTTGGTGCCCCG
      > R G L P Y E R H L D F A F I D A D K V G Y P V Y W A E L V P R
54027 CATGCTCCCCGGCGGGGTCATCGCGGTGGACAACACGTTGCGCGGGGGCCGTGTGCTGCCGATCGCCGACGGGCTGACCCTGGCCCGGGTGCGCTGACG
      > M L P G G V I A V D N T L R G G R V L P I A D G L T L A R V R .
54119 CGTTCAACGACGAGGTGATGGCCGACGTCCGGGTTGGAGCCGGTGCTGCCGGTCGTGTCCGCCTCACCGGGTCGACGAGGGGTGAGGCGGGGTGTT
      > A F N D E V M A D V R V E P V L L P I A D G L T L A R V R .
                                               < R V S R A F Q R A
54210 GGGCCAGCCGACGATCGTGCCAGGTGCCAGGAGAACGGGTTCCACTCGGCGATGCGCTGAGCGCGGAAGGTGAGCGGCAGCAGGATGCCGGAGA
      < A W A V G V A A L V A I I T L G Q W V K D N G L D G A F L A R
54302 GGTGCCGTCCACGGGCCAGGAGAACGGGTTCCACTCGGCGATGCGCTGAGCGCGGAAGGTGAGCGGCAGCAGGATGCCGGAGA
      < T G D V A W S F P N W E A I R Q L W G P A F T L P L L I G S L
54393 GCCCAGGCGACGCCGACGGCCAAGCACCGCGATGATGGTCAGGCCCTGCCGAGGTCGCCGGGCGAGGTCGCCGGGCGAAGAGGGCCCG
      < L L V P Q A V T N M V P A L A D E S K V K L A V G Y S V A S
54485 GCAGCAGCGGCCTGGGCGGAGAGCATCAGGCATTACGGCGAGCAGGTCGCCGATGAACACGTCGAACAGGAGCGGAGCAGGGTGAT
      < T M L A I L A L M L Y A L L D G I F V R L E F L L A L L T I
54577 GTCATCAGCGCGATCAGGGCGAGCATCAGGCATTACGGCGAGCAGGTCGCCGATGAACACGTCGAACAGGAGCGGAGCAGGGTGAT
      < T M L A I L A L M L Y A L L D G I F V R L E F L L A L L T I
54669 GATGACGGGCCTGGGCGGAGCAGCGGCGACGAGCAGCGGGCCCGGCGGGCGAGCGGCTGACCGGTGACCGGGACCGTT
      < I V A Q A L L S V V D R L A R G L L L A L R S V P T V R S R E
```

FIG.11A(47)

```
54853 CGATGACGCCGGCGCAGCTCGGCGATCAGGCCCGAAGAGGCCCGAAGATGGCCAGCAGCACCAGCAGGCCGGCACGAAG
      < I V G A R L E A I L G F G Q F L G G F I A L L V L L G P V F
54945 ATCTTGTACGCCTGGCCTCGGCGCGTTCAGCGCGGGCGAAGAGGAGCAGGCTTGAGCGGGGCGAAGAGAGCAGGTACATCACCGGCTGAAGACGCC
      <I K Y A E A Q T P A N L A P K L L P A F L L L Y N V P Q F V G
55037 GACGAAGACCCAGACCGGATTGCGGAGCAGGAGTTGCATCTGGCGCTGGGCGCTGTGCGGGGCGAACTTCATGATCGGACT
      < V F V W V P N R L L L Q M R Q A V L W T D R A F K M
55127 CCGGGGTGGTCAGGACTCGCGCAGCGCCGGTCTTGGTGAGGAAGACGTCGTCGAGGCTGTGGGGCGTGCAGCTCGAGCTGAGCC
      <    S E R L S R G T K T L F V D D L S P R H L E I S S L R
55218 TGAGGCCGGACTGGTCGAGCCGGCAGGACCTGCAGGAGCTGCGGGATGGGCGGTCAGGCGCAGGCCGCGTCGACGGTT
      < L G S Q D L R R L V Q P I A T A G E D V T L R L G G G D V T
55310 TCCAGCTTGGTGACGTACGGCTCGGTGTCGAGCAGTTGGGCGCGTCGAGCCGCGGGTGCCGGCGCGTCAGCAGCACCTCGCCGGA
      <E L K T V Y P E T D L L Q A A Q P T A A A D L G V L L V E G S
55402 GATCTCCCGCTTCAGCCGCCCGGAGCTGGTGATGAAGACGGTTCATCCCCGGAAAGACATGCGGGGCGATCTCGAGAGCGATCTCGACGGCGATCTGCGGGTCGAGG
      < I E R K L G G P T G E A V V E G H D M I A I R D C L A D A E D
55494 CCAGGTAGTGCGTGGCTCGGCGTCGTCCAGGAAGACGGTTGGGGGGTCGTGGATGATGCCAGTGCCGATCTCGACGCGGGCGATCTGCGGGGCGTCGCCGCGGGATCCGAGG
      < L Y H T T I F V T M G E A R L R R I E D W M H A R S Q P D L
55586 CCGCTGGTCGGCTCGTCAGGAAGACTCGTCCAGGTGAGCTGGAAAGGGGGCCAGTGCTTGTGAAGGGGCGTCGGCCTTGCCGATGCCGTACA
      <G S T P E D L F V I R P D H I I G L A I E V R R Q G G S Y T
55678 CTTGCACTTACGGTCGGCTGTCAGGAAGACCAGTTCCTGCGGGTGAGCTGGAGTCGTCCCGGTGCTGCCGACATAGCGATCCGGCGACCACCTCG
      < K C K R D A Y E T L Q F A A L A R E A R R L A D A K G I G Y M
55770 TCCGGGCGTGCAGGACCAGTCTGCAGCAGTCGGCCTGACCCGGACTCGGCAGCCGGCCGTGGCAGCACCGGAGTGGGGGAGGCACCGAGTGATGAGGTGGGCGACGACCTCG
      < R A H L V L E E R A T S D D W T S G G Q A V Y G I R R R V E
55862 GCCGGGTTCCGCAGCAGGTCGGCCTGCTGGACCGTCAGCCGCATCCGCCAGCATCCGGAGGGGTGATGAGGTGGTCTT
      <A P N R L L D A G A I T A Q G G D P T I L T A L M R L T T T K
```

FIG.11A(48)

```
55954 CCCGGGGCGCGTTGGGGGCCGAGGAAACCGAAGATCTCCCCCTCGGGCGACGTCAGGTCGACGCCGCGCACGGCGTCGACGCGTCTTGTGCTGTC
      < G  A G N P G L F G F I E G E A V D L D V G R V A D V T K H Q  R
56046 GACCGGCGGGGAGGCGAAACGACTTCCGCAGCCCTCTGGTCTGGATCATCTTCGCTCCTGGTCGTCCTTAGCCGGACCGGGGCCGGCCCTC
      < G  A R S R F S K R L G R T Q I M
56136 TCTCCGGAGACGCCACGCCACACGGGTGCCCCGAAACGTCGCGCCGAGGCTAACGCGATATAACTCTAGTCAACTTTGATTAATGGCGA
                                       <  *  R S I V E R T L K S  *  H R
56227 CCGTCGGCCCCCTCCCCCACGTTCCAGCCGTCCTGACTGGCCAACCCTTCGGGCAGATACGGCACGCCGGCCTCGATCCGGTCGGCGACCCG
      <G  D A G E G V N W G D Q S A L G E P L Y P V G A E I R D A V  R
56319 CTCACACCAGGCCACTCTGACCTCTCCCGGGCAATTCTGGAGCTCGTACATCCAGTCTCACGCCGACGGCTTGGAGTCGGGATCCAGGAGG
      <E  C W A V E G R A I N L E Y M W S V G V P K S D R I W S  S
56411 ACTCCATCGAGGCACGCATGGTTTCGAACACTGCCGTGCAGCGTCTGGTGCAGGGCCACCGCGCCTCCGGCTGCTGGGCAGCGCC
      <  E M S A R M T E V S A R L V Q G R S R L A A V A E P R P L  A
56503 GGCAGGAACGCGAACGCCGCCGTCTTCCCCGACTCGACGCAGCACAACAGGCTGCCGCCAGCAGCGTCTGAACTCGTCGACCCC
      <P  L F A F A A V F P D S T Q H N G W L G R L L T E F E D V G
56595 CTTCGGGGGTGATCTCGTTACGTCGGTAGATCGAGCGGGCTGCACGTTGGCCGACCTGTCGCGGAGCAGCCCCTCTGCCGAGCTTGC
      <  K P T I E Y T T R A R R A G V Q E T A V E R L L G E E G L K R
56687 GCAGCGCGTGGTAGAGCGGTGCAACTGTCGGCAGCTGCACGTTGGCCGACCTGTCGCGGGAGACGTCGTAGCCGTGCACC
      <  L A H Y I S G P Q V N A W K D A G W S L L E R R V D Y G H V
56779 GGCTGCATCCACTTGACCAGGCCGAGAATCATGCGAGTGGCAGACACCGGAAAGAGTATTAGACAAGTTTGACTATTCCAAGCATCTG
      <P  Q M W K V L G L I M M
56870 GGGCAGTGCCTCATCCCACACTGAGCGTTAGGGCCGGATCGTTAGGGCCACGACGATCGTCAGTAACATCCCGTCAGTAACTCCCGAGCCACGAG
      >V  R K V L I A N R G E I A V R V I R A C R D A G L G S V A V
56961 GTGCGCAAGGTACTCATCGCCAACCGAGGCGAGATCGCTCCGGTCATCCGCGCCTGGGCAGGTCTGCCGTCT
      >  Y A D S D R D A L H A T L A D E A Y A L G G D T A A E T Y L  R
57052 ACGCGGACTCCGACTCCGACCGGGCGCTGCACGCGACGCTGGCCGACGAGGCGTACGCCCTGGGCGGCGACACCGCCGCCGAGACGTACCTGCGG
```

FIG. 11A(49)

```
57144 ATCGACAAGCTGATCGCGTCGCGGGCACAGGCCGGGGCCGTCCACCCGGGTACGGCTTCCTCGCCGAGAACGCCGACTTCGCCA
      > I D K L I A V A A Q A G A D A V H P C Y G F L A E N A D F A Q
57236 GGCCGTCCTCGACGCGGGCTTACCTGGATCGGCCCGACCCCACAGGCGATCCGCGACAAGGTCACCGCCCGGCACATCGCCC
      > A V L D A G L T W I G P T P Q A I R D L G D K V T A R H I A
57328 AGCGGGCCGGGCCGCGCCCTTGGTCCCGGTACCTCGGACCGGTCTCGGCAGCCGGATCGCATTCGCGGTCGACCACGGCCTGCCG
      > Q R A G A P L V P G T S D P V G S P D E V I A F A V D H G L P
57420 GTCGCCATCAAGGCCGCCTTCGGCGGCCGGGGCCGGGGCCTCAAGGTGGCCCGGACTATGGAGGAGATCCCGCACCTGTTCGAGTCGGCCAC
      > V A I K A A F G G G R G L K V A R T M E E I P H L F E S A T
57512 CCGGGAGGCGGTCGCGCTTCGCGTTCGAGTGTCGTCGGCAGAGTGTTCGTCGAGGACTACCTCGACCAGCCCGCACGTCGAGGCGCCAGTCCTCGCCG
      > R E A V A A F G R G E C F V E R Y L D Q P R H V E A Q V L A
57604 ACCAGCACGGCAACGTGATCGTCGTCGGCACTCGCGACGACGCCAAGGCAATCTGCCGGGAGGCCGGCTACCACGGCGCACGTGGAGTACCT
      > D Q H G N V I V V G T R D C S L Q R R H Q K L V E E A P A P F
57696 CTCACCGACGCCAGCGTCAGCGGCAGATCCACGACGGACGATCTCCTTGAGGTCAACACCCGCCTGCAGGTGGAGCATCCATCGAGTTCCGGATC
      > L T D A Q R R Q I H D S A K A I C R E A G Y H G A G T V E Y L
57788 GGTGGGCACGGACGGCACAGTTCCGGATGCGCGAGCAGTTCCGCATCGCCGATGGCGAGAAGCTGCGCCTGCGCCTGGCACACCGCGTGCCGGGTGCCACGGTGACC
      > V G T D G T I S F L E V N T R L Q V E H P V T E E T A G I D
57880 TCGTCCGCAGGCGATGTTCCGGATCGCCGATGGCGAGAAGCTGCGCCTGCGCCTGGCCGAGGATCCGACTCCGCGGCACTCCATCGAGTTCCGGATC
      > L V R E Q F R I A D G E K L R L A E D P T P R G H S I E F R I
57972 AACGGCGAGGATCCGGGCCGCAACTTCCTGCCGGCCCCGGGCACCGTCACGCTGCGCCTGCCCACCGGCCCGGTGCGCGTGGACAC
      > N G E D P G R N F L P A P G T V T A L R L P T G P G V R V D T
58064 CGGCATCTCCGCCGGCGACGTGATCGGCGGCAACTTCGACTCCCTGCTGGCCAAGGTGATCATCACGGGCGAGACCAGGGAGGCCCTGG
      > G I S A G D V I G G N F D S L L A K V I I T G E T R T E A L
58156 AGCGGGCCGGCCGGCGGGCGCTGGACGAGATGGTCGTCGAGGGAATGGCCACGGCGCTGCCGTTCCACCGCCTGGTACGCGACCCCGCGTTC
      > E R R R A L D E M V V E G M A T A L P F H R L V V R D P A F
```

FIG.11A(50)

```
58248 ACCGCCGGCCGCTTCACCGTGCACACCCGGTGGATCGAGACGGAGTTCGACAACACCGTCCTGCCGTTCACGGCCGCCGCCGGCCCGCCGA
      > T  A  A  P  F  T  V  H  T  R  W  I  E  T  E  F  D  N  T  V  L  P  F  T  A  A  A  G  P  P  A  E
58340 GGGCCCGGCCGAGCGGGAGACCGTCGTGGTCGAGGTGGGCGGCAAGCGCCTGGAGGTGACCCTCCCGGCTGGCCTCGGCGCGGTACGGCCG
      > G  P  A  E  R  E  T  V  V  V  E  V  G  G  K  R  L  E  V  T  L  P  A  G  L  G  A  G  T  A
58432 CCGGGCCCGCGCGGAAGCCCAAGGCCAAGGGCGGGGCGGGGGCAAAGGCCGGAGGGGGAGCCAAGGCCCTCACCTCTCCGATGCAG
      > A  G  P  A  A  R  K  P  A  R  R  G  G  G  A  K  A  G  A  A  V  G  G  D  A  L  T  S  P  M  Q
58524 GGCACGATCGTGAAGATCGCCGTCGCGGACGGGGACACCGTCGCCAAGGGCGACCTGGTCGTGGTGGAGGCGATGAAGATGGAGCAGCC
      > G  T  I  V  K  I  A  V  A  D  G  D  T  V  A  K  G  D  L  V  V  V  L  E  A  M  K  M  E  Q  P
58616 GCTGCACGCGCACAAGGCGGGCACGGTCGGGGGCCTGTCCGCCGAGGTCGGCGCGGTCCTCGCCGCCGGCGCCCCCATCTGCACCATCACCT
      > L  H  A  H  K  A  G  T  V  G  G  L  S  A  E  V  G  A  V  L  A  A  G  A  P  I  C  T  I  T
58708 GAGGTGCAAGGAGGGGCCCCTGTAACGCATTCGGTATATAGGAAGGGCCCTTCCTAACCACGCCGCCCCGGGGGCCGCCCCCAGCCCGGG
      >  .
58800 TACGCGTACCGCCGGGGTGTTTTCCGGACCACCGGGGTGAGGACCCGGAATGATGGCCAGGTGCCGGTTCCTACATGGC
      >                                                                > V  R  F  L  H  G
58891 GCGGTTCCCGGCCACGGGCGACCTACAACGACGTCTTCATGGCCCCGAACCGCTCCGAGGTCGGTTGGAGTCGACTGGCCAC
      > A  V  P  A  H  D  L  T  Y  N  D  V  F  M  A  P  N  R  S  E  V  G  S  R  L  D  V  C  L  A  T
58983 CTCCGACGGCACGGGCACCACCATCCCGCTGGTGGCCAACATGACGGCGGTGGCCGGCCGGATGGCCGAGACTGTCGCCCGGCGGG
      > S  D  G  T  G  T  T  I  P  L  V  V  A  N  M  T  A  V  A  G  R  R  M  A  E  T  V  A  R  R
59075 GCGGCACTCGGGTGCAAGGACATCCCGCAGGACATCGAGGTGGTCAAGCAACGGCACCTGGTGCACGACACG
      > G  A  L  A  V  I  P  Q  D  I  P  I  E  V  V  A  N  V  V  K  Q  R  H  L  V  H  D  T
59167 GCGATCACGCTCGGCCCGACCGATGTCGGCGATGCCATCCATCTGCTGCCGAAACGTTCGCATGGCGCGGTGGTGGTGGACGAGGC
      > A  I  T  L  G  P  T  D  T  V  G  D  A  I  H  L  L  P  K  R  S  H  G  A  V  V  V  D  E  A
59259 CGGTCGGCCGCTGGGCGTGGTGACGGAGGCGGACACCGTCGGGGTCGACCGCTTCGCCCAGCTCCGCCACGTGATGTCGACGGAGTTGCACA
      > G  R  P  L  G  V  V  T  E  A  D  T  V  G  V  D  R  F  A  W  L  R  H  V  M  S  T  E  L  H
```

FIG. 11A(51)

```
59351 CGGTGCCGCGGGAGACGGCGGACCGGCGTACCGGATTCGACCGGCTCTCGGCGGCGGCGGCCGGTGGTGGACGGGCGACGGCCGG
      >T V P A D A D P R T G F D R L S A G R R R L A P V V D G D G R
59443 CTCGTCGGGGTGTTGACCCGCAAGGGCGCGCTCACCGGCGCGACCCTCTACACCCCGGCGGTGGACGACGGGCCGGTCGCGGCGGC
      >L V G V L T R K G A L R A T L Y T P A V D D R G R L R I A A A
59535 CGTCGGCATCAACGGCGACGTCACCGGCAAGGCCGCGCTGCTGGAAGGCGCTGCTGGTGGACGCCCTGGTGGTGGACACCGCACC
      >V G I N G D V T G K A A L L E A G V D A L V V D T A H G H
59627 AGGGCGCGGATGGTCGCCGGCGGTGCGGGGTCGCCCAAGCTTCACCGGGCGGTTCCGGTCCGGCCGGCAACGTGGTCACCGCGATGGGGTA
      >Q A R M V A A L R A V R K L H P G V P V A A G N V V T A D G V
59719 CGGGACCTCGTCGAGGCCGACATCGTGAAGGTGGGCGTCGGTCCCGGATGTGCACCACCCGGATGATGACCGGGGTGGGGCG
      >R D L V E A G A D I V K V G V G P G A M C T T R M M T G V G R
59811 TCCGCAGTTCTCCGCGGTGCTGGACTGCGCGGCCGCCGCCGCAGCGCGGGACCTCGGGCGCCACGTCTGGGCCGACGGCGTACGGCACCCGCG
      >P Q F S A V L D C A A A A R D L G R H V W A D G G V R H P R
59903 ACGTGGCGCTGGCCCTCGCCGCCGGCGCGTCGAACGTGATGATCGGTTCCTGGTTCGCCGGCACGTACGAGTCCCCGGGTGACCTGTACACG
      >D V A L A L A A G A S N V M I G S W F A G T Y E S P G D L Y T
59995 GACGGCGGACGGCGGTACAAGGAGAGCTTCGGGATGGCCTCGTCGCGCGCCGGTCAGCGCGTACGGGACACAGCGGCGTTCGACCG
      >D A D G R R Y K E S F G M A S S R A V S A R T A E D S A F D R
60087 GGCCCGCAAGGGGATCTTCGAGGAGGGCATCTCCTCGGCCGGATGTACCTCGACCCGGCGTCGAGGACCTGATCGACGAGA
      >A R K G I F E E G I S S A R M Y L D P D R P G V E D L I D E
60179 TCATCTCCGGGGTACGCAGCGCGTGCACGTACGCGGGGGCTGAGCCTGCGCCGGAGTTCGCGGAGCGGGCGCTGGTCGGGGTGCAGAGCACG
      >I I S G V R S A C T Y A G A R S L A E F A E R A L V G V Q S T
60271 GCCGGCTACACGGAGGGGATGCCCCTACCGACGAGTTGGTGACCCGCCGCCGCGCCGCACGCGCCGCACTGAGCCGCCCGTCGAGGGTCAA
      >A G Y T E G M P L P T S W .
60362 CAAGGGCCCTTCCTTCGTGCGGCTGGTATCGGCGTGACCGACTGCCGACCGACTGCCGCCGCACGCGCCGCACTGAGCCGCCCGTCGAGGGCCC
```

FIG.11A(52)

```
60454 ACCGAACGGGCGCCGGGGGTCAGTCGAAGAGGCGACGATGACGGTTCCGGGTCCGGGCGGTGCCGGGGCGGGGAGCGCC
       <  *   D   F   L   R   R   I   V   T   R   A   A   A   E   P   D   P   G   T   G   P   P   L   A

60545 CCGGCCAGCCAGAGTGTCACGAAGCGTGCACGATCGACCAGGCGTCCGCTCCTGGTCCGGTTCCCGGCGCGGGAG
      <G   A   L   W   L   T   V   F   G   H   V   I   S   W   A   A   L   A   D   A   E   Q   D   P   T   E   R   R   P   L

60637 GGCGGCCACCCCGGCCAGCCCGGCTGTCGACCGCGAAACCGGCGATCACGGGCGGCTGTCACCTCGGGGTCGTGCGACGGTAGAGCTCGGGGCGGAACA
      <A   A   V   G   A   R   L   A   A   G   A   R   D   R   A   A   T   V   E   P   D   D   R   R   Y   L   E   P   R   F   M

60729 TCACCTCGAAGTGGGCCGGTGCCCGGTGGTCGAGCGCGTACCGCGAACGGTGAGCAGGTGCGCCGCTCGCACAGCGCCGGCC
      <V   E   F   H   A   R   H   D   V   A   F   R   V   Y   A   V   G   A   D   L   L   L   D   G   A   E   C   L   A   G   A

60821 AGCAGGTCGAATCCCTCGACGGCGAGCGCGGTGCAGCCCCGTTGTCGCCGAAGTGGTGCGCGGGGCGGCGACGCAGGTCACCGT
      <L   L   D   F   G   E   V   A   L   A   T   L   L   G   A   K   D   G   F   H   H   A   P   A   A   H   S   V   G   A   R

60913 GCGGGCCAGGTCGCCAGGCTCCAGGGGCCAGCTCCCGGGCCAGCAGCAGCCTAACTTGTCATTGACAAGATAGCCAAGCCAATCTAGGCAATGACAAGTTG
      <R   A   L   D   R   L   S   L   A   A   P   G   A   D   T   I   A   D   V   A   A   L   L   R   R   L   D   G   H

61005 GATGGTAGCCAGGTCCGGTCCGTCATGCGGGCAGCAGCCCTGATCGCTCTCCATGCGCCCTTCGGCCCGGCTACTCAACGTCGACG
      <  H   Y   G   R   P   G   T   M

61095 CCTTCGACCGAGGAGAACCCCGATGGCGCCCCCGCTCGGCCTGGGGGCTGTGGGGCTGCTGCTGCGCCATGTTCCCGGGGATCGCCCACTTCACCTCCGACGGCCCGAC
      >M   V   P   P   R   L   P   H   P   G   L   L   V   T   G   L   L   E   L   A   G   A   V   A   L   L

61187 CCCTGGCCGGCTGGCACCCGCTGCCGCCCCGCCGGTGACCCCTCGTCCCCGCCTCGTGGTCGCTGGTGAGTTGGGCCGCGGTCGCGCGCTGCT
      >L   L   A   M   F   P   A   N   A   S   A   A   R   R   G

61279 CTGGTCGCCATGGTCGCCGCCCACTGTGCCGCCCCCGCGCTGCGCTGCTGTCAGGTGATCTTCCTCACCGCGGCGGCAATCAGCTTCGTTTGGG
      >L   T   A   G   R   P   V   T   P   L   V   P   R   A   L   L   Q   V   I   F   L   T   A   A   A   I   S   F   G

61371 CGTCCCCGGCACGCGGTGGGCGTGGGCGTGCTGCGATGTTCCGGCCGATGTTCCGGCCCTCGAACGCCTCGAACGCCTCGACGCGGGCCCGAC
      >V   P   G   T   A   R   W   A   A   A   G   L   G   L   L   L   L   A   M   F   P   A   N   A   S   A   A   R   R   G

61463 TGACCCTCGGCCGGCCGGCCGGTGACCCGGCTGCTCGTCCTCTCCACCGCGCTGCTGATCTTCCTCACCGCGGCGGCAATCAGCTTCGTTTGGG
      >L   T   L   A   G   R   P   V   T   P   L   V   P   R   A   L   L   Q   V   I   F   L   T   A   A   A   I   S   F   G

61555 CCCTGACTATCAGGGAGCTAACATGAGCCGGCTGATAGGGCTGCGAGAGCTGCCACTCGGCCGGCTGCTGGTGACCGGCCA
      > P   *
```

FIG.11A(53)

```
61645 CGTCGTCGGCAACGGTGGAACCGCTACCTCGCCGAGGAGCACGGCCTCACCCAGGCGGGGCATGGTCACCCTGATGACCCTGGCCCGGCACG
      > V V G Q R W N R Y L A E E H G L T Q A G M V T L M T L A R H
61737 GCGAGCTGCCGCACCGGCGTCGCCGAGGCGTTCATCCGCCCGGCCACCCTAACCGGCATCGTCGACACACTGGAGCGCGACGGCCTC
      >G E L P H R A V A E A C F I R P A T L T G I V D T L E R D G L
61829 GTCGAGCGGCAACGCGACGAGCCGCGACGCGTGCAGCGTCCTGACCCCGGCGGGCGAACGGGTCGCGCGCTCACCAACGT
      >V E R Q R D D V D R R S V R L V L T P A G R E R V A A L T N V
61921 CATGCAGTCCGGACGACCTCGGTGACGCCGATGACCTCGGTGACGCCGGAAGGCCGCCAGTTCCTGCTCGAGGTCATCGGCAGTG
      > M Q S G R P M T S V D A D P A K A A V I R Q F L L E V I G S
62013 GAGAGGAACCTCGGGTGACGCCCCTCGACGCGAGGCTCGATGTCCCGCATGTGATCCGCTGCTGCCCACCTGCCGCCCGTACCGTC
      >G E E P R V T A L D A R P E A P A C .
62105 GACCGCTGGCGGCGGTGCAGTTCGTTGCAGTGGCGCTACATGGCCTCGCTGAGCCTCAACGCGACATCATCGACCAGGG
      > M A L Q F V G T M A S L Y L P S L N A D I I D Q G
62196 TGTGGCCCGGGGCGACACCGGCTACATCATGCGCACCGGCGGGGTGGATGCGCTGTCTCCACGCCGCCGG
      > V A R G D T G Y I M R T G G W M L L V S L V Q I A C S T A A
62288 TCTTCCTCGGCGCGCGAGTCTGCGCGATGGGCTTCGGCCGGGACGTACGGCGCGAGGTCTTCGCCCACGTCAACCGGTTCTCGCCGGAGGTG
      >V F L G A R S A M G F G R D V R A E V F A H V N R F S A R E V
62380 ACCCGCTTCGGCGCACCCTCGCTGATCACCCGCAACACCAACGACGTGCAACAGGTGCAGATGCTCGTCCTGATGAGCTGCACCATGCTGGT
      >T R F G A P S L I T R N T N D V Q Q V Q M L V L M S C T M L V
62472 CGGCCGGCCGATCATGAGCGTGTTCATGGCACTGCGGGAGGACGTGGGCCTGTCCTGGCTGATGCTGGTCAGCGTGCCGGCGC
      > A A P I M S V G G V F M A L R E D V G L S W L M L V S V P A
62564 TGGCCATCGCCCTGATGCTGATCATCCGGCGGATGGTGCCCGGGTTCCGGCTCATGCAGACCAGAGATCGACGCGGTCAACCGCGTGCTGCGC
      >L A I A L M L I I R R M V P G F R L M Q T R I D A V N R V L R
62656 GAGCAGATCACCGGCATCCGGGTGGTCCGCGAGCGTCGTTCCGGGCGCGTACGGGAACGCGCGGCTTCGGCCGCGCGAACGCGACCTCACCGC
      >E Q I T G I R V V R A F V R E P Y E T A R F G R A N A D L T A
```

FIG.11A(54)

```
62748 GACCGCCCTGCGCACGGGTCGGTTGATGGCCCTGATCTTCCCGGTGGTGCTGTTCCCGGTGGTGCTGAACGTCTCCAGCGTGGCCGTGCTGTGGTTCG
      >T A L R T G R L M A L I F P V V T L V L N V S S V A V L W F

62840 GCGCGGACCGCGTCGACGCCGGCCAGGATCCAGGTTCGGCGCGCTTCACCGCGCCTTCCTGCAGTACCTCATGCAGATCCTGATGGCCGTCATGTTG
      >G A D R V D A G Q I Q V G A L T A F L Q Y L M Q I L M A V M L

62932 GCCACCTTCATCCTGATGATGGTCCCGCGCGCCGCGGTCTGCGCCGAGCGGATCGTCGAGGTGCTCGACACCGACTCGACGGTGATCCCGCC
      >A T F I L M M V P R A A V C A E R I V E V L D T D S T V I P P

63024 GGCCGCGCCGACGGCCGAGGTGACCGGCCGCGGGGAACTGGAACTGCGCGGCGTTCCAGTACCCGGGGGCGAGCGCGCCGGTGCTGC
      >A A P T A E V T G R G E L E L R G V R F Q Y P G A S A P V L

63116 ACGACATCTCGTTCCGGGCCACGCCGGGCCGCACCACCGCCATCATCGGCAGCACCGGGGCCAAGACGACCCTGCTGACGCTGATCCCG
      >H D I S F R A T P G R T T A I I G S T G A G K T T L L T L I P

63208 CGGCTGATCGACGCCACCGCCGGGGCGGTGCTGGTCGACGGGGTGGACGTCGACCAACTCGCCGGTACGGCCAGGGCGACGAGCTGTGGCCG
      >R L I D A T A G A V L V D G V D V R D L A P D D L W R R I G L

63300 GGTGCCGCAGCGGATCGCCGTCGTGCAGGCGCGCGACTTCGTCGCCGAGTTGCCCGAAGGGCTGAACGGCACCAATATCTCCGGC
      >G V P Q R P Y L F S G T I A S N L R Y G N P D A T D A E L W A

63392 CCCTGGAGATCGCCCAGGCGCGCGATTCGCCGGGCAGCGCCTGGTCCGCAAGCCGGAGATCTACCTGTTCGACGACTCGTTCTCGGCGCTGGACCTGGG
      >A L E I A Q A R D F V A E L P E G L N A P I T Q G G T N I S G

63484 GGGCAGCAGCGCCTCGCGATCGCCCGCGCTGGTTCGACGTTCACGGCCGATCGTGGCCGACATCGTCGACG
      >G Q R Q R L A I A R A L V R K P E I Y L F D D S F S A L D L G

63576 CACCGACGCCAGGCTGCGCGCCGCGCTGCGCCCGGTGACAGCCGACACGGTGCTCATCGTCGCCCAACTGGCCCGACGACTACCCGACCTACGCCGAGATC
      >T D A R L R A A L R P V T A D A T V L I V A Q R V S T I V D

63668 CCGACCAGATCATCGTCTTGAGGACGGGGGCATCGTCGGCATGGGCCGCCACGCCGAACTCCTGGAAGACTGCCCGACGTACGCGGAGATC
      >A D Q I I V L E D G G I V G M G R H A E L L E D C P T Y A E I

63760 GTCGCCTCCCAGCAGACAGCGGGTGCCATGACGGCCGTACCGGCGGGCCGAGGGCCGACGCCGAA
      >V A S Q Q T A G V P A .
```

FIG.11A(55)

```
63851  GCGGGCTGCCCTCCGGCAACCAGGGCAGGCGGGGCCCGAGGTGGATGAGGCGCCGGCATGCCGGGCCGAGAAGTCGATGAACTTCGGGCCGTCCAC
                                                 >M  S  A  G  M  P  A  E  K  S  M  N  F  G  P  S  T
63941  CCGGCGGCTGCTGCGCCGGCTGCGACCGCCACGCGCCATGTCTGCGGCCGCCTCCTGCTCTCGCTGGTCAGCGTCGGTTGCAACGTGTACG
       >  R  R  L  L  R  R  L  R  P  H  R  L  Q  L  A  A  I  V  L  L  S  L  V  S  V  G  C  N  V  Y
64033  GGCCGAAGGTGCTCGGCCATGCGGACCTGATCTTCAGCGGGGTGATCGGCCGGCAGTTGCCGGCCGGCACCGCCGAGGCGGGTC
       >G  P  K  V  L  G  H  A  T  D  L  I  F  S  G  V  I  G  R  Q  L  P  A  G  T  T  A  E  Q  A  V
64125  GCGGGCCCGGCGCGGCGGCCGGTAACGACAGCTTCGCCGACATGCTGGCCCGGATGGACGTGGTGCCCGGGATCGACTTCACCGCCCT
       >A  A  A  R  A  A  G  N  D  S  F  A  D  M  L  A  R  M  D  V  V  P  G  V  G  I  D  F  T  A  L
64217  GGGCCGGGGTGCTGCTCTTCGTTCTCGCCCTCTACCTGGCGGCCAGCGTGTTGTGGTGGCAGGGCTGGCTGCTCAACGGGGTGGTGCAGC
       >G  R  V  L  L  F  V  L  A  L  Y  L  A  A  S  V  L  L  W  Q  G  W  L  L  N  G  V  V  Q
64309  GCACGGTGCTGCGCCTGCGCGCCGACGTGGAGGACAAGCTGAACCGGCTACTTCGACCGGCAGCCCCGGGGCGAGTTGCTC
       >R  T  V  L  R  L  R  A  D  V  E  D  K  L  N  R  L  Q  L  Q  Y  F  D  R  Q  P  R  G  E  L  L
64401  AGCCGGGTCACCAACGACATCGACAACATCTCGCAGAGCCTCCAGCAGACGCTGTCCCTGCTGCTCACCTCGCTGCTGACCAGCCTGGTGGTGGTCACGAGCTGGTC
       >S  R  V  T  N  D  I  D  N  I  S  Q  S  L  Q  Q  T  L  S  Q  L  L  T  S  L  L  T  V  V  G  V
64493  ACTGGCCATGATGTTCTGGATCTCGCCGCTGTTGGCGCTGGTGTCCCTGGTCGCGGTGGCCCCGATGTCGGTGGTCACCAGCCTGGTCGCGA
       >L  A  M  M  F  W  I  S  P  L  L  A  L  V  S  L  V  A  V  P  M  S  V  V  V  T  S  L  V  A
64585  AGCGGGTCACACAGCGGTTCATCGCCCAGTGGACGCATACCGGAGACTGAACGGCCAGATCGAGGAGGCGTTCACGGACACGAGCTGGTC
       >K  R  S  Q  Q  R  F  I  A  Q  W  T  H  T  G  E  L  N  G  Q  I  E  E  A  F  T  G  H  E  L  V
64677  AAGGTCTTCGGCCGCCAGCGCGAGGTGGAGGCCGCCTTCACCGGCCAAGAGGAGCTGTTCCGGGCCAGCTTCGGCGCCCAGTTCATCTC
       >K  V  F  G  R  Q  R  E  V  E  A  A  F  T  A  K  N  E  E  L  F  R  A  S  F  G  A  Q  F  I  S
64769  CGGGGATCATCATGCCGGCGCAGGCATTCATCCAGTACTCCCTGCAGTTCACCCAGCCGCTGACCCGGGTCGCCTCGATGGCCAACCTGCTCCAG
       >  G  I  I  M  P  A  M  M  F  I  Q  N  L  S  Y  V  A  I  A  V  V  G  G  L  R  V  A  S  G  S
64861  TGAGCATGGGCGACGTGCAGGCATTCATCCAGTACTCCCTGCAGTTCACCCAGCCGCTGACCCGGGTCGCCTCGATGGCCAACCTGCTCCAG
       >M  S  I  G  D  V  Q  A  F  I  Q  Y  S  L  Q  F  T  Q  P  L  T  R  V  A  S  M  A  N  L  L  Q
```

FIG.11A(56)

```
64953 TCCGGGGTGGCCTCCGCCGAGCGGGTGTTCGCGGTGCTCGACGCGGAGGAGCAGAGCCCGGACCCGGCGGTGCCGGCGCGGGTCGCCGACCA
     > S  G  V  A  S  A  E  R  V  F  A  V  L  D  A  E  E  Q  S  P  D  P  A  V  P  A  R  V  A  D  Q
65045 GCGCGGTCGGCGTCGAATTCGACCACGTCTCCATTCCGGTACGAGCCGCGCAAGACCGACCTGTCGCTGGTCGCCGAGCCGGGC
     >    R  G  R  V  E  F  D  H  V  S  F  R  Y  E  P  D  K  P  L  I  T  D  L  S  L  V  A  E  P  G
65137 ACACGGGTTGCCATCGTCGGGCCGACCGGCGCCAAGACCACCCTGGTCAACCTGGTGATGCGCTTCTACGAGCTGGACGCCGGATC
     > H  T  V  A  I  V  G  P  T  G  A  G  K  T  T  L  V  N  L  V  M  R  F  Y  E  L  D  A  G  R  I
65229 ACCCTCGACGGGGTCGACATCACCACGCTGAGCCGCGACGACCTGCGCGGATCGGTGCTCCAGGACACCTGGTCTTCGGTGG
     > T  L  D  G  V  D  I  T  T  L  S  R  D  D  L  R  G  R  I  G  M  V  L  Q  D  T  E  L  F  G  G
65321 CACGATCCGACAACATCGCGTACGGCCCGGACGCGAGCGAGGAGATCGTCGCCGCCGCACGTTCGTGGACGGTTCG
     > T  I  R  D  N  I  A  Y  G  R  P  D  A  S  E  E  E  I  V  A  A  A  R  A  T  F  V  D  R  F
65413 TGCGTAGCCTCCCGACGGCTACGACACCGTCATCGACTCCGAGGGCAGCAACGTCAGCGCGGAGAAGCAGCTCATCACCATCGCCCGG
     > V  R  S  L  P  D  G  T  D  T  V  I  D  S  E  G  S  N  V  S  A  G  E  K  Q  L  I  T  I  A  R
65505 GCGTTCCTGGCCGAGCCGTCGCTGCTCATCCTCGACGAGGCCACCAGTTCGGTCGATCGGACCGAGGTGCTGCTCCAACGGGCCATGGC
     > A  F  L  A  E  P  S  L  L  I  L  D  E  A  T  S  S  V  D  T  R  T  E  V  L  L  Q  R  A  M  A
65597 GGGGCGTCGAGCGACAGGACCAGCTTCGTCATCGCCCATCGTTTGTCCACCATCCGTGATGCCGACCTGATCCTGATGGAGCACGGTC
     > A  L  R  S  D  R  T  S  F  V  I  A  H  R  L  S  T  I  R  D  A  D  L  I  L  M  E  H  G
65689 GCATCGTCGAGCAGGGCACCCACGAGCAGCTCCTGGCCGCCCGGGGCTGACCGTCGTGCCCGGTACATCCCGCCGACCGCAG
     > R  I  V  E  Q  G  T  H  E  Q  L  L  A  A  R  G  A  Y  H  R  L  Y  A  Q  A  F  T  Q  P  D  P
65781 GCCGCGTCCCCGGGCCCCGAGCCCGGGCCCCAGCCGCCCGGGGAAGAGACCAGCGTTGGTGCGCAGAGCCGGAGCGCGAACTCGTCGGGGCCAGCCG
     > A  A  V  G  D  P  E  P  Q  P  P  A  S  V  R  G  .
65872 GGGGCAGCTCCCCGGGGAACATGTCGTCGGCGAAGTGGCCCTCGATGACGTCAGTCGGGCGCGGGGTTCCCGACGTCG
65964 CATCGGGGAACATGTCGTCGGCGCTGCGCATGGGGAGACGGTAGGCGGGAGACGGTAGGCGCGCGATCGCGCGGACACG
66056 TGGTCCGTACCGCGCTGCGCTGCGCAGTCGTCGGCCGCAACCCGGTCGCAGTCGCACCAGTCGGCAACCCGGCACAGCGCCAGCGAGACG
66148 CATCCGGTTACGCCGAAGGGCGACAGGCCGACAGAGCCGCAATCCGCCGGATGCGGATCCGGCAACCGCTCGGGGCCGCCGGCCAC
```

FIG. 11A(57)

```
66240  GGGACCTGCCGGCGGCCCATGGCGGCCCGGTCGTCGGCTACGGGGGTCGGAGCCGCCGCGACACTCGAGGCCCGCCGCGCGACTACGGTCGCCGGCGTCGGC
66332  GATCCGCGACCGCCTCCACCGAGCCCCAGCGGTTGCCGCCCCCAGCGGGTCGCCGAGGTTGCCGCGCCGCCCAGCGGGTCCCCGGCGTCCCCGCGTGCCGGCCC
66424  GACGACCGGTTCGTGGCGGGTGCCGGCGAGGTGGAGCCGCGCCCAGTTACTCGAGCTCGTGGAGCATGAGCTGGCGGGGCGGCCTCGGTGATC
                                                            < .   E  L  E  H  H  L  M  L  Q  R  A  A  E  T  I
66515  GAGCCCGACAGGCTCGGGTAGATGGTCTGGGCCAACTCGTTGACCGTGAGGTTGTTCTCCACGCCATGGTGATCGGCAGGATCAG
       < S  G  S  L  S  P  Y  I  T  I  T  Q  A  L  E  N  V  T  L  N  N  E  V  A  M  T  I  P  L  I  L
66607  CTCGCTGGCCTTCGGTGCCGTGCCACCACGACCGCGTTGGCCGGCGGCAGAACAGCTTCACGAAGCCGTCGGCGAGGTCGT
       < E  S  A  K  P  A  V  V  V  G  G  I  V  Q  G  S  A  P  R  C  G  L  K  V  F  G  D  A  L  D  D
66699  CCATCTTCGCCGGGAGTCGTTGCCGACAGCGGCGGGGTCTTGCCGGGTCTTGCCGGTCTTGCCACCTCGTCCTGGAGACGCCGACG
       < M  K  A  R  A  N  G  S  L  P  L  M  V  Q  R  A  P  T  K  G  A  S  V  E  D  Q  S  V  G  V
66791  GTGGCCAACTCCGGTCGTGAAGACGTTCGGCTACAGCAGCCACGTTGCCGAGCCGTGCACATCGCGAT
       < T  A  L  E  P  D  T  F  V  N  A  A  V  T  R  L  R  P  R  V  A  E  G  L  A  H  W  M  A  I
66883  CCGGCCCTGCATGGCGAGCCGGTCACCGGCAACGGCGGAGCGGAGCTGTAGATCCGGCAGTCGCAGCGTAGATCCCGGGACGTTGGTGCGGACACCC
       < R  G  Q  M  A  A  V  S  A  L  P  L  V  G  T  C  D  G  A  A  Y  I  G  P  V  N  T  R  S  V  R
66975  GGTCGACGGTGAGCCGGTAGCCGGTCGGCCCAGTTCGACCTCGAGGTCGACCGGGAGCAGGGGATCGAGCGACCGGATG
       < D  V  T  V  Y  G  G  R  A  L  E  V  G  T  E  A  L  G  L  N  A  T  N  P  I  S  G  V  A  I
67067  AGCGCGGTGCGAGCCGTGCACCGGCGTTGCACCGGAACGGGAGCGGAACACGCGCTTGGCAGCCCTCGGCGACCCTCTGGCGGAGTTGTT
       < L  A  H  S  G  H  V  L  R  G  D  A  L  E  V  E  V  G  D  A  I  R  Q  V  R  E  A  R  S  N  N
67159  GAGGATCGTCATGCCGGGAGCGGAACGGGAGCGGAACACGCGCTTCTCGTGCGCATCACCCGGTCCCGGCTGAGA
       < L  I  T  M  G  R  S  R  F  V  R  E  I  A  M  A  A  D  A  D  E  H  P  M  V  R  D  R  S  S  V
67251  CGAGGGTGACCGGGACCCGTCGTACACCTGCCGCCAGGTACTCGGCGAACTCGGCTGACGCGGTGCTCGGGCAGG
       < L  T  V  P  V  G  M  A  L  Y  A  S  A  F  E  A  G  T  V  G  S  G  V  V  I  L  H  E  P  L
67343  TGCGGCAGGTCGTACACTGCCGCCCAGGTCAGGATGCTCAGGATGAGCCGCACGGCCGTGGGGGGTGGCCGTGGCGAC
       < H  P  L  D  Y  V  Q  E  W  T  L  I  R  E  G  D  P  V  A  T  P  L  Q  R  P  T  A  G  T  A  V
```

FIG. 11A(58)

```
67435 CAGCACGGTCGACGCGTCGAGTGCTTCTCGGAGCGTCTTCGGCCGTCGAGACGACGCGGTCGGTCTGTGGCCCAGCATGTCCTCGCCGA
      < L  V  T  S  A  D  I  S  H  K  E  S  G  D  A  P  T  V  V  V  R  H  T  H  G  L  M  D  E  G  L
67527 GCCGGGCCGTGCCGGCCACGAAGGTGACGCCGGCTTTCACCAGCTTCGCTGGATGTCGGCGGACTGGGCCAGGGCGAGCCGCTTGACCCGC
      < R  A  T  G  A  V  F  T  V  G  A  K  V  L  K  A  H  I  D  A  S  Q  A  L  A  L  R  K  V  R
67619 TCGTGCACGGCCCGGCGTCGACGGTGACGGTTTTCGACGGTACGGTCCCAGCCGTCGAGTGCACCCCGAACTCCTCGTGTCCGGTACCGGTGACCACCTC
      < E  H  V  A  R  A  D  V  T  V  A  E  L  G  D  S  H  V  G  F  E  E  T  D  R  Y  G  T  V  V  E
67711 CGAGCTGGCGATGAACGTTTTCGACGGTACGGTCCCAGCCGTCGAGTGCACCCCGAACTCCTCGGCCTCCACCACGGTGACATCAGCGT
      < S  S  A  I  F  T  K  S  P  V  C  D  S  L  V  C  A  G  G  A  G  E  A  E  V  V  T  V  D  A  D
67803 CCAACTGGGCGGCGACCAGGGCGACACGGTCGACCGCCTGTACCCGGCCGCGATGATCACGATCTGCTCACAGCTCTGCCCCTCGTCCGT
      < L  Q  A  A  V  L  A  A  E  Y  G  A  P  G  G  G  I  I  V  I  Q  S  V                  > V  R
67893 GCTCACAGTGACTTTCTCCCCGACACCGTCTATTCTCCCCAGCCTGTCGGCTATCGTCATCGCCGTGCG
                                                                                              > V  R
67984 TCACTACGCCGCTACGGCTCAAACTGGACCCGGCTCGAATGCCGGCAACTGCCCGCACTCCCGGATGTCGGCGTGGCTGGCTGGAGG
      > H  Y  A  A  Y  G  S  N  L  D  P  A  R  M  R  A  U  C  P  H  S  P  M  V  G  V  G  W  L  E
68076 GCTGGGGCTCACCTTCGCGGGTGAGGGCGCGATCGGCGAGGGCGCAGCGACCATCGTCGAGTCCCCGGGTGATCGGGTGTTCGTG
      > G  W  R  L  T  F  A  G  E  G  A  I  G  E  G  A  V  S  T  I  V  E  S  P  G  D  R  V  F  V
68168 GCGCTCTACGACATCCACCCGTACGACGCCGTCCAGCTCGACGAGATCGAGGGGTGGCCTCCGGGACGTACGCAAGCTGCACGTCCGCGT
      > A  L  Y  D  I  H  P  Y  D  A  V  Q  L  D  E  I  E  G  V  A  S  G  T  Y  R  K  L  H  V  R  V
68260 CTTCGACGGCTACGAGGGCGGCCTGCCGACCGCGTGGTACCTGTCTGAGATCTCGTCGGAGATCG
      > F  D  G  Y  E  G  G  L  P  T  A  W  Y  L  S  E  I
68352 CCAACGCCGCGGAGAAGGCGGGCGCGCCCGACGACTACGTCAGCGAGCTGCGTTCCCGGACACGGGCACCGCGTCGGCGTAGCGCGTCTC.
      > A  N  A  A  E  K  A  G  A  P  D  D  Y  V  S  E  L  R  S  R  P  T  G  T  A  S  A  .
```

FIG.11A(59)

```
68443 CCACACTCCCAGTCTGCTCCGCCGAGACGGGGCCGCCGGGGGTGTCTGTCACACATCATGGTCGCGCCCGTCACA
         < A T A A P V T R E Y M D T V R E Y M D T V                                                 V

68534 CCGCCGTGGCGGTGGGGACGGTGCGCTCGTGCTCCAGGCCATCTCGCGCAGCCGGGTGTAGAGCGGTCGCCGGGGAGGTC
         < A T A A P V T R E Y M D T W R M E R L G V S R Y L T A P S T

68626 GGGTTGGTCAGGTGACGGTGCCGAGGCCGGTGCCGCCGTCCCTTCGCGTGAAGGCCGTAGACCCCACAGCGGCGGCCGACCCC
         < P N T L D V G L G A H R R G K A A Y V T F A R W L L A A G V G

68718 GTGCGCCGGTACTTCGGACACGACAGGGTCCGACGAGTCCTGTTCCAGGCCTGTCGGACTGGAGCTGCAACGCGCGGCCG
         < H R R Y K P L V S L T R V W G S D Q W L A Q D S S Q L A G A P

68810 GCTCCCCGTCGACCTTCGGCGACGAACCACTCGTCGTAGATCCGGTGTGTCGTAGATCCGGTGGAACAGGCCAGGTCGTCCTCGCCGGCCAGTTGGTCGTACCCGGCCGGCTCG
         < E G D V E A V F W E D W T R D Y A P L R E R W H D Y G A P E

68902 TAGTCCGGGGTGTCCCGGAACAGCGCGTGTCGTAGATCCGGTGTGTCGTAGATCCGGTGGAACAGGCCAGGTCGTCCTCGCCGGCCAGTTGGTCGTACCCGGCCGGCTCG
         < Y D P T D R F A T D Y I R H F L R L D D E D G A R L P R V T V

68994 CCCGGGTGGGGGCCGGCGGCCAGCGGCCAGTCAGCCAGTCATCCGTACGTTCACCGCTGAAACCGGCTCGGTCA
         < G P P P P E A P L G A L D R S M R V Y R K V R S F G A E T L

69086 GCTCCGTCACCCAGCGGGGTCTCCGGCGGGTAGGCCGGAGGCCGGGCAGCTCAGCGCGCAGGCTCCGCTCCGCCGCTCGGCGACCGG
         < E T V W R T E P P Y A S A R V T L A P L S R E A A R E A V R

69178 TCCAGCATCCAGAGCGAGCAGGCGGGACCGCGTACCGGCCCTCGGCGCGCCTCGACGAGGACGTCGACGAACTCCGGCCACCCGGTCGG
         < D L M L A L L P A R V A E A R E P D V L V D V F E R G V G T P

69270 GTTGTCCACCACGGCGACGAGCCGCACCGGCCCTGCTGACCAGGAGTCGCGCGGCCGGTCGAAGAAGGGGGCCGTCAGGG
         < N D V V D Q A V L R G Q P D S V L W S D R A P D F F P A T L A

69362 CGGCCTTGACGTCTTCGGCGTCGAAGTCCGGCGTGGCCGATCGCGAAGGTGTCTGCGGTGCAGACGGGAGGATCCAGGACGTCGTCG
         < A K V D E A D F D P H G I A F T D A A H V V A L I G P V D D

69454 AGGGTGGGGCGCGCGGCCGCCCAGTCAGCGGCGATCCTGGCAGCCACCCGGTCCCGGCGCACCCTCATTTCAACCGC
         < L T P R R A A W D A P L T V
```

FIG.11A(60)

```
69545  CCCGCGCCCTGCCCCGCCGCCGCACGCGCTGCGCGGCGAGAGGGACCCTTTCTACCCCAGGCGTTAGTAAGGGCCCTTCCTTGCACCAC
       <.  Y  P  A  R  G  Q  V  V

69637  GGCGCGTGCGGTGGTGTCAGCAGGTCGAGCAGCGCGGTGCCCTCGGCCGTGAGCCCGGAATCCGGTGACACCGGTCGGTCACCG
       <A  R  A  T  T  L  L  D  L  L  A  T  G  E  A  P  T  L  A  R  F  G  T  S  V  L  R  D  R  V  A

69729  CCTCCGACCACACCAGCGCGGTCCCAGCGGGTACGGCCCAGCGGCGCAGCCAGGGTGCGCCCCCGGCCTCCCGGC
       <E  S  W  L  R  R  R  V  L  P  G  V  R  P  Y  P  P  P  W  G  C  A  L  A  G  A  E  G  E  P

69821  CGGCCAGCACCGCCTCAGCCGTCATCCCGCGTACGCGCCCAGCAGGTACGCCCGGCGAAGTGCTCCGAAGCAGCAGCCC
       <G  A  L  V  A  E  L  P  T  M  G  G  A  R  V  A  L  L  Y  A  G  A  F  H  E  R  L  L  L  L  G

69913  GGCGGCGGCACGGGGCCCGGTGTGTCCGGCGGCGGCCCGCAAAGAGTGGCATCCCGCTGGCGTCCGCGGCGTCGA
       <A  A  A  R  A  G  P  T  D  D  P  P  P  V  A  R  W  A  A  F  L  P  ,  G  S  A  D  A  A  D  V

70005  CCACCCGGTGCAGCGATCACGCGGGCACGGCGGTCAGGTGCTGCTCACCGGCCAGCACTCGGCCAGGTTCGCC
       <V  R  H  L  L  T  A  L  R  I  V  G  P  V  A  T  L  H  E  S  G  W  R  C  C  E  A  L  N  A

70097  GTGGCCACCTCCAGCGGTGCAGCGGCGGCGGCCCGGGTGAAGCCGAGGGCCGGCTCAC
       <T  A  V  E  L  P  A  H  V  R  A  A  A  D  W  G  S  A  V  A  D  P  A  V  F  G  L  A  A  S  V

70189  CGTGGCGGGCCCGACTCGCGCAGCACCCCGAGCCGGCGATGTGGAAGGCCCAGCAGCGGAGATGCCCAGACAGAGGGCCGGTGCAGGG
       <T  A  A  G  V  D  G  L  V  G  A  R  G  A  I  H  F  A  Q  G  S  I  G  L  L  R  A  R  H  L  T

70281  TGGCCGGGCAGCGGGCGAACATCTCCCGAGCTTGCTCGCGGCGACCTGCTCCGGCGTCATCGGGTTCAGTCT
       <A  P  C  R  A  F  M  E  G  L  E  L  V  L  P  K  S  A  A  A  V  Q  E  P  T  M  <.  D

70372  GCCCCGCGGGCCTTCCGTGACAGCCCGTGCGGCGCCGCTCGATCGCCCTCGATTCGCGGCTGCGGCGGGGT
       <A  G  G  P  G  E  T  V  A  G  D  E  A  D  V  A  E  I  A  G  E  I  E  G  T  R  R  Q  A  A  T

70464  GACGGGCCCGTTCCGGCCTTCCGCCGGCCAGCTTCCGCCTGAGTTCCTGCGCCTGCTGGCCTGGGATCGCTCCAGCTGCGGCCAGGACC
       <V  A  R  E  A  A  R  R  A  L  K  R  R  S  L  E  Q  E  A  A  R  S  R  E  L  E  A  L  S  R
```

FIG.11A(61)

```
70556  GCTCGATGCCGGTCAGTTCCTCGGCACCGTCGTGCTCGGCCCTCCGGCCCAGTTCCGCCTCGGCCCTGGTCGGTACGCGCC
       < E  I  G  T  L  E  E  A  G  D  H  E  A  E  V  A  G  A  L  E  A  E  R  E  Q  D  T  R  A

70648  CGGCGCCAGTTCCCGTTCAGCATCCGGCCGTTGCCGCCGCACGGGCCCGCTCGGCCGCGCGCTCCCGGCGGGCGCTTCGCGCGG
       < R  A  L  E  R  E  L  M  R  R  Q  R  A  R  E  A  R  A  A  R  E  A  E  R  A  A  R  K  A  R  P

70740  TGGTGGGTGGGCCCGGAGCAGCGTGGCCGTGTCCTCGCCGTGACCAAACGGAGCTCGGGGCACCTCGCCGAAGCCGGTAGTCGGCGG
       < P  P  H  T  P  P  Q  E  E  G  G  T  V  L  R  L  Q  P  R  P  V  E  G  F  G  A  Y  S  A  A

70832  CCCGCAGCAGCCGGCCGGAGCCGCCCTCGGCGTGCAGGCCACTCGCCTCGTGTCGGAGAGCCGCGCCTTCCACCTCGCCAGCGAGC
       < R  L  L  R  G  S  R  V  Q  G  A  V  E  T  D  S  L  A  A  D  L  T  A  E  V  E  G  L  P  L

70924  TTCCCGGCCGGCGGGGCCGCCCTCGGGGCGCCCTCGCCGGCTCGCGCTCAGGTCGGGTCAGTTGGGTCAGGTCGGCGACCAGCTCGGGGCGCGGCA
       < K  G  A  P  P  G  G  E  A  D  A  A  L  R  R  A  E  A  V  L  A  A  V  A  A  R  R  Q  A  S  L

71016  TTCCCGCAGCCGCGGGGCCGGCGGCTCGCGCTGGCCGAGGCGCTCGCGGCCGAGCTCGCGGCGATCGCGGCGCGCGGCGGCA
       < E  R  L  R  P  G  R  L  D  R  Q  A  R  R  L  A  E  A  L  Q  T  L  D  A  V  L  E  P  R  R  L

71108  GGGCGAGCAGGTTGACGTAGAGGCTCTTCCGCCGGGTGGCCGACGAACTTCTCCGGCAGAAGAGGCTCTGCGGGCAGCGCCGGGGCCACGGCTC
       < A  L  L  N  V  L  W  A  A  V  T  P  R  R  L  R  A  I  E  R  A  T  A  P  D  G  S  R  R  A

71200  TCGGCGAGGCCGTCGTGTGCAGGGAGGGTGGCAGGAGCCGCTGCCCGGCTCGAGGCTCGGTAGTCGGTCACAGCCGGTCGGTTGAGGACGGCGAGGCGTTGTCG
       < E  A  V  A  A  D  R  T  A  V  F  K  E  P  P  E  T  Y  L  R  R  L  L  S  Q  P  P  P  V  < .

71291  AGACGTCGAGCCGCTGCCCGGCTCGAGGCTCGGAAGGCTCGAAGCTCGAGCACCTCGAGAACTTCGACGTGGTAGCGGTCGCTCGGTCGGGATGAAGTCGAGCACCTCGAGAACTTCGACGTG
       < V  D  L  R  S  G  P  O  E  L  R  Q  U  D  T  G  S  L  A  A  Y  Q  R  N  L  V  A  L  G  N  D

71383  TTGAGCAGCCCGTCGTGTGCAGGGCTGCAAGGCTGAAGCTCGCGGAGGCCACCGGGCGGCCTCCGAGGCGCCGCCGGGGGTGCCACCAGGGCGTCGCACCGGGGCGTG
       < N  L  G  D  H  L  A  F  A  R  R  P  A  V  A  R  I  F  D  L  V  E  S  F  K  S  W  P  A  H

71475  GATCGGCGCGAAGAGAGTGGTGCCACGGGGTGTCCTCGGGGGCGTCCTCCGGGGTGGTAGACGACGTCGTTCAGCAGATACCCGA
       < I  P  A  F  L  T  D  V  P  A  D  E  P  A  A  V  L  A  D  G  P  H  Y  V  V  D  N  L  L  Y  G  L

FIG.11A(62)
```

FIG.11A(63)

```
72852 TCGCGGGTGGCCCTCGGCGTGCCGGTGGCGGTGCTGCTTGCGGGTGTCGACCGCGGCGGCCGGCGTCAACGCGCC
      >F A V A L G V P P V A V L L A V L R R R R R P P A P A V N A P
                                                  <.  R  A

72943 GCCGCCAGTGCCCGCAGCGCTCTGCACCATGACCCGGGTGATGGCCCCCTCGTCGACGTCGAAGCGAGCCGGTGCAGGT
      > P P V P A A R S A P .
      <A A L A R L A T Q V M V R I G V A I A G E D V D F S A R H L D

73034 CGACGTTCGGGCTCCGAGGCGGGGCCGAGCGCGCAGCGGGACGTACTCCAGGTACCAGGAGAAGTCCTCGCCCCATGCTC
      <V N P G S R G V G L R A L A G P V Y E L Y W S F D E G G M S

73126 TGCGGGGTCTCCGACCCCTCCGGGCGGTGCCCCGGTGCGCGTGTTGGTCACGGCGG
      <Q P T E A V G E P G L A A H T A A T L V Q I A R A D N T V P P

73218 CCGGCCGCCGGTAGGTACTCCAGGTCGCCATCACCACCTGAGCGACGATCTTGGGGCCTGGTCCC
      <R G R L Y E L D V T A G T P A I V D R V V Q A V I K P A Q D W

73310 AGGTGTCGGCGGTCCATCACCACCAGGGTGGCCGGGACTGACCAGGGATCCGGTGACGGTGACCAGGTCGAC
      <T D R D M V R L T G S A S A E S P I V N Y R T G A S A H G F

73402 ACGAGCAGGCAGGATCCAGCCGGTGTCCCGGACGGTGTGCCGGGACGGGTGATCGGGCGGGACCCGCAGGC
      <V L L L G S N A P V R R S V L A P V E T V L R G L A D V L D V

73494 GGTCAGGTGCGCAGGGGCTGGTTGGGGTGCCAGTGCCGGTCGAAGATCTGCAGACGTCGAGACCGCCTGATGACCTCCAGCGAG
      <T L H P R A T H G G P G T L R V T V N D A A T I P G V E L G

73586 CGACCTTGCCGACGCAGGATCAGCCCGGCTGGAAGATCAGCCGGTCTTGGTGGACCGGTAGGGCACGTCCTTGACGTCGG
      <V K G V P Q N P D V H L A F I Q V V D D L G G A E I V E L S

73678 CCGCAGGGCAGGCAGGATCTCCTGGCTGGATGTGTGCCGGTCGGGAAGGTTGGCGAGTTGGCGAGTTGGGCGAGTTGGGCAGCACGCC
      <G C P L I E E A P Q F I L R V R G D L E G L N A L Q A L L V G

73770 GACGGCCGAGCAGCAGGTTGGTGCACGTCGTGGCCGCAGGCGTGGCAGACACCGTCCTTGGTGGACCGGTAGGGCACGTCCTTGACGTCGG
      <V G L L V T T H V D H G C A H C V G D K T S R Y P V D K V D T
```

FIG.11A(64)

```
73862  TCAGCGGCAGCGCGTCGATGTCGGCGGCGGGAGCGCGACCACCGGGCGGCCGTCGATGTCGCAGATGACCCGTTGCCCTTTGGC
       <  L  P  L  A  D  I  D  A  R  L  A  V  V  P  G  D  P  R  G  D  I  V  G  N  G  K  P
73954  AGCAGGCGCGGGCAACCCGGCGACAGCGACTCGCGGCGATCTCGAACTCCTCGCCGGCAGAGTCTCCGGGTGGGAGTG
       <L  R  P  R  L  G  A  L  S  L  E  R  A  I  L  A  A  T  E  F  E  E  G  S  L  E  P  H  S  H
74046  GATGTGCCGGGGGTGGCGATAAGGCCGGGACATCCGAGGGCATCGAGCAGAGGCTGCGACGGCAAAGGCTGCGACGGCGACT
       <I  H  R  R  T  A  I  L  G  P  M  R  L  A  L  L  H  D  L  E  F  P  L  P  Q  S  G  S  P  S  E
74138  CCGGCCAGGCCGACGCCAGGTGGCCGTTCGGCAGCGTCAACGCACTCGTCGAAATCTCGAATCTCGATCACTAGAAACGGATGGATC
       <  P  W  A  S  S  A  L  H  S  G  N  P  L  T  L  A  S  T  V
74229  ATCAGGGATGACAGCGCCAGCCTTCTTGTGCAACATCATTCCGTAGGCGATGCGACTCTACAACCGGCGCAGGCGTCACGAATAC
                                      <  F  R  D  S  P  R  Y  T  G  W  V  Q  R  L  T  G  C  V  E  G  V  T  A
74321  CCTGGTGGAAGGGCTCCATAATCACCGTCGATCTGCGGGACAGGTAGATCGCGGTTGAACGCGTCATCTCTGCCCCACCTCTACAACCGA
       <  R  A  R  L  A  E  K  M  P  H  L  V  N  A  T  G  E  A  A  A  R  L  E  G  L  A  R  E  V  A  D
74413  TTCGGCGGTCACGAAATCACCGTCGATCGGAGACTCCGACTCGTCGATTGTCGCACTGTGTCGTTAACTGCGCTCGGACAAGTAAC
       <  S  D  R  E  V  R  L  K  A  L  R  E  A  Q  A  A  E  I  T  P  D  V  R  L  P  E  Y  P  E  D  A
74505  CGACCGCACTCGGCCAGTCCGACTCCCGGGTGGCTGCCCCGGGCTGCACACACACCAGGCAGCCCGAACGGTTACGCCCGCGACCC
       <  D  V  T  F  R  N  L  G  V  V  V  R  E  G  S  D  I  E  Q  A  I  R  Y  A  S  Q  E  I  E  R
74597  TTACCCACTGCCCCGAGACAAGGGGTCAGAACCCGGTCGCTCCTTCGGGCCCAGTCACACACCGGCGCAGCCGCTCGACCGTGGCC
74689  CTCATCCGAGACAAGGGGTCAGAACCGGTCGCTCCTTCGGGCGCCCAGCGCGCTCGGCGGCCGGCCGCGCCGCTCGACGGCGTC
       <  R  A  R  L  A  E  K  M  P  H  L  V  N  A  T  G  E  A  A  A  R  L  E  G  L  A  R  E  V  A  D
74780  CGGGCCCGCCAGCGGCCCTCCTTCATCGGGTGCAGCGACGTTCGCAGTACCCTCGGCGGCGGCCGGCCGCGCCGCTCGACGGCGTC
74872  GCTGTCGGCGACCGGTGAACCGGTTCCACTCTGCTTGGCCAGCTTGGACCCGGACCTGGGGTCGATCGTCGATCGTACGGCTCGTCGG
       <  S  D  R  E  V  R  L  K  A  L  R  E  A  Q  A  A  E  I  T  P  D  V  R  L  P  E  Y  P  E  D  A
74964  CGTCGACCGGTGAACCGGTTCGAGCCCGGTTGCGGTCGACACCAGGCCGGTGATCCTCCCGAGTCGATCTCGGGGATCCGGATCTCCCGC
       <  D  V  T  F  R  N  L  G  V  V  V  R  E  G  S  D  I  E  Q  A  I  R  Y  A  S  Q  E  I  E  R
75056  TTCTGGAAGCCGCCTTCGGCGAAGAGATCGCTGATGGCCGTCGACGTCGACCACGAGCCGTGGTCGGCACGTCCACCACCGCGCTCGATCTCGGCGGT
       <K  Q  F  G  A  E  I  A  D  V  V  S  G  H  D  A  V  R  E  M  L  E  V  V  A  A  E  I  E  A  T
```

FIG.11A(65)

```
75148 CATCGCCTCCACCACGTACGACCCGGGCGAACGGGTCAGGTTCGACGGTGTGGGCGTCTCGTACGGAGCACCTGCTGGGTGCGCAGGCCA
       < M  A  E  V  V  Y  S  G  A  F  P  D  V  T  A  T  L  D  T  E  Y  A  L  V  Q  Q  T  R  L  A  L
75240 GCCGGGCGGCCTTCTGGGTCAGCGGCCATGGCCTGTCGAAGCTGTTCGTGTGTAGCGACTGGGTGCCGCCGAGCACGCGCCAGCCC
       < R  A  A  K  E  T  P  L  A  I  A  E  D  F  S  N  T  H  L  S  Q  T  G  G  L  V  A  G  L  G
75332 TGGATCGCCACCCGGACCAGGTTCACCTCGGGCTGCTGGGCGGTGAGCTGCCCGTCTGGGTGTGGAAGCGCAGCATCATCGACTT
       < Q  I  A  V  R  V  L  N  V  E  P  Q  Q  A  T  L  Q  V  G  A  T  Q  T  H  F  R  L  M  M  S  K
75424 CGGGTTCTTCGCGCGATCTCGCCGAACTCGTCGCGCATCAGCCCAGATCCGCGGCCACGAACTTCGCAGACCTCCTCCAGCAGGTGGTCC
       < P  N  K  A  G  F  E  D  R  M  L  R  A  Q  I  R  R  A  A  R  F  K  A  V  E  E  L  L  T  T  R
75516 GGGCGACGAAGAAGAACGACAGCCGGGCGCGAAGTCGTCCACCGCGAGCTCGGGCCATGTGGTAGCCGGACATGTGTTCCACTTCGGCACCTCCGC
       < A  V  F  F  F  S  L  R  P  A  F  D  D  V  A  L  G  A  A  L  A  A  R  V  Y  E  V  G  N  A
75608 AGCGTGAACGGCGATCTCCTGCGCGACGGCGACGCCAGCGGAGCGGCCATGTGGTAGCCGGAGATGGTGTTCCACTTCGGCACCTCCGC
       < L  T  F  A  I  E  Q  A  P  S  A  G  A  E  A  M  H  Y  G  S  I  S  I  T  N  W  K  P  V  E  A
75700 CCGGCAGTAGGCGAACGTGTCGCCAGCAGCCGACCAGCGGCAGGGCTTCGGGGAAGATGTACGTGCCCGGGATGTACTCCTTGAGGATGT
       < R  C  Y  A  F  T  S  A  V  L  R  L  S  P  K  P  F  F  I  Y  T  G  R  A  I  Y  E  K  L  I  D
75792 CGTTCTGGATGGTCATGCCGAGGTGGAAACCTTGTCCAAGGGGATGCGTGGAACAGCGGACCCATGTCCTCGAGTGGACGCCGACCTT
       < N  Q  I  T  G  N  L  A  A  G  P  V  G  A  E  E  A  V  L  Q  Y  L  L  L  L  V  S  G  P  A
75884 TTGATCGTCATGCGAGGTGGAAACCTTGTCCAAGGGGATGCGTGGAGTCGTGAAGCAGATCAAAAGCACGGAGAGGCCCATGTGCCGGGC
       < N  I  T  M  S  T  S  V  K  D  L  P  I  G  H  F  L  L  R  M  D  E  I  S  D  I  A  V  G  V  K
75976 GCCGACCTCGCCGTGGGCGTAGCGGTGCTGCGAGTCGTGCCAGCAGTCGTGGGCAGATCAAAAGCACGGAGAGGCCCATGTGCCGGGC
       < G  V  E  G  H  A  I  P  D  D  S  D  Y  G  M  Q  T  P  L  D  F  A  V  S  L  G  M  T  G  A  R
76068 GCAGGAGCTGGTGGTAGCGGCTGGTGCTCCGCTTGCTCTCGCCGTCGAAGCTGCATCGTCCACGGACCCGCTCGGGAGGTGTACATGGTG
       < L  L  Q  H  Y  R  A  N  S  E  T  A  T  G  F  G  A  Y  Q  R  M  T  W  P  R  S  T  Y  M  T
76160 GAGTAGACCCCACGGGTGTACGGGAACTCCCGGCAGCCCTCGGGTAGGTAGACACCCTT
       < S  Y  V  G  R  T  Y  P  F  E  G  P  F  E  G  L  R  E  P  L  G  E  P  L  D  R  Q  T  Y  V  G  K
```

FIG.11A(66)

```
76252 GATCGGGAAGCCGGACTCGCTGACCGCGGTTCACTCATCCCCGGATGTAGGACGTGCCACCGCGCCGGAGGGTGAGGGATTGCACAT
      < I P F G S E S S R P E S M
76343 CGCACCCCTGTCTTTCCCGCGACTCCGAGGGTGAACACCTGGCTCGCTCCGATTAGTAAACGTTCCCGCGTCGGGTTTCGCA
76435 TCGGGCGTCGGAACCAGCAAGATAGAGGAGGTTGTGTCCAGCCCCTCGATTCTTCTGTGACTCAGATCCCGACGTGGA
76527 GCGGGCGGACCAGTCAGCCCCACGTGGCGGACACGTCGCCGTGCCACAGACACCCTGGCGTGCCGGTGTGACTCGCTCCGGTGGGCAATGGC
76619 GGCATGGGACGGTCTGGCGTGCCAGAGACACCCTGGCGTGCCGGTGTGCGGCGGTGAAGGAGGTCGTGCTTCCGCGCGGCCTCGCCCCGA
      > M G T V W R A T D T L L R R D V A V K E V L P P G L A P
76710 GCGACCGCGACGCCATGTACGAACGCCACGCCCGCGACGGCCCATCCAGCACCGGCTGGTCCAGGTGTACGACGTG
      > S D R D A M Y E R T L R E A R A A A I Q H P A V V Q V Y S V
76802 GTCACCGAGGGGTGGTCGCCCCTGGATCGTGCAATGGCCTGGCCTGCTGGACATGGTCGATCGAGGACGGGCCGGTGGCCCC
      > V T E G G R P W I V M E L L D A R S L A D M V I E D G P V A P
76894 CGGCGCGGTCGCCAAGATCGGCCATCGCCCTGCTCGGCGCGCTGGAAGGTGGCCACGCGATCGGGGTGCTGCACCGCGACGTGAAGCCGGCCA
      > R A V A K I G I A L L G A L E V A H A I G V L H R D V K P A
76986 ACGTGCTGATCTGCACCGACGGCCGCTGCGTGCTGACCGACTTCGGGGTGGCCAAGCTCCCCACCGACGTGCAGCTCACCACGCCGGGGATG
      > N V L I C T D G R C V L T D F G V A K L P T D V Q L T T P G M
77078 GTGCTCGGCTGCCGCCACTTCATCTCCCCGAGCGGGCCATGGGCCAGGAGTTCGGCCCGCCGAGCGACCTGTTCTCCCTGGCGTCACGCT
      > V L G S P H F I S P E R A M G Q E F G P P S D L F S L G V T L
77170 CTACACGGCGGTGGAGGGGCCGCCGTTCGACTTCGACAGGGGCGATCGAGACCATGCACGCCGTGGTGGAGGACCCGCCGGCCACGCCGC
      > Y T A V E G R P P F D F D R G D P I E T M H A V V E D P P A T P
77262 AGCGCAGCGGCCCGCTGACCCGGGTGCTGATGGGGCTGCTGGAGAAGGACCCGGCACGCCGCCGCCTGGACGTGCACACCGCGCGCATGCTC
      > Q R S G P L T R V L M G L L E K D P A R R L D V H T A R M L
77354 CGGGAGCTGCTGGCCGGGCCGCTGACCAGCACCGCGACCGCGGTGAACTCGGTCACCGACCCGTACGCGGTGGTGCCGGTCAAGCAGCGCCC
      > R E L L A G P L T S T A T A V N S V T D P Y A V V P V K Q R P
```

```
77446 GGCCGTCGCCCCACCGCCCTCCGCTGCGGAGCCGAAGCCGAGCGGGCAGATCGGCGGGCGGGGGCGGGGATGCTGCCCCGGGCGAGTCGCTGACCG
      > A V A P P P S A A E P K P S G Q I G G R A M L A P G E S L T
77538 ACCGGCTGGCGGCCCTGCGCCGCGGAGAAGAGGAAGAGACGCGGAAGAAGACGACGCGCTGGACGACACGGCGACGCGCTT
      >D R L A A L R R G E K T R K R K T T T A A L D D T S A D A L
77630 GCCGGGCCGCTGCACACCCCGGATGCCGGGGCATGCCCGGCCGCGCCCCCGGCCGGAACGGGTTCGTCGGAGGCCACCAGCGGGT
      > A G P L H T P G A M P A P P P A G R T Y G G S S E A T Q R V
77722 CGACGGGGACGGGACCGCGCCGGAGGCCACCCAGCGGATGACGTACGGCGGCAGCGCCCCGGACGCCCAGCAGGTGTCCCCACGGGAGCGGCCCGT
      > D A G T A P E A T Q R M T Y G S P P D A T Q R V S H G S G P
77814 CGGAGGCCACCCAGCGGGTGCCCTACGGCGGTGCCCTCGGCGGCTCGGCGGACGCCCAGCAGGTGCCCTTCGGTCGCCGCCCCGACGCCACGCAGCGG
      > S E A T Q R V P Y G G G S A D A T Q Q V P F G R R P D A T Q R
77906 GTCCCCTACGGCAGCCAGCCCGGTGCCGGCGCCACCCAGCAGGGCTTCGGCGACGCCGTGCCCGGCTTCGGCGCCTCGCCCGACGCCACCCAGCGGGTCGGCGGCGCCTACGG
      > V P Y G S Q P G A T Q P V P G F G A S P D A T Q R V G G A Y G
77998 CGGGCAGTGGTCGGTGCCCGGCACCGGCCAGCCGTGGGCCACGCCCGCCACCGCAGCTCCGGCCGTGCTGCTGCTGATCGGTGTCG
      > G G Q W S V P G T G Q P W A T P A T A P A P A V L L L I G V F
78090 GCCGGCCTCGTCGCCGACGACCCCGAGCAGCCGACCACCCCGCAAGGGCTGCCGCAGCTGCAGGGCCACCCCGACGCGTGTGGGCCACCCGGGCCAGGGTGGAGATGCA
      >G R L V A T V K G W P R K V Q L A A A G G V A V L L I G V F
78182 GCCCTCTTCGGGGACGACCCCGAGCAGCCGACCACCCCGCAAGGGCTGCCGCAGGGTCAGGGCCCCGGGCCAGGCGCGTGTGGGTGTCGACTACATCGATC
      > A L F G G D D P E Q P T T P Q G Q P S A G A P A G P G V E M Q
78274 GGAGCAGTGCCAAGGGCGTCACGGTGCAGGTCCAAGGTGCCCAAGGGCTGGGAGCGGCGGCACGTCGAGCGCTGGGCCGGAACCGCGAACGGCTGCGG
      > E Q S A K G V T V Q V P K G W E R R S A D G G V W V D Y I D
78366 CGGAGGACAACAGCCGGAAGGTGCGCATCCTCGCGGAGCGGTGGAGCGGCAGCACGTCGACCCGGTGGGCTGAGACTGCGGCCAACGGCTGCGG
      >P E D N S R K V R I L A E R W S G T S T R W A E T A A N G L R
78458 ACCCGGTCGGCCTTCCTGCCAGAAGCGTACAACAAACCAGGTGTCGATGACCGTGAGCAGGAGCTCGACGGCAAGGCGGCAGCCGAGTTCGAGTACAC
      >T R S A S C Q K P Y N Q V S M T E Q E L D G K A A A E F E Y T
```

FIG.11A(68)

```
78550 CTGCGGGCGACGGGCGAGGGCAAGCGGCACGGGCGTGTGGCGCGGGGTGGTGCACGAGGGCAAGGTCTACTCGTTCTACTCTCGACCGACG
      > C  G  D  G  E  G  K  R  H  G  V  W  R  G  V  V  H  E  G  K  V  Y  S  F  Y  L  S  S  T  D
78642 CCCGCTTCGCCGAGAGCAAGCCGATCTTCGACCAGATGGTGGCGTCGTTCAAGCTCCGGGGCGACTGAGCCGGGCCGGGGCCGGACGC
      > A  R  F  A  E  S  K  P  I  F  D  Q  M  V  A  S  F  K  L  R  G  S  D  .
78733 GACGCCGGCCGGGGCCGGGGCCGAGCGTGGTGGTGAGCGATGGCGGACACCACTGACCTGACGACACG
                                                > M  A  A  D  T  T  D  L  D  D  T
78824 CGCGATCTGGACGACCTTCGCGACCCCGGCCTCGACGACGACCCCGACGAGCTGGAGGCCGTGGTCGA
      > R  D  L  D  D  L  R  D  R  A  R  R  W  L  D  D  D  P  D  P  A  T  R  D  E  L  E  A  V  L  D
78916 CGGGCTGCCGGCGAGCGCGGCCGAGCTGGCCGACCGGTTCGCGGGCCCACTGACCTTCGGCACCGCCGGCCTCCGCGGCCCGCTGCGCGCCG
      > G  L  P  A  S  A  A  E  L  A  D  R  F  A  G  P  L  T  F  G  T  A  G  L  R  G  P  L  R  A
79008 GCCCCAACGGGATGAACCTCGCCGTCACCCAGGCCGCGGCTCGTCGCCAGGAGCGCACCGCCCAGGACGCCACCGGCCCGCTGGTC
      > G  P  N  G  M  N  L  A  V  V  T  Q  A  A  A  G  L  V  A  W  L  A  A  Q  D  A  T  G  P  L  V
79100 ATCGGGTACGACGCCCACCCCGTGCTGGCCGTACGCCAGCTGCAGCTCGGCCGTGCGACCAGCTGCCCCAGCCACACCCGCCCC
      > I  G  Y  D  A  R  H  G  S  R  E  F  A  E  R  T  A  Q  V  A  T  G  A  G  R  P  A  L  L  P
79192 CCGCCCGGCTGCCAACCCGTCTACCTCGTGGCGTGCTGGCGTACGCCGTGGCGCAGCTCGGCGCCCAGCTGGGCGCGCAGATCGTGCCGCCCGACACCGGCATC
      > R  P  L  P  T  P  V  L  A  Y  A  V  R  Q  L  D  A  A  A  G  V  M  V  T  A  S  H  N  P  P
79284 AGGACAACGGCTACAAGGTCTACCTCGGCGCCAGCTGGGCGCGCAGCTGGGCGAGCTGGGCGCGGGCGCGCAGATCGTGCCGCCCGACACCGGCATC
      > Q  D  N  G  Y  K  V  Y  L  G  A  Q  L  G  G  E  L  G  A  G  A  Q  I  V  P  P  A  D  T  G  I
79284 AGGACAACGGCTACAAGGTCTACCTCGGCGCCAGCTGGGCGCGCAGCTGGGCGAGCTGGGCGCGGGCGCGCAGATCGTGCCGCCCGACACCGGCATC
      > Q  D  N  G  Y  K  V  Y  L  G  A  Q  L  G  G  E  L  G  A  G  A  Q  I  V  P  P  A  D  T  G  I
79376 GAGGCCGCCATCCGGGCGGTCGGCCCGCTGGCCGACGTACCCGCTGGCCGGCGACGTCGTCGGCGACGTGGTCGTGTCGTACGT
      > E  A  A  I  R  A  V  G  P  L  A  D  V  P  L  G  P  A  G  Q  V  V  G  D  D  V  V  S  Y  V
79468 CGACCGGGCCGCGCCGCGGTGGTCGACCCGGGCCGGGCCCCGGCAGGCCCCCGAAGCTGGCCTACACGCCGCTGCACGGCGTGGGCGCGGCCGTGCTGA
      > D  R  A  A  A  V  V  D  P  A  G  P  R  S  L  K  V  A  Y  T  P  L  H  G  V  G  A  A  V  L
```

FIG.11A(69)

```
79560 CCGCCGCCTTCGCCGCCGGCTTCGGCATCCCCGGGGTTGTGCCCGAGCAGGCGGTGCCGGACCCGGACTTCCGGACCGTCAGCTTCCCC
     >T  A  A  F  A  R  A  G  F  G  I  P  G  V  V  P  E  Q  A  V  P  D  P  D  F  R  T  V  S  F  P
79652 AACCCGGAGGAGCCGGGGGCGGTGGACCTCCTCGTCGCGCTCGCCGAGCGCACCGGCGACCTGGCGATCGCCAACGACCCGGACGCGGA
     >N  P  E  E  P  G  A  V  D  L  L  V  A  L  A  E  R  T  G  A  D  L  A  I  A  N  D  P  D  A  D
79744 CCGCTGCGCGGTGGCCGTCCGCGACGGCCGGGCCGCGGGCCCGGCACCGGTGAGTGGGGGCGCCTGGCGGATGCTGCGGGGACGAGGTGG
     > R  C  A  V  R  D  G  R  A  A  G  P  A  P  V  S  G  G  A  W  R  M  L  R  G  D  E  V
79836 GGGCGCTGCTCGCCGACCATCTCATGCGCCGTGGCGTCACGGCCTGTGTCCTGTACGCCATGTGC
     >G  A  L  L  A  D  H  L  M  R  R  G  V  H  G  L  Y  A  T  T  I  V  S  S  L  R  A  M  C
79928 GCCGCCCGTGGCCTGCCGTACGACGAGACGCTGACCGGCTTCAAGTGGATCGTCCGGGCCGCGGCGGTGGGTGAGGCCGGCTCCGA
     >A  A  R  G  L  P  Y  D  E  T  L  T  G  F  K  W  I  V  R  A  G  G  P  L  G  E  A  G  S  D
80020 CCCGGCTGGTCTTCGGCTACGAGGAGGCGCTGGGCTACTGCGTCGCCCCGGAGCACGTCCGCGACAAGGACGGCATCACCGCGCTGACCG
     > P  L  V  F  G  Y  E  E  A  L  G  Y  C  V  A  P  E  H  V  R  D  K  D  G  I  T  A  A  L  T
80112 TCGCCGAGCTGGACGAGCTGGCCGCGGAATTCGGCGTGCACCACACCCCGGGCCGCACCCTGACCGACCGCCTGGACGAGCTGGCCGCGGAGTTCGGCGTGCACCACACC
     >V  A  E  L  A  A  G  L  K  A  Q  G  P  T  L  T  D  R  L  D  E  L  A  A  E  F  G  V  H  H  T
80204 GACCAACTCTCGGTGCGCGTGGACGATCTGCGGATCATCGCCGACGCGATGGCGCGCGTACGCGTGGTGATCCGCCCGTCGGGCA
     >D  Q  L  S  V  R  V  D  D  L  R  I  I  A  D  A  M  A  R  V  R  A  A  T  P  T  T  L  L  G  R
80296 CCCGGTGACCGAGGCGCGGGACCTGCTCCCCGAGGCGGACGTGGTGATCCTGCGGACCGATGGGGCCCGGGTGGTGATCCGCCCGTCGGGCA
     > P  V  T  E  A  R  D  L  L  P  E  A  D  V  V  I  L  R  T  D  G  A  R  V  V  I  R  P  S  G
80388 CCGAGCCGAAGCTCAAGGCGTACTTGGAGGTGGTGGAGCCGGTGGCGGACGGCGACGTGCCGGCGGCCCGCACGCGCGCCGCCGCGACGCTG
     >T  E  P  K  L  K  A  Y  L  E  V  V  E  P  V  A  D  G  D  V  P  A  A  R  T  R  A  A  A  T  L
80480 GCGGCACTCGACGAGGTGAACCCGGGCGCCCTGTTTGAGCGTGTACGGCCGAAGCCACTGGCAGTCGCCAGTGTCACATCGTCACGCGGGGCTTTCCCGTT
     >A  A  L  R  T  E  I  A  A  L  V  Q  G  .
80571 CAGGTTCGTGGTGATATGCGGCCAGTAAGCCCTGCCACTATCCATGTCGTAGAACATGATGCGTGCCACTTGGATGTAGTAG
80663 GTGACCAATGAGAGGTGAACCCGGGCGCCCTGTTTGAGCGTGTACGGCCGAAGCCACTGGCAGTCGCCAGTGTCACATCGTCACGCGGGGCTTTCCCGTT
```

FIG.11A(70)

```
80755  AGCGCTCGCGTAGCTCAGCGCAGGAGACATCCTCCCGCCATAGGATACAGCAGCTGGCTGCTGGTGTATCCCTTTCTCGAAGGGCTTTGCAG
80847  GTTCTGCGGCCAAGGGCGAGAGGTCCTGGGCCTCGTCTTGATCACGATCTCGTAGAGCGGACATCGGCCGTCTCGGTGTTGTACGCCAGG
80939  ATGACCGGCACCGGCCAAGGTGTTTGGGAGGGGTGACCGGAACTGAACCCGGTCCGGGCGCTCGTCGGCCGTGCCGGCTTTCCACCCTCGCCGT
81031  GGCGGGCCCGTCCGAGGAATAACTACGGAACCATCCAACATGCCGTCTCTGTTGTTGTACAGGAACAGCCACTGCCGCTTTCCACCGTCTTCGTTG
81123  TCACCTCGAAGGGCGTACGGCGCTGTTGCCGGTAAGGGCATCGTAGAGCATGGACATACCGCCTGTCGTTCTGCACGACGGAACGACGAGGT
81215  TCCACAACCTGCCACACGGGCTGTTGCCGGTAAGGGCATGGACATACCGCCTGTCGTTCTGCACGACGGAACGGCCGTGCCGT
81307  CCACCCCTTCCGAGCATTGGCTGTAGAACAGCACGGGCCACTGTAGTGCCGTCGAAATGCAGAGATATCGTCGGTGAACCCTGGTCCGAGTTGGACA
81399  CATTGCTGTTGTAGAGACATTCCGGAGTGACATGGGTTTACCCCGTCCTAGGGATCACTGCTTCTCAACAGATCATCAAGCGGTGTGCCAGGCTGCA
81491  TCATAGAGACATTCCGGAGTGACATGGGTTTACCCCGTCCTAGGGATCACTGCTTCTCAACAGATCATCAAGCGGTGTGCCAGGCTGCA
81583  CAATCGGGTGGAAGAAGAGCCAGCATGTCGTCGGGCGTGTCGAAGGTGCGGCTACCCCGGTCGCGAGCAGGGTGCCTCCGCGTCACGGGT
81675  AGCGTTCCGCGCATCTGTCGTCGGGCGTGTCGAAGGTGCGGCTACCCCGGTCGCGAGCAGGGTGCCTCCGCGTCACGGGT
81767  TCTGCCACGAGGCGCCGGCCAGGACCGGCGAACGCGGCACGCTCACCCCGCGTCTTCTTGCCGACGCAGCTGCTCACCCAGTCCCGACGAGCGCCGCTC
81859  CGGCGGCCCTCCGCGCCGGCGAACGCGGCACGCTCACCCCGCGTCTTCTTGCCGACGCAGCTGCTCACCCAGTCCCGACGAGCGCCCATATCAGCA
81951  CAGGCCCCACCATTACCCGGCACCAAATGGCTCGACCGTGCCGACCAAATGGCTCGACCGTGCCGACGCAGCTCGGCAGGCAGCTGCTCACCCAGTCCCGACGAGCGCCCATATCAGCA
82043  TGCACGGTGCGTGAAACAAATGGCTCGACCGTGCCGACGCAGCTCGGCAGGCAGCTGCTCACCCAGTCCCGACGAGCGCCCATATCAGCA

82134  TCGACGCGGGCCGGCCGGGCTGAGCTGCTGCTCGCGGCAGAAGCTCTGGCGGATCGAGCGGGGCTGACCTCGGCCAAGACACCGGACGTCCGG
       > V  P  R  R  Q  L  G  R  L  L  T  Q  L  R  E  S  A  H  I  S
82226  GTGCTCTGCGAGCTGTACCGGGCCGACCAGGCCGCCGTGCTGCTGGGCCTCGCCGAGGTGAGCCGGGCTGAGGTGAGCCGGGCTGTGGCACGC
       > I  D  A  A  A  G  E  L  D  C  S  R  Q  K  L  W  R  I  E  R  G  L  T  S  A  K  T  P  D  V  R
82318  CCACGGCAGCCAGTCCCGTGCCGCCTGGTTCTCGCTCTACGTCGGCCTGGAGAACGTCGGCAGCAGCATTCGGCACTACAACGCGGAGCTGGTGC
       > V  L  C  E  L  Y  R  A  T  P  D  Q  A  S  V  L  G  L  A  E  V  S  R  A  E  G  W  H  A
82410  CGGGGCTGTTGCAGACCCCGGCTACGCGGCCACCGCCCTCTTCGAGCACAACCCCGAGCTGGGCGAGGAGGAGAGGAAAGAAGGCGGTGGGC
       > H  G  S  S  V  P  A  W  F  S  L  Y  V  G  L  E  N  V  A  S  S  I  R  H  Y  N  A  E  L  V
       > P  G  L  L  Q  R  P  G  Y  A  T  A  L  F  E  H  N  R  P  E  L  G  E  E  E  R  K  K  A  V  G
```

FIG.11A(71)

```
82502 TTCCGGACTCAGGGCAGGGGCTGCTGGCCCGGCTGCGCCGGCGCCTGCCCCGGCCCCGAGCTGACCGTGATCCTCAGCGAGGCGGTGCTGCGCCGCCC
      >F  R  T  Q  R  Q  G  L  L  A  R  R  L  P  P  A  P  E  L  T  V  I  L  S  E  A  V  L  R  R  P
82594 GGTGCCGGGGCCGATCGGTGATGGCCGACCAGCTCCGGCACCTGCTGGCCGTCGGCGAACATCACGTACGGGTGCTGCCGCTGG
      >V  P  G  R  S  V  M  A  D  Q  L  R  H  L  L  A  V  G  E  R  H  N  Q  T  V  R  V  L  P  L
82686 CCGCCGGGCCCGCTGGCCGCCGAGGCCGGCACGTTCGTGCTGCTGGACTTCCCGCTCTCGGCGCTCGGCAGCCCGACCGAGCCGCCGACC
      >A  A  G  P  P  L  A  A  E  A  G  T  F  V  L  L  D  F  P  L  S  A  L  G  S  P  T  E  P  P  T
82778 GTCTACGTCGAGGGGCTCACCGGCGCGCTCTACCTGTACCTGGACCAGCCTGAGATCGCCGCGTACGAACGGGTCTGGAGGGGTCTGGATTCGCT
      >V  Y  V  E  G  L  T  G  A  L  Y  L  Y  L  D  Q  P  T  E  I  A  A  Y  E  R  V  W  R  G  L  D  S  L
82870 CGCCCTCGGCGCGCAGCAGAGCGCGGAGCTCATCGACGCGATCCGGGGAGAGTGCTATGAGTGATCGAGCCCGCTGGCGACCAG
      >A  L  G  A  R  Q  S  A  E  L  I  D  A  I  R  G  E  C  Y  E  *
82961 CACCCGCAGCGGCACCAGGGACTGCGTCGAGGTGGCCGACAACCTCACCGGCATCGTCGGCGTCCGGGACAGCAAGGACCCGGGCG
      >                                                                                              
      <  A  R  K  G  L  A  A  D  V  A  K  G  L  A  T
83053 GGCCGGCCCTGACGGTCGTCCGCGCCTTGTGTCCGCCTTCAAGGCCACCGCTGACACGCTGACAGTCTCGACACGAA
      <  V  V  L  A  V  S  P  R  V  V  S  D  D  L  S  V  T  G  S  F  G  A  G  A  I  E  E  L  R  R
83145 CCAACCCCGGCTACGCCTCAGACGCGCCCCACGCGCTGCCCAGGGCTGCCGAGACAGCAGCGCCGGCGCCTCAGACGTGCCTGCGCCTCAGAC
      <  R  A  D  V  A  A  D  G  T  L  G  L  A  P  E  M  R  L  V  A  V  L  T  A  L  A  A  T  A  E
83237 AGCCCGGGATCTGCCCGGCGAGGGCGCTGCGCCTCAGGGGCGTGCGCCCTGCCGAGGGCGGCGCCGCCTTGCCCAGGGCGGT
      <  D  P  I  Q  G  G  A  L  A  E  A  L  R  R  S  D  R  R  V  T  A  D  T  P  Y  R  H  V  H
83328 GACGACCAGGCCACCGAGGGCACCAGAGCGCCGGTCGTCCAGGTCGTCGTCGACGATCTCCTCAGCCGAC
      <  V  V  L  A  V  S  P  R  V  V  S  D  D  L  S  V  T  G  S  F  G  A  G  A  I  E  E  L  R  R
83420 GCCCGGGCCGTGCCGGCCGTGCTCGCCAGGCCCGAGCGTGGCCAGGGTGCCAGGCGGCCGTCGCCTCG
      <  R  A  D  V  A  A  D  G  T  L  G  L  A  P  E  M  R  L  V  A  V  L  T  A  L  A  A  T  A  E
83512 TCGGGGATCTGCCCGGCGAGGGCGCTGCGCCTCAGGGGCGTGCGCCCTGCCGAGGAGTCCTCCTCGACCAGGCGCCGGTAGCGGTGCACGTG
      <  D  P  I  Q  G  G  A  L  A  E  A  L  R  R  S  D  R  R  V  T  A  D  T  P  Y  R  H  V  H
83604 GATGAAGCCCAGTCTGGTCTCCTCAGCGTCCTCCTCGGTGAGGATCCGGCCGAGGATCCGGTCGCGGTGCCAGGCCGTGGGCGCAGCC
      <  I  F  G  L  E  T  E  E  V  D  R  V  V  G  R  A  V  L  D  G  L  I  R  D  R  L  G  H  R  L  R
```

FIG.11A(72)

```
83696  GCTGCACCCAGGAGGACGGGGTGTGCGGGCGTGTGCCCGGTGGGCGCGGGGTCC
       < Q V W S S P T H P T D A A M R G L V E D L I P E G T P A P D
83788  GTGACCACCAGGTTCCCATGCGACGTACGGCGACCCGGCGGAGGGCCAGCTCGATCAGGACGGCGGCCATCCCGAGGTCGAGGCTGAT
       < T V V L N G D V Y A V R G A L A L E I L V A A M G L D L S I
83880  CCGGGCATGGTCGCCTTGCCGGATTCGTCGTCGGAGGAGCAGCAATTCCTGGCAGGCAACACCAGTCATGGCGGGAGACGG
       < R P M
83970  TAGGCCTGAGCGCCACCCGTGCGCCCCAACTCGCCAGGAGCGCACTCGCCCGGTGAGAGGGGAACCCGTGAGGCGTTAACA
                < ·     F R P M G G F Q R D G A D G L G P V I F M R D
84062  GGGGGCCCTTCCTTGCGATCAGAAGCGGGGCATACCGCCGAACTGCCGGTCGCCGAGGCGGTCGCGGCACGATGAACATCCGGTCG
84153  TTGAGGCTCTCGTCGATCGCGGGCGGTGACGAGGCGGTCAGCCGGACTGCTCCAGCCGGGCGATGCCGGCGGCGAGCACGCA
       < N L S E D I A A T V L R L P L G S Q E L R A I G V P A A L V C
84245  GAGCACGGTGATGTCGGTGCAGCCCGCTCGGCCTGCAGCAGTGCTCCAGGAGCGGCCAGCATCCGGTCGAGGACCA
       < L V T I D T C G R E A L R C C H E L S G G T A L M P D L V L
84337  GCACGGGCAGGCGACTCGGGGAGCAGGCGAGGGCCAGGCGCGTCGGCCAGCGCGTCGGCCCGGCGCGGGGTTGGCCAGCCG
       < V P L G A L D R P L S E M Y A R P E Y T E E D R A L G V F G
84429  ATGGACGACTCGGGGAGCAGGCCAGGGCGCGTCGGCCATGCGAGAACCCGCCAGCAGCGGGTACCAGCAGCGAGGGCGAGCG
       < M S S E P L L A L A A D A M G L G A R L V P V L L P P N A L R
84521  GGTGCCCTCGGGCTGCGGCCTGGTCGACGGGCCCGGGTACTTCTGACGGGAAGGAGCGGGCGGCCTCGTACGAGCATGGTGGTGAGCT
       < T G E A D T V P T Q V P P Y K E V P F S R A A E Y V L M T T L E
84613  CGTGCAGGCGCGGCCCGGAAGTTGGAGGAGTCGGTGCGCGAGCTGGGCGAGCGACTGGGCGAGCGGATGGTCAATGACGTGT
       < H L A A R F N S S D T R A S R M
84705  AGTCCACGATCGCCCAACCTACGGAACGCCCGGGCCCCGAGAGACGCCGCTCACCCGGTGCGCAACCCTCGACGGT
84797  TGGCGTTCGAAGGTAGGGCCAGGTGCCCAAGGTCGCCCAAGGTCGCCCCAGATCACGAGGCGTGCGTGCGGGT
84889  CATGACGCGACAGCGACAGCGGGACGAGCGGCTTTGCGAACTTCCTGACGCCGCCG
       > M T A T S A R S D L S E L G R S E T A L R N F L H G L P
```

FIG.11A(73)

```
84980 GGCGTGGACCAGGTCGGCGCGGAGCAGCGGGCGGCCCAGCTTCGGCACCCGCTCGATCAAGACCACGGCCAAGGCCCGGGCGATCGACCTGGC
     > G  V  D  Q  V  G  A  E  Q  R  A  A  Q  L  G  T  R  S  I  K  T  T  A  K  A  R  A  I  S  L  A
85072 GATCCGGATGGTCGACCTGACCACCCTGGAGGGGCCGACACCCCCGGGCAAGGTGCGCTCGCGGCCAAAGCACTGCGCCCGACCCGG
     > I  R  M  V  D  L  T  T  L  E  G  A  D  T  P  G  K  V  R  A  L  A  A  K  A  L  R  P  D  P
85164 CCGACCCGTCCTGCCGCCACGTCGGCGCAGTCTGCTCTACCGCGGCGATGGTCCCGGCGGAGGTGCTGCGCGGATCGCGCGGGTCC
     > A  D  P  S  C  P  H  V  G  A  V  C  V  Y  P  A  M  V  P  Y  V  A  E  V  L  R  G  S  A  G  S
85256 GGGCGGCCGTCCGGCGGACCGGACGGCAACGCGCCGGCCCAGCCGTGGTGCACCTGGCCAGCGTGGCCACGCGTTCCGTCCGGGCA
     > G  R  P  S  G  G  P  D  G  N  A  P  A  G  P  G  V  V  H  L  A  S  V  A  T  A  F  P  S  G  Q
85348 GGCACCCCTGGAGGTCAAGCTCGACACCCGGGCCGCAGTGGCCGCGGTGGCCGCGGGAGATGACATGGTGATCAACCGGGGCGTTCC
     > G  R  P  S  G  G  P  D  G  N  A  P  A  G  P  G  V  V  H  L  A  S  V  A  T  A  F  P  S  G  Q
85440 TGGCCGGCCTACGCGGAGGTCTACGACGAGATCGTGGCCACCAAACAGGCGTGCGGGGACGCCCACCTCAAGGTGATCCTGGAAACCGGC
     > A  P  L  E  V  K  L  A  D  T  R  A  A  V  A  A  G  A  D  E  I  D  M  V  I  N  R  G  A  F
85532 GAGCTGGCCACGTACGACAACGTGCGCCGCGCCAGCTGGCTGGCCATGCTGGCCGGCGGCGACTTCATCAAGACCTGACGGGCAAGGTTCC
     > L  A  G  R  Y  R  E  V  Y  D  E  I  V  A  T  K  Q  A  C  G  D  A  H  L  K  V  I  L  E  T  G
85624 CGTCGGGCGACCCTCCCGGTGACGCTGATGCTGGAGGGCGGTGCCCGGCGACTTCCGCCACCGGGCGGCCAGGTCGGCGTGAAGCCGG
     > E  L  A  T  Y  D  N  V  R  R  A  S  W  L  A  M  L  A  G  G  D  F  I  K  T  S  T  G  K  V  P
85716 CCGGGCGGCCATCAAGAACACGCGATCAAGTACCTGGTTATGGTCAACGAGACGCGTCGGCCCGGACTGGCTGGCGACCCGGACTGGTTC
     > V  A  A  T  L  P  V  T  L  V  M  L  E  A  V  R  D  F  R  A  A  T  G  R  Q  V  G  V  K  P
85808 CGGTTCGGCGCGTCGTCAGCCTGCTCAACGACCTGCTCATGCAGCGCACCAAGCTCGGTGGACCTCAAGCCCTCGTACGGGCTGTTCGTCGACGG
     > A  G  G  I  K  N  T  K  D  A  I  K  Y  L  V  M  N  E  T  V  G  P  D  W  L  D  P  D  W  F
85900 GGGGCGGCCGGGGGGGCTTCAAGTCGGTCAACCCGGCCTCCGAGGAGGTGCTGGCCGAGATCGCCGAGGGCGGGCCAGCG
     > R  F  G  A  S  S  L  L  N  D  L  L  M  Q  R  T  K  L  T  T  G  V  Y  S  G  P  D  Y  F  T  L
85989 GGAGTTCGTCGACCCGGCCGATGGCGGCGGCTTCAAGTCGGTCAACCCGGCCTCCGAGGAGGTGCTGGCCGAGATCGCCGAGGGCGGCAGCG
     > E  F  V  D  P  A  D  G  G  G  F  K  S  V  N  P  A  S  E  E  V  L  A  E  I  A  E  A  G  S
```

FIG.11A(74)

```
86081 CCGACGTGGACCGGGCGGTCCGCGCCGCCCGGACGGCGTACGAGAAGGTGTGGGGCCCGATGCCGGGCCGGGACCGGGCCAAGTACCTGTTC
       >A  D  V  D  R  A  V  R  A  A  R  T  A  Y  E  K  V  W  G  P  M  P  G  R  D  R  A  K  Y  L  F
86173 CGGATCGCCCGGATCATCCAGGAGCGCTCCCGCGAGCTGGCCGTGCTGGAGTCCCTGGACAACGGCAAACCGATCCGGGAGTCCCGGGACGT
       >R  I  A  R  I  I  Q  E  R  S  R  E  L  A  V  L  E  S  L  D  N  G  K  P  I  R  E  S  R  D  V
86265 CGACCTGCCGCTGGTCGCGGCGCACTTCTTCTACGGGGCTTGGGCAGACAAGCTGCCGTACGCGGGCTTCGGCCCCAACCCCCGGCCGC
       >  D  P  L  V  A  A  H  F  F  Y  A  G  W  A  D  K  L  P  Y  A  G  F  G  P  N  P  R  P
86357 TCGGCGTGGCCGCGCAGGTCATCCCGTGGAACTTCCCGCTGCTCATGCTGGCCCAGAAGATCGCCCCGGCGCTGGCCGGCAACACGGTG
       >L  G  V  A  A  Q  V  I  P  Q  N  F  P  L  L  M  L  A  Q  K  I  A  P  A  L  A  A  G  N  T  V
86449 GTGCTCAAGCCGGCCGAGACCACCCCGCTGACCGCGCTGCTGTTCGCCGAGATCTGCCAGCAGGCCGAGGTCGCTGCTCGGTCAACAT
       >V  L  K  P  A  E  T  T  P  L  T  A  L  L  F  A  E  I  C  Q  Q  A  E  L  P  A  G  V  V  N  I
86541 CGTCACCGGCGCGGTCGGGACGGCCGGCGACCGGGCGCTGGTCGAGCACCCTGGAGTGGACAAGGTCGCGTTCACCGGCAGCACCGAGGTCGGCAAGG
       >V  T  G  A  G  D  T  G  R  A  L  V  E  H  P  G  V  D  K  V  A  F  T  G  S  T  E  V  G  K
86633 CCATCGCCCGGAGCGTCGCGGGCACGGGCAAGAAGGTCACCCTGGAGCTGGGCGGCAAGGCCGAACATCGTCTTCGACGACGCCCCGGTC
       >A  I  A  R  S  V  A  G  T  G  K  K  V  T  L  E  L  G  G  K  A  A  N  I  V  F  D  D  A  P  V
86725 GACCAGGCCGGTCGAGGGGATCGTCAACGGGATCTTCTTCAACCAGGGGCATGTCTGCTGCGCCGGGTCGGAGCTGCTGGTCCAGGAGTCGGT
       >D  Q  A  V  E  G  I  V  N  G  I  F  F  N  Q  G  H  V  C  C  A  G  S  E  L  L  V  Q  W  S  V
86817 CGCCGAGCAGGTCCTGGAGTCCCTGAAGCGCCGCATGGCCCTGTTGAACAAGAACACCGATATCGGGGCGATCA
       >A  E  Q  V  L  E  S  L  K  R  R  M  A  L  L  R  V  G  D  P  L  D  K  N  T  D  I  G  A  I
86909 ACTCGGCCGCCCAGCTGGCCCGCATCCGCGAGCTGTCCGCAGGGGTCACCCAGGGTCACGGCCACGCCCCGGAGAGCCCGTGCGAGCTGCCC
       >N  S  A  A  Q  L  A  R  I  R  E  L  S  A  A  G  E  A  E  G  A  E  R  W  S  P  P  C  E  L  P
87001 GAGCGCGGGTTCTGGTTCGCCCCGACGATCTTCACGGGGGTGACGGCCGTGCAGCACCGCATCGCCCGGGAGGAGATCTTCGGTCCGGTGCTGTC
       >E  R  G  F  W  F  A  P  T  I  F  T  G  V  T  Q  A  H  R  I  A  R  E  E  I  F  G  P  V  L  S
87093 CGTGCTGACCTTCCGCACCCCGGCCGAGGCCGTGGAGAAGGCCAACAACACGCCGTACGGGCTGTCGGGGATCTGGACCGACAAGGGCT
       >V  L  T  F  R  T  P  A  E  A  V  E  K  A  N  N  T  P  Y  G  L  S  A  G  I  W  T  D  K  G
```

FIG. 11A(75)

```
87185  CCCGGATCCTGTGGATGGCCGACCGGCTGCGCGACGTGGTGTGGGCCAACACGTTCAACAAGTTCGACCCGACCTCGCCGTTCGGCGGG
      >S  R  I  L  W  M  A  D  R  L  R  A  G  V  V  W  A  N  T  F  N  K  F  D  P  T  S  P  F  G  G
87277  TACAAGGAGTCGGGCTACGGTCGCGGCGAGGGCGGCCGGCACGGTCTGGAGGGGTACCTCGGTGTCTGAGCGGGGGTACGCAAGACGTAC
      >  Y  K  E  S  G  Y  G  R  E  G  G  R  H  G  L  E  G  Y  L  G  V  .        >  V  Q  S  A  N  V  S  L  A  S  R  K
87368  AAGCTCTTCATCGGCGGGAAGTTCCCGCAGCTCGGACGAGTCGGAGTGCTCGTATCTCGTGCAATCCGGAACGTGTCGCTGGCCTCCCGCAAG
87458  GACGCGCGGGACGCCGTGGTCGCCGAGACGCGCGTGGTCGCCCCCGTGAAGGGCTGGGCCGGGTACAACCGGGTTCAGATCCTCTACCGGGT
      >  D  A  R  D  A  V  V  A  A  R  A  A  V  K  G  W  A  G  A  T  A  Y  N  R  G  Q  I  L  Y  R  V
87550  CGCCGAGATGCTGGAGGGCCGTCGCGAGCAGTTCGTCGCGCTCGGCGTGCCGGCCGACGAGGTCGACGCGGCGATCGACCGCTGGGTCTGGT
      >  A  E  M  L  E  G  R  R  E  Q  F  V  A  L  G  V  P  A  D  E  V  D  A  A  I  D  R  W  V  W
87642  ACGCGGGCTGGTCCGACAAGCTCCCCCAGGTGTACGGCGGCGCCAACCCTGTCGCGGGCCCGTACTTCAACCTGTCCGCCCCGAGCGACG
      >  Y  A  G  W  S  D  K  L  P  Q  V  Y  G  G  A  N  P  V  A  G  P  Y  F  N  L  S  A  P  E  P  T
87734  GGGGTGGTCGCCGTGGTGGCCCCCGAGGCTGCCCTGCTCGGGCTGCTCGGTGAGCATCGTCGCCGAGGTGCTGGCCACCTGCGAGGGTGGTCAACGTGGT
      >  G  V  V  A  V  V  A  P  E  A  P  A  L  L  G  L  L  V  S  V  I  A  P  A  I  V  T  G  N  T  V  V
87826  GGTGCGCGGGCCTCGCCGACGTGACCGAGACCGTGCCCCAGCCGGTCAAGAGGTCGGACCTGCCGGGGGGTGTGGGGACGCGTCC
      >  V  A  A  S  P  T  Q  P  L  A  S  V  T  L  A  E  V  L  A  T  S  D  L  P  G  G  V  V  N  V
87918  TGACCGGTGCTGATCACCGAGACGGTGCCCACGCTCGCGGCACACCTCGACGTCAACATCGATTCCGGACGGTGCGCGACGCCGGCCTC
      >  L  T  G  A  I  T  E  T  V  P  T  L  A  A  H  L  D  V  N  A  I  D  L  T  G  V  G  F  A  S  L
88010  GCCACCGAGCTGGAGGTCAGGGCGGGAGCGGAGAACCTCAAGCGGGTCATCCGCCCCAAGGGCGTCTGAGCCGTACGACCACGACCCGGCCT
      >  A  T  E  L  E  V  R  A  A  E  N  L  K  R  V  I  R  P  A  P  A  D  H  D  W  Y  A  D  P  G  L
88102  CACCCGGATGACGACGCTGCTGGAGACGAAGACGGTCTGGCACCCCAAGGGCGTTGGGGTGAGGGGTAGGATTGCCGTGACTCGGTTGGGTGATCTTGAGC
      >  T  R  M  T  T  L  L  E  T  K  T  V  W  H  P  K  G  V  .
88193  CCGGCCGCCGGAGGCAGGGAGTGGGCGGCGGGGT
```

FIG. 11A(76)

```
88284  GGGCGGTGATGGACGTGCTGTGGGACACCGTCCCGGGCACGTCGGACGGGGTGCCGAGGTGCGCGAGGCCCTCGACGGCCGCGA
            > M  D  V  L  W  D  T  V  P  G  T  S  D  G  V  T  V  R  E  V  A  E  A  L  D  G  R  E
88375  GCTGGGCGTACACGACGGTGATGACCGTGCTGCTGGACCGGCTCGCCGGCAAGGGCATGGTGCGCCGGCAGCGGGAGGGCCGGGCCTACC
         > L  A  Y  T  T  V  M  T  V  L  D  R  L  A  G  K  G  M  V  R  R  Q  R  E  G  R  A  Q  R  Y
88467  AGGCCGCGGCCAGCCGCGAGGCGCACATCGCCCAGCTCATGCTCGACGCGCTGGACCTCGGCGGCAGCCGGGACGCGGCGCTGGTGCGCTTC
         > Q  A  A  A  S  R  E  A  H  I  A  Q  L  M  L  D  A  L  D  L  G  G  S  R  D  A  A  L  V  R  F
88559  GCCCGGTCGGTGACCGGCACCGAGGCGAGGTGCTGCGCGCCCTCGGCGCCGAGGCCGGGCCCGCTGACCGACCGCGTCGACGCGCC
         > A  R  S  V  T  G  T  E  A  E  V  L  R  A  A  L  G  A  E  A  G  G  P  L  T  D  R  V  D  A  P
88651  GCGGGCCGACCGGGCCGGGCAGCCCCTAGCCGACGAGGCCACCGACCGGTAGGGCCCCGTCATGGCGTACGTCCACTTCGCCG
         > R  A  D  R  A  G  Q  P  A  L  A  D  E  A  T  D  R  .        > M  A  Y  V  H  F  A
88741  CGACGGTCCTGGCCTGCTACCTGACCGCTCAGGTCCTGGCCGTCCACCTGAGCACGTGGACCGGATCGTCTGTCTGGCAG
         > A  T  V  L  A  C  Y  L  T  A  Q  V  L  A  A  S  T  W  R  A  P  R  I  A  I  V  C  W  Q
88833  GCCGGTCGGGCTGGCTCTCCGGGATGGGCCTGCCGATGGCGCTCGGCATGGGCCTGCCGATGGCGCTGGGCGTACGACCGGCAGCCGGTTGCT
         > A  V  G  L  A  L  G  L  S  A  M  G  L  P  M  A  L  G  V  A  A  Y  D  R  P  T  G  S  A  L  L
88925  CGCCCTGGCCCACCACGACCTGACCGACGGTGCCAGGCTGCAGGGACCGTCCAGGCACCTCGGTCTGGGGTTCGGCATCGGGGG
         > A  L  A  T  D  L  T  H  G  T  L  P  A  G  L  G  A  V  H  L  G  L  V  G  G  F  G  I  G
89017  CGGGCGGCTGCTCGCCGACGCGGTACAGCAGCGTCCAGGCGACCGTCCGGGCCCAGGCGACCGTGCGGGCGCAGCGCCAGCACCGGCGAGCAGCCTGCTGCGCCCGGGTGGTCAGCGC
         > A  A  L  L  A  T  T  V  R  S  V  Q  A  T  V  R  A  Q  R  Q  H  R  D  L  L  A  L  V  A  R  R
89109  GACCCGGAGGTGCCGGGGGCGCTGGTGCTGGACCATCCGAGCGCGGCGGCGTACTGCCTGCCCGGGGTGTGCCGCCCGGGTGGTCAGCGC
         > D  P  E  V  P  G  A  L  V  L  D  H  P  S  A  A  A  Y  C  L  P  G  V  R  P  R  V  V  S  A
89201  CGGGGCGCTCAGCATGCTCGACCGGGCCGAGCTGGCGGGTGCTGACCGACGAGCGCGCACACGCCCAGGAGCGCCACGACCTTGTCTGC
         > G  A  L  S  M  L  D  R  A  E  L  A  A  V  L  T  H  E  R  A  H  A  Q  E  R  H  D  L  V  L
89293  TGCCGTTCACCGCGCTGTGCCGTGCCCTGCCGTGGTTCCGTTGGGTACGCGACGCGCACGAGCGGGTCGCCCTGCTGGTCGAGATGCGCGCC
         > L  P  F  T  A  L  C  R  A  L  P  W  F  R  W  V  R  D  A  H  E  R  V  A  L  L  V  E  M  R  A
```

FIG. 11A(77)

```
89385 GACGACAAGGCCCGGGAGCTGCACGCCGAGGCTCCCCTGGCGGGGGCTGGCGGCCCTGGCGGGGGCGTTGCGCGCGGCCACCGGATCGCGCGGCGG
      > D  D  K  A  R  E  L  H  A  E  A  P  L  A  G  A  L  R  R  G  A  A  G  H  R  I  A  P  A  G

89477 CACCCTCGGCCTGGGCGACCTGGACGTCCAGCGGGTCCAGGTCCGGGTCCTGTCGCGCGTCAGCGGCTGCGCGACGGCCCCGCTGATCGGGGCGCGC
      > T  L  G  L  G  D  R  D  L  D  V  R  V  Q  R  L  L  V  A  D  R  P  P  R  L  I  G  A  A  A

89569 TGGCGGTGGCGGTCACCCTGGTCGCGCTGCCCGGTCTCCCCTTCCTGAGCTGACGACGTCCGGACACGTCCGACACGCGCGAC
      > L  A  V  T  L  V  A  L  P  V  S  L  F  L  S  .

89660 CGGACACGTCCGACCGGACGCCTCGCCGGAGTTGGGCCCGTGTCCCACGGGGCCCTCGCCTGCCCGTTGCCGGCCACCGACATGCGGG
                                                                   > M  D  Q  L  L  L  A  R

89752 GCGATAGGTAGAGAGACTACGTGTAGTCTTCCTACGACAAGGGAGCCTACTACCGGAGGGCGGCCATGGATCAACTGCTCCTCGCCCGTC
      > L  L  V  G  L  V  T  L  L  V  T  L  L  F  V  V  T  L  G  L  V  T  L  L  V  G  L  Q  T  A  W

89842 TCCAGTTCGCCACGACCACCTCGCTGCACTTCCTCTTCGTCGTCGTTCGGTCTCGGTCACCCTGCTCGTCGGGCTCCAGACGGCCTGG
      > L  Q  F  A  T  T  S  L  H  F  L  F  V  V  T  L  G  L  V  T  L  L  V  G  L  Q  T  A  W

89934 ACGATCACCGGCAATCCCGTCCACGAGCGGCTGACCCGGTTCTGGGGCTACGTCTACGTCTACTACGTGCTCGGCATCGCCACGGGCCT
      > T  I  T  G  N  P  V  H  E  R  L  T  R  F  W  G  Q  L  T  V  I  N  T  V  L  G  I  A  T  G  L

90026 GCTCATGGAGTTCCAGTTCGGGCTGAACTGGAGCGGCCTGTCGCGCTACGTCGTCGGCAACGTCTTCGGCGCCGATCGAGACCCTGG
      > L  M  E  F  Q  F  G  L  N  W  S  G  L  S  R  Y  V  V  G  N  V  F  G  A  P  L  A  I  R  T  L

90118 TCGGTTCTTCCTGGAGTCCACGTTCCTCGGGATGTGGATCTTCGGCTGGCACCGCCTGCGCCGCGGCGTGCACCTCGCGCTGCTGTGGGGC
      > V  A  F  F  L  E  S  T  F  L  G  M  W  I  F  G  W  H  R  L  R  R  G  V  H  L  A  L  L  W  G

90210 GTGGCGCTGACGCGTACGCCGGTCTTCGGCTACGGCGAACCCGGTTCGGCTGCAGAACCCGGTCATGAGGTGCGGCGACGGGGT
      > V  A  L  T  A  Y  A  S  A  F  W  V  M  V  A  N  A  W  L  Q  N  P  V  G  Y  E  V  R  D  G  V

90302 GGCCCACCTGACCGACTTCGGCGCGTTGCTGACCAACATCCCACCTTCGGCCTTGGCCTTCGGCCACGTGGTCGCCGCCCTGCTCACCGGCG
      > A  H  L  T  D  F  G  A  L  L  T  N  P  T  F  G  L  A  F  G  H  V  V  A  A  L  L  T  G

90394 GGATGCTGATGGCGGCCGGTCTCGATCAGCGCGTGAGCGCTGGCCTGGCACCGCGCTGTTCCGCACGTGGATCGGGATCGGCTGGTC
      > G  M  L  M  A  A  V  S  A  W  H  L  I  R  R  T  P  D  H  A  L  F  R  T  S  L  R  I  G  L  V

90486 ACCGGCGGCCGGTCTCGATCAGCCTGGTTGCAGGGCTTCGGCTTCGGCCCAGTTCGCGGCCAGACGCAGCCCACCAAGTTCGGCGGCGG
      > T  A  A  V  S  I  S  L  V  Q  G  F  F  G  F  A  Q  F  G  P  V  G  Q  T  Q  P  T  K  F  G  G
```

FIG.11A(78)

```
90578  CGGGCAGCGCGACGCCCTGGTCGCCGAATGGACCTCCCGGTTCGGGCCCGGAGACTACACCCCGCCGGTGCTGGCCGACGTCGGGCTCGGTT
       > A Q R D A L V A E W T S R F G P G D Y T P P V L A D V G L G
90670  TCATGATCCTGGGCCTCCTCTGTGGCCTGTGGCTGCTCCTCCCCCTGCTCTGGCGGGACTGGTTCATCCGGCTGCGCTTCCCGCTC
       > F M I L I G L L L G C L W L L L P L L W R D W F I R L R F P L
90762  TGGCTGATCCTGGCCCTGCCCTTCGTCGCCGTGATCCTCGGCTGGATCGCCCGGGAGGTGGGCCGCCAGCCGTGGGTCGCGTA
       > W L I L L A L P F V A V I L G W I A R E V G R Q P W V A Y
90854  CGGGCTGCTCTCCACCGAGCGGGCCGTCTCGCCGGTCGCCCCCGGGGTGATGCTCGCGTCGCTCATCGGCTTCACCCTGCTCCTGGGCGGC
       > G L L S T E R A V S P V A P G V M L A S L I G F T L L L G G
90946  TCGCCGTGGCCAACTGGGTGCTGTTCGCCCGGTACGCCGGGCTGAGGAGGCCCGTCGTGGAACTCGCTGTGGCTCTTCCTGCCGGCTACC
       > L A V A N W V L F A R Y A A R G A A D P A L G R R P G P A A D
91038  GAGTCCGCCCGGTCCCGTCCCTGGGCGTCGCCGGCGCCCTCGCTCGGCCCTCACCGCGGTGGGC
       > E S R P V P L G .      > V E L A W Y A L L G L F L A G Y
91127  TGGTCCTCGGCTACGACTACGGGCTCCTCGCCCGGGGCGGCCCTCGCTCGGCGGCCCTCACCGCGGTGGGC
       > L V L G G Y D Y G V G L L A R G G P P A R R A A L T A V G
91219  CCGTTCTTCCTGGCAACGAGGTCTGGCTGGTGGCCGTCACCGTCGGCATTCTGTTCGGCGCGTTCCCCACCCTGGAGGGGAACTGCTGTCCGG
       > P F F L G N E V W L V A T V G I L F G A F P T L E G E L L S G
91311  CTTCTACCCCGTCGTCGCCGCCGCCCTGGCCGGGGTGATCATGGTGACCGTGCAACTGCAGCCGCCGACGACGAGCCGACCC
       > F Y P V V A A A L A G V I M V T V G V Q L R S R P T D E P T
91403  GCGCCGCCTGGGACCGGATGGTGGCCGCGGGAGCCTCGCTGCTCGCCGCTGCTCCAGGGCGTACCG
       > R A A W D R M V A A G S L L A A F G W G A L L A G L L Q G V P
91495  CTGGCCGCCGACGGGCACGTCACGGGGCGTCGGCGATGAGCCCTGGTGGCGGT
       > L A A D G H V T G V G H V A T P F A A L A G L A M T A L V A V
91587  GCACGGTGCGACGTTCCTCACGCTCCGGCTGTCGCCGCCGACGCCGCTGGCTCG
       > H G A T F L T L R L S A A D A A P L A R T A R R L V A V A L
```

FIG. 11A(79)

```
91679 CCGCCGTCGCCCTGGCCGCCGTCGCGGGGCGCGCTCTCCGATCGGGTACGCGCCGACGCAGCGCCCGTGCCGGCCGTACTGCTGCCGTTG
     >A A V A L A A V A G A L S D R V R A A R Q R P L P A V L L P L
91771 GTACTGGTGGCGGCGCTGCTGGTCGCCCGGGCGGCGCACGCACCTGCCCGGGTTGGCCTTCGCCGCCACTTCGGCGGCGCTGGCGCT
     > V L V A A L L V A R A A H A R H L P G V A F A A T S A A L A L
91863 GCCGGTGGCGGGAGTCGGCGGCGCGTTGTGGCCCTACGCGCTGGTCTCCACCGCATCGCTGAGCGTGACGGACGCGGCGG
     > P V A G V G A A L W P Y A L V S T V A P T A S L S V T D A A
91955 CCAGCGGGCCGACGCTGACGGTGCTGGGCTGGCTCGCGCTACGCGTCCTCCAGGCTTCCAGGCGATGTGCTGGTGGTGTTC
     >A S G P T L T V L G W L A L P L L P A L L G F Q A M C W W V F
92047 CGGGACGAACCGACGGCAGGGCGCGGGCTCGTGGGGCTGCTGGTCGTGGGGCAGGCCACCGCTGGCCACGGTGCTGGCCGCCGCG
     > R G R T D G R A P V Y W .
92138 CGACCTCGCCGTGCTCGGCGGTCGCGGTGCTGGCGGTGGGGCAGGCCACCGCTGGCCACGGTGCTGGCCGCCGCG
     > V L A V L G G L T A L L V V G Q A T A L A T V L A A A
92229 CTCGACGGGCGGTTGGCCCGCCGGTTCCTGGCGGCCGTCGGCGGCCTTCGCGCTGCGCCGGGGCACGGTGGC
     > L D G R L A R P A L A G F L A A V V G R A L V A W A Q G T V A
92321 GGCGCGGGGCCGCGACGGTCAAGGCGCACCCTGCTGGCCGCGGTCGGACGCCGTCACTTCGCCGGTCGCCGGGCAGC
     > A R A A A T V K A A L R A D L L A A V G R H G P G W V A G Q
92413 GGGCCGGGCCAGCTGGCCACCCTGGCCCGTGGGCGGCTCGACGCCCTCGACGCCTACTTCACCGGGTACCTTCCGCAGCTCGTCAGCGTC
     > R A G Q L A T L A G R G L D A L D A Y F T G Y L P Q L V L S V
92505 ACCGTTCCCGGTCGCCGTGCTGCTGCCAGGGCTGCCCCGGATCACCTTCGCCGACTGGGGCTCCGGCGTCATCGTCCTGACCCTGCCGATCCCGGTCTT
     > T V P V A V L A R I T F A D W G S A V I V A L T L P L I P V F
92597 CGGGGCCTGCTCGGCTGCTGCAGGCGCGGTTCGGCGGGGATGGCCGGATGGCGGGAACGGGCCAGGTGGTCCGGCGGATGGCCGACGTCGTCAGGTCG
     > G A L L G W Q A Q A A T E R Q W R R L S T L G G H F L D M V
92689 CCGGCCTGCCACGCCTGCGGCCGTTCGGCCGCGAGGCGGCACGCGAAGCGGCCGGATGCGAACGGGCACCGGCGACGATG
     >A G L P R L R A F G R A R G Q V E V V R R M A D G H R A A T M
```

FIG. 11A(80)

```
92781 CGCACGCTGCGGATCGCGTTCCTGTCCGCGTTGGTGCTGGAGCTGGTTGCCGCCCTTGTCGCGGTTGGCGCTGTCGCGGTTGGGCATCCG
      >R T L R I A F L S A L V L E L V A T L S V A L V A V P V G I R
92873 GCTGCTCGGCGGGCTGGCGCTGTCCACGGCGCTGTTGCTGCTGCTCACCCCGGAGGCGTACTTGCCGCTGCGGGCGGCCGGCAGCC
      >L L G G L A L S T A L L V L L L T P E A Y L P L R A A G S
92965 GGTTCCACGCCAGCATGGAAGGGCTGGCCGCGCTGGACGAGGCGCTCACTCTGAGCGCTGCCGACCCGACGGCTACGGGCAGCGAC
      >R F H A S M E G L A A L D E A L T L S A A D P T A T A G S
93057 CGGCCCGTCCCCGACGGCGCGCGCGAGATCGGTGCTGAGGGCGTGACGGTGGCGTACGAGCGGACGGTCGCGCTGCGCGACGTGACGCTGAC
      >R P V P D G R A E I P F E G V T V A Y E R T V A L R D V T L T
93149 AATCCGGCCCGGCGAGCGCATCGCGATCGTCGGGCCCAGCGGCGCGGGCAAGAGCACCCTGCTCAACCTGCTGCTCGGCTTCGTCGCCCGA
      >I R P G E R I A I V G P S G A G K S T L L N L L G F V A P
93241 CGCAGGGCCGGGTCACCGTGGGTGGCGTCGACCTGGCCGGAGCCGACCCGGACGGCTGGCGCGTCAGGTCGCCGCAACGGGCC
      >T Q G R V T V G G V D L A G A D P D G W R R Q V A W P Q R A
93333 CACCTCTTCGCCGCTTCGCTGACCGACAACATCCGGCTCGGGGCCCCGGGCACGCCCGACGCGGCTCGCGGGCGCGCAGCGGGG
      >H L F A A S L T D N I R L G A P G T P D A A L A G A V A A A
93425 GCTGGACGAGGTGGTTGCTGCGGCCCTGCCGGACGGGCTCGACACCGTCCTCGGCGAGCGCGGCCACGGCCTGTCCAGCGGCCAGCGGCAGCGGG
      >L D E V V A A L P D G L D T V L G E R G H G L S S G Q R Q R
93517 TCGCCCCTGCGGCCGGTTCCTGCGGACACGGCCAGCGAGGCCGGGGTG
      >V A L A R A F L R D A P V V L L D E P T A R L D T A S E A G V
93609 CTGGCCGCCACCCGCCGCCTCGTCGCCGGCCGAACCGCCCTGTTGGTGGCCCACCGCCCGGCCCTGCTCTCCGACGCGGATCGCCTGCGG
      >L A A T R R L V A G R T A L L V A H R P A L L S D A D R I L R
93701 GGTCGAGGAAGGCCGGGTCACCGAGCTGACCACCACCCCGGCCACCGGGGTGACCCCGGGCCCGGGCGAGGCGGCCGCCGGGCCCGGCGGCC
      >V E E G R V T E L T T T P A T G V T P G P G E A A A G P A G
```

FIG.11A(81)

```
93793 AGGTCGCCCCCGGCCCCGGCCGGAGAGGGGCGGCCCGATGAGCACCGGTCCCGCCGACGACGCCTTCGCCATCCCGCTGCCGGCCGACGGG
      > Q  V  A  P  A  P  A  G  E  G  A  A  R  .
      >M  S  T  G  P  A  D  D  A  F  A  I  P  L  Q  A  D  G

93884 GCCCCGGTGGCCGGCGGCAGCGTCCGGGCCGAGCGCGTGCTCCGGCTGGCCCGGCCGTACCTGGGCCGTCTGGTCGGCGCGGGTCT
      > A  P  V  A  G  G  S  V  R  A  A  E  R  A  V  L  R  L  A  R  P  Y  L  G  R  L  V  G  A  G  L

93976 GCTCGCCGCCACCGAGTTCGCCGGGCTGGCCCTGATGGCCACCGCCACCTGGCTGCTGATGAGCGCCGCCGGTCGGCCACCACTGGACC
      > L  A  A  A  T  E  F  A  G  L  A  L  M  A  T  A  T  W  L  L  M  S  A  A  G  R  P  P  L  D

94068 GGCTCACCGTGGCGATCGTCGCGGTCCGGGCGCTGGCGATCAGCCGCGGCGTGTTCCGCTACACCGAGCGCCTCGCCGGCCACGATGCGTG
      > R  L  T  V  A  I  V  A  V  R  A  L  A  I  S  R  G  V  F  R  Y  T  E  R  L  A  G  H  D  A  V

94160 CTGCGGGATGATCACCGACGTCCGGGCCGGGGTCTTCGCCGCCCTGGCCGCGCGCCGCGACGCGGCCAGCGACCGGACCGGCGACGCGCTGAG
      > L  R  M  I  T  D  V  R  A  G  V  F  A  A  L  A  A  R  R  D  A  A  R  Q  R  T  G  D  A  L  S

94252 CCGGCTCGTGTCCGACGTGGAGGCCGTGCAGGACCTGCTGCTGCGGGTGCTGCCGGGGGCCGCGGCGACGGTGGTCAGCGTGCTGGCCG
      > R  L  V  S  D  V  E  A  V  Q  D  L  L  L  R  V  L  V  P  G  A  A  A  T  V  V  S  V  L  A

94344 TGGCGCGGGTCACCGCCACGCGCTCGCCCGCGCCGGGGTACGCGCTGGACGCCGCGATCGGGCGCCGGCGCCGGCTCGAACGACGCCTGGACCTT
      > V  A  G  A  T  T  I  S  L  P  A  A  G  V  A  L  G  L  L  V  A  G  V  A  L  P  L  A  A  T

94436 GCGCTGACCCGGCACGCCGCCGATCGGGTCGCGCCCCTGCGCGGCGCCCTGGCCCGCGACGCCGTGGACCTTGTCCACGGCGCCGACCT
      > A  L  T  R  H  A  A  D  R  V  A  P  L  R  G  A  L  A  R  D  A  V  D  L  V  H  G  A  A  D  L

94528 GGCCGCGTTCGGTGCCGCCGGGTACGCGCTGGACGCGGCCGCCGCCGATCGGGCCCGGGCCCGGCGCCTGGAACGACGGCTCGCCGCCACCG
      > A  A  F  G  A  T  G  Y  A  L  D  A  A  A  D  R  A  R  R  R  L  E  R  R  L  A  A  T

94620 GCTTCGCCGTGGACGCCGCCGGGGCCCTGGTCGGGGTGACCGGTGCCGGCACCGTGGTGGTCACCCTGCGCGACGGCGTCGGCGGGGTG
      > G  F  A  V  D  A  A  G  A  L  V  A  G  V  T  A  G  T  V  V  V  T  L  R  D  G  V  G  G  V

94712 CTGGTCGGGGTGCTGGCGGTCGGTTCCCTGGCCGCCGTCGAGGTGGCCCTGGCCGTGGGCGCCGCCAGCTCCGGGC
      > L  V  G  V  L  A  V  G  S  L  A  A  V  E  V  A  L  A  L  V  G  A  A  R  Q  R  T  R  L  F  A

94804 CGGGCTGGTCCGGGCGGTGGCCGCCCTGCTGACCGCCAGGCCCGCCGGACGCCGATCCGGCCGCCGCCGCCGTCG
      > G  L  V  R  V  A  A  L  L  T  A  P  Q  A  D  A  P  A  A  T  P  P  G  A  A  R  A  A  A  V
```

FIG. 11A(82)

```
94896 GTGCCGGCCCGACGACGTGCGCTTCGACGCGGTGCGCTACCGGGTGCGGTACCGGGCCGGCACCCTGGACCTG
      > G  A  G  P  H  D  V  R  G  D  A  V  T  V  R  Y  R  A  G  T  A  P  A  L  D  R  V  T  L  D  L
94988 CCGGCCGGCCGCCGCCGTGGTCGGGCCGAGCCCCTCGCCGTCCTCACCGGTGCGACCGGTGCAAGAGCACCCTCGCCGTCCTCACGGGCACCGTGCGACCCGAGCA
      > P  A  G  R  R  V  A  V  V  G  P  S  G  A  G  K  S  T  L  A  A  V  L  T  G  T  V  R  P  E  Q
95080 GGGCCGGGTCACCCTCGACGGGGCCGACCTGTCGGCGTACCCGGTCGAGGAACTGCCCCGGGCCGTGGGCGGCCTGCTCGCCGAGGGCTACG
      > G  R  V  T  L  D  G  A  D  L  S  A  Y  P  V  E  E  L  P  R  A  V  G  G  L  L  A  E  A  Y
95172 TCTTCCACGCCACGGTCCGGGAGAACCTGCTGCTCGGGCGCCCGGCCGCGGACGAGGCGGAGCTGACCGCCGACCGGCGGGCCGGCCTG
      > V  F  H  A  T  V  R  E  N  L  L  L  G  R  P  A  A  D  E  A  E  L  T  A  A  T  R  A  A  G  L
95264 CTGGACTGGGTGCACGCCCAGCCCGGCGGGTGGGACACCGTGGTCGGGGAGGAGGGCCAGCTCTCCGGCGGCCAGCGCCAGCGCCTCGC
      > L  D  W  V  H  A  Q  P  A  G  W  D  T  V  V  G  E  E  G  Q  L  S  G  G  Q  R  Q  R  L  A
95356 GCTGGCCCGGGCCGTGCTCGCGGGCGCTGCCGGACCCCGCGGGCCGGGGGCTGTCCGCGCCGTCCGACCCCGAGGGGCTCGACCGGTGCTCG
      > L  A  R  A  L  L  A  A  P  G  V  L  V  L  D  E  P  T  E  G  L  D  P  S  A  A  D  A  V  L
95448 CCTCGGCGCTGGCGCTGGCGACCCCGCGGGCCACTGGTTCAGCGGTCTCGCGCACCGGCTCAGCGGCCTCGCGGACCTCGACGAGATCGTGGTG
      > A  S  A  L  A  A  T  P  A  G  H  S  V  L  L  I  S  H  R  L  S  G  L  A  D  L  D  E  I  V  V
95540 CTCGACGCCGGCCGGGTCCAGCGTGGTCGGCCGTGGCCCGGCGGACAGGAGTTGGTCGCGCGACCAGTGGCGTGCTGCTCCAGGAGGC
      > L  D  A  G  R  V  V  Q  E  G  R  H  D  E  L  V  A  A  P  G  W  Y  R  D  Q  W  L  L  Q  E  A
95632 GGCCGAGCGCGGGTACCTGGCCCTGACGCCCCGCCCCTGAGCCGCTGGCAGTGCGTCGGCAGTCACCGCATGGCCAGGCT
      > A  E  R  G  Y  L  A  L  T  P  R  P  .
95723 CGTCGCATGGTGCGCTGCGACGACGTACTCGTGAAGGAGCGGCTGCGCGAGTTGAGCGACCGGCTGCACGGCCGCAAGGCCG
      > M  V  R  C  D  D  V  L  V  K  E  R  L  R  E  L  S  D  R  L  H  G  P  A  R  L  K  A
95814 ACCTGCTGGCCGAGGCCCGCCACGCCCTTGCAGGACGCCGTTGCAGGACGCCGTACGGCGTCGAGGCGTACCGGCGCGGAGGCCGAGGCCGGGCA
      > D  L  L  A  E  A  R  H  A  L  Q  D  A  V  E  A  Y  R  D  G  G  L  P  A  A  E  A  E  R  R  A
95906 GTGGCCGAGTTCGGCGAGCCGGCCCGCCTGGCGCCGGCCTACCAGGCCGAGCTGGCCGCGGGCAGCCTGCGCGGCCTGTCCCTGCGGGTGCT
      > V  A  E  F  G  E  P  A  R  L  A  P  A  Y  Q  A  E  L  A  A  G  S  L  R  G  L  S  L  R  V  L
```

FIG.11A(83)

```
95998 CGCGGTCGCGCGGCGTCCTGGTCGTCGCGGGCGATCTGACCTGGCAGGGTCGAGCTGGAGCGGCGGCCCCGGCGGCGGCCTACCGCC
      > A  V  A  G  V  L  V  V  A  G  D  L  T  W  Q  G  S  S  W  S  G  G  P  G  P  P  A  A  Y  R
96090 TGCTGTCCGCCTCGGTGGACGGCATCTGGGCGCGGTTGCTGTCGTCGGGGGCGGTTGCTGTCGCCGCTCGGCCCCGGTGGGCG
      >L  L  S  A  S  V  D  G  I  W  L  G  A  V  V  L  S  V  A  G  L  L  L  V  A  A  S  A  R  W  A
96182 CACCCGGCCCTGCCCCGGCTAGCCCTGACCGGTCTCGGGCTCACGGCCACGCTCGTCCTGGGCGTGGCGACCGGCGCCCTGTACGC
      >H  P  A  L  P  R  L  A  R  L  T  G  L  G  L  T  A  T  L  V  L  G  V  A  T  G  A  A  L  Y  A
96274 CTGGTCGATCGGGCTCTGGGAGGCGGCCCGCACCTGGCCCCGATGCTCGTCGGCGCGCTGGTCTGCGGCGCGGGGTTCTTCTGGATCGGTC
      > W  S  I  G  L  W  E  A  A  R  T  W  P  P  M  L  V  G  A  L  V  C  G  A  G  F  F  W  I  G
                                                                                          junction
marker
96366 GGGCGGCCCGGTCCTGCTGCTCTCGGCACGCCGGCCGGCCGGACCGGCCGTAGTCGGGTGGGCGCGGTCAGGCCGGCGTGGCGG
      >R  A  A  R  S  W  L  L  S  A  R  R  P  A  G  P  A  .           <- .  A  P  T  A  P
96457 GGGTGTCGCCGAGGAACTGCCGCTGAACTCCCGCCAGCCCCGTTCCCCGGAGGGCCCGGAGTCGGATCCGGAGCTGGCGCGGAGCCAGC
      < T  D  G  L  F  Q  G  V  T  A  S  F  E  R  W  G  A  R  E  G  A  L  A  R  R  G  S  D  T  L
96549 TCGTAGGTGCGGCAGATCGAGGCTGCCCTCGCTGCCGGGCCCTGGCCGTGCAGCCGTCAGCCGTTCCAGCACCGCGA
      < E  Y  T  R  R  E  R  G  N  V  T  S  W  S  S  V  V  H  G  A  R  E  L  R  R  L  A  P  Y  I  T
96641 CCCGGTAGGCGCGTCTGAGGGTGTCCGTGAGGCGCCTGGCCGTGTCGTGGCCTTCATAGGTAGCAAGACTACTTGTGGGCCACTCGGCGCCGCCACCGGGTGCGG
      < G  T  P  L  D  L  S  G  E  S  R  A  R  L  A  E  I  I  A  Y  G  H  L  A  G  R  E  L  V  A  L
96733 GCAGCAGCGCGTCGAGGTGCCGTGAGGTGAGGTATGTGCCAGAGTCACTCGGCGGGAGACAGCGGGTGGGCAGCCCGAAGCACAC
      < L  L  A  D  L  H  G  H  L  A  Q  A  K  M
96824 GCACCGGGCCTCCTAAGCCGCCCACTAGGGTATGTGCCAGAGTCACTCGGCGGGAGACAGCTGAGCTCGACGCCGCAGAGGTCGAAG
                                                             > V  G  S  P  K  H  T
96914 GGAGGTCAGGCGTGGCCCGACCGTGCCCAACGGCCAGTGCCCCCAACGGCCAGTGCCGCCGGCGGCCGCTGAGCTCGACGACCGACAGGAGCTCGACGACGAGAGGTGAAG
      > E  V  S  V  A  R  Q  S  P  Q  R  P  D  A  D  E  P  E  L  D  E  T  D  G  T  A  A  E  V  E
```

FIG. 11A(84)

```
97006 AGGACGGGCGCGCCCGTCGGCGAGGACGCGGACGCGCGCTCTGGGACGAGCTGCGCATCGACCCGGTCGAGATCGCCCTGCCCGCCGGC
      >E  D  G  A  R  P  S  A  Q  D  A  D  R  A  L  W  D  E  L  R  I  D  P  V  E  I  A  L  P  A  G
97098 ACCGGCTACACGCTGCGGGCGTACCGGCCGGCACGGGAGTTGACCCCGACCGACGTCGCCGAGCGCGACCAGGACGACCCGTTCCTGGCCCG
      >T  G  Y  T  L  R  A  Y  R  P  A  R  E  L  T  P  T  D  V  A  E  R  D  Q  D  D  P  F  L  A  R
97190 CCGGCAGGCGGTCGAGACGGACGAGGACGAGGACGAGGTCATCATCCTCGACGAGGAGGTCGCCGCGAGTTCGCCGAGGCGGACGCGGAGG
      >  R  Q  A  V  E  T  D  E  D  E  D  E  V  I  I  L  D  E  E  V  A  A  E  F  A  E  A  D  A  E
97282 AGGCCGGCGGGAAGTCCCGCTCCCGCAAGCCCCGCGCCGACTCCGACGACGCCGGGGCCAGGCTGCTGTTCAAGACGCCCGAATC
      >E  A  G  G  K  S  R  S  R  K  P  R  A  D  S  D  D  A  G  A  A  T  D  A  D  A  E  E  E
97374 CCGGACTCCGACGAGGACGAGGCGGGCGGCGACGAGGAGGTTCCGGTCTTCCTCAGCCACCGGGGCAGGCTGCTGTTCAAGACGCCCGAATC
      >P  D  S  D  E  D  E  A  G  D  E  E  V  P  V  F  L  S  H  R  G  R  L  L  F  K  T  P  E  S
97466 CCTCGTCAGCTTCGTCCGGTCCGGGGACACCTAGAGCACTGGAATGAACTGCGCGGGGTGGAGCACCTGCGGCACTCGGCGCTGCTGATC
      >  L  V  S  F  V  R  S  G  A  P  N  D  M  S  Q  L  D  S  W  N  E  L  S  E  R  V  E  P  A  D
97558 TGCGTCCCCGCTCGACGAGGACACCTACGAGCTCGACCTCGTCGAGAACCTGCGGGGTGGGCACACCTGGGACTCGGCGCTGCTGATC
      >I  V  P  L  D  E  D  T  Y  E  L  D  L  V  V  E  N  L  R  G  G  H  D  T  W  D  S  A  L  L  I
97650 GAGCCGGCGAGGTGGCCCGCGCCAACGGCCCAACGGCAAACGGCCACATGTCTCCGCCGGCTCCAGCCTGCCCGCGGCTCCGACGACCTG
      >E  P  A  R  W  P  G  T  S  R  M  P  C  V  C  P  P  C  W  T  C  S  P  P  A  P  A  S  T  T  W
97742 GACGAGGCGCTGCGCGGCGCTGCGCGCCAACGGCTCGTGGCGTCGTGGACTGCGTTCCTGGCCGCAGACGCGGCGAGTC
      >  T  R  R  C  A  P  R  P  T  A  G  S  G  A  S  S  A  A  G  G  .
97833 TCGGTTGGCGCACCATTGTCGCAAGATCTCTGGCAGAGCATCAGTCTCTGGCAGAGAAAG
                                                    BamHI
                                                    junction marker 97925 ACCAGTCCCGGAGGAGGACGACGCTGTGGCCTCGTGGGCGTCTGGCCGGCGATCCGGCGCGGATCCGGCCGACCGGCCTCGGCC
98017 GGTTCGGCGCTGACGTCGCTGTGGCGAGCAGGCTCGGCGTGCTGCTCCATGTGTCGCGAGATCGGCGACGCCAGCCGGCTACGCTCAGCT
98109 GGTCGTCGTACTCGTGGAGGCCCGAGCGGGCGGCGGGCGGCTCGGCGGCCCGACGACAGCGACGACCACCACCGGTCACCTCGCTGCTGAGTG
```

FIG.11A(85)

98201 CCGCCGGGCGTCCACTGGCGATCGCGGACGACGACTCGCGCCGAGCGGTTCGCCGAGACGACTCGCTGGAGGAGATGCA
                                                                          > M Q

98292 GTCCGCGCCGGAGCGGCGGGCGGTCGGGCTCGCGGCGCTCCAGGCGGCGCTCCAGGCGGGCGTCACCCTCCCCGGGATC
      > S A P A E R R A V G L A R A L Q A G A L S A V T L P A R D

98384 TCGCCGGGCTACAAGCAGGTCCTCTCGGCGCACGCGGCCCTCGCCAGCGGCCGCCACTCGGCCGCGGTGCTGCGCGAG
      > L A G Y K Q V L S A H A A L A S G R H S A A V A L R E V L R E

98476 CTCTACCCGGCTGCCCTGCGCGCCTACCCGGACCCGGCCGAGCCGGTGTTGGACGCCCTGCCCGAGCCCGGGATGCTGGG
      > L Y P A A L R A Y P D P A E P V A L V L D A L P E P G M L G

98568 CGGGACGATCGCCCGGGGCCGGGAGGTGTCGTCGGCCGCCGACGCCATCGCCGAGACCCCCCGGCGCGCGGCGGTGTCG
      > G T I A R G R E V S V A A D A I A A H L A A D G V A D E G K

98660 TCAACGATGCGGTGACCGCGCTGCGCGTGGCCATCGCCGAGACCCCCCGGCGCGCGGCGGTCAGCCGCGCTCACCTCCG
      > I N D A V T A L R V A I A E T P R R A A V S R A L T S A V A E

98752 ACGGTCCGTCAGGCGGTGGCCTCGGTGCGCTGCGACGCGGCCCTGCTGCGCTCGCTCGACGCGCGGGTCACCACCCCCAG
      > T V R Q A V A S V R A C D A G C E A L V G A L D A R V T T P T

98844 CCCGGTCCCCCGGCGCGCCGCCGCCCGAGGCGAGCCCGTCGAGTTGCCCGGCGCTGCGCGCTCTGCGCCCACTGGGCCCTC
      > P P G R R A A A R G E P V A E L P G A G L R A L R P T E

98936 CCGGAGCCGGTCCCCGGCCGCCGGTCCCGCGAGCCCGAGCCCGTCCCGGCAGCCGGTCCCGCTGGCCCGCCGCGGTC
      > P E P V P G R R S R P E P V P G G S L P A Q P R P L G P P P V

99028 GCGCCGGAGCCGGTCGCCCCGCCGCCGGTGGCCCCGCGGCCGATCACCCCCGGCCGCCTCGGCGTCTCCGGGCCGTCGCC
      > A P E P V A P P P V A P R P I T P A A S A T P P V S G P P S P

99120 CGAGCCGGCCGCCTGATCGACAACCCGGCCAACCGGCCACCGGGATCACCCGGATCCCGAGCC
      > E P R R L I D N P A N R P V S A P P P P P G I T P I A P S

99212 AGCGCGAGCGCGGGGTCGTGCCGCCGGCCGAGGCCGGTTCCGGCCCACGCTGACCACCGCCGCCATCCAGAACGCGCGGGAG
      > Q R E R G S V P P A E A G E P F R P T L T T A A I Q N A R A E

FIG. 11A(86)

```
 99304 CGGCAGGCGCACCATCATCCCGCCTCTGCCCCCAAGAGACGGGCGAGTCCGCGCCCCACCGGGCGGCTTCAGCGCCACCGACCTGAGCGT
      >R  Q  R  T  I  I  P  P  R  P  K  T  T  G  E  S  A  P  P  P  T  G  G  F  S  A  T  D  L  S  V
 99396 CCCGGTGCCGACCCCGCTCCCGGCCAGGAGTCCGCTCCCCCCGGCTCCGGGGCGAACTGGCCGCTGGTCAACAACCCGGAGGACCCGGCCG
      > P  V  P  T  P  R  P  G  Q  E  S  A  P  P  G  S  R  A  N  W  P  L  V  N  N  P  E  D  P  A
 99488 ACAGCTCCCCGAACAATCCGGTGGCGCGCCGGCCCCTTGGAGGATCGGGAAGCGCAGATCGACGCCGACCCAGTGGTCCCGCCGGCC
      >D  S  S  P  N  N  P  V  A  R  R  P  L  E  D  R  A  K  R  Q  I  D  A  P  T  Q  V  V  P  P  A
 99580 GAGGGCCGGGTCACCCCGCCCTGGCTCGCCGACCTGCCCCAGGAGCCACCGATGCTGCGGCTGGTCGAGCCGCCGCTGGCCGACCG
      >E  G  R  V  T  P  P  W  L  A  D  D  L  P  Q  R  P  P  M  L  R  L  V  E  P  P  L  A  D  R
 99672 GGCACTGCGGGATGGGCCGGGCCAGGCTGCCGCCGACCCGCGCCTGGAGCCGCCGCTGCGGCTGGTCGACCGCGGCGAGGCAGCCGCCG
      > A  L  R  D  G  P  G  Q  A  A  D  P  R  L  E  P  P  L  R  L  V  D  R  G  E  A  A  R  A
 99764 GCCGTCCCGCCGGAGCCCCGAGCCGTCGCAGCGCCCTTGGTTCGCGTCCCGCTGGGTCAGCGGGTCCCGCTTGGAGGAGCGGCCCGAC
      >G  R  P  A  P  E  P  R  P  E  R  A  P  A  E  H  R  S  P  L  G  Q  R  V  P  L  E  E  R  P  D
 99856 ATGGAACATCGGACCGCGCCGCCCCAGCCGTCGCGGTCCGCGCCGATGGAGCGGCGTACCCCGCCGATCTCCGACGAGGGGACGGCGACCT
      >M  E  H  R  T  A  P  P  Q  P  S  R  S  A  P  M  E  R  R  T  P  P  I  S  D  E  G  D  G  D  L
 99948 GCTGATCTTCGCCGCCGCCAAGTCGGCCTGGTTCGTCGGGCACGGCGATCCGAGATGGACTGGTCGAGCACTGGCCGGGTGGC
      > L  I  F  A  A  A  K  S  A  W  F  V  G  H  G  D  E  S  E  M  D  W  S  S  T  A  S  T  G  W
100040 AGGCCGCGAGCAGGCCGCGGCCCGGCCGGTGGGGCGCCGATACCAAGGCCGGTTGCCAAGCGGTTGCCGCAGGCCAACCTGGTTCCGGGC
      >Q  A  A  E  Q  A  A  R  P  A  V  G  A  D  T  K  A  G  L  P  K  R  V  P  Q  A  N  L  V  P  G
100132 TCCCCCCTGCCCGAGGAGCGTCCCCTACGGATAGTCCGCGACGCCGCGAGAACACGACCGGCTACTTCCGGGGCTGGCGTCG
      > S  P  L  R  E  E  R  P  L  R  I  V  R  D  A  A  S  L  A  E  N  T  T  G  Y  F  R  G  W  R  R
100224 CGGGCAGGAGAGATCGGCGGGTTCGCGGTCGGCGGGCGTCCGGGCCGGGGCGAGGCGGCTGGGACTTCACCCGGGACACCGGCGACCGAG
      > G  Q  E  I  G  G  F  A  V  G  G  R  P  G  R  E  A  A  G  G  W  D  F  T  R  D  T  G  D  R
100316 ACGACGACCGGGAGTACGAGTACCGGTCCGCGGTCCTGACCATCGCGCTCCTGGCGGGTGGCGGCACCGAAGAGCAACCGGTGGGACCCCG
      >D  D  D  R  E  Y  E  Y  R  S  A  G  Y  R  S  .
100407 CCGTGCTGGCGTACGGCCGTAGCAACCCGACGCCCACCCGACGCTGGGACCGGTGGGACCGGTGGGCGGCCGCCTGACGTC
```

FIG.11A(87)

```
100499  CCGCAGGGACGGTGACGGCTACTGGCCGTCCCCCGGGAAGGTTGCGAGGCGGTCGGGGCGCACAGGCGCTGTCAGGCCGCTCCTGAGCCG
100591  CCCTACGGAATGGGCTAGCCCTACGAATCGAGCGCCGCCGGTGCCGTCGAGTTGCCTCCAGCCGGTCCCCAAACAGCCGGAC
100683  GCGCCCGACGGCCCGGGTGCCGGGGTGCCGTCGGGCGCGTCGTCCCGTCGATCAGCCGGCCGGCGACCGCGAGCGCGCATCGTGAGCA
                    < .   A  P  A  V  A  R  S  R  R  M  T  L  V
100774  CGTACTCGACCAGCGAGATCAGCACGTGCTTCGTCGACTCCCGGTTCCGGCAGCCGTCCACCGCCACCAGGCCAGTGGAGAGATCGCGAGC
           < Y  E  V  L  S  I  L  V  H  K  T  S  E  R  N  R  A  D  C  A  V  V  P  V  D  H  S  I  A  L
100866  GCGTCCCGGACGTTCCTGCGGGTCGTGGTTGCGATCGCATCCCGTCGAAGCAGTTGATGGCCACCAGGTACGGCCGATGCTCGAAGAAGTC
          < A  D  R  V  D  Q  P  D  H  Y  Q  M  G  D  F  C  N  I  A  V  L  Y  P  L  R  R  H  E  F  F  D
100958  GATGGCCGGAAGCAGTCGGCGGACGTGTGCAGGAGGACACGGGTCCTGACGATCAGGTTCCCGGTCGATCGAGATACGGCCGAAGTTCCACCGTGGTCGTC
          < I  A  A  F  C  D  A  L  R  R  T  D  V  L  V  V  A  G  I  A  G  R  C  L  E  D  W  M  F  W  F
101050  ACCGGGTCTGGCCCCCACTCCTGCGGGAGTCGGAAGTCCATCGCGAAGTTCATCGAGATCGCCTCAGGCGTGATCTCCGAGACCGAGCC
          < R  T  Q  G  P  T  G  F  L  Y  L  I  L  D  R  D  I  S  I  R  G  F  D  M  A  V  T  T  T
101142  TCGCCCCGAAGTCTGCCGGGTCACCGACGATGACGTTGCCGACACCAGCGACCTCGGGACAGGCGGGGTGCGACA
           < E  G  P  V  Q  R  T  D  D  V  G  V  G  A  S  T  M  I  A  E  T  T  L  P  T  I  E  S  V  S  G
101234  GACCAGCGGTCGTCTTGCCGAAGTCCACTCAGCACCCTCTCCAGCGATAACGATCTTCGCCAGGCAGTCAGTTCGGAAGTCGTCAGGATGGTCGGCGTGGA
          < V  L  T  T  K  G  V  G  F  G  G  A  I  V  I  K  A  S  T  V  R  G  S  P  V  P  P  R  H  S  M
101326  TGTCAGAGGCTGCGAAGTCCACTCCAGCACCCTCAGGCCGGCTCCGAGGCATGTCCACCTCGGAGGCGGCCACCGCACGCGCGCACGTCGT
           < <  .   L  R  R  L  G  S  L  V  R  E  L  L  E  T  G  V  A  D  D  S  D  D  L  I  T  P  E  H  V
101417  CTGCGACCAGGCCGCTCGACACGCGGTCCGTCGGCGATGAGCACCTAGCACGCCGAGCGAGCTGCATCCGCGGATCTCGGCAAGCGAC
          < A  V  L  G  D  T  A  M  D  A  I  L  V  R  A  V  G  L  P  L  Q  M  R  A  A  I  E  A  L  S
101509  TGCACGCGTCCGTCGCACAGCCGGCCTCGTCGCCATGTCGGCGATGTACTGGTGCTCTGCCACCGTTGCTACTGGCCAGCGCCCGACCGCCACCGTCGT
          < Q  V  R  G  D  C  L  A  A  I  Y  Q  H  E  R  G  Q  G  G  N  S  S  A  A  R  G  R  V  T  T
101601  CTGACGAGCGCCTCCAACGCGATGTCCAGCCGGACGCGGGTCGACCGGTACGGACGGGCGTACGACGGACCAACGCCGCCAGTCGGCTCGT
          < E  V  L  A  E  L  A  I  D  L  R  P  R  T  R  G  R  T  V  A  Y  P  R  V  L  A  G  T  P  E  D
```

FIG.11A(88)

```
101693 CACGGATCCATGTCGCCGCTCACCTCCTTCGTCCCCGACACCGGCTGAACCCGGTCGTTCTTGTCCTTGCCACCCCGCCGAC
       < R  D  M  D  G  S  V  E  K  T  G  S  V
101784 CCATCGGCCAGCCGCGTGGGTCAGCCCCACAGTCGTACGCGGCTGCCGGGGTCAACGCGTCGCCACCCGGTCGACCAGGAGGC
       <.  G  M  M  G  V  T  T  R  P  Q  P  T  L  A  D  G  V  R  D  V  L  L  A
101875 CATCTCGTATCCGACTCGCGCCCGACGTCTGCAGCAGCACGGTCTGCGGCGGCAGCCGCACCGCGAAGGACAGCCCCTGCGCTCGAAGCAGCTGCCCTCGAGAAGATGGACATCAGGAACAGGAAGC
       <M  E  Y  G  V  Q  G  V  D  C  S  R  A  A  L  V  A  F  S  S  G  D  S  I  S  M  L  F  L  F  G
101967 CGTTGTCCATCTCGACCACGGTCGGCCTGTCACGCGGGTCCGGTCCCTGCGCTGACGGCTGAGGCTGAACGCGGACCCGCTGAGGCTGACAGCCTGACGGCTGCGACACC
       < N  D  M  E  V  V  T  Q  L  V  A  G  G  E  F  C  R  A  A  G  Q  T  L  S  V  L  G  S  A  I
102059 GCGGCGAGCTGGTCGGCCACCGTCGGCGAAGTTGGCCAGCAGCCAACGAGATCCTGCGTAGTTGTCATCCTTGTTGCTCCTTCTGCCGCTCCTCCGGCCACCG
       <A  A  L  Q  D  A  R  D  R  P  L  D  R  S  S  A  L  L  G  D  A  S  V  A  H  A  V  G
102151 GGGCACCCGGTCGGCGAAGTTGGCCAGCAGCCAACGAGATCCTGCGTAGTTGTCATCCTTGTTGCTCCTTCTGCCGCTCCTCCGGCCACCG
       < P V                         < G Q Q E K Q G S G A V P
102242 GGCCTGAGCCAGACTGCGAGGATTGCTGCCCACCGGAGCTGCCTCCGGGTTGGTTGCCGTCGGGCTCGGTACGCCCACGCTGCACG
       V  G  S  G  S  Q  S  S  Q  Q  G  G  P  A  A  E  E  P  N  T  P  N  G  D  P  E  T  R  G  R  Q  V
102334 CCTCGATGGTATGCCAGGACAGAGCAGCGGCGGACAGCGCTGGACGTGGTGGGCTTCTCCACCCCGCGCCAGGCACGAG
       < G  R  H  Y  A  S  L  L  G  R  V  G  E  P  T  R  R  Q  V  S  T  T  P  K  E  V  G  G  P  V  L
102426 TTGGGCACCCCGCAGGCCTTCGGCGCCTTGCGCGGTGGTCTCGCCGGGACCTCGGTGGCCGCGAGGCCGCCAGCGTCGT
       < Q  A  M  P  V  R  K  P  L  G  K  R  T  T  E  A  V  P  V  E  T  A  A  S  A  A  R  W  S  P  P
102518 CCGCGGCCAGTCTGCCAGGCGTCTGCCGGCCATTCCTCCCGGCCATCTGCTGCCGGTGTCTGCGGGTCTCCCGGGTGCTGGTCTGGACGGGCCG
       V  A  A  T  Q  W  A  H  A  Q  P  T  P  R  R  G  A  F  G  E  A  P  G  P  R  T  G  G  N  T  P
102610 GACCCGTTGTCGCGGAACCGTCGACGTCGACGGAGAACATTCCTCCCGGCCATTGTTGGGTCTTGCGCTGTCGTCCCGGGTTGCTGGTGTCGCGACGGCCG
       < S G N  D  R  P  M  G  G  A  M  P  R  D  A  M  P  A  N  G  T  T  G  P  A  P  T  Q  V  P  R
102702 GCCGGTGACGTCGACGTCGCGCCAGAACTGTTGGGTCACGGGCCGTTCGCCGGGCTTCGTCGGCCATTGGTCGTCGTCGCGACTGCCGG
       < G  T  V  D  V  A  S  F  Q  Q  T  V  A  A  N  A  P  S  G  A  G  N  T  A  R  Q  A  V  G  A  T
```

FIG. 11A(89)

102794 TCTCCTCCGAACCCGAGCGGGTACGGAGCCGACTCGAGCTCCGAAGATCGGCAGCTCCATCGTCTCCGTACCGCTGC
       < E E S G S R R T R G W A S E L E R G I P L E M T E D A Y R Q
102886 TGCCGGTTCTGGGCTTCTGCACGGGCTGCGACGGCGTCGTCGGCGTGCGGTGCTGCGGCGTCGGTGCTCGG
       <Q R N Q A Q V P T S R A P T P T T P Q T A P T S P V E T S P
102978 CACCCGGGGCAGCTCCGTGGTCATGTCCAGGGCTGCGCCGAGGGCCTCCGGCGCGGTGACCGCGGCCACGCGGCGCC
       < V R P L E T T M D L A A A L R E P V P P T V P E P A A V P P W
103070 AGGCCGGCGGCGGCCACGGGCCTGCCGGCACCGGCCGTGGCCAGCCGACTGGGCGAGTACGGCTGACCGGGAAACCGG
       < A P P A V P A Q A D P V P R S P L P Q A S Y P Q G S V P T G
103162 AACGGCTGACCGGAGACACCGGCGGCACCGGAACGGCTGCCGAACGGGGTGCCGGCAGCTGTCGGGGATGGCCGGCTGCT
       <F P Q G S V P T G F P Q G S V P P V S V P P V S V P F V S V P
103254 CGGTGCGGACACCGGCGGCACCGGAGACACCGGCGGCACCGGAGACCGGGTGCCGGCAGCTGTCGGGGATGGCCGGCTGCT
       < P A S V P P V S V P P P T W G R A E P S S P L Q R P I A P Q Q
103346 GGCCGCTGCTGGCCGGATCGCCGGATCGCCGGATCGGCGGAAA
       < G S S A P D G D G S A R R Q P L P D S S Q G N S T R G A A A
103438 CCGGCCAGGCTGCCACTGGCCGTCAGGTCGAACCAGGCCGGGTTACCTGGTTGCCCGGGTGCCGGTGTGCTGGCCGTGTGCG
       < G D A T G S A G T L D S W A P M S R M S G T S A P T G H G N R
103530 CGAGGCCCGGGTCGAACGCACCCAGGGGTGCAGGTGCAGGTGCAGGGTCCCGGGCGGAGGCGGCCAGGCGCGGGCTGC
       < S A P D G D R G G L T V Q N G S H G P R Q T P A P T A P N N G
103622 CGAAGGCCGCGGGAAGGCCGCACCACCCAGGAGGGCCAGGCCGGGCCGGGCCGTGGCCAGCCGTGGCCAGCTC
       < F A A F A G L A P P A G G P Q S S T L S A P P A P L A G P Q
103714 TGGAACCGGCTGCCGGGACGCCTGCGTCACGACCCCGAGGGCGGCCAGGCCAGCTC
       <Q F R G S L A R P V L V T T P L T V D A V T G R D T G P R L E
103806 GACCTTGACCCGCTGCCGGGACGCCAACGGCGACCACGTCCACCTGCGGCGGAGGCGA
       < V K V G H R S A L R A V V V L G M M R S V A V D V Q P P S A L

FIG.11A(90)

```
103898 GGCGGTGTCGTTGAGGTCGTGTAGCTGCTCGGGCGCTGATGCCCGGTCCTCGACGTAGAGGTTGGCCCGGTCGCCGACCCGGCGGGCC
       < R  D  N  L  D  H  L  Q  E  A  S  I  G  I  G  R  D  E  V  Y  L  N  A  R  D  G  V  R  R  A
103990 TCCACCATCACCTGCGAGTCGGGCGGCGAGAAGGCGGTCGCGTTGTCGAACAGCTCGGCGACCAGTTGACCAGTCGTTGACCGTGCGC
       <E  V  M  V  Q  S  D  P  P  S  F  A  T  A  N  D  G  L  E  A  V  L  H  V  L  D  N  V  A  H  A
104082 GGCGACCTCGATGTCACGGTCGACACCCGAACTCGATCGGACTGGTAGTGCTGACGCAGCACGTCGATCAGTG
       <A  V  E  I  D  R  D  I  V  G  F  E  I  R  T  Y  H  E  V  E  S  Q  A  A  R  L  V  D  I  L  A
104174 CCGCCGGCTCGCGCTGCACGCGGGTGGAGTCGGCCTCCTCGCGGCTGGCATCCGGGTCGTTGCGCAGCCAGGAGGTGGTCG
       < A  P  E  R  Q  V  R  T  S  D  A  G  A  L  V  L  L  N  E  D  N  R  R  M  R  T  A  L  H  D
104266 AGCTGGAAACAGCTCGGCCAGGTTGACGAACATGGTCGGCAGCGGCCTCCTGCTCCGCGAGGTGGCCTCCAGGTACGGCCTCGACCAGGATCTGCGA
       <L  Q  F  L  E  A  L  R  D  P  D  E  E  G  R  E  L  R  D  L  H  F  I  L  R  D  V  L  I  Q  S
104358 ACGGGCGGGCCAGGTTGACGAACATGGTTGCTGCCAGCCACATCTGTCCTTGCTGCGACCAGGCAGCTCGGAGCTGGCCTGCACCGGGAGAGCTGG
       < R  R  A  L  N  V  F  M  T  A  V  S  A  R  L  A  A  Q  E  A  A  T  R  V  A  E  L  H  V  A  N
104450 TGAACGCCTCGGTCACCTGGCACCTGAATGCGCCGGCAACGGCTGGGCAACCTGGGGCAACGGCTGGGCGACGGTCGCGCAGCGA
       < F  A  E  T  V  Q  G  F  E  D  K  S  R  V  P  L  P  E  A  I  Q  N  A  A  Q  V  P  S  L  Q
104542 CTGGAAAACTGCGACCGGCGACATCGCGCAACGGCTGGGCAACAGGATGGCCAGCAGCATGCCGAGCACCCTGAGGCTCTGGAGGAACACCGTGCGCT
       <S  S  G  Q  P  D  R  L  R  A  V  A  Q  P  L  G  T  Q  A  I  S  L  A  G  Q  R  L  D  R  L  S
104634 GCGGGCCATCGACCGGCGAGCGAGGCGCAGGTCGGCGCTGCTTGACCACGTCGTTGCCGTCACGATCAGTTGGGCGTCGTGGCGACCATG
       < R  A  M  S  R  A  V  L  Y  A  F  L  I  A  L  L  L  M  G  L  L  G  T  Q  L  F  V  T  R  Q
104726 GTACGTCGGAGGCGAGCGAGCGCCCGGTCGGCCGGTCCCATGCGCGTTGGCATGCGCGTTGGCGTVNGCTGAGCAGCCGGTGTAGTTCTGGCCTCGCT
       < V  D  S  R  L  A  D  A  Q  K  V  V  N  G  D  L  K  A  E  V  T  R  I  L  K  A  S  A  V  M
104818 GCCGGTCCCACTGGTCCGATCCGGCCGAAACGGCGCGTTGGCCATGCGCGTTGGTGTTGCCGTVGTTGCCGGTAGTTCTGGCCTCGCG
       <A  A  D  W  Q  D  P  G  F  P  A  N  A  M  S  G  N  T  N  G  D  L  W  G  T  Y  N  Q  A  E  R
104910 CCGGTCGCCGGCCGGCGACGGTCTGGTCGTCGAGGTCCAGGTCTGCAGGTCCACCGGTCTGAAGCTTTGCAGTGCCTTGCTGCTGCCGG
       <R  D  G  G  A  V  T  Q  D  H  L  D  S  E  D  L  S  A  V  A  K  F  S  Q  L  A  Q  Q  Q  G  T
```

FIG. 11A(91)

```
105002  TGCCGCTGGCGATGTAGTCGGTGCGCAGGATGGGGTCAACTCGCTGGATCAGGCCGGTGCACCACGAGCCCGGCGACCGAGAGGTAT
        < G  S  A  I  T  D  T  R  L  I  P  T  L  E  R  Q  I  L  A  R  H  V  V  R  R  V  S  L  Y
105094  TCCTTCTCCCGGCGACGGCTGCCGGCGCCATCCGGTCGCTCAGGTCGTTGTCACCGGCGAGTGGCGAGTCGCGGATGGACAG
        <E  K  E  R  A  V  A  A  A  A  R  M  R  D  S  L  D  N  D  G  A  L  H  T  A  S  D  R  I  S  L
105186  CAGGTCGTTGATCAGGCCCTCGTACGGCCTGATGGCGTCGATGATCTTCAACTTGCCGTTGAAGACCTGGCTGCGGGTGCCGGAGGTCCT
        < L  D  N  I  L  G  E  T  A  Q  M  A  D  I  I  K  L  K  G  N  F  V  Q  S  R  T  G  P  L  D  K
105278  TCAGGTTCTGGTCGATCCGTCGAGGAGGCCCTCCAGGCTGCGGCAGGCCGTGTTGACCTCGACCTCTGGGAGGTACGGCACCTTGTCC
        < L  N  Q  D  I  G  D  L  L  G  E  L  S  S  P  L  G  D  V  E  G  R  Q  Q  L  Y  P  V  K  D
105370  TGGTGCAACCCGGATGTTGACCGGGTTGTACGCCGTCCTGGTACGCCTCGCCCGAGCAGCAACACGCGGAGGT
        < Q  D  V  R  I  N  V  R  N  Y  A  E  Q  Y  A  K  A  Q  D  G  S  A  G  L  L  L  V  A  S  T
105462  GCGTTCGTCCTGAGGCCACTGTGGTGCCGACGACCAGTCGCCGATAGCCACCAGATTGGCCACGATCATGATGGACCAGATCGGCATGTC
        < R  E  D  Q  L  S  N  V  L  D  G  S  Y  G  V  L  N  A  L  D  G  S  R  N  A  N  N  L  T  E  L
105554  GGTTGTCGACGAGGCCACTGTGGTGCCGACGACCAGTCGCCGATAGCCACCAGATTGGCCACGATCATGATGGACCAGATCGGCATGTC
        < N  D  V  L  G  S  T  G  V  V  V  T  A  I  T  P  V  I  M  I  L  G  L  K  S  E  I  P  M
105645  GCGGAGCCGGGCCCTTCGGGGCTCCTCGCTGCTGCAGTCGCGCAGCAGTCAGCAGCTCAGGCAACGCCGGGCGACCCGGTGACCTCCGAGATTCCATCACGCCGTGTTCCAAAGAGAAAGCCCA
        <H  R  L  V  L  L  A  G  P  S  G  S  G  K  S  T  I  A  Q  Q  T  G  L  P  V  L  C  L  D  D  F
105737  GTTCGCGCGTTGCCCCGGCAACGCTCAGGCAACGCCGGGCGACCCGGTGACCTCCGAGATTCCATCACGCCGTGTTCCAAAGAGAAAGCCCA
        > Y  K  D  G  D  D  P  T  L  P  R  Q  N  G  L  V  D  W  D  S  P  Q  S  W  D  A  G  A  A  V
105829  GGCTGGCCGTGCCGAGGTGTGATGAGAGCCGAAGTGCCGGTTATGCGAGTAATGGATCACCCC
        > M  D  H  P
105919  CACCGCCTCGTCCTGCTGCGCTGCGCGCGGGCCCTTCGGGCTCCTCGCTGCTGCAGTCGCGCAGCAGTCAGCAGCTCAGGCAACGCCGGGCGACCCGGTGACCTCCGAGATTCCATCACGCCGTGTTCCAAAGAGAAAGCCCA
        >H  R  L  V  L  L  A  G  P  S  G  S  G  K  S  T  I  A  Q  Q  T  G  L  P  V  L  C  L  D  D  F
106011  CTACAAGGATGGTGATGACGTTACGCGCCAGTTCTTGTGACTGGGACTCACCCAGTCGTGGGACGCCGGCGGCCGTGG
        > Y  K  D  G  D  D  P  T  L  P  R  Q  N  G  L  V  D  W  D  S  P  Q  S  W  D  A  G  A  A  V
106103  AAACGATTGCCGGCGTGCCGGCGCTGGCCGAGGTGATGAGAGCCGAAGTGCCGGTTATGCGAGTAATGGATCACCCC
        >E  T  I  A  R  L  A  R  D  G  K  A  E  V  P  P  V  Y  A  I  G  A  D  R  R  V  A  T  R  T  F  E
```

FIG.11A(92)

FIG.11A(93)

```
107205  CGAACCCGGGCGACGACGCCTCGACCACCTCGTCCAGGTGTCCGCTCGTCTGCGGGGGCGAACCGCACCTCGGCGTAGACG
        < F  G  A  V  V  A  E  V  V  E  D  L  T  L  D  R  E  L  H  Q  E  P  A  F  R  V  E  A  Y  V

107297  ACCCCGTCGGCGCCAGTCCAGCGCGCACTCCTGGGCGCACTGCGGGCGGTCTGCATGACGCCACGGTGTGGGCGAACGT
        > V  G  D  A  A  L  D  L  A  C  E  Q  A  V  R  R  L  A  P  A  T  Q  M  V  A  V  T  H  A  F  T

107389  CTCCAGGTAGCGCTCGACGAGCGAGTTCGCCGACGAGTTCGCCGAGCGCTTCGGGTCGGTCGGTGGGCACCTTGACGATGTCCTCG
        < E  L  Y  R  E  L  S  G  S  N  A  A  V  F  W  R  G  L  A  E  P  D  T  T  P  L  E  H  G  V

107481  CCTCGGGCGGCAGCTCGACGATGTCGTCCAGGACCCTAGTGCTGCAGCAGCGCCTTGGGCGACGCGAGGATGTCCAGGTGATGGACCCC
        < E  A  A  L  E  V  I  T  A  P  R  L  G  G  D  L  H  D  H  L  L  A  K  P  V  K  I  D  E

107573  TATGAGATTGCGACCATGCCCAGACCCTAGTAGGCACGGACCGGTCGCCGACGACGTGGAGGATGTCCAGGTGATGGACCCC
        < Y  S  I  A  V  M                                                    > M  D  P

107662  CGGCATCGTCGACCGGCTGCGTTGCCCGGTCTGCGCCGAGCCAACCGCTCACCCGAGGCTCACCCCGGCGCTGCCCGCCG
        > R  I  V  D  R  L  R  C  P  V  C  A  E  P  L  T  E  A  A  G  T  T  R  A  L  R  C  P  R  R

107754  GCACAGCTTCGACGTGGCCCGCCAGGGGTACGGTCAGGGGTACGACACGACCTGCTCGCGGGCACGTGGGCGACACGGTAGAGATGGTGGCGCC
        > H  S  F  D  V  A  R  Q  G  Y  V  D  L  L  A  G  R  A  P  H  V  G  D  T  A  E  M  V  A  A

107846  GCGCCGACTTCCTCGCCGCCGGCCACTACGACACGCTCTCGGCCGCGCTCGCCGCCGCTGCCGCCGGGCCACCGCCTGAGCCACGCCCCCCACCCCCGGGAGGCC
        > R  A  D  F  L  A  A  G  H  Y  D  T  L  S  A  A  L  A  A  A  A  A  L  S  H  P  P  E  A

107938  CCCGGAGCGGACGGCCGGCGCGACGGCAAAGACGGCCGGACAGCGCGGGCAGGATGCCCAAGCCGTCCTGGACATGACGCGTCCGCGGACAGCC
        > P  G  A  D  A  S  A  G  K  D  G  Q  D  A  Q  G  R  D  A  S  A  G  H  D  A  S  A  G  Q  P

108030  GGCCGTCGGGACGTACCCGCTGGTGGACGCCGGCGCACCTCGGCGGCTGCCGGCGTGCTGCCCGACGCGCTGCCCCCGACGCCGTGG
        > A  V  G  T  Y  P  L  V  V  D  A  G  A  G  T  G  R  H  L  A  A  V  L  A  A  L  P  D  A  V

108122  GCCTGGCCCTGGACGTCTCCAAGCCGTCGCTCGCCCGTGCTGCGCGACGTCTTCGCCCGGCACCTCGGCGGG
        > G  L  A  L  D  V  S  K  P  A  L  R  R  A  A  R  A  H  P  R  A  A  A  L  A  D  T  W  R  R

108214  CTTCCGCTGCCGGCGGACGCCAGCGTCGCCGTGCTGCTCGACGTCTTCGCCCCGCAACGGCGGAGTTCCGCCGGGTGCTGCACCCGGCCGG
        > L  P  L  A  D  A  S  V  A  V  L  L  D  V  F  A  P  R  N  G  A  E  F  R  R  V  L  H  P  A  G
```

FIG.11A(94)

```
108306  CGCGCTGCTCGTGGTCACCCCGCGAGGA CACCTCGCCGAACTGGTCGACTGCTCGAACTGGACGACAAGGCGGACC
         A  L  L  V  V  T  P  A  E  D  H  L  A  E  L  V  D  S  L  D  L  L  K  V  D  P  D  K  A  D
108398  GGGTCGCCGGGAGCCTGGCCGGCCACTTCGAGCAGACCGCCGAGAGCGTGCTGCGGGCCCGGCTGGAACTCACCGGCCGGCAGGTGGCCACC
         R  V  A  G  S  L  A  G  H  F  E  Q  T  A  E  S  V  L  R  A  R  L  E  L  T  G  R  Q  V  A  T
108490  CTGGTCGGGATGGGACCGAGCGCTGGCACGCACCGACACGACCCGGCCACCCTCGCCGCGATCGCCGCGCTACCGGAGCCGGTCCGGGTGACCCT
         L  V  G  M  G  P  S  A  W  H  T  D  P  A  T  L  A  A  R  I  A  A  L  P  E  P  V  R  V  T  L
108582  CGCGGTACGGCTCGGCGTGTACCGCCCGCGCTGACCGGGGCGCGGCCGCTCAGGTGGAAAGGTCGACCTCTTCCCAGCCGCGGTC
         A  V  R  L  G  V  Y  R  P  R  *       T  S  L  D  V  E  E  W  G  P  P  E
108674  CTCGTGGTAGGGCCCTCGCAGGACCACCTCCAGCCGCCCACTCCAGGCGCTGCCGATCGCTGGCGTGCCGATCGCGTTGGCGGTGCCGGGCCGGGCGGACC
         L  V  V  G  P  S  Q  D  H  L  Q  P  P  T  P  G  A  A  D  R  W  R  R  R  R  G  D  R  W  R  R  G  T
108766  GCCCGTCGCGCTCCAGTCCAGGTACGGCCAGTAGTGCAGGTCGAGGCAGGCAGTCAGGTCCCGCGCGTCGGCCGGTGCTGGGGCGCGGCC
         A  R  R  A  P  V  Q  V  R  P  V  V  Q  V  E  A  G  S  Q  V  P  R  V  G  R  C  W  G  A  G  L
108858  AGGATGCGGGAGCGCCACTGCTGAAGCTCTCCCGCGCGATGTGCCAGCAGCGGCGTCGTCGACCAGCGCTCGTTGACCGGCAGCGTCGGGTC
         R  M  R  E  R  H  C  *  S  S  P  A  R  C  A  S  S  G  R  R  R  P  A  L  V  D  R  Q  R  R  V
108950  GAGCTGCTTGGCCAGGCCGAGCCAGGCCAGGTGACCAGGCAGGTGACCAGGTGAGTTGAGCAGCTCATCGCCGCCTGCCGGCATGCCGAAACACCGG
         E  L  L  A  R  P  S  Q  A  R  *  P  G  R  *  L  S  S  S  S  H  R  R  L  P  A  C  R  H  A  E  H  R
109042  CGAACTGCCACTCCGGGCGGGGGTGACCAGGTGCAGCAGTCAGCTCGATCTCGACGGCTCGGCCGGATCTCGTCGCCGCCAGCTCGAGCCAGGGGAA
         R  T  A  T  P  G  G  G  *  P  G  A  A  V  S  S  D  L  D  G  S  A  G  I  S  S  P  P  A  R  A  R  G  N
109134  GCCAGGATCACGTGCAGCACGGCAGCCCCAGGCCGGATGCCGCTCGATCTCGAACGTGCCAGCAGTGCCCACTCAGGGGAA
         A  R  I  T  C  S  T  A  A  P  G  R  M  P  L  D  L  E  R  A  S  S  A  H  S  G  E
109225  ACTGGCTCGGTGGCAGCGGCAGGCCCAGCCGGGACAGCTCGTCAGGCTGGTCAGGTCACGGAGGGGAAACGGCACG
         T  G  S  V  A  A  A  G  P  A  G  Q  L  V  R  L  V  R  S  R  R  G  K  R  T
109317  GCTCAGATCCCTGTCAGTCAGTCGCCATCGGCTCGCATCGGCCGGTCGTCCCCTTGGCCTGGGAGGATAGCGGTTCACGAGGCACCACGGCGGG
         A  Q  I  P  V  S  Q  S  P  S  A  R  I  G  R  S  S  P  L  A  W  E  D  S  G  S  R  G  T  T  A  G
109409  CGGGGGCGGGCCCGGTTCAGCCGGGGCGGTCGATGACCAGGCCGGTCGGGGCGGTCGGGAGATCCGTACCGGACCGGCCGCCTCG
         R  G  R  A  R  F  S  R  G  G  R  *  P  G  R  S  G  D  P  Y  R  T  G  R  L
                                                      BamHI
109501  GCCAGGCGCCGCCGGGATCC
```

FIG.11A(95)

FIG. 12A

```
1235 GAC CTG GAG CGA CGG GTC GAC GAG GCG GTG CAC GCC GGA TCG GCG CGT GCG GTG TCC AAG CAG CAC CGG GGC AAG AAG ACG GCG CGG
   >D   L   E   R   R   V   D   E   A   V   H   A   G   S   A   R   A   V   S   K   Q   H   R   G   K   K   T   A   R
1325 GAG CGG ATC GGG CTC CTG GAC CTG CTC GGC GAG GGG TCC TTC GTC GAG CTG GAC GGC TTC GCG CGG CAC CGG TCC ACC CGG AAC TTC GGC CTG GAC CGC
   >E   R   I   G   L   L   D   L   L   G   E   G   S   F   V   E   L   D   G   F   A   R   H   R   S   T   N   F   G   L   D   R
1415 ACC CGC CCG TAC CTC GAC GGC GTG ATC ACC GGC TAC GGC GTC ATC ACC GGC GTC CAG GAC TTC GCG CAG GAC TTC ACG GTC TTC
   >T   R   P   Y   L   D   G   V   I   T   G   Y   G   V   I   T   G   V   Q   D   F   A   Q   D   F   T   V   F
1505 GGC GGC TCC CTC GGC GAG GTG TTC GGG GAA AAG ATC GTC AAG GTG ATG GAC CTG GCC ATG AAG ATC GGC TGC CCG GTC GTC GGC ATC AAC
   >G   G   S   L   G   E   V   F   G   E   K   I   V   K   V   M   D   L   A   M   K   I   G   C   P   V   V   G   I   N
1595 GAC TCC GGC GGC GCC CGC ATC CAG GAG CGC CTC TAC GGC GTC TCT CCG GCC GTG ATC GGC GCC AGC GGC GTC
   >D   S   G   G   A   R   I   Q   E   R   L   Y   G   V   S   P   A   V   T   D   F   T   V   M   V   D   Q
1685 ATC CCG CAG ATC TCC CTG ATC ATG GGC CCC GCC GAC GTC ACC GAC GAG ATG GAA GAA CTG GGT GCC CGC ACC
   >I   P   Q   I   S   L   I   M   G   P   C   A   G   V   T   D   V   T   G   M   E   E   L   G   A   R   T
1775 ACC TCG CAC ATG TTC ATC ACC GGC CCC GAC GTC ATC CTC GAC GCC ATC AGC GAC GGG CTG CAG TTC CTG GAG GTC CAG CCG TCG TAC GCG CTC CCG
   >T   S   H   M   F   I   T   G   P   D   V   I   K   T   V   I   E   Y   V   K   A   L   L   S   Y   L   P
1865 CAC AAC GCG CGG AGC GGC AAC GCG CAC TAC CTG TTC GAC CGC CCG GCC GAC GTC ATC GAG TAC GTG AAG GCG CTG CTC CAG CCG TCG TAC GCG
   >H   N   A   R   S   G   N   A   H   Y   L   F   D   R   P   A   D   V   I   E   Y   V   K   A   L   L   S   V   P
1955 TCG GCC AAC CAG CCG TAC GAC ATG CAC CGG GTC ATC GAG CAC GTG CTG GAC GAC GAC GGC GAG TTC CTG GAG GTC CAG CCG CTG TAC GCG
   >S   A   N   Q   P   Y   D   M   H   R   V   I   E   H   V   L   D   D   D   G   E   F   L   E   V   Q   P   L   Y   A
2045 GAC TCG GCC ATG GTG GTG GGT CGA ATC GAG GGA CGA CCG GTG GGC GTG GCC GTC AAC CAG CCC GTG ACC CTG TTC GTG GAC CTG GAC
   >D   S   A   M   V   V   G   R   I   E   G   R   P   V   G   V   A   N   Q   P   M   H   L   A   G   T   L   D
2135 CAG AAC ATG GTC GGC TTC GGT CGA ATC GAG GGA CGA CCG GTG GGC GTG GCC GTC AAC CAG CCC ATG CAC CTC GCC GGC ACC CTC GAC
   >Q   N   M   V   G   F   G   R   I   E   G   R   P   V   G   V   A   N   Q   P   M   H   L   A   G   T   L   D
2225 ATC GCC GCG TCG GAG AAG GCC GCC CGG TTC GTG CGC ACC TGC GAC GCC TTC AAC ATC CCC GTG CTG ACC TTC GTG GAC GTG CCC GGG TTC
   >I   A   A   S   E   K   A   A   R   F   V   R   T   C   D   A   F   N   I   P   V   L   T   F   V   D   V   P   G   F
```

```
6821 GAA GTC GGT GCC GAA GAT GCC GTC GAA GGC CGG CTC GCC GGT GCG GAC GCT GTG CGC CAG GCC GTC CCA GGC CGT GGT CAT GGC CGG GTC
    < F   D   T   G   F   I   G   D   F   A   P   E   G   T   R   V   S   H   A   L   G   D   W   A   T   T   M   A   P   D

6911 GGT CAG CAT CCG CAG CGG CAC CCG GTC CCC CAT CGG GGC GAG CGC GAA CGC GGC GAG GCC GTC CGG CTC GCC CAA CTC CTG
    < T   L   M   R   A   L   P   R   L   T   G   P   R   D   G   R   L   L   A   G   M   P   A   L   A   F   R   G   P   T

7001 GGT CTC GAG CAC CTC GCC GGC CAG CGC GGC CAT GGT GTC CGC TCG GGC GTC CAG CAC CCG CAG CTC GTA CCG CAG CCC CAA CTC CTG
    < T   E   T   L   V   R   L   A   A   L   A   R   L   V   R   F   M   T   D   A   R   A   D   Y   R   L   A   L   E   Q

7091 CGG GGT GCG CTC GTC GCC GAT CGC GTC GGG CAG GTA GCC CCG GCT CAG CCG GAC GTC CGT GGC CAT CCC GCC GAA CAC CAA
    < P   T   R   E   D   D   G   I   A   D   P   L   G   L   R   V   C   Y   G   V   L   R   S   A   M   G   G   F   V   L

7181 CCG CAT CAG CAG CTC CGG CCA GGC GTC GCC CGC CAG CGC CGC GGT CGT GGG CTC GTC CGT GGC TGC GCTCGTCCGTGTCCGGGA
    < R   M   L   E   P   W   A   A   D   A   G   T   Q   A   R   R   A   S   P   E   D   T   T   A   R   E   D   T   D   P   V

7276 CGG TCA TCG GAC CGG CTC GCC CGG CAG CCC GAT GCG CGG CAG GTA GTC GAC CGG TTC GCC GTC GCC CGG GCG GTC CAG
    < T                                                                                                                         
        M
        V   R   M   L   E   P   W   A   A   D   A   R   E   V   P   S   Y   D   G   D   P   R   D   L

7366 GTC CAG CTC GCC CAC CAG CGG GCT CGG CTG CCG CAG CCC GGT CAT GAA CCG GGT GCC CGT GTT GGC CAC GGT GTG CAC CAG GAA CGG
    < D   L   E   G   V   P   Q   L   S   P   Q   G   A   M   F   R   P   T   G   T   N   A   V   P   T   H   V   L   F   P

7456 GTG GCA CAG CAG GTA GAC CGG TTC GGT GGC TCC GGT GGC CGG GCC GGG GAC GTC GAG CTC GGT GTC GAG GTA GGT GTC CGG CTC
    < H   C   L   L   Y   V   D   G   A   R   G   T   A   S   A   L   P   R   D   R   G   V   D   G   V   D   L   Y   T   G   E

7546 GTG GTG GCC GCC GTT CTG GGG CCC CAG CGG ACC GGC CAG CAG CGG CGG CGG CAG GTG GGA GCC GTT GCA GCG CTC GTC CAG GTC CTC
    < P   G   Y   P   E   L   L   P   P   V   D   L   H   S   G   A   R   G   R   V   L   T   P   A   E   R   E   D   T   D   S   F

7636 GAG GAA CAG CAG CTG CTG GGG GCC CAG CCG GGC CTG CGC CAG CCG GAG GTT GCA GCG CTC CGC TTC GTA GTT GGG CCC GTA GTC GAG GAA
    < L   F   L   L   L   A   R   G   Q   L   R   Q   P   E   L   L   A   R   S   R   L   N   C   R   F   V   E   A   Y   N   P

7726 CTC CCA GTT CTG GGG CCA GGG CTG CGC CAG CCG GTC GTC GGC CAG GAA ACT GGC CAG GTG CGG CCA GTG GAT ATC CAC GCG CCC CAC GAG CTG GCC
    < E   W   N   Q   P   G   L   R   Q   R   D   D   A   L   F   S   A   D   I   H   W   G   R   V   L   Q   D   F   A   A   H

7816 CTT GGG CAC CGG GAA CGG GAC GGG CGG GAA GGT GCC CAA CGG GTC CGT GAT CCG GAT CAG CGA GTC TTG CCA GCG GTA GGG GGC GTG
    < K   P   V   P   F   R   V   P   F   T   G   I   R   D   L   P   K   W   R   G   V   L   Q   D   F   A   A   H
```

```
11289 TTC CGC GCC ATC GCC GCC CTG GTG GCC GAG CGG ACC GGT CGG GCC GAG GTG CCG GTG CTG GCC GTG CCC CCG GAC GAG GCC CGG GTC
     >F   R   A   I   A   A   L   V   A   E   R   T   G   R   A   E   V   P   V   L   A   V   P   P   D   E   A   R   V
11379 AGC GAC TTC CAC GAC ATG GTC GTT GAC TCG GCC TTC CAG GCG GCG GTC ACC GGG TGG GCC CCG GTG CCG TTG CGC CTC GCG CTG GAC
     >S   D   F   H   D   M   V   D   S   A   F   Q   A   A   V   T   G   W   A   P   R   V   P   L   R   L   A   L   D
11469 CGC ACC GTC GCG GCG CTC GCC CGC GAC GAC AGC GGC CCC GAG CCC GGC GTC CCG GCG ACG CGG GAT CAG GCC CGG
     >R   T   V   A   A   L   A   R   D   D   S   G   P   E   A   P   G   G   V   P   A   T   R   A   D   Q   A   R
11553 AAG CCG GAC TCG ATC TCC AGG CAG GTC CGG TAG TCGGGCAGCAGCAACCACGGGGAGCGCCTGTTGAAGGTGATCGCGGTGCGGATCGGTTCGAC
     >K   P   D   S   I   S   R   Q   V   R   •
11663 GTCCTCGGGGATGGGACAGGCCCGGGTCGAGGCGGTCGAAGACGTACTCCTGGGACACAGGACGTGTCGGCCAGGGCGACGAAC
11784 ATGTGCGCGGAGACCCCGACCGGCAGTCCCGCTGTCGAGGACCACCAGCTCGGTGAGCCCACGTCGGTGAGCACCAGGTCGAGCACCC
11905 GGCCGTGCGCGGAGAGGAACTTCCGGGTACCGGGGGTCCCCGCGCTGTAGTCGTGCCGCCACGGGGAACAGCGGGTA
12026 CCCGACCGTGTCCCGGAACAACGAGTCGAGATACGCGCCTTCGACGGTGGGGCGCGAAGGCGTGGCGGAAGGGGCGGGGCGGACACC
12147 GGCGGG
```

FIG.12K

EVERNINOMICIN BIOSYNTHETIC PROTEINS

This application is a divisional application of U.S. patent application Ser. No. 09/758,759; filed Jan. 11, 2001 now U.S. Pat. No. 6,861,513, now allowed, which claims the benefit of U.S. Provisional Patent Application No. 60/175,751; filed Jan. 12, 2000 each of which is herein incorporated by reference in its entirety.

FIELD OF THE INVENTION

This invention is directed to nucleic acid molecules which encode proteins that direct the synthesis of the orthosomycin everninomicin. The present invention also is directed to use of DNA to produce compounds exhibiting antibiotic activity based on the everninomicin structure.

BACKGROUND OF THE INVENTION

Everninomicin Biosynthesis

Everninomicin is an oligosaccharide antibiotic belonging to the orthosomycin group of antibiotics produced by *Micromonospora carbonacea* var. *africana* (ATCC 39149, SCC 1413) and is useful as a human medicine. Everninomicin chemically consists of several glycosyl residues attached to modified orsellinic acid. Everninomicin's antibiotic activity is believed to be due to its inhibition of protein synthesis by a mechanism that involves binding of the antibiotic to a ribosome (McNicholas et al., Abstract C-846, ICAAC, San Francisco, Calif., 1999). Everninomicin is structurally similar to the antibiotic avilamycin produced by *Streptomyces viridochromogenes* Tu57.

The biosynthesis and enzymatic steps necessary for synthesis of homologs of the chemical moieties contained in the everninomicin structure have been studied in other systems. These include synthesis of orsellinic acid (Type I polyketide), glycosyl group synthesis (deoxysugars), and glycosyltransferase responsible for covalent attachment of glycosyl groups. Orsellinic acid biosynthesis in *Penicillium patulum* and *Streptomyces viridochromogenes* Tu57 has been investigated (Beck et al., European Journal of Biochemistry, 1990, 192:487-498; and Gaisser et al., Journal of Bacteriology, 1997, 179:6271-6278). Glycosyl biosynthesis has been reviewed (Hung-wen et al., Annual Review of Microbiology, 1994, 48:223-56; Williams et al., "The Carbohydrates: Chemistry and Biology" Vol. 1B, 1980, 761-798; and Johnson et al., Current Opinion Chem. Biol., 1998, 5:642-9), and been studied in the erythromycin biosynthetic cluster (Summers et al., Microbiology, 1997, 143:3251-3262). Glycosyltransferases have been studied in a number of systems (Olano et al., Molecular Gen. Genetics, 1998, 3:299-308; Fernandez et al., Journal of Bacteriology, 1998, 18:4929-4937; and Wilson et al., Gene, 1998, 214:95-100).

Polyketides are synthesized via a common mechanistic scheme thought to be related to fatty acid synthesis. The cyclic lactone framework is prepared by a series of condensations involving small carboxylic acid residues (acyl groups). Modifications of the structure, such as ketoreduction, dehydration and enolylreduction, also occur during the processing. The synthesis is driven by a set of large multifunctional polypeptides, referred to as polyketide synthases.

PCT Publication No. WO 93/13663 describes the organization of the gene encoding the polyketide synthase of *Saccharapolyspora erythraea*. The gene is organized in modules, with each module effecting one condensation step. The precise sequence of chain growth and the processing of the growing chain is determined by the genetic information in each module. This PCT publication describes an approach for synthesizing novel polyketide structures by manipulating in several ways the DNA governing the biosynthesis of the cyclic lactone framework. In order to adapt this methodology to other polyketides, however, the DNA molecules directing the biosynthetic processing must first be isolated.

Combinatorial biosynthesis with bacterial deoxy-sugar biosynthetic genes has been demonstrated (Madduri et al., 1998, Nature Biotechnology, 16:69-74) with the antitumor drug epirubicin (4'-epidoxorubicin) produced by *Streptomyces peucetius*. The heterologous sugar biosynthetic genes avrE from *Streptomyces avermitilis* and eryBIV from *Saccharopolyspora* were introduced into an *S. peucetius* dnmV mutant blocked in the biosynthesis of dausosamine, the deoxysugar component of epirubicin. Product yields were enhanced with avrE complementation demonstrating heterologous expression of sugar biosynthetic genes in combinatorial biosynthesis. Glucosylation of the glycopeptide antibiotic vancomycin (Solenberg et al., Chem Biol, 1997, 4:195-202) demonstrated that the heterologous glycosyltransferases gtfB and gtfE from *Amycolatopsis orientalis* expressed in *E. coli* produced glycosyltransferase capable of adding glucose or xylose to the vancomycin heptapeptide. Additionally, expression of gtfE from *Amycolatopsis orientalis* in *Streptomyces toyocaensis* resulted in glucosylation of A47934, producing a novel antibiotic. Thus, cloned glycosyltransferases can be used to produce novel hybrid antibiotics by glycosylation. In order to adapt this methodology to other glycosyl synthetic genes or glycosyltransferases, however, the DNA molecules directing the biosynthetic processing must first be isolated.

Orsellinic acid is synthesized by AviM, a Type I polyketide synthetase in *Streptomyces viridochromogenes* Tu57. An acetyl-CoA is used as the "starter" unit and three manonyl-CoAs are used as "extender" units for the synthesis of orsellinic acid. AviM has been shown to synthesize orsellinic acid by introduction of aviM into *S. lividans* TK24 (Gaisser et al., Journal of Bacteriology, 1997, 179:6271-6278). AviM has homology to the *Penicillium patulum* Type I polyketide synthase for 6-methylsalicylic acid (MSAS). The *M. carbonacea* EvrJ protein has homology to both AviM and MSAS and contains polyketide synthetic active site motifs resembling acyl carrier proteins, β-ketoacyl:ACP synthetases, and acetyl-CoA/Malonyl-CoA:ACP acetyltransferases. Thus EvrJ contains motifs necessary for the condensation of malonyl extender units with the starter acetyl-CoA unit.

The *M. carbonacea* EviI protein has homology to DpsC from from *S. peucetius* ATCC 29050. Purified DpsC has been shown to use propionyl-CoA as substrate and to be acylated by propionyl-CoA at the Ser-118 residue (Bao et al., J. Bacteriol, 199, 181:4690-5). This has led to the proposal that DpsC is responsible for the choice of propionyl-CoA as the starter acyl unit in the biosynthesis of daunorhubicin by acting as an β-ketoacyl:acyl carrier protein (ACP) synthetase three (KSIII), and catalyzes the first condensation of the propionate-starter unit with malonyl-ACP. Thus EvrI may be responsible for specifying the choice of acetyl-CoA as the starter acyl group in orsellinic acid biosynthesis and condensation with the first malonyl extender unit. EvrI contains a possible Cys-127 acylation site to form the EvrI-Cys-S-acetyl moiety. This active Cys is similar to the active Cys found in the *Streptomyces glaucescens* FabH (KSIII) enzyme.

The success in cloning and manipulating biosynthetic pathways for the products mentioned above demonstrates a need in the art to isolate and harness the biosynthetic pathway for everninomicin. Moreover, there is a need to employ everninomicin biosynthesis in the development of novel molecules by combinatorial biosynthesis.

Genetic Manipulation of Actinomycetes

The ability to insert genes into the actinomycete chromosome is important to avoid plasmid inhibition of secondary metbolite production and to allow the construction of recombinants that do not require antibiotic selection to maintain cloned genes. Vectors have been developed for use in actinomycetes that contain att/int functions for site-specific integration of plasmid DNA. The two systems available make use of the att/int functions of bacteriophage phiC31 (U.S. Pat. No. 5,190,870) and plasmid pSAM2 (U.S. Pat. No. 5,741,675). However, there is a need for additional vectors with att/int functions for site-specific integration in *M. carbonacea*.

The present invention addresses these and other needs in the art.

SUMMARY OF THE INVENTION

The present invention advantageously provides the DNA sequence for the gene cluster responsible for encoding everninomicin biosynthetic genes, which provide the machinery for producing everninomicin. As a result, the present invention provides the information needed to synthesize novel everninomicin-related compounds based on everninomicin, arising from modifications of this DNA sequence designed to change glycosyl and modified orsellinic acid groups contained in everninomicin.

Thus, in one embodiment, the invention provides a nucleic acid comprising an everninomicin biosynthetic pathway gene product from a *Micromonospora carbonacea*, e.g., encoding a protein as set forth in Tables 1a and 1b, and in a specific aspect having a coding region (CDR) as set forth in Tables 1a and 1b.

The invention further provides expression vectors, host cells, and related methods of expression of protein gene products, comprising the isolated nucleic acids of the invention.

In addition, isolated polypeptides corresponding to an everninomicin biosynthetic pathway gene product are provided. Specific open reading frames and amino acid sequences of the polypeptides are set forth in FIG. 11 (SEQ ID NOS: 2-175) and FIG. 12 (SEQ ID NOS: 183-204).

Furthermore, the invention provides modified *M. carbonacea*, in which an everninomicin biosynthetic pathway gene is knocked-out, or, alternatively, over-expressed (or both). Similarly, the invention provides for metabolic engineering of new everninomicin analogs.

A particular advantage of this invention is the discovery of various everninomicin resistance genes, which can be used as selection markers. Thus, the invention provides a vector comprising an *M. carbonacea* everninomicin biosynthetic pathway resistance gene, and related methods of selection of transfected or transformed host cells.

In a related but distinct aspect, the inventors have discovered a *Micromonospora* site-specific integrase. The gene for the integrase can be incorporated in a vector for integration into any actinomycete, and, particularly *Monospora*. Thus, the invention further provides a method for introducing a heterologous gene into an actinomycete chromosome using this particular vector.

These and other aspects of the invention are better understood by reference to the following Detailed Description and Examples.

DESCRIPTION OF THE DRAWINGS

FIG. 1. The structure of everninomicin.

FIGS. 2A-C. (A) Map of cosmid clones and subclones that span the whole region of the everninomicin biosynthetic locus and surrounding genomic DNA. Heavy cross-hatching indicates sequenced regions; light cross-hatching indicates regions for which a cosmid restriction map was obtained. (B) Restriction map of cosmid pSPRX272. (C) Restriction map of cosmid pSPRX256. In (B) and (C), cross-hatched regions have been sequenced and cloned fragments are indicated by clone designations beneath the fragment.

FIGS. 3A-D. Map of the everninomicin biosynthetic region of *Micromonospora carbonacea* var. *africana* DNA. Distances in bf are shown relative to the beginning of the DNA region. Open reading frames (ORF) are indicated by block arrows. The restriction sites for BamHI, BglII, EcoRI, KpnI, PstI and XhoI restriction enzymes are indicated.

FIGS. 4A-B. Proposed biosynthetic pathway for orsellinic acid synthesis by evrJ and malonylCo-A synthesis by evbD. (A) Orsellinic acid biosynthesis. (B) Malonyl-CoA biosynthesis.

FIGS. 5A-B. Biosynthetic pathway for D-6-deoxysugar and L-6-deoxysugar biosynthesis by evrV, evrW, and evrX.

FIG. 6. Map of pSPRH830B *E. coli-Micromonospera* shuttle vector.

FIG. 7A B(1)-(4). (A) Map of pSPRH840 integrating vector. (B) Sequence of integrase gene (SEQ ID NO: 176) and deduce amino acid (SEQ ID NO: 177).

FIG. 8. Map of pSPRH826b insertion plasmid.

FIGS. 9A-B. Analysis of *M. carbonacea* and *M. halophytica* pSPRH840 insertion site att-B/attP region. A(1)-(2) Alignment of pMLP1 attP region with religation clone edge sequences. (B) pMLP1 attP.

FIG. 10. Schematic of specific resistance gene-containing fragments for cloning in the pSPRH830 vector.

Figure 11A:
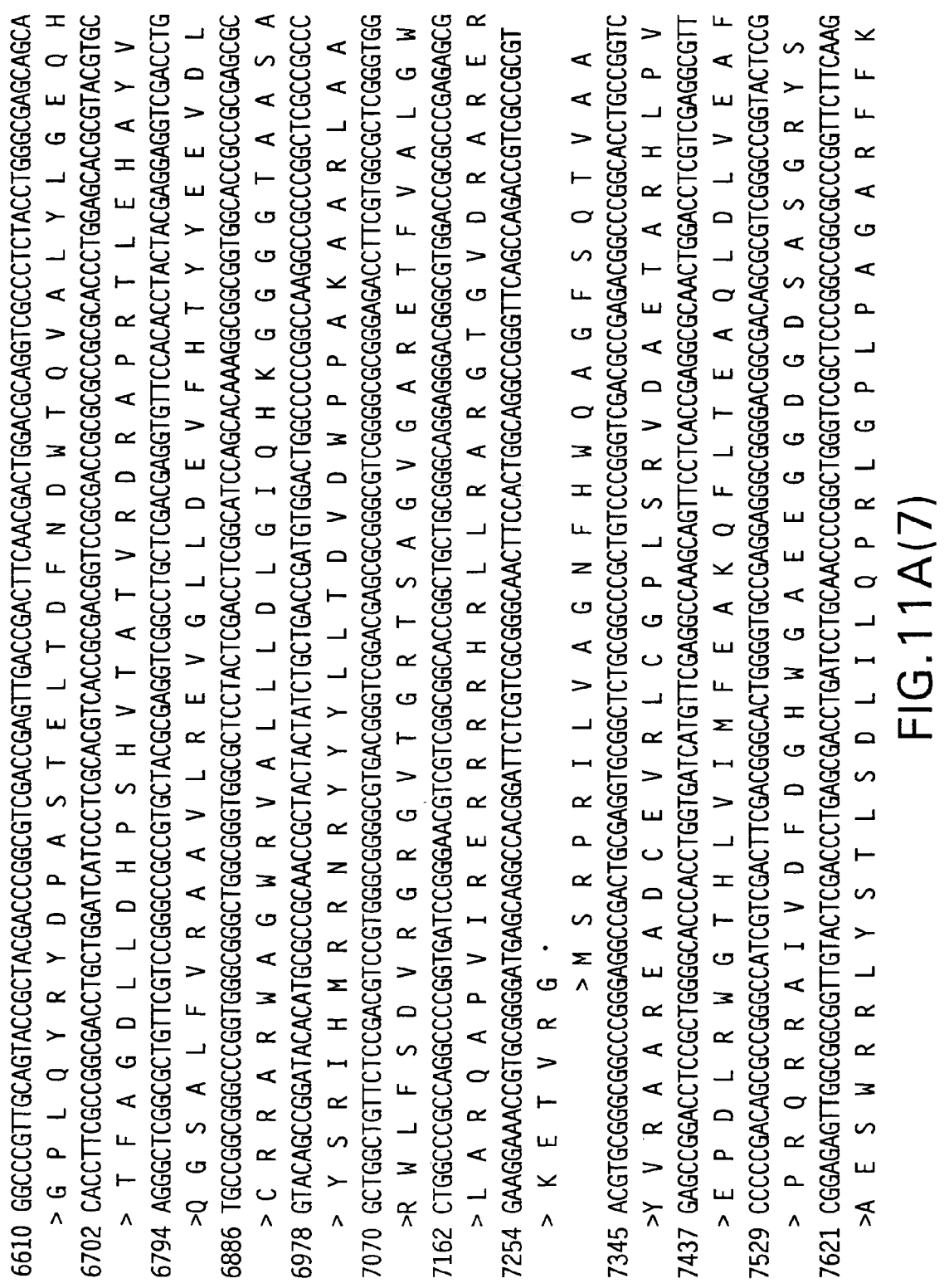
Figure 11A:
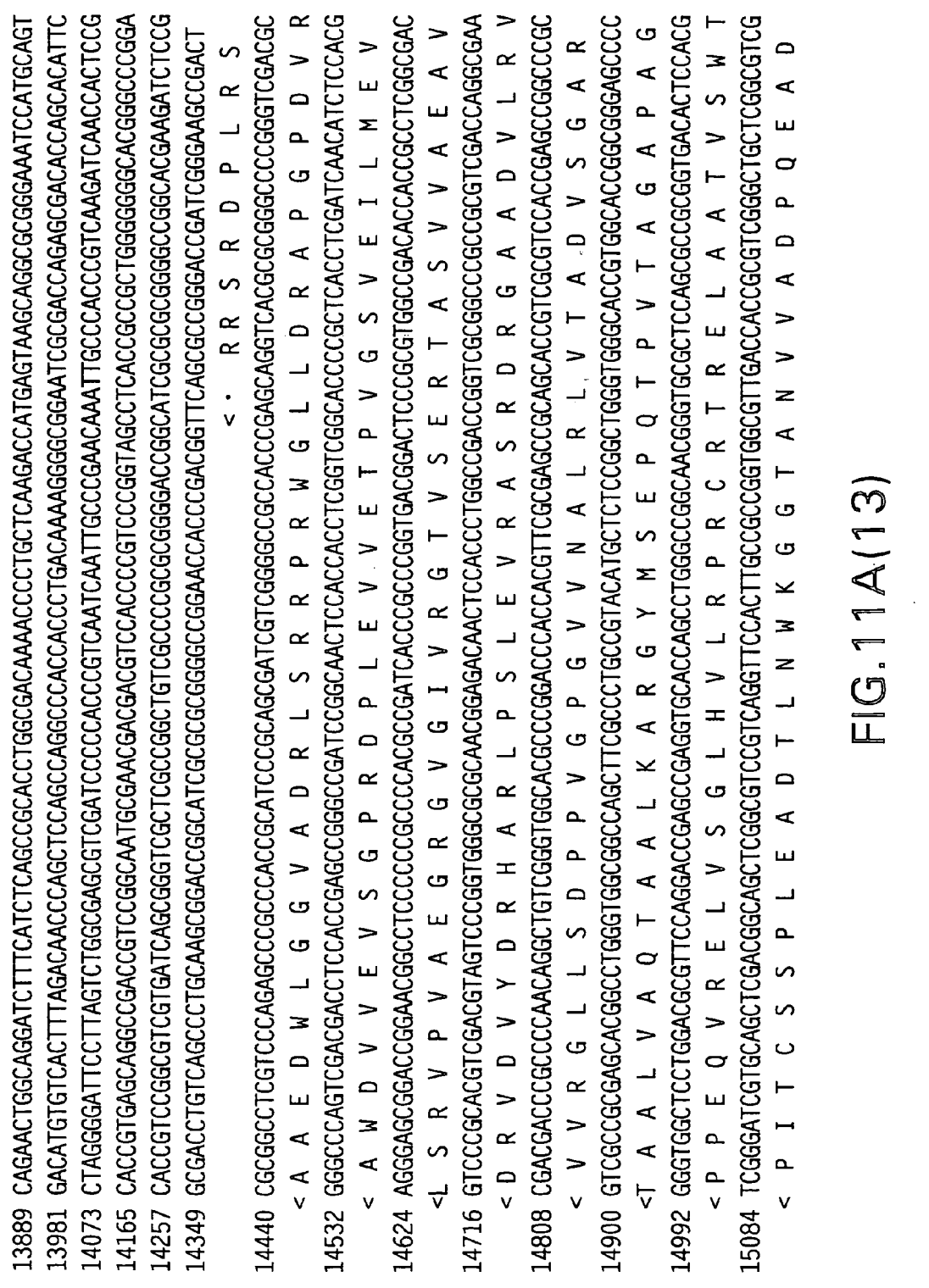
Figure 11A:
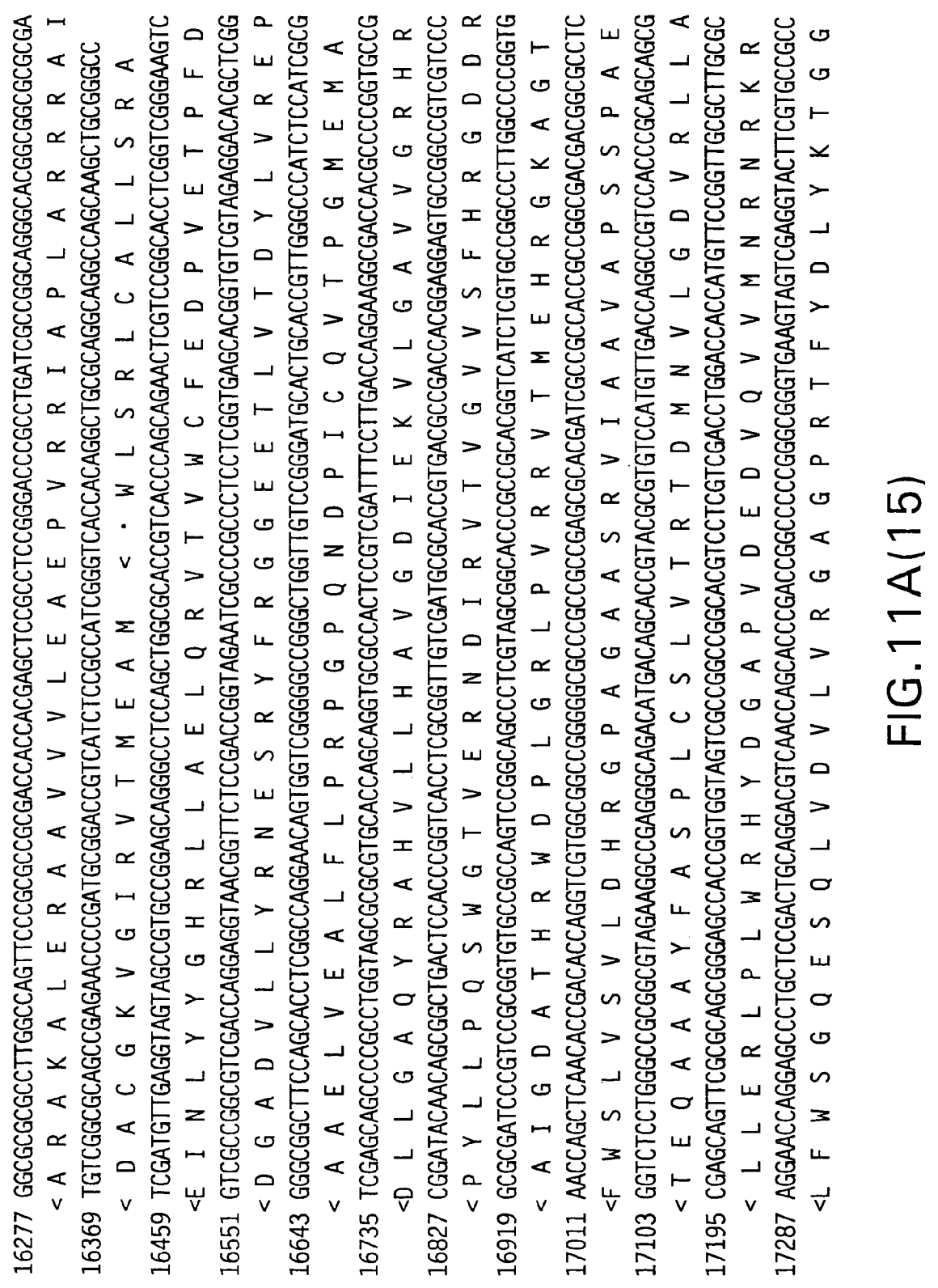
Figure 11A:
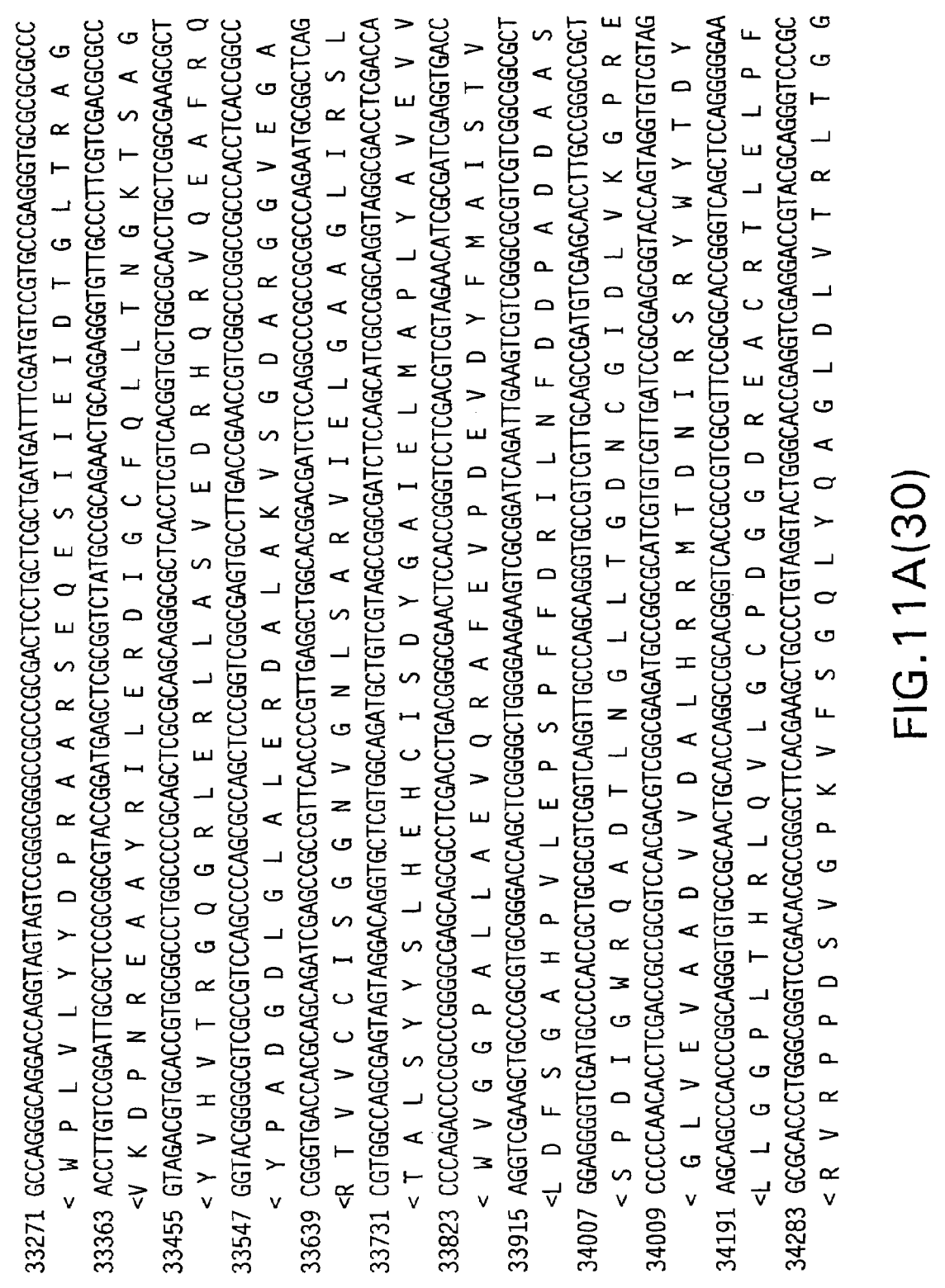
Figure 11A:
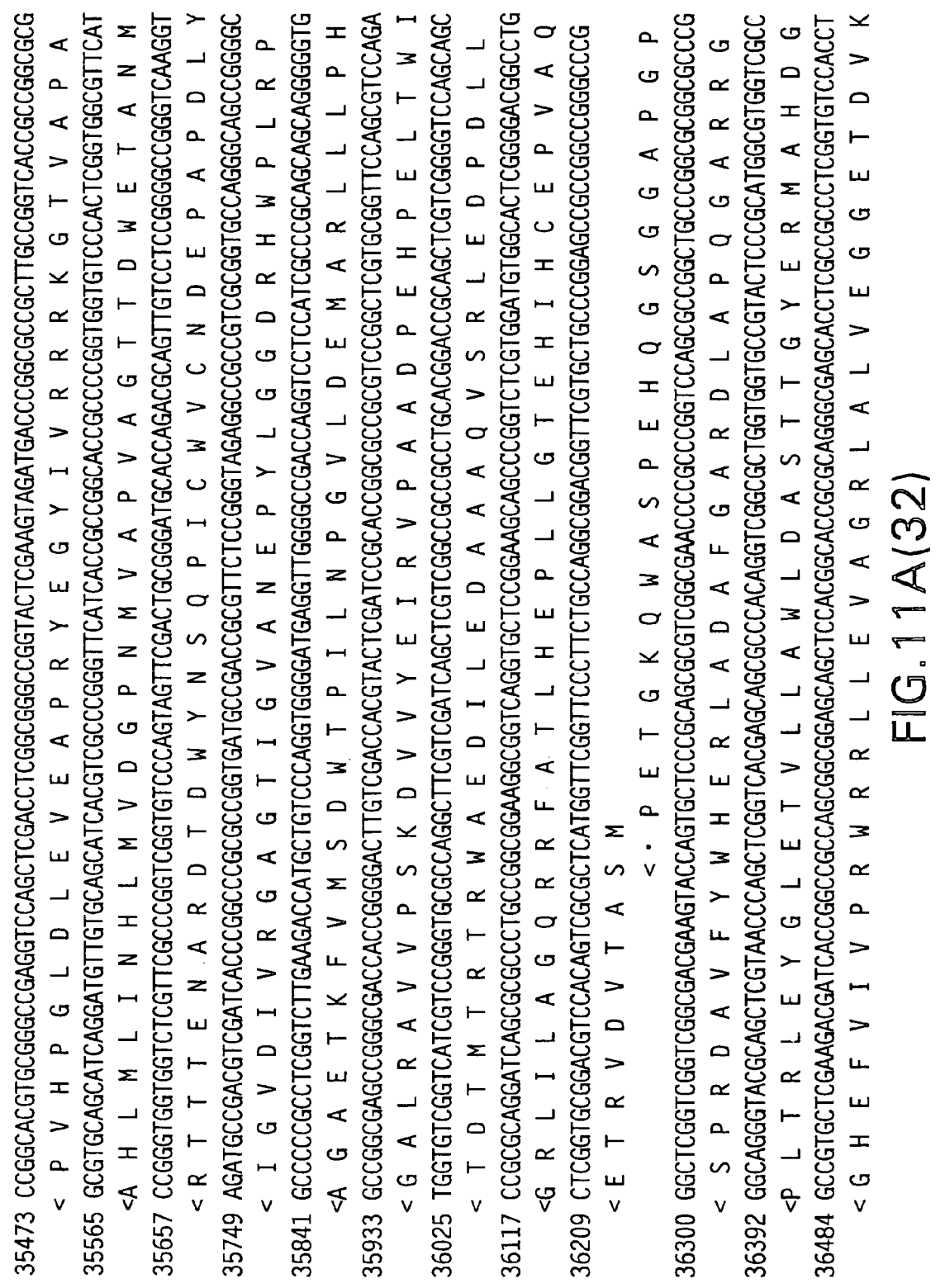
Figure 11A:
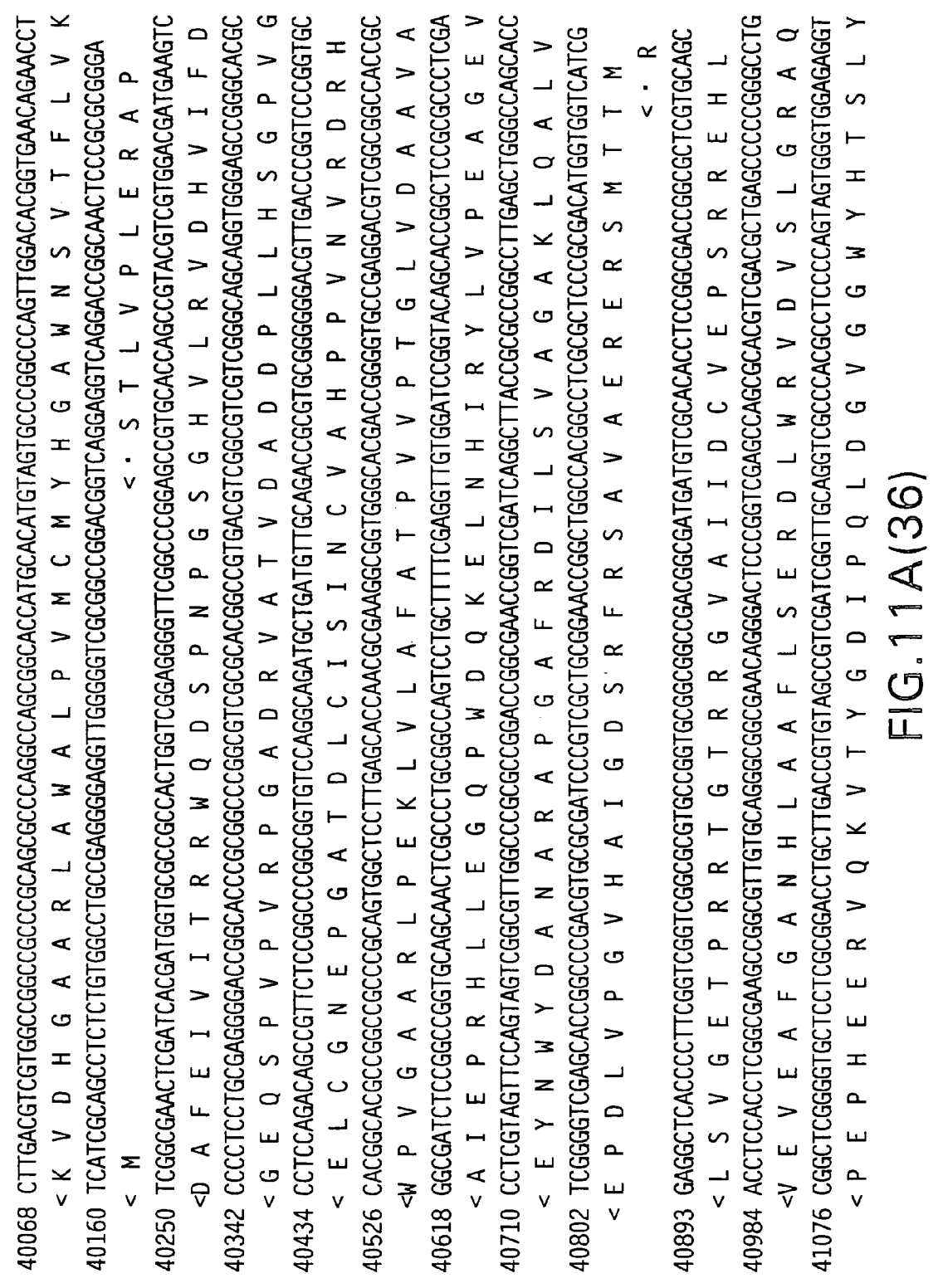
Figure 11A:
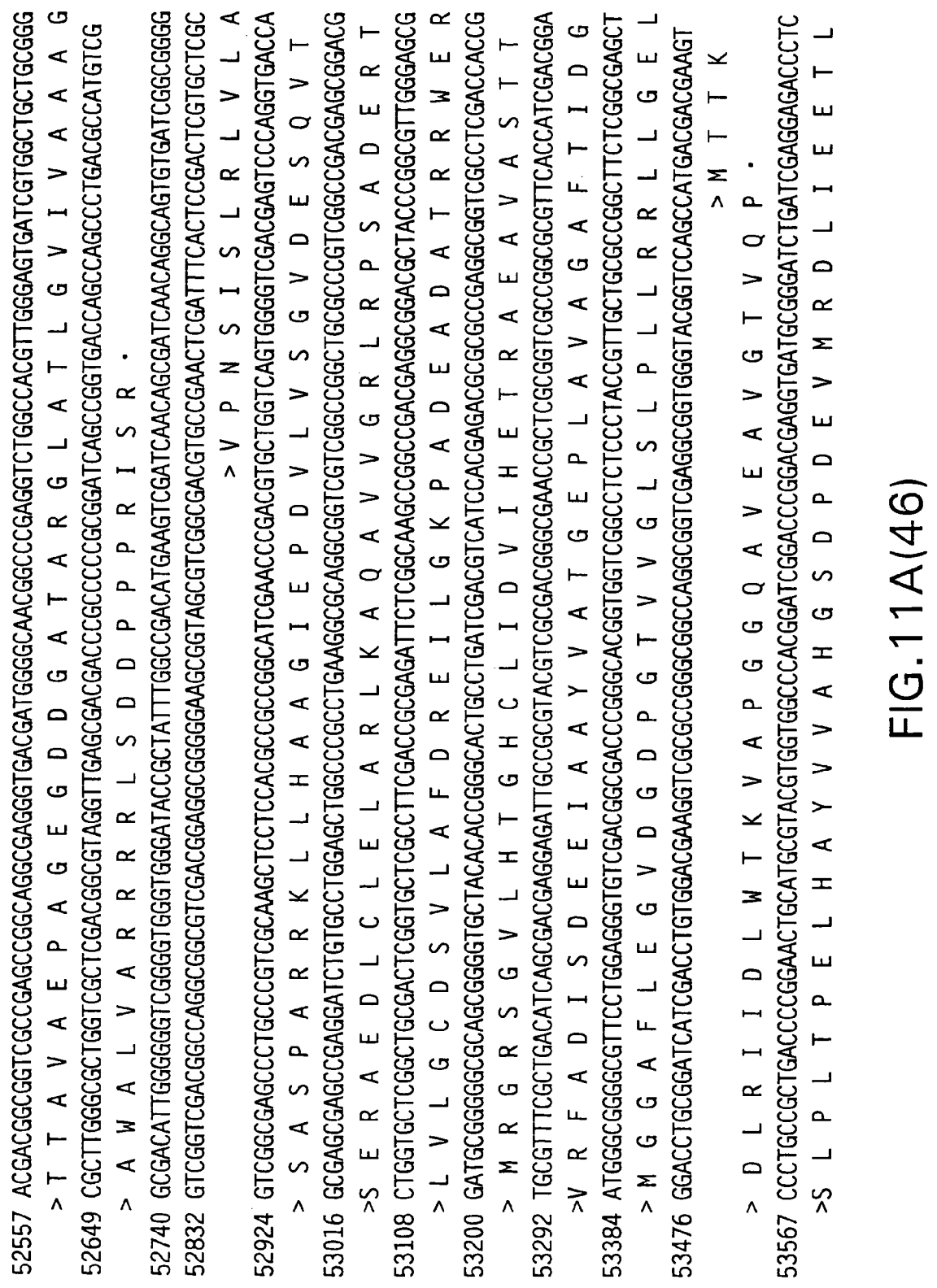
Figure 11A:
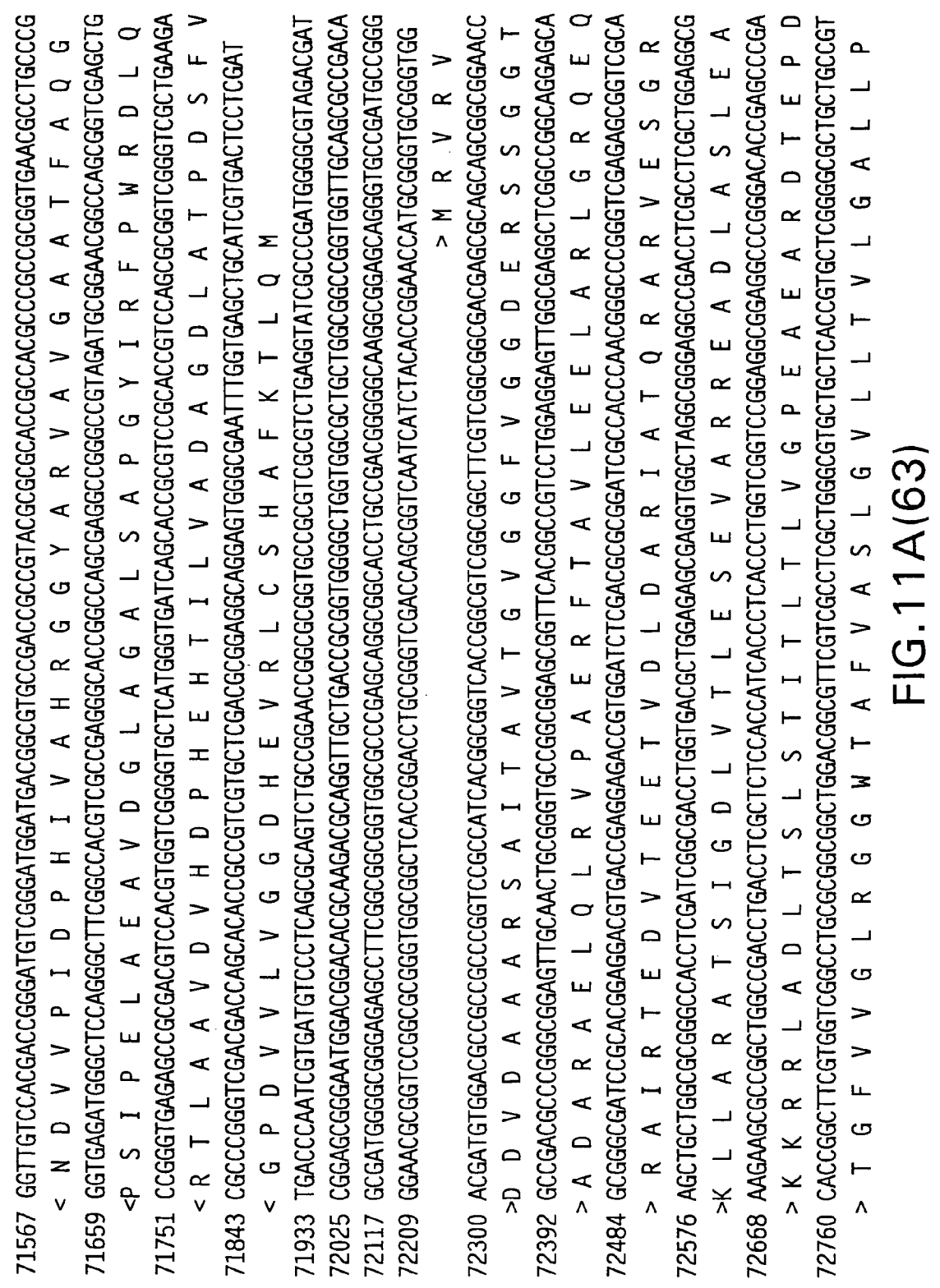
Figure 11A:
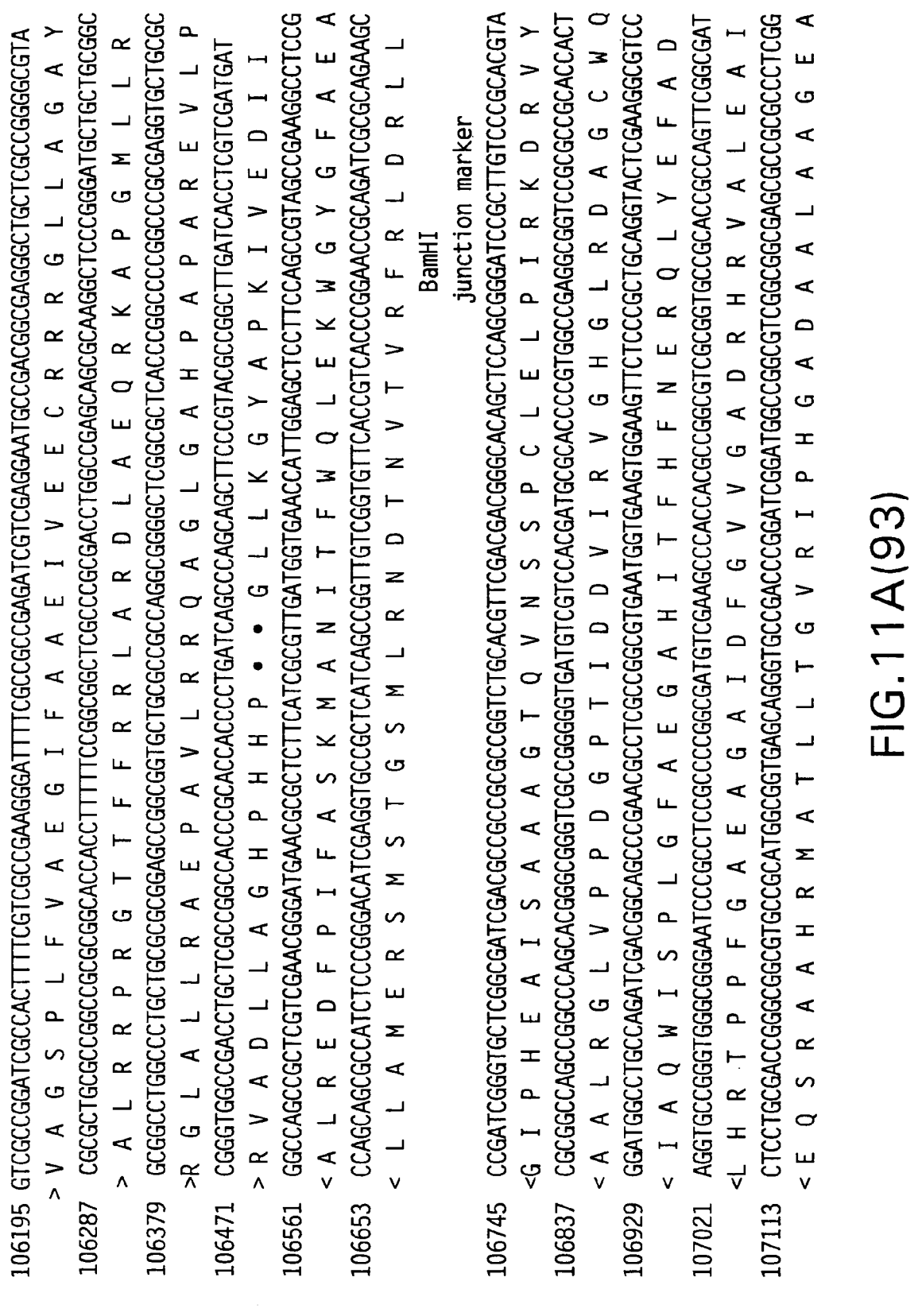

FIG. 11A(1)-(95). Everninomicin biosynthetic pathway locus sequence (SEQ ID NO:1) with open reading frames and deduced amino acid sequences (SEQ ID NOS: 2-175).

Figure 12A:
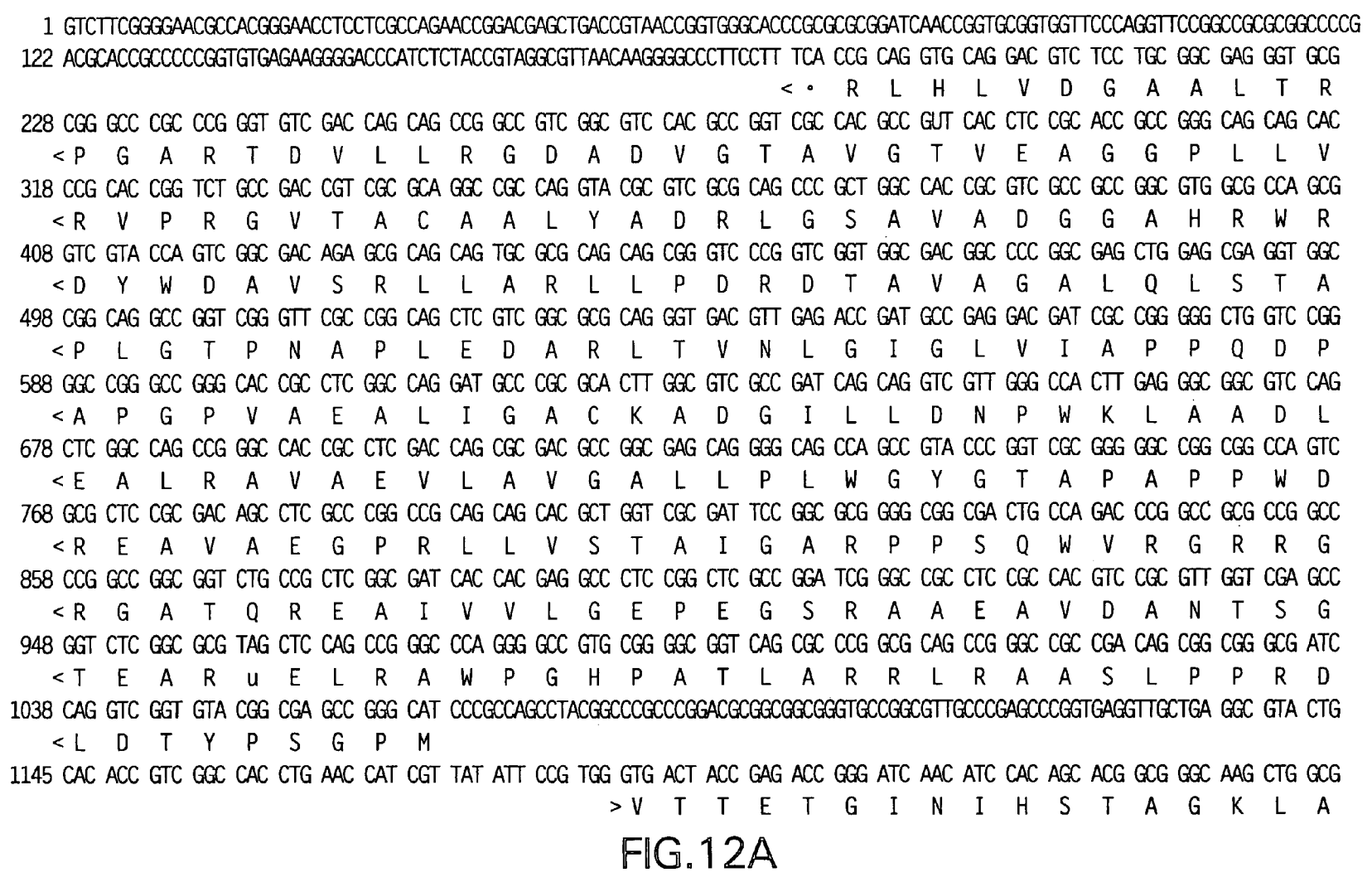
Figure 12C:
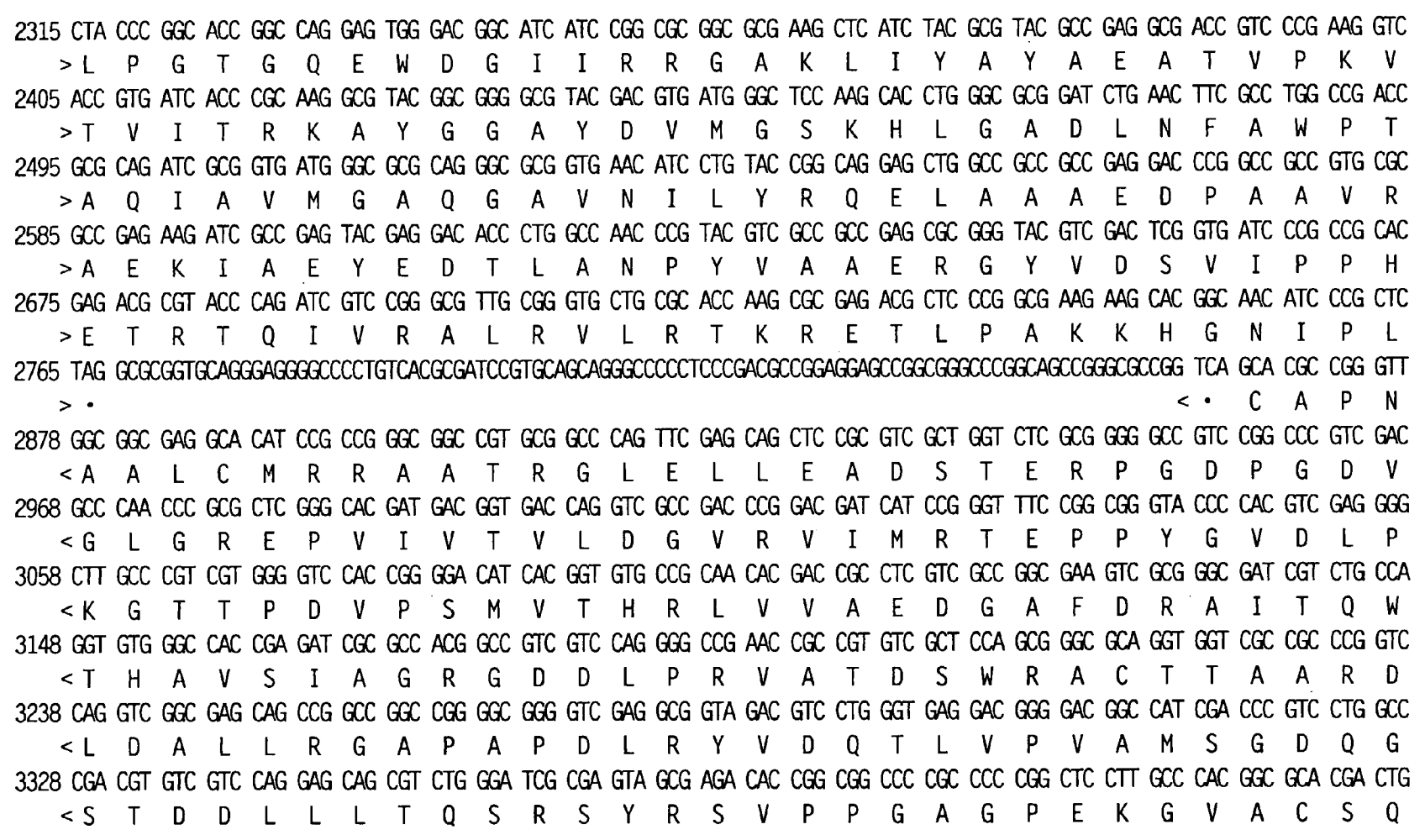
Figure 12D:
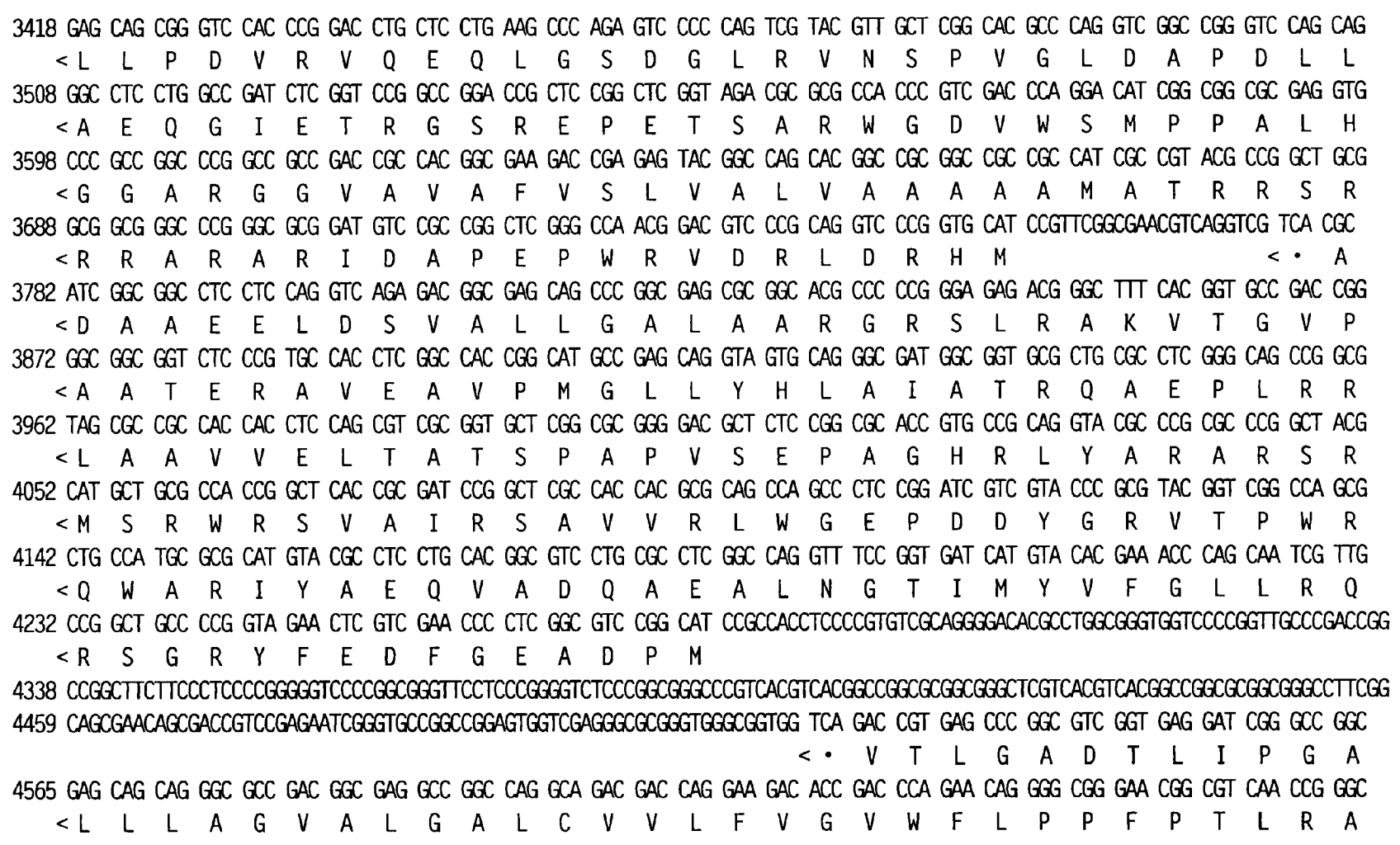
Figure 12F:
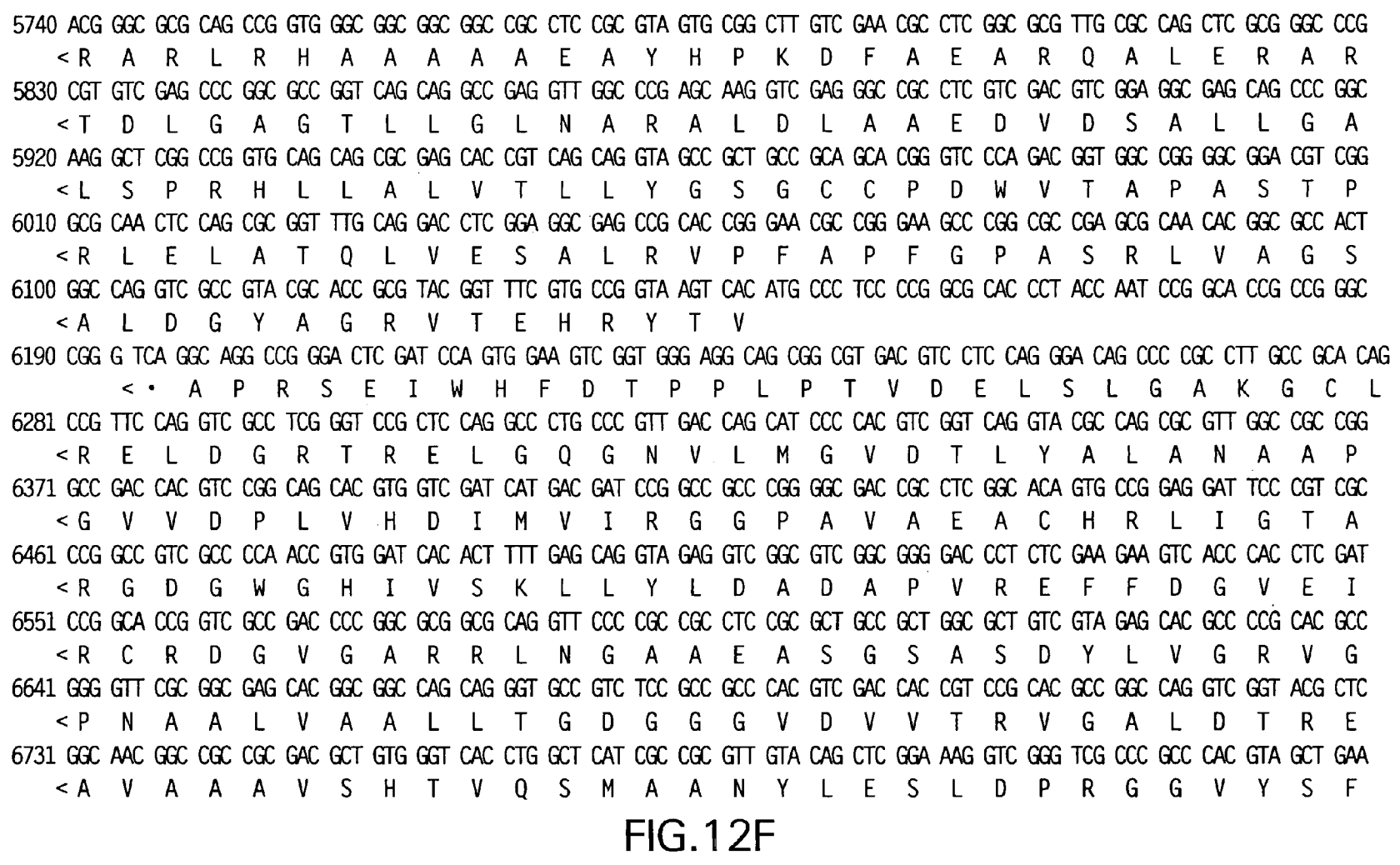
Figure 12H:
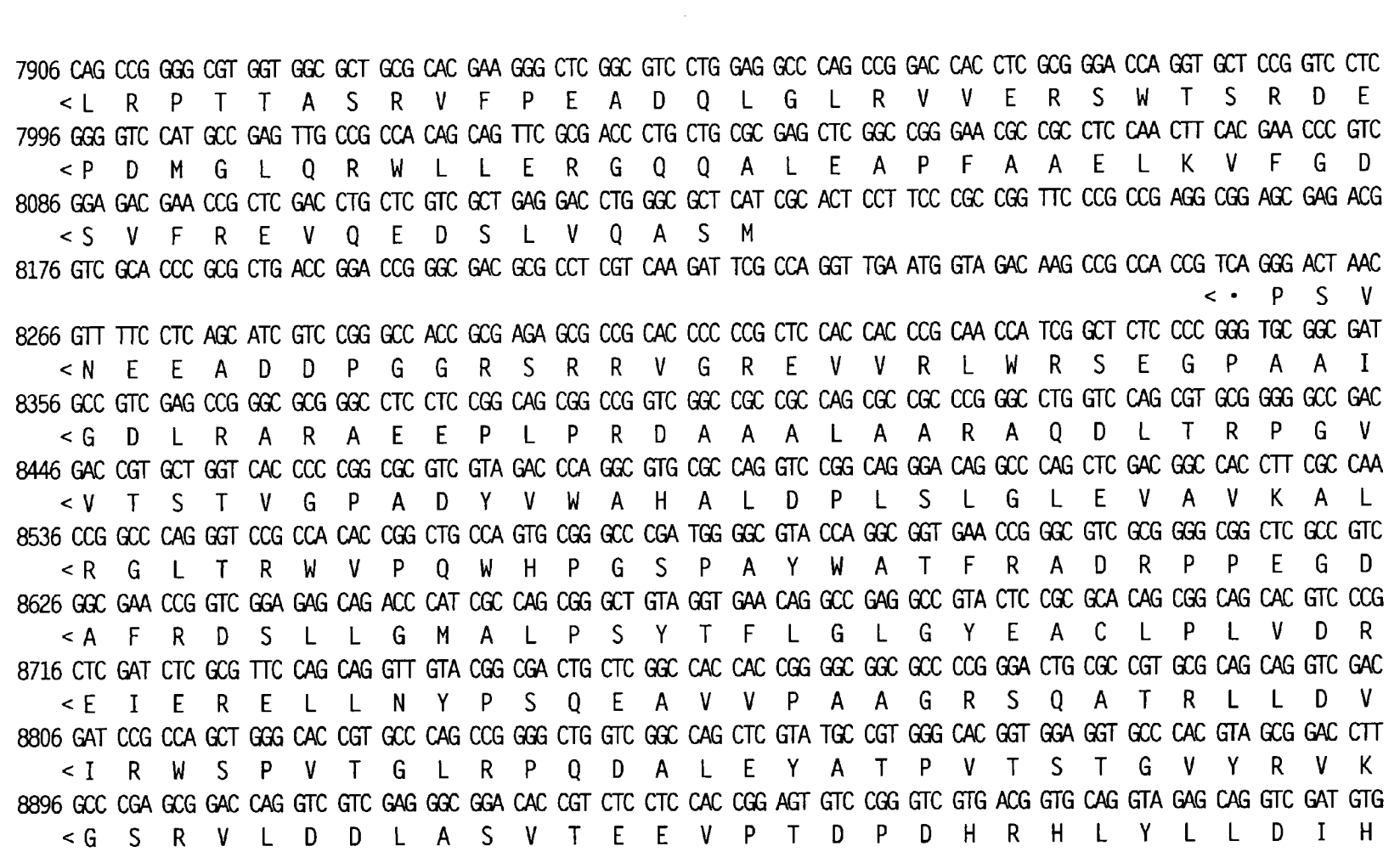
Figure 12J:
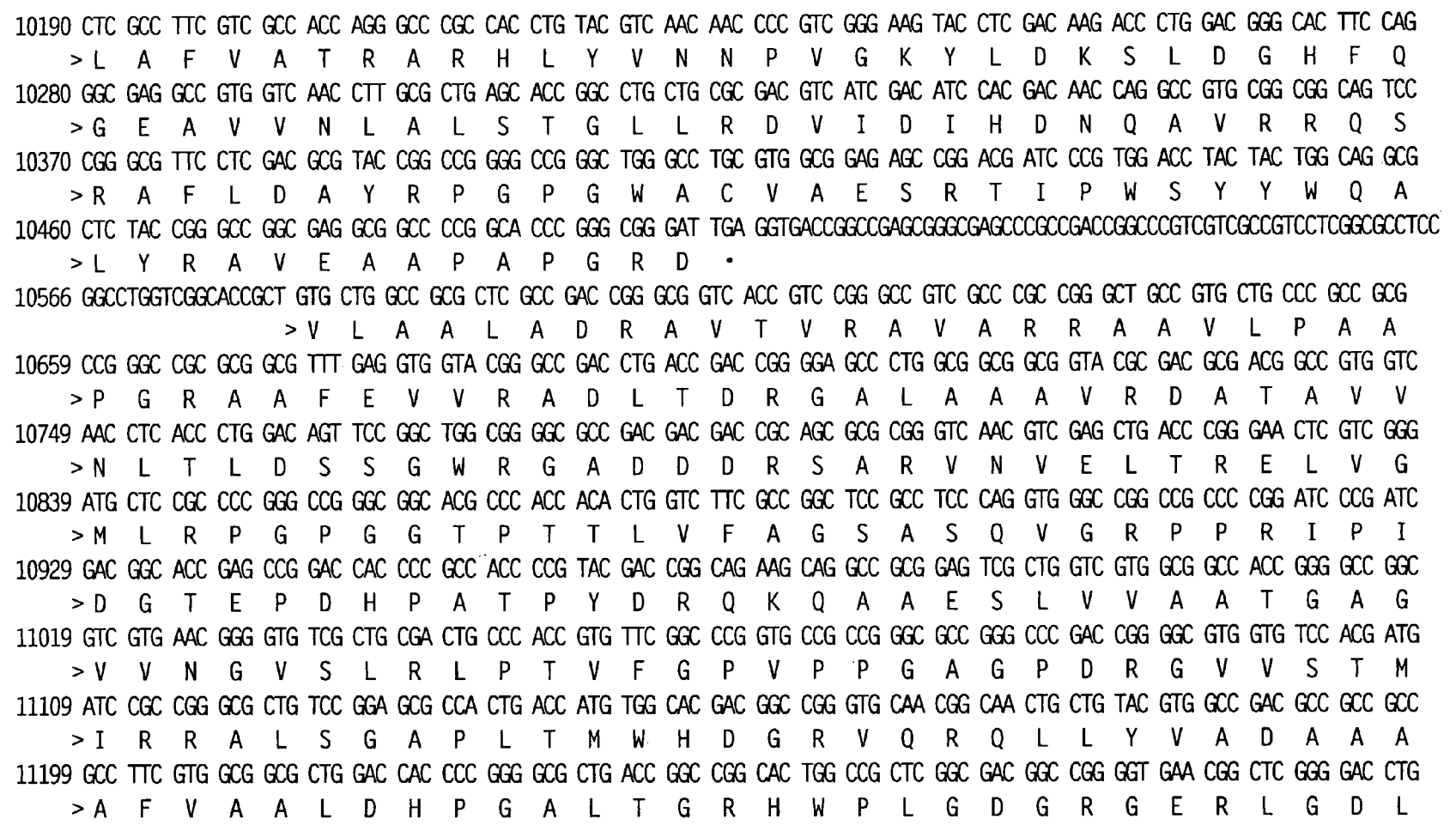

FIGS. 12A-K. Everninomicin biosynthetic pathway locus sequence (SEQ ID NO: 182) with open reading frames and deduced amino acid sequences (SEQ ID NOS: 183-204).

DETAILED DESCRIPTION

*Micromonospora carbonacea* var. *africana* produces several antibiotics, including everninomicin, thiostrepton, chloramphenicol and lasilosid. As noted above, the present invention advantageously provides the DNA sequence for the gene cluster responsible for encoding everninomicin biosynthetic genes, which provide the machinery for producing everninomicin. As a result, the present invention provides the information needed to synthesize novel everninomicin-related compounds based on everninomicin, arising from modifications of this DNA sequence designed to change glycosyl and modified orsellinic acid groups contained in everninomicin.

The invention also advantageously provides an *M. carbonacea*-specific integrase gene and integration sites (see, FIGS. 7B, 9A, and 9B). Use of the pMLP1 att/int site specific integration function allows for increasing a given gene dosage and for adding heterologous genes that lead to the formation of new products, such as hybrid antibiotics. This procedure has many advantages over methods involving autonomously replicating plasmids. In particular, a plasmid containing pMLP1 att/int functions would integrate as a single copy per chromosome. Plasmids comprising the site-specific integrating function would introduce the gene of choice into the chromosome of actinomycetes. Vectors lacking actinomycete origins of replication can only exist in their integrated form in actinomycetes. Integrated vectors are extremely stable which allows the gene copies to be maintained without antibiotic selective pressure. The site-specific nature of the integration allows analysis of the integrants.

"Everninomicin" refers to a lipophilic oligosaccharide antibiotic of the orthosomycin family of antibiotics, which contain at least one acidic phenolic hydrogen, and two orthoester linkages associated with the glycosy residues (FIG. 1; see, PCT Publication No. WO 93/07904). These include for example everninomicin, curamycin, avilamycin and flambamycins (Ganguly et al., J.C.S. Chemical Communication, 1976, pp. 609-611; "Kirk-Othmer, Encyclopedia of Chemical Technology", Vol 2, 1978, Third Edition, John Wiley and Sons, pp. 205-209; Ollis, et al., Tetrahedron, 1979, 35:105-127). These lipophilic oligosaccharide antibiotics exhibit broad spectrum biological activity against gram positive and some gram negative bacteria in various in vitro assays, and in vivo activity, for example, in animal models such as murine models of gram positive infection.

Figure 2A:
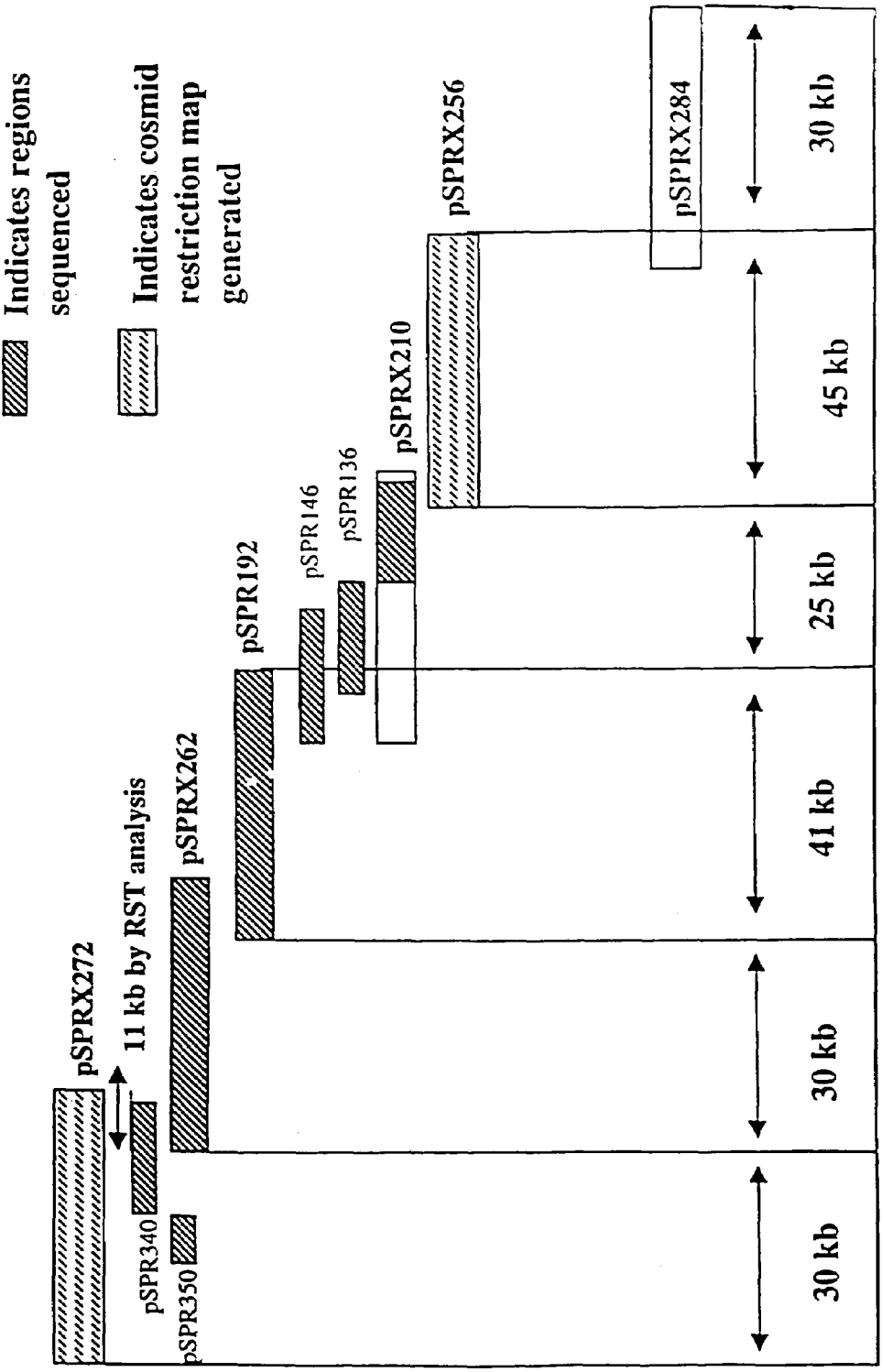

An "everninomicin (EV) biosynthetic pathway gene product" from a *Micromonospora carbonacea* refers to any enzyme ("EV biosynthetic enzyme") involved in the biosynthesis of everninomicin. These genes are located in the EV biosynthetic locus on the *M. carbonacea* chromosome. This locus is depicted in FIGS. 2A and 3. Since everninomicin is only known to be produced in *M. carbonacea*, for the sake of particularity the EV biosynthetic pathway is associated with this microorganism. However, it should be understood that this term encompasses EV biosynthetic enzymes (and genes encoding such enzymes) isolated from any *M. carbonacea*, and furthermore that these genes may have novel homologues in related actinomycete bacteria that fall within the scope of the claims here. In specific embodiments, these genes are depicted in FIG. 11 (SEQ ID NO:1; open reading frames and polypeptides designated as SEQ ID NOS: 2-175) and FIG. 12 (SEQ ID NO: 182; open reading frames and polypeptides designated as SEQ ID NOS: 183-204). It is noted that the sequences of FIGS. 11 and 12 are linked (contiguous) or connected such that they are part of the same cluster, i.e., the sequence in FIG. 12 precedes that of FIG. 11. Moreover, the present inventors have identified specific categories into which many of the genes from the EV biosynthetic pathway fall, including but by no means limited to, orsellinic acid biosynthetic enzymes, sugar biosynthetic enzymes, glycosyltransferases, tailoring enzymes, regulatory enzymes (serine-threonine kinases), and resistance mechanism enzymes (rRNA methylases and transporter enzymes). These categories are discussed in greater detail, infra. The gene products are listed in Tables 1a and 1b.

TABLE 1a

Gene Products and Putative Enzymatic Functions Involved in Everninomicin Production

| Gene Product | CDS[1] | RBS[2] | SEQ ID NO.[4] | Enzymatic Function (Protein ACC No; BLAST Score) | Class |
|---|---|---|---|---|---|
| evdA length 416aa | (132 . . . 1382)* | (1389 . . . 1394)* | 2, 3 | similarity to hydroxylase (CAA11782; 6.5e−137) | sugar biosynthetic |
| evdB length 373aa | (1490 . . . 2611)* | (2618 . . . 2622)* | 4, 5 | hexose aminotransferase, dnrJ homolog (daunorubicin) (P25048; 2.8e−65) | sugar NH2 addition |
| evdC length 412aa | (2622 . . . 3860)* | (3867 . . . 3870)* | 6, 7 | similar to flavoprotein, oxidase (S39965; 4.4e−92) | sugar biosynthetic |
| evdD length 389aa | (4143 . . . 5312) | (4134 . . . 4138) | 8, 9 | dNTP -hexose glycosyltransferase (AAC01731; 4.6e−49) | Glycosyl transfer |
| evdE length 308aa | (5309 . . . 6235) | | 10, 11 | hexose dehydratase (CAA18814; 8.0e−58) | sugar biosynthetic |
| evdF length 347aa | (6232 . . . 7275) | (6226 . . . 6229) | 12, 13 | dNTP-hexose glycosyltransferase (CAB07092; 3.4e−18) | Glycosyl transfer |
| evdG length 351aa | (7272 . . . 8327) | | 14, 15 | unknown | unknown |
| evdH length 340aa | (8342 . . . 9364) | (8333 . . . 8336) | 16, 17 | dNTP-hexose glycosyltransferase (CAA19930; 0.8) | Glycosyl transfer |
| evdI length 253aa | (9463 . . . 10,224)* | (10,232 . . . 10,235)* | 18, 19 | hydrolase (AAB81835; 6.8e−10) | sugar biosynthetic |
| evdJ length 250aa | (10,424 . . . 11,176) | | 20, 21 | unknown | unknown |

TABLE 1a-continued

Gene Products and Putative Enzymatic Functions Involved in Everninomicin Production

| Gene Product | CDS[1] | RBS[2] | SEQ ID NO.[4] | Enzymatic Function (Protein ACC No; BLAST Score) | Class |
|---|---|---|---|---|---|
| evdK length 415aa | (11,208 ... 12,455) | | 22, 23 | hexose dehydratase or empimerase (CAB08849; 3.3e−26) | sugar biosynthetic |
| evdL length 304aa | (12,108 ... 13,022)* | (13,027 ... 13,030)* | 24, 25 | dNTP-hexose glycosyltransferase (S37028; 0.010) | Glycosyl transfer |
| evrA length 317aa | (14,410 ... 15,363)* | (15,369 ... 15,373)* | 26, 27 | hexose epimerase (CAA12010.1; 1.3e−40) | sugar biosynthetic |
| evrB length 344aa | (15,380 ... 16,414)* | | 28, 29 | hexose oxidoreductase (ACC01734; 1.3e−65) | sugar biosynthetic |
| evrC length 484aa | (16,419 ... 17,873)* | | 30, 31 | hexose dehydratase (CAA12009; 2.2e−107) | sugar biosynthetic |
| evrD length 354aa | (17,870 ... 18,934)* | | 32, 33 | GDP-mannose 4,6-dehydratase (BAA16585; 1.0e−88) | sugar biosynthetic |
| evrE length 510aa | (19,374 ... 20,906) | | 34, 35 | multidrug efflux transporter (CAB15277; 1.4e−59) | resistance mechanism |
| evrF length 492aa | (21,064 ... 22,542) | (21,056 ... 22,542) | 36, 37 | similar to non-heme oxygenate/halogenase (CAA11780; 4.3e−58) | orsellinic acid chlorine addition |
| evrG length 474aa | (22,748 ... 24,172) | (22,736 ... 22,740) | 38, 39 | oxidase (Q12737; 5.5e−67) | tailoring |
| evrH length 348aa | (24,177 ... 25,223)* | (25,230 ... 25,233)* | 40, 41 | unknown (AAB89073; 3.2e−6) | unknown |
| evrI length 358aa | (25,550 ... 26,626) | | 42, 43 | acyl starter unit fidelity (daunorubicin homology) (AAA65208; 5.7e−56) | PKS acyl Carbon choice |
| evrJ length 1264aa | (26,685 ... 30,479) | (26,672 ... 26,676) | 44, 45 | orsellinic acid synthase 6-methylsalicilic acid synthetase (CAA72713; 0.0e) | polyketide synthetase |
| evrK length 439aa | (30,557 ... 31,876)* | (31,885 ... 31,888)* | 46, 47 | Na/H antiporter (BAA16991; 2.1e−14) | unknown |
| evrL length 313aa | (31,941 ... 32,882)* | | 48, 49 | similar to gene essential to heme biosynthesis (BAA12681; 0.0012) | unknown |
| evrM length 412aa | (33,167 ... 34,405)* | (34,414 ... 34,418)* | 50, 51 | similar to p450 hydroxylase (S18530; 3.8e−70) | tailoring |
| evrN length 253aa | (34,449 ... 35,210)* | (35,219 ... 35,221)* | 52, 53 | methyl transferase (CAB10751; 0.00061) | tailoring |
| evrO length 314aa | (35,294 ... 36,238)* | | 54, 55 | unknown (BAA20094; 0.56) | unknown |
| evrP length 242aa | (36,235 ... 36,963)* | | 56, 57 | unknown (CAB05421; 0.00020) | unknown |
| evrQ length 342aa | (36,998 ... 38,026)* | | 58, 59 | similar to oxidoreductase and heat stress protein (P80874; 7.8e−31) | tailoring |
| evrR length 164aa | (38,072 ... 38,566)* | | 60, 61 | low similarity to hexaheme nitrite reductase regulator (P30866; 0.0034) | regulatory (methyl transferase) |
| evrS length 423aa | (38,892 ... 40,163)* | | 62, 63 | dNTP-hexose glycosyltransferase (AAD15267; 1.9e−36) | Glycosyl transfer |
| evrT length 224aa | (40,216 ... 40,890)* | (40,899 ... 40,902)* | 64, 65 | similar to L-proline hydroxylase (BAA 20094; 5.5e−7) | tailoring |
| evrU length 229aa | (40,887 ... 41,576)* | | 66, 67 | methyltransferase (CAB02029; 5.6e−6) | tailoring |
| evrV length 342aa | (41,679 ... 42,707)* | (42,714 ... 42,717)* | 68, 69 | dTDP-glucose epimerase (AAB84886; 3.5e−36) | L-dTDP-glucose biosynthetic |

TABLE 1a-continued

Gene Products and Putative Enzymatic Functions Involved in Everninomicin Production

| Gene Product | CDS[1] | RBS[2] | SEQ ID NO.[4] | Enzymatic Function (Protein ACC No; BLAST Score) | Class |
|---|---|---|---|---|---|
| evrW length 329aa | (42,810 ... 43,799)* | (43,807 ... 43,811)* | 70, 71 | dTDP-glucose dehydratase (CAA72715; 5.1e–136) | D-dTDP-glucose biosynthetic (GDH) |
| evrX length 355aa | (43,799 ... 44,866)* | | 72, 73 | dTDP-glucose synthetase (A26984; 1.2e–118) | D-dTDP-glucose biosynthetic |
| evrY length 248aa | (45,014 ... 45,760)* | (45,767 ... 45,770)* | 74, 75 | dehalogenase (P24069; 5.8e–8) | drug resistance |
| evrZ length 250aa | (45,962 ... 46,714)* | (45,952 ... 45,956)* | 76, 77 | similar to muramidase/lysozyme (P25310; 1.2e–77) | drug resistance |
| evsA length 692aa | (47,156 ... 49,234)* | | 78, 79 | serine threonine kinase (BAA32455; 2.0e–76) | regulatory |
| evsB length 362aa | (51,627 ... 52,715) | (51,620 ... 51,622) | 80, 81 | similar to proteases | unknown |
| evsC length 222aa | (52,889 ... 53,557) | | 82, 83 | similar to MAF involved in septum formation (BAA18425; 1.3e–21) | unknown |
| evbA length 217aa | (53,554 ... 54,207) | | 84, 85 | O-methyl transferase (AAC44130; 8.6e–38) | tailoring; possible resistance |
| evbB length 251aa | (54,362 ... 55,117)* | (55,125 ... 55,128)* | 86, 87 | membrane pump, homolog mithramicin resistance (AAC443581; 2.9e–24) | resistance mechanism |
| evbC length 319aa | (55,135 ... 56,094)* | (56,100 ... 56,103)* | 88, 89 | membrane pump, homolog mithramicin resistance (AAC44357; 1.0e–69) | resistance mechanism |
| evbC2 length 198aa | (56,184 ... 56,813)* | | 90, 91 | ankrylin like (AAC44356; 0.0041) | resistance |
| evbD length 582aa | (56,961 ... 58,709) | (56,947 ... 56,951) | 92, 93 | acyl-CoA carboxylase (CAB07068; 7.3e–201) | malonyl-CoA biosynthesis |
| evbE length 479aa | (58,873 ... 60,312) | | 94, 95 | IMP dehydrogenase (CAA15452; 4.1e–165) | tailoring |
| evbF length 185aa | (60,472 ... 61,029)* | (61,038 ... 61,040)* | 96, 97 | hypothetical protein Rv0653c, *mycobacterium* (CAB07128; 3.8e–06) | regulator |
| evbF1 length 90aa | (61,288 ... 61,560) | | 98, 99 | unknown | unknown |
| evbF2 length 152aa | (61,610 ... 62,069) | (61,597 ... 61,599) | 100, 101 | ORFI *Streptomyces peucetius* (CAA06602; 0.024) | regulatory/ resistance |
| evbG length 557aa | (62,122 ... 63,795) | | 102, 103 | ABC transporter (Q11046; 2.7e–170) | drug resistance |
| evbH length 645aa | (63,891 ... 65,828) | (63,884 ... 63,887) | 104, 105 | ABC transporter (Q11047; 5.6e–166) | drug resistance |
| evbI length 467aa | (66,469 ... 67,872)* | (67,883 ... 67,886)* | 106, 107 | lipoamide dehydrogenase (CAA17075; 1.6e–140) | tailoring |
| evbJ length 151aa | (67,979 ... 68,434) | | 108, 109 | hypothetical protein Rv3304 [*Mycobacterium tuberculosis*] (CAA17076; 7.6e–40) | unknown |
| evbK length 321aa | (68,529 ... 69,494) | | 110, 111 | protease synthase and sporulation regulator; homology to resistance proteins *Streptomyces* (029729; 7.3-7) | regulatory |
| evbL length 249aa | (69,610 ... 70,359)* | | 112, 113 | acetyltransferase/ phosphotransferase | tailoring |
| evbM length 306aa | (70,365 ... 71,285)* | | 114, 115 | hypothetical protein Rv 1584c [*Mycobacterium tuberculosis*] (CAB09085; 0.32) | unknown |

TABLE 1a-continued

Gene Products and Putative Enzymatic Functions Involved in Everninomicin Production

| Gene Product | CDS[1] | RBS[2] | SEQ ID NO.[4] | Enzymatic Function (Protein ACC No; BLAST Score) | Class |
|---|---|---|---|---|---|
| evbN length 209aa | (71,289 ... 71,918)* | (71,926 ... 71,929)* | 116, 117 | hypothetical protein SC3A7.08 [S. coelicolor] (CAA20071; 4.0e−40) | unknown |
| evbO length 230aa | (72,284 ... 72,979) | | 118, 119 | putative lipoprotein [S. coelicolor] (CAA19252; 2.6e−20) | unknown |
| evbP length 420aa | (72,933 ... 74,195)* | | 120, 121 | peptidase (CAA17077; 6.5e−88) | unknown |
| evbQ length 527aa | (74,707 ... 76,290)* | | 122, 123 | methylmalonyl-Coa mutase (BAA30410; 1.8e−149) | acyl precursor biosynthesis |
| evbR length 696aa | (76,622 ... 78,712) | | 124, 125 | protein serine/threonine kinase note eukaryotic type (BAA32455; 1.1e−71) | regulatory |
| evbS length 576aa | (78,791 ... 80,521) | | 126, 127 | phosphomannomutase (CAA17080; 5.4e−91) | sugar biosynthesis |
| evbT length 286aa | (82,073 ... 82,933) | | 128, 129 | hypothetical protein SC5C7.22c (CAA20634; 5.7e−28) | 10–28 |
| evbU length 202aa | (83,280 ... 83,888)* | | 130, 131 | glucose-6-phosphate 1-dehydrogenase low BLAST homology (S61167; 0.00039) | unknown |
| evbV length 193aa | (84,080 ... 84,661)* | | 132, 133 | uracil phosphoribosyl transferase (CAA17081; 5.6e−60) | unknown |
| evbW length 338aa | (84,890 ... 85,906)* | | 134, 135 | deoxyribose-phosphate aldolase (AAA79343; 1.3e−54) | unknown |
| evbX length 477aa | (85,909 ... 87,342) | | 136, 137 | aldehyde dehydrogenase (AAB84440; 4.2e−103) | tailoring |
| evbY length 245aa | (87,422 ... 88,159) | (87,407 ... 87,411) | 138, 139 | aldehyde dehydrogenase (CAA71003; 3.4e−16) | tailoring |
| evbZ length 137aa | (88,292 ... 88,705) | (88,280 ... 88,282) | 140, 141 | hypothetical protein (CAB06141; 1.3e−16) | unknown |
| evcA length 301aa | (88,716 ... 89,621) | | 142, 143 | hypothetical protein, putative integral membrane protein [Streptomyces coelicolor] (CAB06143; 4.5e−28) | unknown |
| evcB length 416aa | (89,817 ... 91,067) | | 144, 145 | cytochrome D oxidase subunit I (P94364; 3.0e−65) | tailoring |
| evcC length 335aa | (91,078 ... 92,085) | (91,068 ... 91,072) | 146, 147 | cytochrome D oxidase subunit II (CAA71118; 1.9e−15) | tailoring |
| evcD length 561aa | (92,148 ... 93,833) | | 148, 149 | ABC transporter (CAA22219; 2.6e−107) | resistance |
| evcE length 613aa | (93,830 ... 95,671) | | 150, 151 | ABC transporter (AAC44070; 3.4e−32) | resistance |
| evcF length 229aa | (95,729 ... 96,418) | | 152, 153 | unknown | unknown |
| evcG length 111aa | (96,440 ... 96,775)* | | 154, 155 | unknown (AAB84787; 1.9e−8) | unknown |
| evcH length 303aa | (96,894 ... 97,805) | | 156, 157 | unknown (CAA17083; 9.2e−5) | unknown |
| evcI search length 691aa | (98,287 ... 100,362) | | 158, 159 | unknown (CAA19992; 6.0e−6) | unknown |

TABLE 1a-continued

Gene Products and Putative Enzymatic Functions Involved in Everninomicin Production

| Gene Product | CDS[1] | RBS[2] | SEQ ID NO.[4] | Enzymatic Function (Protein ACC No; BLAST Score) | Class |
|---|---|---|---|---|---|
| evcJ length 197aa | (100,733 ... 101,326)* | | 160, 161 | putative ATP/GTP binding protein (CAA19989; 7.9e−59) | unknown |
| evcJ2 length 134aa | (101,328 ... 101,732)* | | 162, 163 | unknown (CAA19986; 8.6e−23) | unknown |
| evcK length 117aa | (101,803 ... 102,156)* | | 164, 165 | unknown (CAA19991; 1.7e−36) | unknown |
| evcL search length 1145aa | (102,204 ... 105,641)* | | 166, 167 | unknown (CAA19992; 4.6e−99) | unknown |
| evcM length 201aa | (105,907 ... 105,641) | | 168, 169 | putitive uridine kinase (CAA19591; 1.0e−9) | unknown |
| evcN length 358aa | (106,513 ... 107,589) | | 170, 171 | unknown (CAA17085; 7.5e−120) | unknown |
| evrMR length 320aa | (107,653 ... 108,615) | (107,637 ... 107,641) | 172, 173 | homology to 23S rRNA methylase for mycinamicin resistance (myrA) (BAA03674; 1.4e−79) | resistance |
| evrMR2 length 193aa | (108,635 ... 109,216) | | 174, 175 | homology to gene linked to myrA | resistance |

Although the term "enzymes" is used to refer to the EV biosynthetic pathway gene products, such gene products may be proteins with non-enzymatic functions. Such proteins are also contemplated as falling within'the scope of the present invention.

An "EV biosynthetic pathway bottleneck gene" is a gene encoding a product whose level limits the rate of synthesis of everninomicin. Examples of such gene products include, though are not limited to, evrJ (involved in orsellinic acid biosynthesis); evrV, evrW, and evrX (involved in dTDP-glucose synthesis); evbD (involved in malonyl-CoA-synthesis, which is required for orsellinic acid synthesis); and oxidases responsible for oxidation of the amino group on the terminal sugar to produce everninomicin that contains a nitrososugar group. Other likely bottleneck genes include those encoding glycosyltransferases (evdD, evdF, evdH, evdL, and evrS) and tailoring enzymes, particularly sugar modification enzymes.

A modified *Micromonospora carbonacea* refers to a microorganisms that has been genetically engineered to over-express or suppress expression of an EV biosynthetic pathway gene product (enzyme). Such genetic engineering and manipulation is described in detail, infra. Preferably, to increase the level of production of everninomicin, the modified microorganism overexpresses one or more bottleneck genes. To produce an everninomicin analog or homolog, various tailoring enzyme genes (e.g., evdB, a hexose aminotransferase that produces an amino sugar; evrF, a non-heme halogenase that chlorinates the orsinillic acid; or an oxidase gene that produces a nitrososugar by oxidation of an aminosugar) may be knocked out. Other knock-outs may be made of putative key genes, resulting in all likelihood in blockage of everninomicin biosynthesis. These include the orsellinic acid synthase (evrJ), dTDP-glucose synthases (evrV, evrW, and evrX), and glycosyltransferases (evdD, evdF, evdH, evdL, and evrS). A knockout of the glycosyltransferase that adds the terminal glycosyl group is expected to produce an everninomicin analog lacking the terminal glycosyl group.

Such genetic construction can be replicated in a different actinomycete, such as a *Streptomyces*, as described infra, by introduction of all or part of the modified everninomicin biosynthetic pathway described here into such a host cell.

A *Micromonospora carbonacea* "everninomicin biosynthetic pathway resistance gene product" is a protein or enzyme that confers resistance to everninomicin (and related compounds) to a host cell. Expression of such a gene on a vector provides an alternative selection mechanism for transformed host cells in vitro or in vivo, and thus can be used in molecular biological manipulations of cells independently of the EV biosynthetic pathway. For example, such a vector can be used to select for a transfected or transformed host cell by culturing the cell in the presence of an amount of everninomicin that is toxic to the host cell lacking the vector.

A *Micromonospora* site-specific Att/Int functions consist of an integrase protein and AttP site, e.g., as depicted in FIG. 7B (SEQ ID NO: 177) and in a specific embodiment encoded by a nucleic acid having a sequence as depicted in FIG. 7B (SEQ ID NO: 176), that permits site-specific integration of a vector into an actinomyce, and particularly a *Micromonospera*, genome.

General Definitions

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure, more preferably, at least 90% pure, and more preferably still at least 99% pure. Purity can be evaluated by chromatography, gel electrophoresis, immunoassay, composition analysis, biological assay, and other methods known in the art.

Methods for purification are well-known in the art. For example, nucleic acids can be purified by precipitation, chromatography (including preparative solid phase chromatography, oligonucleotide hybridization, and triple helix chromatography), ultracentrifugation, and other means. Polypeptides and proteins can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction, and countercurrent distribution. For some purposes, it is preferable to produce the polypeptide in a recombinant system in which the protein contains an additional sequence tag that facilitates purification, such as, but not limited to, a polyhistidine sequence, or a sequence that specifically binds to an antibody, such as FLAG and GST. The polypeptide can then be purified from a crude lysate of the host cell by chromatography on an appropriate solid-phase matrix. Alternatively, antibodies produced against the protein or against peptides derived therefrom can be used as purification reagents. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting [FACS]). Other purification methods are possible. A purified material may contain less than about 50%, preferably less than about 75%, and most preferably less than about 90%, of the cellular components with which it was originally associated. The "substantially pure" indicates the highest degree of purity which can be achieved using conventional purification techniques known in the art.

In a specific embodiment, the term "about" or "approximately" means within 20%, preferably within 10%, and more preferably within 5% of a given value or range. Alternatively, especially in biological systems, the term "about" means within about a log (i.e., an order of magnitude) preferably within a factor of two of a given value, depending on how quantitative the measurement.

The use of italics indicates a nucleic acid molecule (e.g., enrJ cDNA, gene, etc.); normal text indicates the polypeptide or protein.

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. The term "variant" may also be used to indicate a modified or altered gene, DNA sequence, enzyme, cell, etc., i.e., any kind of mutant.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their sequence similarity, whether in terms of percent similarity or the presence of specific residues or motifs at conserved positions.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when the encoded polypeptides are at least 35-40% similar as determined by one of the algorithms disclosed herein, preferably at least about 60%, and most preferably at least about 90 or 95% in a highly conserved domain, or, for alleles, across the entire amino acid sequence. Sequence comparison algorithms include BLAST (BLAST P, BLAST N, BLAST X), FASTA, DNA Strider, the GCG (Genetics Computer Group, Program Manual for the GCG Package, Version 7, Madison, Wis.) pileup program, etc. using the default parameters provided with these algorithms. An example of such a sequence is an allelic or species variant of the specific everninomicin biosynthetic genes of the invention. Sequences that are substantially homologous can be identified by comparing the sequences using standard software available in sequence data banks, or in a Southern hybridization experiment under, for example, stringent conditions as defined for that particular system.

Cloning and Expression of EV Biosynthetic Pathway Genes

The present invention contemplates analysis and isolation, and/or construction, of a gene encoding a functional or mutant EV biosynthetic enzyme, including a full length, or naturally occurring form of an EV biosynthetic enzyme, and any antigenic fragments thereof from any source. It further contemplates expression of functional or mutant EV biosynthetic enzyme protein for evaluation, diagnosis, or, particularly, biosynthesis of everninomicin or other secondary metabolic products.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. ÊPerbal, *A Practical Guide To Molecular Cloning* (1984); F. M. Ausubel et al. (eds.), *Current Protocols in Molecular. Biology*, John Wiley & Sons, Inc. (1994).

Molecular Biology-Definitions

"Amplification" of DNA, as used herein, denotes the use of polymerase chain reaction (PCR) to increase the concentration of a particular DNA sequence within a mixture of DNA sequences. For a description of PCR see Saiki et al., Science, 239:487, 1988.

A "nucleic acid molecule" refers to the phosphate ester polymeric form of ribonucleosides (adenosine, guanosine, uridine or cytidine; "RNA molecules"); or deoxyribonucleosides (deoxyadenosine, deoxyguanosine, deoxythymidine, or deoxycytidine; "DNA molecules"); or any phosphoester analogs thereof, such as phosphorothioates and thioesters, in either single stranded form, or a double-stranded helix; or "protein nucleic acids" (PNA) formed by conjugating bases to an amino acid backbone; or nucleic acids containing modified bases, for example thiouracil, thio-guanine and fluoro-uracil. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A "polynucleotide" or "nucleotide sequence" is a series of nucleotide bases (also called "nucleotides") in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids.

The polynucleotides herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Furthermore, the polynucleotides herein may also be oligonucleotides modified with a label capable of providing a detectable signal, either directly or indirectly. Exemplary labels include radioisotopes, fluorescent molecules, biotin, and the like.

A "coding sequence" or a sequence "encoding" an expression product, such as a RNA, polypeptide, protein, or enzyme, is a minimum nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG, though as shown herein, alternative start codons can be used) and a stop codon.

The term "gene", also called a "structural gene" means a DNA sequence that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including a 5'-untranslated region (UTR) and 3'-UTR, as well as the coding sequence.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control of" or "operably (or operatively) associated with" transcriptional and translational control sequences in a cell when RNA polymerase transcribes the coding sequence into mRNA, which is then trans-RNA spliced (if it contains introns) and translated into the protein encoded by the coding sequence.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as mRNA or a protein. The expression product itself, e.g. the resulting mRNA or protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a heterologous nucleic acid into a host cell. The term "transformation" means the introduction of a heterologous gene, DNA or RNA sequence to a host cell, so that the host cell will express the introduced gene or sequence to produce a desired product. The introduced gene or sequence may also be called a "cloned" or "heterologous" gene or sequence, and may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include plasmids, phages, viruses, etc.; they are discussed in greater detail below.

Vectors typically comprise the DNA of a transmissible agent, into which heterologous DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells can further be used for screening or other assays, as described infra. In a preferred aspect, a host cell of the invention is an actinomycete, preferably of the genus *Streptomyces* (e.g., a host cell as described in Ziermann and Betlach, BioTechniques, 1999, 26:106) or alternatively *Micromonospera*. Additional examples include, but are not limited to, the strains *S. pristinaespiralis* (ATCC 25486), *S. antibioticus* (DSM 40868), *S. bikiniensis* (ATCC 11062), *S. parvulus* (ATCC 12434), *S. glauescens* (ETH 22794), *S. actuosus* (ATCC 25421), *S. coelicolor* (A3(2)), *S. ambofaciens, S. lividans, S. griseofuscus, S. limosus*, and the like (see also Smokvina et al., Proceedings, 1:403-407).

The term "expression system" means a host cell and compatible vector under suitable conditions, e.g., for the expression of a protein coded for by foreign DNA carried by the vector and introduced to the host cell. Common expression systems include *E. coli* host cells and plasmid vectors, although the actinomycte host cell expression systems are preferred for biosynthesis of everninomicin and related products.

The term "heterologous" refers to a combination of elements not naturally occurring. For example, heterologous DNA refers to DNA not naturally located in the cell, or in a chromosomal site of the cell. A heterologous gene is a gene in which the regulatory control sequences are not found naturally in association with the coding sequence. In the context of the present invention, an *EV biosynthetic enzyme* gene is heterologous to the vector DNA in which it is inserted for cloning or expression, and it is heterologous to a host cell containing such a vector, in which it is expressed, e.g., a K562 cell.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of EV biosynthetic enzyme, or to detect the presence of nucleic acids encoding EV biosynthetic enzyme. In a further embodiment, an oligonucleotide of the invention can form a triple helix with a EV biosynthetic enzyme DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

EV Biosynthetic Pathway Nucleic Acids

A gene encoding EV biosynthetic enzyme can be isolated from any everninomicin-producing *Micromonospora* source. Methods for obtaining EV biosynthetic enzyme gene are well known in the art, as described above (see, e.g., Sambrook et al., 1989, supra). The DNA may be obtained by standard procedures known in the art from cloned DNA, by chemical synthesis, by cDNA cloning, or by the cloning of genomic DNA (e.g., DNA having a sequence as deposited with the ATCC and accorded accession no. 39149), or fragments thereof, purified from the desired cell (see, for example, Sambrook et al., 1989, supra; Glover, D. M. (ed.), 1985, DNA Cloning: A Practical Approach, MRL Press, Ltd., Oxford, U.K. Vol. I, II). Whatever the source, the gene can be molecularly cloned into a suitable vector for propagation of the gene. Identification of the specific DNA fragment containing the desired *EV biosynthetic enzyme* gene may be accomplished in a number of ways. For example, a portion of an *EV biosynthetic enzyme* gene exemplified infra can be purified and labeled to prepare a labeled probe, and the generated DNA may be screened by nucleic acid hybridization to the labeled probe. (Benton and Davis, Science, 1977, 196:180; Grunstein and Hogness, Proc. Natl. Acad. Sci. U.S.A., 1975, 72:3961). Those DNA fragments with substantial homology to the probe, such as an allelic variant from another species, will hybridize. In a specific embodiment, highest stringency hybridization conditions are used to identify a homologous *EV biosynthetic enzyme* gene.

Further selection can be carried out on the basis of the properties of the gene, e.g., if the gene encodes a protein product having the isoelectric, electrophoretic, amino acid composition, partial or complete amino acid sequence, antibody binding activity, or ligand binding profile of EV biosynthetic enzyme protein as disclosed herein. Thus, the presence of the gene may be detected by assays based on the physical, chemical, immunological, or functional properties of its expressed product.

Other DNA sequences which encode substantially the same amino acid sequence as an *EV biosynthetic enzyme* gene may be used in the practice of the present invention. These include but are not limited to allelic variants, species variants, sequence conservative variants, and functional variants.

The genes encoding EV biosynthetic enzyme derivatives and analogs of the invention can be produced by various methods known in the art. The manipulations which result in their production can occur at the gene or protein level. For example, the cloned EV biosynthetic enzyme gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of EV biosynthetic enzyme, care should be taken to ensure that the modified gene remains within the same translational reading frame as the *EV biosynthetic enzyme* gene, uninterrupted by translational stop signals, in the gene region where the desired activity is encoded, unless the gene will be used to knock-out or disrupt an endogenous EV biosynthetic enzyme.

Additionally, the EV biosynthetic enzyme-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Such modifications can also be made to introduce restriction sites and facilitate cloning the *EV biosynthetic enzyme* gene into an expression vector. Any technique for mutagenesis known in the art can be used, including but not limited to, in vitro site-directed mutagenesis (Hutchinson, C., et al. J. Biol. Chem., 1978, 253:6551; Zoller and Smith, DNA, 1984, 3:479-488; Oliphant et al., Gene 1986, 44:177; Hutchinson et al., Proc. Natl. Acad. Sci. U.S.A., 1986, 83:710), use of TAB linkers (Pharmacia), etc. PCR techniques are preferred for site directed mutagenesis (see Higuchi, "Using PCR to Engineer DNA", in *PCR Technology: Principles and Applications for DNA Amplification*, H. Erlich, ed., Stockton Press, 1989, Chapter 6, pp. 61-70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Finally, the vector may include a fusion polypeptide sequence such that the construct with the EV biosynthetic enzyme encodes a chimeric protein, such as a poly-histidine tag, FLAG tag, myc epitope tag, or some other such sequence for ease in purification.

Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired.

Expression of EV Biosynthetic Enzyme Polypeptides

The nucleotide sequence coding for EV biosynthetic enzyme, or antigenic fragment, derivative or analog thereof, or a functionally active derivative, including a chimeric protein, thereof, can be inserted into an appropriate expression vector, i.e., a vector which contains the necessary elements for the transcription and translation of the inserted protein-coding sequence. Thus, a nucleic acid encoding EV biosynthetic enzyme of the invention can be operationally associated with a promoter in an expression vector of the invention. Such vectors can be used to express functional or functionally inactivated EV biosynthetic enzyme polypeptides.

The necessary transcriptional and translational signals can be provided on a recombinant expression vector.

Expression of EV biosynthetic enzyme protein may be controlled by any promoter/enhancer element known in the art, but these regulatory elements must be functional in the host selected for expression. Promoters which may be used to control EV biosynthetic enzyme gene expression include, but are not limited to, prokaryotic expression vectors such as the β-lactamase promoter (Villa-Komaroff, et al., Proc. Natl. Acad. Sci. U.S.A., 1978, 75:3727-3731), or the tac promoter (DeBoer, et al., Proc. Natl. Acad. Sci. U.S.A., 1983, 80:21-25; see also "Useful proteins from recombinant bacteria" in Scientific American, 242:74-94, 1980). Among regulable promoters which can be used in the context of the present invention, mention may be made more especially of any regulable promoter which is functional in actinomycetes. These can comprise promoters induced specifically by an agent introduced into to the culture medium, such as, for example, the thiostrepton-inducible promoter tipA (Murakami et al., J.Bact., 1989, 171:1459), or thermoinducible promoters such as that of the groEL genes, for example (Mazodier et al., J.Bact., 1991, 173:7382). They can also comprise an actinomycetes promoter which is specifically active in the late phases of the proliferation cycle of actinomycetes, such as, for example, certain promoters of genes of the secondary metabolism (genes for the production of antibiotics, in particular).

Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2-dimensional gel electrophoresis, chromatography (e.g., ion exchange, affinity, immunoaffinity, and sizing column chromatography), centrifugation, differential solubility, immunoprecipitation, or by any other standard technique for the purification of proteins.

Antibodies to EV Biosynthetic Enzymes

According to the invention, any EV biosynthetic enzyme polypeptide produced recombinantly or by chemical synthesis, and fragments or other derivatives or analogs thereof, including fusion proteins, may be used as an immunogen to generate antibodies that recognize the EV biosynthetic enzyme polypeptide. Such antibodies include but are not limited to polyclonal, monoclonal, chimeric, single chain, Fab fragments, and an Fab expression library. The anti-EV biosynthetic enzyme antibodies of the invention may be cross reactive, e.g., they may recognize EV biosynthetic enzyme from different species. Polyclonal antibodies have greater likelihood of cross reactivity. Alternatively, an antibody of the invention may be specific for a single form of EV biosynthetic enzyme, such as murine EV biosynthetic enzyme. Preferably, such an antibody is specific for human EV biosynthetic enzyme.

Various procedures known in the art may be used for the production of polyclonal antibodies to EV biosynthetic enzyme polypeptide or derivative or analog thereof. For the production of antibody, various host animals can be immunized by injection with the EV biosynthetic enzyme polypeptide, or a derivative (e.g., fragment or fusion protein) thereof, including but not limited to rabbits, mice, rats, sheep, goats, etc. In one embodiment, the EV biosynthetic enzyme polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum*.

For preparation of monoclonal antibodies directed toward the EV biosynthetic enzyme polypeptide, or fragment, analog, or derivative thereof, any technique that provides for the production of antibody molecules by continuous cell lines in culture may be used. These include but are not limited to the hybridoma technique originally developed by Kohler and Milstein (Nature, 1975, 256:495-497), as well as the trioma technique, the human B-cell hybridoma technique (Kozbor et al., Immunology Today, 1983, 4:72; Cote et al., Proc. Natl. Acad. Sci. U.S.A., 1983, 80:2026-2030), and the EBV-hybridoma technique to produce human monoclonal antibodies (Cole et al., in Monoclonal Antibodies and Cancer Therapy, Alan R. Liss, Inc., 1985, pp. 77-96).

According to the invention, techniques described for the production of single chain antibodies (U.S. Pat. Nos. 5,476,786 and 5,132,405 to Huston; U.S. Pat. No. 4,946,778) can be adapted to produce EV biosynthetic enzyme polypeptide-specific single chain antibodies. Indeed, these genes can be delivered for expression in vivo. An additional embodiment of the invention utilizes the techniques described for the construction of Fab expression libraries (Huse et al., Science, 1989, 246:1275-1281) to allow rapid and easy identification of monoclonal Fab fragments with the desired specificity for an EV biosynthetic enzyme polypeptide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an EV biosynthetic enzyme polypeptide, one may assay generated hybridomas for a product which binds to an EV biosynthetic enzyme polypeptide fragment containing such epitope. For selection of an antibody specific to an EV biosynthetic enzyme polypeptide from a particular species of animal, one can select on the basis of positive binding with EV biosynthetic enzyme polypeptide expressed by or isolated from cells of that species of animal.

The foregoing antibodies can be used in methods known in the art relating to the localization and activity of the EV biosynthetic enzyme polypeptide, e.g., for Western blotting, imaging EV biosynthetic enzyme polypeptide in situ, measuring levels thereof in appropriate physiological samples, etc. using any of the detection techniques mentioned above or known in the art.

In a specific embodiment, antibodies that agonize or antagonize the activity of EV biosynthetic enzyme polypeptide can be generated. Such antibodies can be tested using the assays described infra for identifying ligands.

Techniques of isolating bacterial DNA are readily available and well known in the art. Any such techniques can be employed in this invention. In particular DNA from these deposited cultures can be isolated as follows. Lyophils of *E. coli* XL1-Blue/pSPRX272, *E. coli* XL1-Blue/pSPRX2262, *E. coli* XL1-Blue/pSPR192, *E. coli* XL1-Blue/pSPRX210 or *E. coli* XL1-Blue/pSPRX256 are plated onto L-agar (10 g tryptone, 10 g NaCl, 5 g yeast extract, and 15 g agar per liter) plates containing 100 µg/ml ampicillin to obtain a single colony isolate of the strain. This colony is used to inoculate about 500 ml of L-broth (10 g tryptone, 10 g NaCl, 5 g yeast extract per liter) containing 100 µg/ml apramycin, and the resulting culture is incubated at 37° C. with aeration until the cells reach stationary phase. Cosmid DNA can be obtained from the cells in accordance with procedures known in the art (see, e.g., Rao et al., Methods in Enzymology, 1987, 153:166).

DNA of the current invention can be sequenced using any known techniques in the art such as the dideoxynucleotide chain-termination method (Sanger et al., Proc. Natl. Acad. Sci., 1977, 74:5463) with either radioisotopic or fluorescent labels. Double-stranded, supercoiled DNA can be used directly for templates in sequence reactions with sequence-specific oligonucleotide primers. Alternatively, fragments can be used to prepare libraries of either random, overlapping sequences in the bacteriophage M13 or nested, overlapping deletions in a plasmid vector. Individual recombinant DNA subclones are then sequenced with vector-specific oligonucleotide primers. Radioactive reaction products are electrophoresed on denaturing polyacrylamide gels and analyzed by autoradiography.

Fluorescently labeled reaction products are electrophoresed and analyzed on Applied Biosystems (ABI Division, Perkin Elmer, Foster City, Calif. 94404) model 370A and 373A or Dupont (Wilmington, Del.) Genesis DNA sequencers. Sequence data are assembled and edited using Genetic Center Group (GCG, Madison, Wis.) programs GelAssemble and Seqed or the ABI model 670 Inherit Sequence Analysis system and the AutoAssembler and SeqEd programs.

Polypeptides corresponding to a domain, a submodule, a module, a synthesis unit (SU), or an open reading frame can be produced by transforming a host cell such as bacteria, yeast, or eukaryotic cell-expression system with the cDNA sequence in a recombinant DNA vector. It is well within one skilled in the art to choose among host cells and numerous recombinant DNA expression vectors to practice the instant invention. Multifunctional polypeptides of polyketide everninomicin synthase can be extracted from everninomicin-producing bacteria such as *Streptomyces ambofaciens* or translated in a cell-free in vitro translation system. In addition, the techniques of synthetic chemistry can be employed to synthesize some of the polypeptides mentioned above.

Procedures and techniques for isolation and purification of proteins produced in recombinant host cells are known in the art. See, for example, Roberts et al., Eur. J. Biochem., 1993, 214: 305-311 and Caffrey et al., FEBS, 1992, 304: 225-228 for detailed description of polyketide synthase purification in bacteria. To achieve a homogeneous preparation of a polypeptide, proteins in the crude cell extract can be separated by size and/or charge through different columns well known in the art once or several times. In particular the crude cell extract can be applied to various cellulose columns commercially available such as DEAE-cellulose columns. Subsequently the bound proteins can be eluted and the fractions can be tested for the presence of the polyketide everninomicin synthase or engineered derivative protein. Techniques for detecting the target protein are readily available in the art. Any such techniques can be employed for this invention.

In particular the fractions can be analyzed on Western blot using antibodies raised against a portion or portions of such polyketide everninomicin synthase proteins. The fractions containing the polyketide everninomicin synthase protein can be pooled and further purified by passing through more columns well known in the art such as applying the pooled fractions to a gel filtration column. When visualized on SDS-PAGE gels homogeneous preparations contain a single band and are substantially free of other proteins.

Actinomycetes are prolific producers of secondary metabolites with antimicrobial and antifungal activity and represent a significant source of active compounds for pharmaceuticals. The genus *Streptomyces* produces a wide variety of secondary metabolites including antitumor, antifungal, and antimicrobial agents. The biosynthesis of these compounds has been shown to be directed by large multifunctional proteins or a number of proteins each catalyzing specific steps in the biosynthesis of the secondary metabolite (REF-Biotechnology of AB etc.) The genes encoding actinomycete secondary metabolite biosynthesis have been found to be clustered on contiguous segments of each producing organisms genome (Strohl, William R, 1997, Biotechnology of Antibiotics, 2$^{nd}$ Ed., Marcel Dekker, Inc., New York, N.Y.). This makes it feasible for complete pathways to be cloned, analyzed, genetically manipulated and expressed in surrogate hosts.

Components of The Everninomicin Biosynthethic Pathway

Orsellinic Acid Biosynthesis

The term "polyketide" refers to a class of molecules produced through the successive condensation of small carboxylic acids. This diverse group includes plant flavonoids, fungal aflatoxins, and hundreds of compounds of different structures that exhibit antibacterial, antifungal, antitumor, and anthelmintic properties. Some polyketides produced by fungi and bacteria are associated with sporulation or other developmental pathways; others do not yet have an ascribed function. Some polyketides have more than one pharmacological effect. The diversity of polyketide structures reflects the wide variety of their biological properties. Many cyclized polyketides undergo glycosidation at one or more sites, and virtually all are modified during their synthesis through hydroxylation, reduction, epoxidation, etc.

For the purposes of the present invention, "polyketide" refers to the orsellenic acid moiety in everninomicin. Thus, the invention provides, in particular, the DNA sequence encoding the polyketide synthase responsible for biosynthesis of this orsellinic acid moiety of everninomicin, i.e., the everninomicin orsellinic acid synthetase. The everninomicin orsellinic acid synthase DNA sequence, which defines the orsellinic synthase gene cluster, directs biosynthesis of the orsellinic acid polyketide by encoding the various distinct activities of orsellinic synthase. The skilled artisan recognizes, however, that the everninomicin orsellinic synthase genes are useful in the production of other polyketides, e.g., by recapitulating all or part of this component of the biosynthetic pathway, or by modulating biosynthetic pathways (see, the discussion about combinatorial biosynthesis, infra).

Figure 4A:
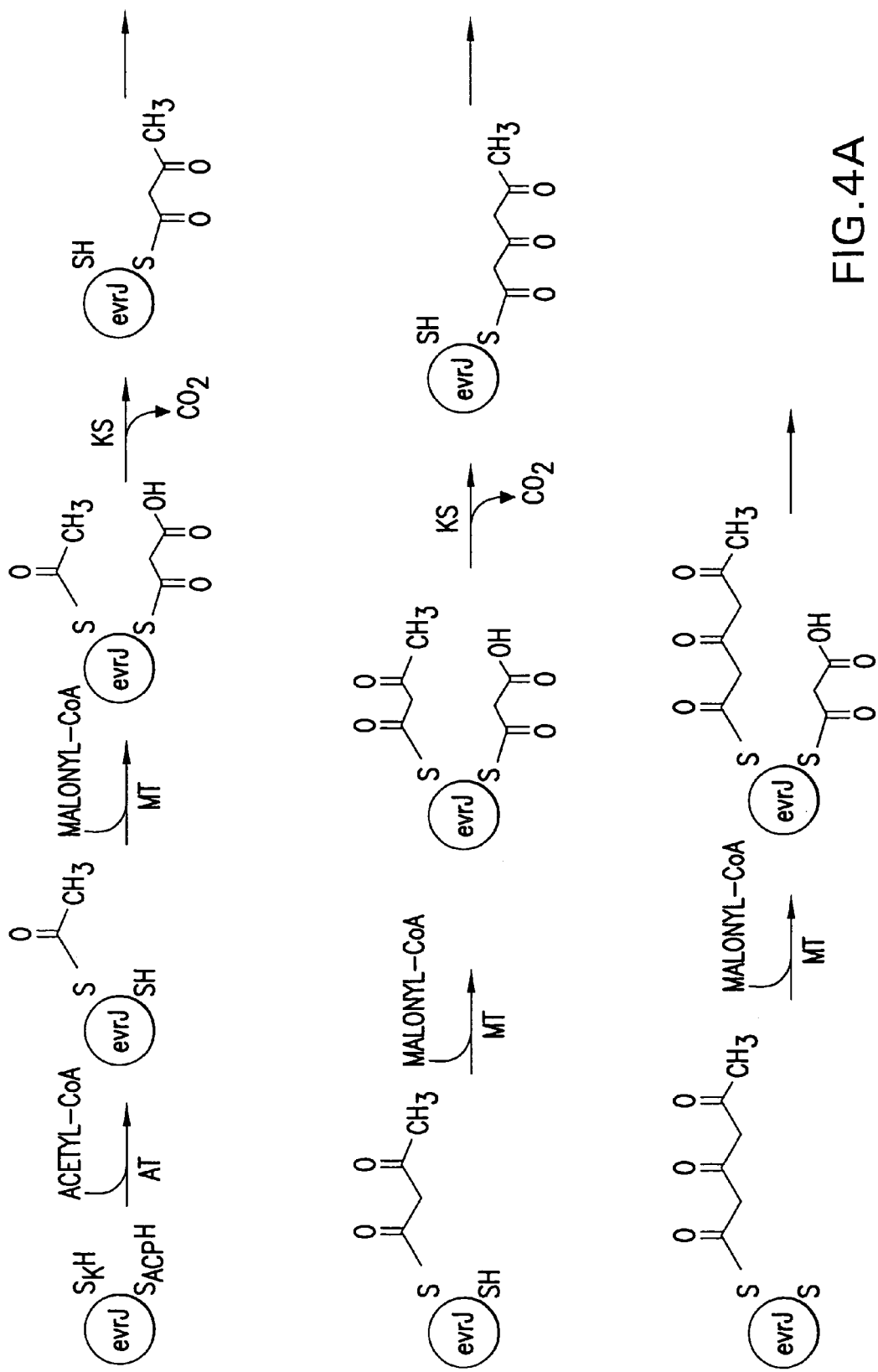
Figure 4B:
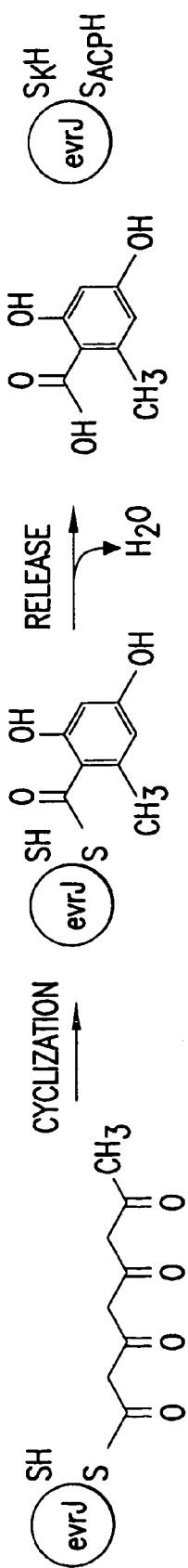
Figure 5:
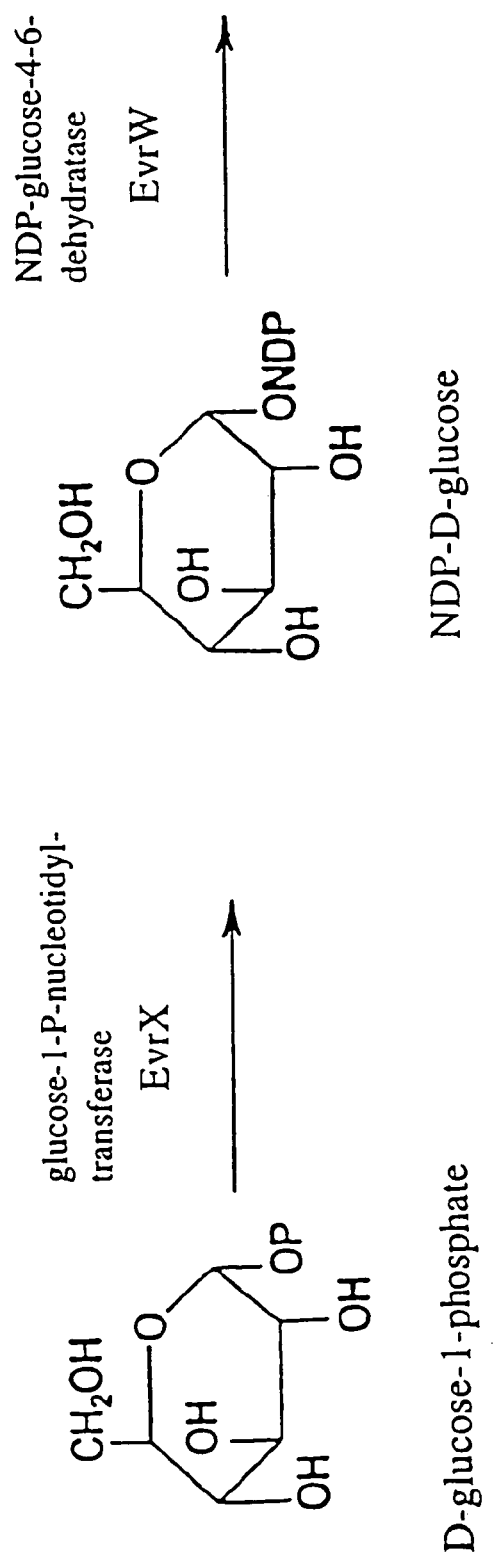
Figure 5:
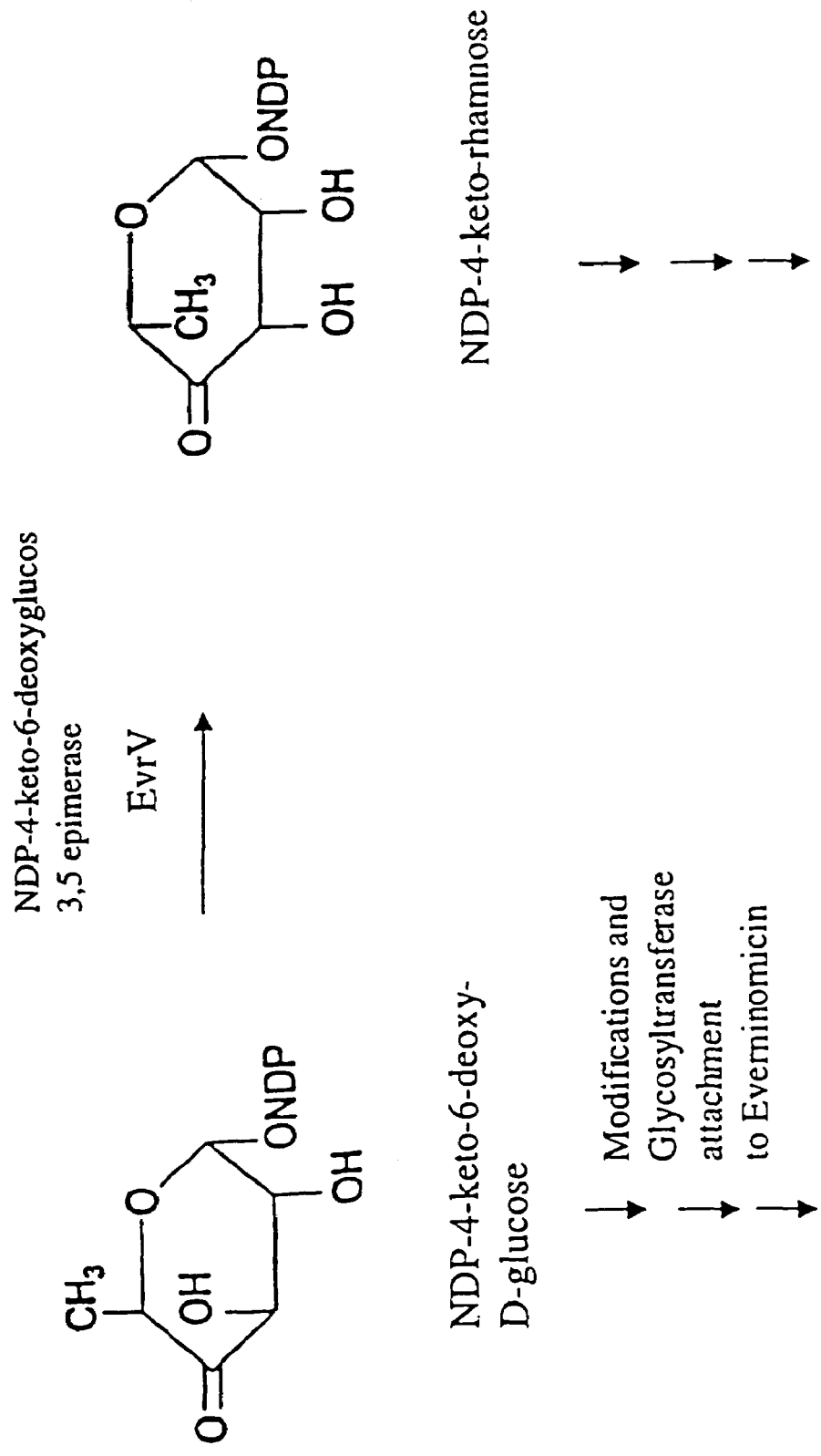

The gene cluster for orsellinic synthase, like other Type I polyketide biosynthetic synthase genes whose organization has been elucidated, is characterized by the presence of an ORF encoding a multi-functional protein which contains separate, active sites for condensation of acyl groups as defined above. The map of the orsellinic synthase gene derived from *Micromonospora carbonacea* var. *africana* is shown in FIG. 3. The accompanying synthetic pathway and the specific carboxylic acid substrates that are used for each condensation of orsellinic acid synthesis are indicated in FIG. 4.

Polyketides are complex secondary metabolites synthesized from the condensation of acetyl-coenzyme A (CoA) or related acyl-CoAs by polyketide synthetase enzymes. Other acyl groups forming the acyl-CoA include malonyl, proponyl, and butyryl. Condensation of extender units requires the action of β-ketoacyl ACP synthetase, acetyltransferase and acyl carrier protein enzymatic sites. Each module processes one condensation step and typically requires several activities accomplished by several active sites including acyl carrier protein (ACP), β-ketosynthase (KS), and acyltransferase (AT). The specific gene products identified with orsellinic biosynthesis are listed in Table 2.

TABLE 2

Orsellinic Acid Biosynthetic Gene Products

| Gene Product | CDS | SEQ ID No. | Enzymatic Function |
|---|---|---|---|
| evrF | 21,064 . . . 22,542 | 36, 37 | non-heme oxygenase/ halogenase addition |
| evrI | 25,550 . . . 26,626 | 42, 43 | acyl starter unit |
| evrJ | 26,685 . . . 30,479 | 44, 45 | Orsellinic acid synthase/6-methylsalicilic acid synthase |
| evbD | 56,961 . . . 58,709 | 92, 93 | acyl-CoA carboxylase |
| evbQ | 74,707 . . . 76,290* | 122, 123 | Methylmalonyl-CoA mutase |

Polyketide synthetases are classified as either iterative Type I, iterative Type II or modular polyketide sythetases. Iterative Type I synthetases resemble the multifunctional fatty acid synthases from animals and are composed of multifunctional proteins with separate protein domains encoding each active sites. This is exemplified by the actinomycete *S. erythrea* polyketide synthetase for the biosynthesis of erythromycin, the *Streptomyces viridochromogenes* Tu57 AviM synthesis of orsellinic acid and the *Penicillium patulum* polyketide synthase for 6-methylsalicylic acid (Hutchinson et al., Annual Review of Microbiology, 1995, 49:201-238; Gaisser et al., Journal of Bacteriology, 1997, 179:6271-6278; Beck et al., European Journal of Biochemistry, 1990, 192:487-498). Iterative type II synthetases have seperate proteins for each active site. These are exemplified by the polyketide synthetases from *S. coelicolor, S. violaceoruber* and *S. glaucescens* synthesizing the aromatic polyketides actinorhodin, granaticin and tetracenomycin respectively (Hopwood, et al., Annual Review of Microbiology 1990, 24:37-66). The modular polyketide synthetases are large proteins that contain several domains with each domain containing several active sites. An example of a modular polyketide synthetase is the 6-deoxy-erythronolide B synthetase from *Saccharopolyspora erythraea*. Recent reviews of polyketides and polyketide synthetases elaborate on these pathways (Hopwood, et al., Annual Review of Microbiology, 1990, 24:37-66; Hutchinson et al., Annual Review of Microbiology, 1995, 49:201-238).

Although not wishing to be bound to any particular theory or technical explanation, a sequence similarity exists among domain boundaries in various polyketide synthase genes. Thus, one skilled in the art is able to predict the domain boundaries of newly discovered polyketide synthase genes based on the sequence information of known polyketide synthase genes. In particular, the boundaries of submodules, domains, and open reading frames in the instant application are predicted based on sequence information disclosed in this application and the locations of the domain boundaries of the everninomicin synthase (Donadio et al., GENE, 1992, 111:51-60). Furthermore, the genetic organization of the everninomicin synthase gene cluster appears to correspond to the order of the reactions required to complete synthesis of everninomicin. This means that the polyketide synthase DNA sequence can be manipulated to generate predictable alterations in the final everninomicin product.

Acyl Precursor Formation

EvrJ (orsellinic acid synthetase) requires one acetyl-CoA starter and three malonyl-CoA extender units to synthesize orsellinic acid. The acetyl-CoA and malonyl-CoA units most likely are derived from glycolysis and fatty acid biosynthesis (Tang L, et al., Ann. N Y Acad. Sci., 1994, 721:105-16). The malonyl-CoA can also be derived from acetyl-CoA by carboxylation by acetylCoA carboxylase, (Scott Eagleson, Concise Encyclopedia of Biochemistry, $2^{nd}$ Ed., Walter de Gruyler; Berlin, 1988). The *M. carbonacea* EV region contains an evbD which has strong homology to know acetyl-CoA carboxylases. Thus evbD is responsible for the synthesis of the malonyl-CoA unit required for orsellinic acid biosynthesisas shown in FIG. 4.

Sugar Biosynthetic Products and Glycosyltransferases

Glycosyl groups (6-deoxysugars) are synthesized by a common mechanism involving hexose-1-P nucleotidyltransferase, dTDP-D-glucose synthetase and dTDP-D-glucose 4,6-dehydratase. L-deoxysugars are synthesized by the action of a NDP-4-keto-6-deoxyhexose 3,5-epimerase. Deoxysugars can be modified by deoxygenations, transaminations, methylations and isomerization or epimerizations prior to covalent attachment by a glycosytransferase.

Biosynthesis of the sugars (see Liu and Thorson, Annu. Rev. Microbiol., 1994, 48:223) that are attached to the orsellinic acid/polyketide, and the enzymes that mediate attachment of the sugars, are also key elements of the everninomicin biosynthetic pathway. Genes encoding such sugar biosynthetic enzymes and glycosyltransferases are typically found in the biosynthetic pathway locus (see Summers et al., Microbiology, 1997, 143:3251). The genes identified from the EV biosynthetic locus are listed in Tables 3 and 4.

TABLE 3

Sugar Biosynthetic Gene Products

| Gene Product | CDS | SEQ ID No. | Enzymatic Function |
|---|---|---|---|
| evdA | 132 ... 1382* | 2, 3 | Hydroxylase |
| evdB | 1490 ... 2611* | 4, 5 | hexose aminotransferase |
| evdC | 2622 ... 3860* | 6, 7 | oxidase (flavoprotein) |

TABLE 3-continued

Sugar Biosynthetic Gene Products

| Gene Product | CDS | SEQ ID No. | Enzymatic Function |
|---|---|---|---|
| evdE | 5309 ... 6235 | 10, 11 | hexose dehydratase |
| evdI | 9463 ... 10,224* | 18, 19 | Hydrolase |
| evdK | 11,208 ... 12,455 | 22, 23 | hexose dehydratase or epimerase |
| evrA | 14,410 ... 15,363* | 26, 27 | hexose epimerase |
| evrB | 15,380 ... 16,414* | 28, 29 | hexose oxidoreductase |
| evrC | 16,419 ... 17,873* | 30, 31 | hexose dehydratase |
| evrD | 17,870 ... 18,934* | 32, 33 | GDP-mannose 4,6-dehydratase |
| evrV | 41,679 ... 42,707* | 68, 69 | dTDP-glucose epimerase |
| evrW | 42,810 ... 43,799* | 70, 71 | dTDP-glucose dehydratase |
| evrX | 43,799 ... 44,866 | 72, 73 | dTDP-glucose synthetase |
| evbS | 78,791 ... 80,521 | 126, 127 | Phosphomannomutase |
| evbU | 83,280 ... 83,888 | 130, 131 | Glucose-6-phosphate 1-dehydrogenase |
| ORF9 | 8254 ... 9318 | 199, 200 | Oxidoreductase |
| ORF11 | 10,584 ... 11,585 | 203, 204 | Deoxyhexose ketoreductase |

TABLE 4

Glycosyltransferases

| Gene Product | CDS | SEQ ID No. | Enzymatic Function |
|---|---|---|---|
| evdD | 4143 ... 5312 | 8, 9 | DNTP-hexose glycosyltransferase |
| evdF | 6232 ... 7275 | 12, 13 | DNTP-hexose glycosyltransferase |
| evdH | 8342 ... 9364 | 16, 17 | DNTP-hexose glycosyltransferase |
| evdL | 12,108 ... 13,022* | 24, 25 | DNTP-hexose glycosyltransferase |
| evrS | 38,892 ... 40,163* | 62, 63 | DNTP-hexose glycosyltransferase |

These genes are important targets for modulation. They are likely to be bottleneck genes, and thus increased expression using an exogenous or integrating vector can increase the yield of everninomicin (or its analog). Alternatively, knocking out these genes may result in complete elimination of everninomicin biosynthesis.

Tailoring Enzymes

Various types of EV biosynthetic enzymes fall into the tailoring enyzme category. These are listed in Table 5. Increasing or decreasing expression of these enzymes permits production of everninomicin analogs. Moreover, expression of these enzymes in other actinomycetes permits production of novel secondary metabolites by the action of the everninomicin tailoring enzymes on these metabolites.

TABLE 5

Tailoring Gene Products

| Gene Product | CDS | SEQ ID No. | Enzymatic Function |
|---|---|---|---|
| evrG | 22,748 ... 24,172 | 38, 39 | oxidase |
| evrL | 31,941 ... 32,882* | 48, 49 | heme biosynthesis |
| evrM | 33,167 ... 34,405* | 50, 51 | p450 hydroxylase |
| evrN | 34,449 ... 35,210* | 52, 53 | methyl transferase |
| evrQ | 36,998 ... 38,026* | 58, 59 | oxidoreductase/heat stress protein |

TABLE 5-continued

| Tailoring Gene Products | | | |
|---|---|---|---|
| Gene Product | CDS | SEQ ID No. | Enzymatic Function |
| evrT | 40,216 . . . 40,890 | 64, 65 | L-proline hydroxylase |
| evrU | 40,887 . . . 41,576 | 66, 67 | methyltransferase |
| evbA | 53,554 . . . 54,207 | 84, 85 | o-methyltransferase |
| evbE | 58,873 . . . 60,312 | 94, 95 | IMP dehydrogenase |
| evbI | 66,469 . . . 67,872* | 106, 107 | lipoamide dehydrogenase |
| evbL | 69,610 . . . 70,359* | 112, 113 | acetyltransferase/ phosphotransferase |
| evbX | 85,909 . . . 87,342 | 136, 137 | aldehyde dehydrogenase |
| evbY | 87,422 . . . 88159 | 138, 139 | aldehyde dehydrogenase |
| evcB | 89,817 . . . 91,067 | 144, 145 | cytochrome D oxidase subunit I |
| evcC | 91,078 . . . 92,085 | 146, 147 | cytochrome D oxidase subunit II |

Regulatory Products: Serine-Threonine Kinases

Protein serine (Ser), threonine (Thr), and tyrosine (Tyr) kinases play essential roles in signal transduction in organisms ranging from yeast to mammals, where they regulate a diverse cellular activities. Genes that encode eukaryotic-type protein kinases have also been identified in different bacterial species, suggesting that such enzymes are also widespread in prokaryotes. Although many of them have yet to be fully characterized, several studies indicate that eukaryotic-type protein kinases play important roles in regulating cellular activities of these bacteria, such as cell differentiation and secondary metabolism (Cheng-Cai, Molecular Microbiology, 1996, 20:9-15). Examples that have been studied include the pknD Ser/Thr kinase from *Anabaena* sp. PCC7120, which is involved in nitrogen metabolism control (Zhang et al., Molecular and General Genetics, 1998, 258:26-33); the pkn9 Ser/Thr kinase from *Myxococcus xanthus*, which is involved in development of fruiting bodies (Hanlon et al., Molecular Microbiology, 1997, 23:459-71); and the afsK Ser/Thr kinase from *Streptomyces coelicolor*, which is involved in aerial myceliaum formation (Ueda et al., Gene, 1996, 169:91-95). These genes from the EV biosynthetic locus are listed in Table 6.

TABLE 6

| Regulatory Gene Products | | | |
|---|---|---|---|
| Gene Product | CDS | SEQ ID No. | Enzymatic Function |
| evrR | 38,072 . . . 38,566 | 60, 61 | hexaheme nitrite reductase regulator/ methyltransferase |
| evsA | 47,156 . . . 49,234* | 78, 79 | serine-threonine kinase |
| evbF | 60,472 . . . 61,029* | 96, 97 | |
| evbF2 | 61,610 . . . 62,069 | 100, 101 | |
| evbK | 68,529 . . . 69,494* | 110, 111 | protease synthase/ sporulation regulator |
| evbR | 76,622 . . . 78,712 | 124, 125 | protein serine-threonine kinase (eukaryotic type) |
| evcJ | 100,733 . . . 101,326* | 160, 161 | ATP/GTP binding protein |
| ORF1 | 189 . . . 1064* | 183, 184 | Transcriptional regulator biotinylation |
| ORF4 | 3776 . . . 4276* | 189, 190 | ECF sigma factor |

The evsA and evbR proteins within the everninomicin cluster have a high degree of homology to Ser/Thr kinases and may play a role in regulating the expression of the pathway. Manipulation of the evsA and evbR proteins could enhance the expression and yield of everninomicin from *M. carbonacea* by providing positive signals for biosynthesis. Thus, these genes are preferred elements in a vector to enhance the efficiency of everninomicin biosynthesis.

Resistance Mechanisms

Actinomycetes utilize a variety or mechanisms to confer resistance to secondary metabolites they produce. These include membrane pumps, rRNA methylases, O-phosphorylation, N-acetylation, and production of resistant target proteins (Cundliffe, Annual Review of Microbiology, 1989, 43:207-33). The genes from the EV biosynthetic locus that have this function are listed in Table 7.

TABLE 7

| Resistance Mechanism Genes | | | |
|---|---|---|---|
| Gene Product | CDS | SEQ ID No. | Enzymatic Function |
| evrE | 19,374 . . . 20,906 | 34, 35 | multidrug efflux transporter |
| evrY | 45,014 . . . 45,760* | 74, 75 | dehalogenase |
| evrZ | 45,962 . . . 46,714* | 76, 77 | muramidase/lysozyme |
| evbB | 54,362 . . . 55,117* | 86, 87 | membrane pump |
| evbC | 55,135 . . . 56,094* | 88, 89 | membrane pump |
| evbC2 | 56,184 . . . 56,813* | 90, 91 | ankrylin-like |
| evbG | 62,122 . . . 63,795 | 102, 103 | ABC transporter |
| evbH | 63,891 . . . 65,828 | 104, 105 | ABC transporter |
| evcD | 92,148 . . . 93,833 | 148, 149 | ABC transporter |
| evcE | 93,830 . . . 95,671 | 150, 151 | ABC transporter |
| evrMR | 107,653 . . . 108,615 | 172, 173 | 23S rRNA methylase |
| evrMR2 | 108,635 . . . 109,216 | 174, 175 | |
| ORF6 | 5392 . . . 6147* | 193, 194 | rRNA methyltransferase |

Multi-drug transporters are membrane proteins that are able to expel a broad range of toxic molecules from the microbial cells. These multidrug transporters belong to the ATP-binding cassette (ABC) family of transport proteins that utilize the energy of ATP hydrolysis for activity. In microorganisms, multidrug transporters play an important role in conferring antibiotic resistance on pathogens, and in actinomycetes confer resistance to the antibiotic secondary metabolites produced by these organisms themselves (Fath et al., Microbial Reviews, 1993, 57:995-1017). A second class of membrane transporters that are found in actinomycetes include MDR (multiple drug resistance) type pumps found in eukaryotes (Guilfoile et al., Proc. Natl. Acad. Sci. USA, 1991, 88:8553-8557). The EV cluster contains evbB and evbC, which are homologouse to the ATP-binding cassette (ABC) family of transport proteins and specifically to the mithramycin resistance pump from *Streptomyces argillaceus* (Fernandez et al., Molecular and General Genetics, 1996, 251:692-698). In addition the EV cluster contains evrE, an MDR type pump with homology to the *Streptomyces peucetius* drrA MDR type pump that confers resistance to daunorubicin. Ribosomal methylases have also been found to confer resistance to producing organisms. The tlrB 23S rRNA methylase from *Streptomyces fradiae* and the myrA 23S rRNA methylase from *Micromonospora griseorubida* have been found to confer resistance to tylosin and mycinamicin respectively.

The EV cluster also contains evrMR, a 23 RNA methylase with (loc.) homology to both tlrB and myrA.

The EV pathway also contains evrZ, a gene with homology to muramidases. Muramidases (lysozyme) cleave β1,4 linkages between N-acetylglucosamine and N-acetylmuramic acid (Scott and Eagleson, Concise Encyclopedia Biochemistry, $2^{nd}$ Ed., Walter de Gruyter: Berlin, 1988 p. 353). Thus, evrZ may inactivate everninomicin by cleavage within the glycosyl bonds.

Increased levels of expression of one or more of these resistance genes is expected to enhance the efficiency of everninomicin biosynthesis in an enhanced biosynthetic system by reducing toxicity to the host cell.

Furthermore, these resistance genes are good candidates for use as positive selection markers in recombinant systems. By including an everninomicin resistance gene in a vector, a host cell successfully transformed with the vector will demonstrate everninomicin resistance. Thus, everninomicin becomes a useful tool for selecting transformed host cells.

Biosynthetic Production And Modification of Everninomicins

There are a number of uses for the cloned *Micromonospora carboonacea* EV cluster DNA. The cloned genes can be used to improve the yields of everninomicins and to produce novel everninomicins. Improved yields can be obtained by introduction of a second copies of genes for enzymes that are rate limiting in the pathway ("bottleneck genes"). This can be accomplished by cloning genes onto vectors, preferably integrating vectors, then obtaining integrants in the chromosome. Alternatively, a rate limiting enzyme gene can be modified by associating it with a strongly expressing promoter sequence and then integrating this construct into the chromosome. Manipulation of regulatory proteins including the Ser/Thr kinases can enhance yields by obtaining mutants that express EV pathway genes at higher levels than parental organisms.

Novel everninomicins can be produced by using cloned fragments to disrupt steps in the biosynthesis of everninomicin. Disruptions can lead to the accumulation of precursors or "shunt" products. To generate disruptions, DNA fragments of internal segments of genes (lacking 5' and 3' sequences) can be cloned into insertion vectors. These constructs can be introduced into the parental organism and homologous recombinants selected for that result in two copies of the gene in the chromosome. One copy lacks 3' sequences and the second copy lacks upstream native promoter sequences and 5' sequences. Alternatively, DNA fragments of genes containing internal deletions or insertions can be cloned into gene replacement vectors. Recombinants can be obtained that contain internal deletions or insertions of genes, which results in a non-functional chromosome copy of the gene. Constructs that allow a frequency of recombination into the chromosome to obtain disruptions should contain fragments of sufficient size for recombination to occur (300 to 600 bases). Modified everninomicins produced by disrupting the genes may be antibiotics themselves, or serve as substrates for further chemical modification, creating new semi-synthetic everninomicins with unique properties or spectra of activity.

Novel everninomicins can also be produced by mutagenesis of the cloned genes, and replacement of the mutated genes for their unmutated counterparts in the everninomicin producer. Mutagenesis may involve, for example, (1) manipulation of the orsellinic acid PKS TypeI gene by introduction of KR, DH or ER domains (see, Donidio et al., 1993), e.g., to yield a modified orsellenic acid nucleus; (2) manipulation of the glycosyltranferase to relax substrate or glycosyl specificity, e.g., to yield everninomicin containing novel glycosyl groups or additional glycosyl groups; and/or (3) manipulation of glycosyl biosynthetic genes, e.g., to yield novel glycosyl groups and everninomicin containing novel glycosyl groups.

The DNA from the everninomicin biosynthetic cluster can be used as a hybridization probe to identify homologous sequences. Thus, the DNA cloned here could be used to obtain uncloned regions flanking the region described here but not yet isolated. In addition DNA from the region cloned here may be useful in identification of non-identical but similar sequences in other organisms.

The modified strains provided by the invention may be cultivated to provide everninomicins using conventional protocols.

Genetic Manipulation of Actinomycetes

Protocols have been developed to genetically manipulate actinomycete genomes and biosynthetic pathways. These include *E. coli* actinomycete shuttle vectors, gene replacement systems, transformation protocols, transposon mutagenesis, insertional mutagenesis, integration systems and heterologous host expression. These techniques are reviewed in numerous articles (Baltz et al., Trends Microbiol., 1998, 2:76-83, Hopwood et al., Genetic Manipulation of *Streptomyces*: A Laboratory Manual, 1985; Wohlleben et al., Acta Microbiol. Immunol. Hung, 1994, 41:381-9 [Review]).

The development of vectors for the genetic manipulation of actinomycetes began with the observation of plasmids in actinomycetes and the development of a transformation protocol of actinomycete protoplasts using polyethylene glycol (Bibb et al., Nature, 1980, 284:526-31). Many standard molecular techniques for *Streptomyces* were developed by Hopwood and colleages for *Streptomyces coelicolor* and *Streptomyces lividans* (Hopwood et al., Genetic Manipulation of *Streptomyces*: A Laboratory Manual, 1985). These techniques have been adapted and expanded to other actinomycetes.

Vectors incorporating antibiotic-resistance markers (AmR, ThR, SpR) that function in *Streptomyces* spp. and other features have allowed the development of vectors for (a) integration via homologous recombination between cloned DNA and the *Streptomyces* spp. chromosome, (b) autonomous replication, and (c) site-specific integration at the bacteriophage phiC31 attachment (att) site or pSAM2 attachment site, and (d) gene replacement vectors. Homologous recombination between the cloned DNA and the chromosome can be used to make insertional knockouts of specific genes. Autonomously replicating plasmids and integrating plasmids can be used to introduce heterologous genes into actinomycetes for complementation or expression studies.

Many actinomycetes contain restriction systems that limit the ability to transform organisms by protoplast transformation. More recent gene transfer procedures have been developed for introducing DNA into streptomycetes by conjugation from *Escherichia coli*. This employs a simple mating procedure for the conjugal transfer of vectors from *E. coli* to *Streptomyces* spp. that involves plating of the donor strain and either germinated spores or mycelial fragments of the recipient strain. Conjugal plasmids contain the 760-bp oriT fragment from the IncP plasmid, RK2 and are transferred by supplying transfer functions in trans by the *E. coli* donor strain. Other recent developments that increase the frequency of recombination of non-replicating plasmids into the recipient actinomycete chromosome include transformation of non-replicating plasmids into protoplasts using denatured plasmid DNA (Oh and Chater, J. Bacteriol., 1997, 179:122-7) and conjugation of non-replicating plasmids from a methyl minus strain of *E. coli*. (Smith et al., FEMS Microbiol. Lett., 1997, 155:223-9).

Various strategies have been used to obtain gene replacements in streptomycetes, for the construction of mutations and the modification of biosynthetic pathways (Baltz et al., 1998, supra; Hopwood et al., supra; Wohllenben et al., 1994, supra; Baltz and Hosted, TIBTECH, 1996, 14:245; Baltz, Curr. Op. Biotech., 1990, 1:12-20). These methods have typically employed a two or three step procedure that results in allelic exchange. Initial crossover events between a non-intergrating phage, non-replicating plasmid, or temperature sensitive plasmid and the streptomycete chromosome are selected for by antibiotic resistance. Subsequent recombination events that result in gene replacement can be detected by screening the progeny of the initial recombinants by PCR analysis, Southern analysis, appearance of an expected phenotype or screening for the loss of a resistance marker which had previously been exchanged into the loci to be replaced. The last of these methods has been employed by Khosla et al., Mol. Microbiol., 1992, 6:3237-49; Khosla et al., J. Bacteriol., 1993, 175:2197-204, to successfully modify the polyketide biosynthetic route of *S. coelicolor*. The strategy employed by Khosla et al., 1992, supra, also has the advantage of allowing placement of non-selectable and phenotypically silent alleles into chosen positions of the chromosome. Donadio et al., Proc. Natl. Acad. Sci. U.S.A., 1993, 90:7119-23 has also successfully reprogrammed the erythromycin pathway of *Saccharopolyspora erythrae* by gene replacement.

Non-replicating plasmids for gene replacement were initialy utilized by Hilleman et al., Nucleic Acids Res., 1991, 19:727-31, who used a derivative of pDH5 to construct mutations in the phosphinothricin tripeptide biosynthetic pathway of *S. hygroscopicus*. Plasmid-integration events were obtained by thiostrepton selection, subsequent screening of the primary recombinants indicated that 4 of 100 isolates had undergone a double-crossover gene replacement.

Use of counterselectable or negative selection markers such as rpsL (confers streptomycin sensitivity) or sacB (confers sucrose sensitivity) have been widely employed in other microorganisms for selection of recombination that results in gene replacement. In *S. coelicolor*, Buttner utilized glk as a counterselectable marker in att minus phiC31 phage to select for recombination events to construct gene replacement mutants of three *S. coelicolor* RNA polymerase sigma factors (Buttner et al., J. Bacteriol., 1990, 172:3367-78). Hosted has developed a gene replacement system utilizing the rpsL gene for counterselection (Hosted and Baltz, J. Bacteirol., 1997, 179:180-6).

The construction of recombinant streptomycete strains to produce hybrid secondary metabolites has been accomplished. Current procedures use recombinant DNA techniques to isolate and manipulate secondary metabolic pathways and to express these pathways in surrogate hosts such as *Streptomyces lividans*. Heterologous expression of diverse pathways, polyketide, oligopeptide and β-lactam biosynthetic pathways, has been achieved. Furthermore novel polyketide structures have been generated through the manipulation of polyketide genes forming chimeric pathways. Recently novel polyketide modules have been isolated from environmental sources using PCR amplification and expressed in *Streptomyces* to yield novel chemical structures (Strohl et al., J. Industr. Microbiol., 1991, 7:163; Kim et al., J. Bacteriol., 1995,77:1202; Ylihonko et al., Microbiology, 1996, 142:1965).

Knowledge of the everninomicin synthase DNA sequence, its genetic organization, and the activities associated with particular open reading frames, modules, and submodules of the gene enables production of novel everninomicins that are not otherwise available. Modifications may be made to the DNA sequence that either alter the structure or sequence of addition of building blocks. The principles have already been described above. In addition, any product resulting from post-transcriptional or post-translational modification in vivo or in vitro based on the DNA sequence information disclosed here are meant to be encompassed by the present invention.

Combinatorial Biosynthesis

The EV biosynthetic enzymes described here are ideal candidates for combinatorial biosynthesis to generate libraries of orthomycins, particularly everninomicin analogs and homologs, for testing and drug discovery (see Altreuter and Clark, Curr. Op. Biotech., 1999, 10:130; Reynolds, Proc. Natl. Acad. Sci. USA, 1998, 95:112744). Moreover, unlike chemical synthesis, which may depend on the efficiency of a specific reaction to determine product yield, a biosynthetic system can be amplified and propagated to produce high yields of the desired product.

Actinomycetes are well known microbial biosynthetic factories, and have been modified to produce novel compounds by mutation of specific biosynthetic genes (see Hutchinson, Bio/Technology, 1994, 12:375; Piepersberg, Crit. Rev. Biotech., 1994, 14:251). In addition to mutagenisis in situ, rapid evolution by DNA shuffling, particularly with related genes from other species or from the EV biosynthetic locus itself, provides for more directed evolutionary mutagenesis (Stemmer, Nature, 1994, 370:389). This technique can be practiced, for example, by shuffling EV biosynthetic gene products with their closest homologs, as determined by BLAST (or some other homology algorithm) analysis. For example, gene shifting of two or more transferases can yield new enzymes with altered function. Similarly, sugar biosynthetic genes, orsellinic acid biosynthetic genes, and tailoring genes can be manipulated by the techniques of directed evolution, e.g., gene shuffling, to produce mutants with novel enzymatic and synthetic function. Tailoring enzymes are particularly attractive targets for mutagenesis, since these will not affect synthesis of the core structure, but yield a variety of novel products.

An Integration Vector for *Micromonospera*

In a specific embodiment, the present invention relates to a new nucleic acid sequence, to vectors for its expression and to its use in fermentation processes in actinomycetes. This nucleic acid sequence encodes a *Micromonospera*, and particularly *M. carbonacea*, var. *africana*, att/int functions and thus permits development of an integrating vector. In a specific embodiment, the att/int functions has an amino acid sequence as depicted in SEQ ID NO: 177. In a more specific embodiment, the integrase is encoded by a nucleic acid having a nucleotide sequence as depicted in SEQ ID NO: 176 (FIG. 7B). A preferred integrating plasmid is shown in FIG. 7A.

Advantageously, the integrative vectors derived from this novel integrase also comprise a recombinant DNA sequence coding for a desired product, including but by no means limited to an EV biosynthetic gene. The product can be a peptide, polypeptide or protein of pharmaceutical or agrifoodstuffs importance. In this case, the system of the invention makes it possible to increase the copy number of this sequence per cell, and hence to increase the levels of production of this product and thus to increase the yields of the preparation process. The desired product can also be a peptide, polypeptide or protein participating in the biosynthesis (synthesis, degradation, transport or regulation) of a metabolite by the actinomycete strain in question. In this case, the system of the invention makes it possible to increase the copy number of this sequence per cell, and hence to increase the levels of production of this product, and thus either to increase the levels of production of the metabolite, or to block the biosynthesis of the metabolite, or to produce derivatives of the metabolite.

Plasmids comprising the site-specific integrating function of the invention can be used to permanently integrate copies of a heterologous gene of choice into the chromosome of many different hosts. The vectors can transform these hosts at a very high efficiency. Because the vectors do not have actinomycete origins of replication, the plasmids cannot exist as autonomously replicating vectors in actinomycete hosts. The plasmids only exist in their integrated form in these hosts. The integrated form is extremely stable which allows the gene copies to be maintained without antibiotic selective pressure. The result is highly beneficial in terms of cost, efficiency, and stability of the fermentation process.

Those skilled in the art will readily recognize that the variety of vectors which can be created that comprise this fragment is virtually limitless. The only absolute requirement is that the plasmid comprise an origin of replication which functions in the host cell in which constructions are made, such as *E. coli* or *Bacillus*. No actinomycete origin of replication is required. In fact, in a specific embodiment the plasmid comprising the inetegrase comprises no actinomycete origin of replication. Other features, such as an antibiotic resistance gene, a multiple cloning site and cos site, are useful but not required. A description of the generation and uses of cosmid shuttle vectors can be found in Rao et al., (Methods in Enzymology, 1987, 153:166-198). In short, any plasmid comprising the integrase is within the scope of this invention.

The integrating vectors can be used to integrate genes which increase the yield of known products or generate novel products, such as hybrid antibiotics or other novel secondary metabolites. The vector can also be used to integrate antibiotic resistance genes into strains in order to carry out bioconversions with compounds to which the strain is normally sensitive. The resulting transformed hosts and methods of making the antibiotics are within the scope of the present invention.

The integrase of the invention may thus be used in any actinomycete, in the genome of which the vector of the invention or its derivatives are is capable of integrating. In particular, they may be used in fermentation processes involving strains of Streptomyces, of mycobacteria, of bacilli, and the like. As an example, there may be mentioned the strains *S. pristinaespiralis* (ATCC 25486), *S. antibioticus* (DSM 40868), *S. bikiniensis* (ATCC 11062), *S. parvulus* (ATCC 12434), *S. glauescens* (ETH 22794), *S. actuosus* (ATCC 25421), *S. coelicolor* (A3(2)), *S. ambofaciens*, *S. lividans*, *S. griseofuscus*, *S. limosus*, and the like (see also, Smokvina et al., Proceedings, 1:403-407).

In this connection, European Patent Publication No. EP 350,341 describes vectors derived from plasmid pSAM2 having very advantageous properties. These vectors are capable of integrating in a site-specific manner in the genome of actinomycetes, and possess a broad host range and high stability. Moreover, they may be used for transferring nucleic acids into actinomycetes and expressing these nucleic acids therein. U.S. Pat. No. 5,741,675 describes tools capable of improving the conditions of industrial use of the vectors derived from pSAM2 by increasing the copy number of pSAM2 or its derivatives, since the free forms are present in a high copy number per cell. This patent also describes cassettes for the expression of this gene, vectors containing it and their use for inducing the appearance of free copies of pSAM2 or integrative vectors derived from the latter.

Alternatively, U.S. Pat. No. 5,190,871 provides methods for increasing a given gene dosage and for adding heterologous genes that lead to the formation of new products such as hybrid antibiotics using plasmids comprising the site-specific integrating function of phage phi.C31.

EXAMPLES

The following examples are provided for illustration purposes only and are not intended to limit the scope of the invention, which has been described in broad terms above.

Example 1

Sequencing of Orsellinic Acid Synthetase

The DNA sequence of the *Micromonospora carbonaceae* var. *africana* (ATCC 39149) everninomicin biosynthetic region was obtained by sequencing inserts of recombinant DNA subclones containing contiguous or overlapping DNA segments of the region indicated in FIG. 2A. All sequences representing the everninomicin region were fully contained in the overlapping cosmid clones pSPRX272, pSPRX262, pSPR192, pSPRX210, and pSPRX256 (FIG. 2A). The sequence was obtained by subcloning and sequencing fragments bounded by restriction site as indicated in FIG. 2A.

Figure 2B:
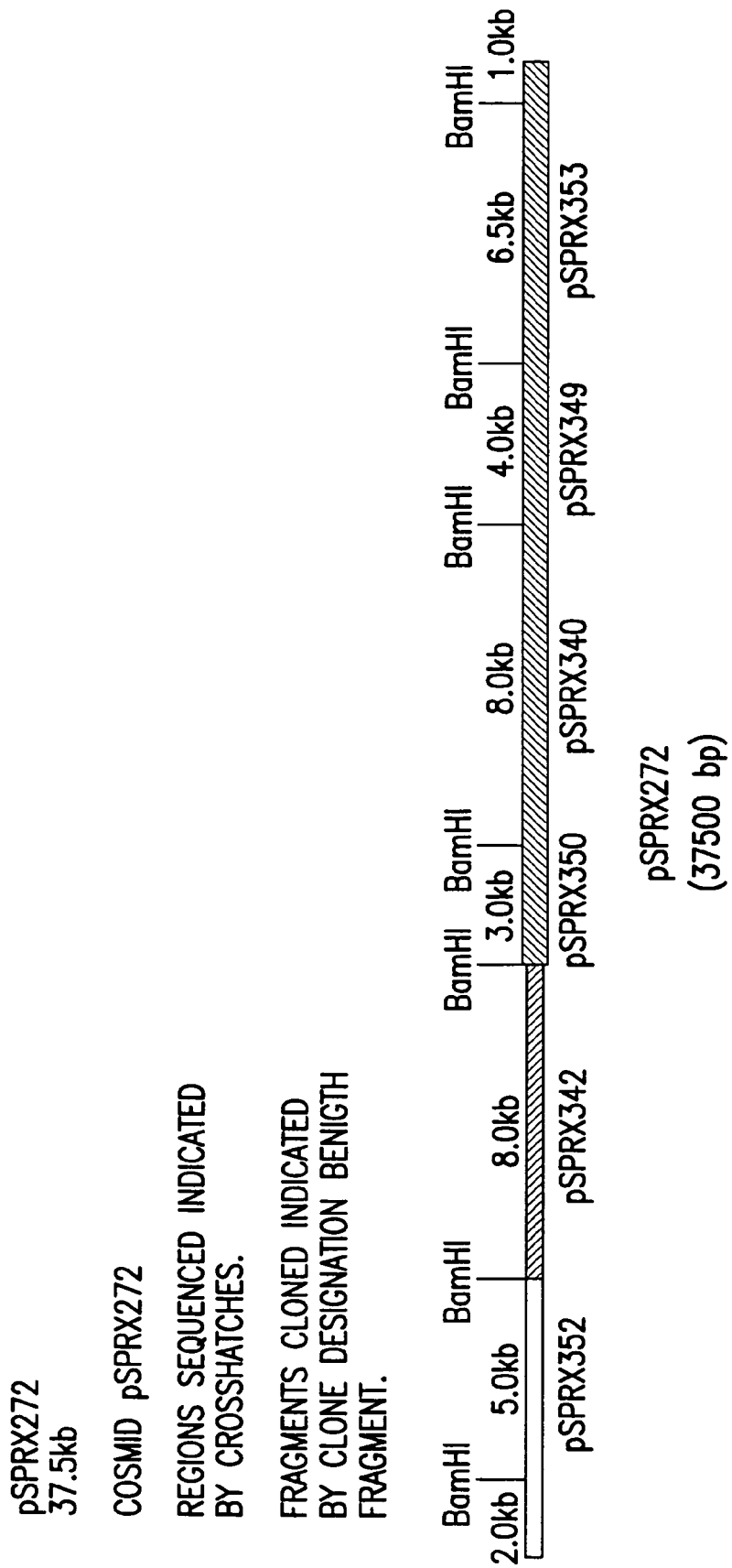
Figure 2C:
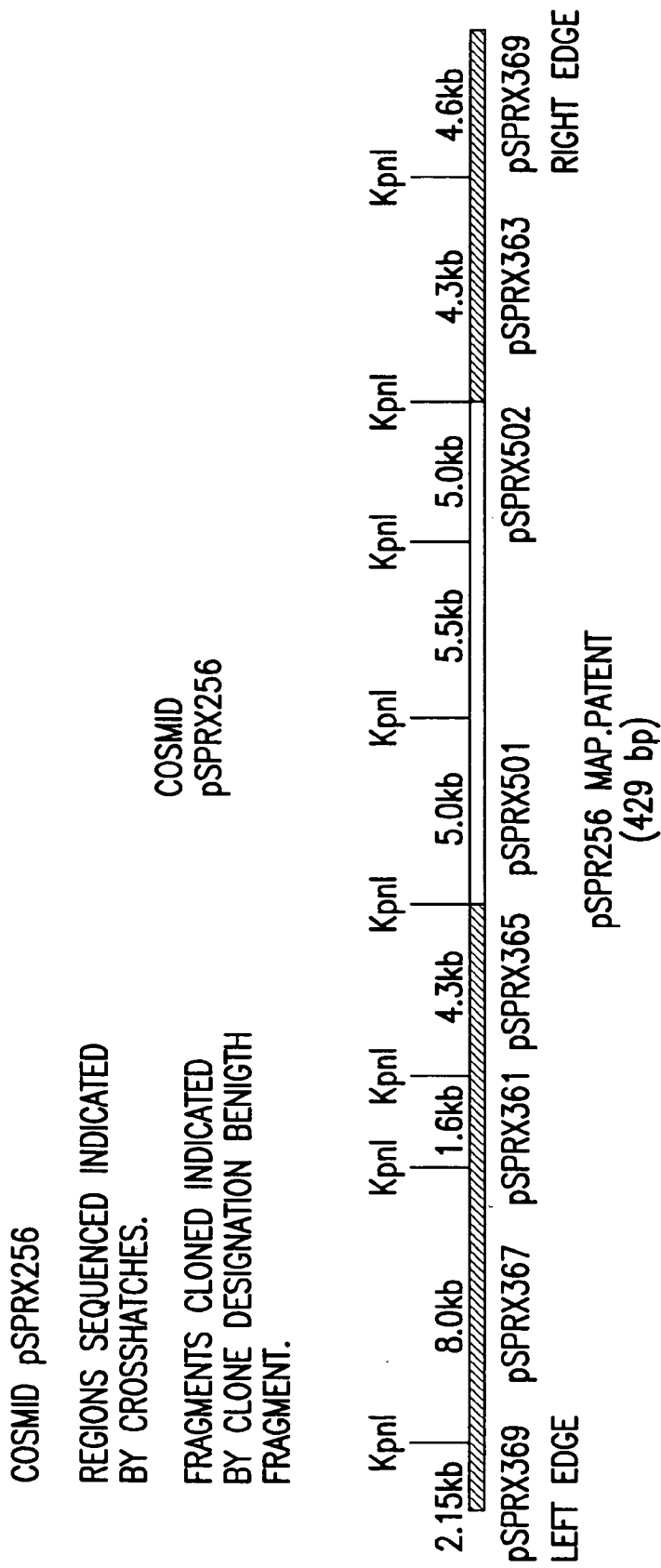
Figure 3A:
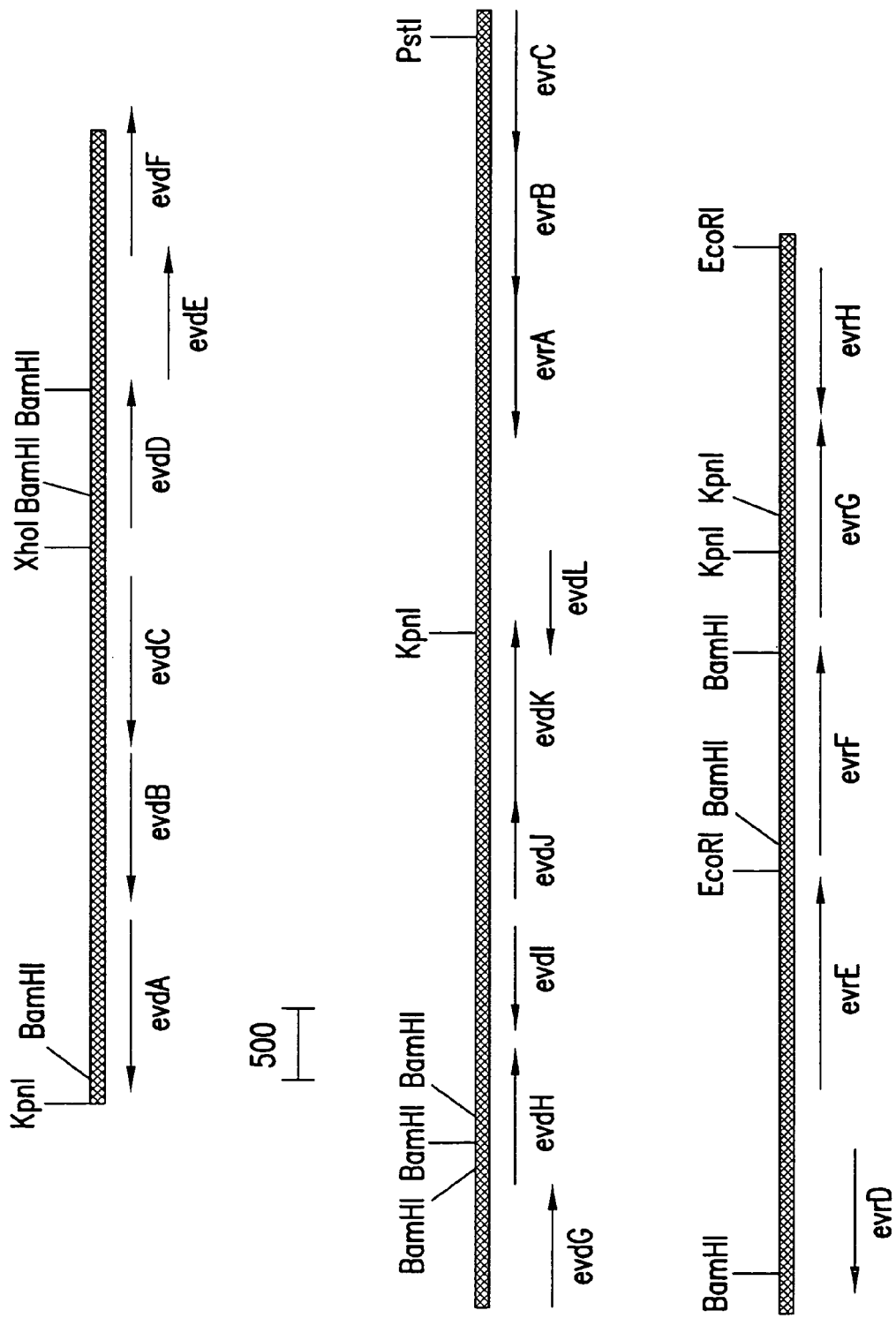
Figure 3B:
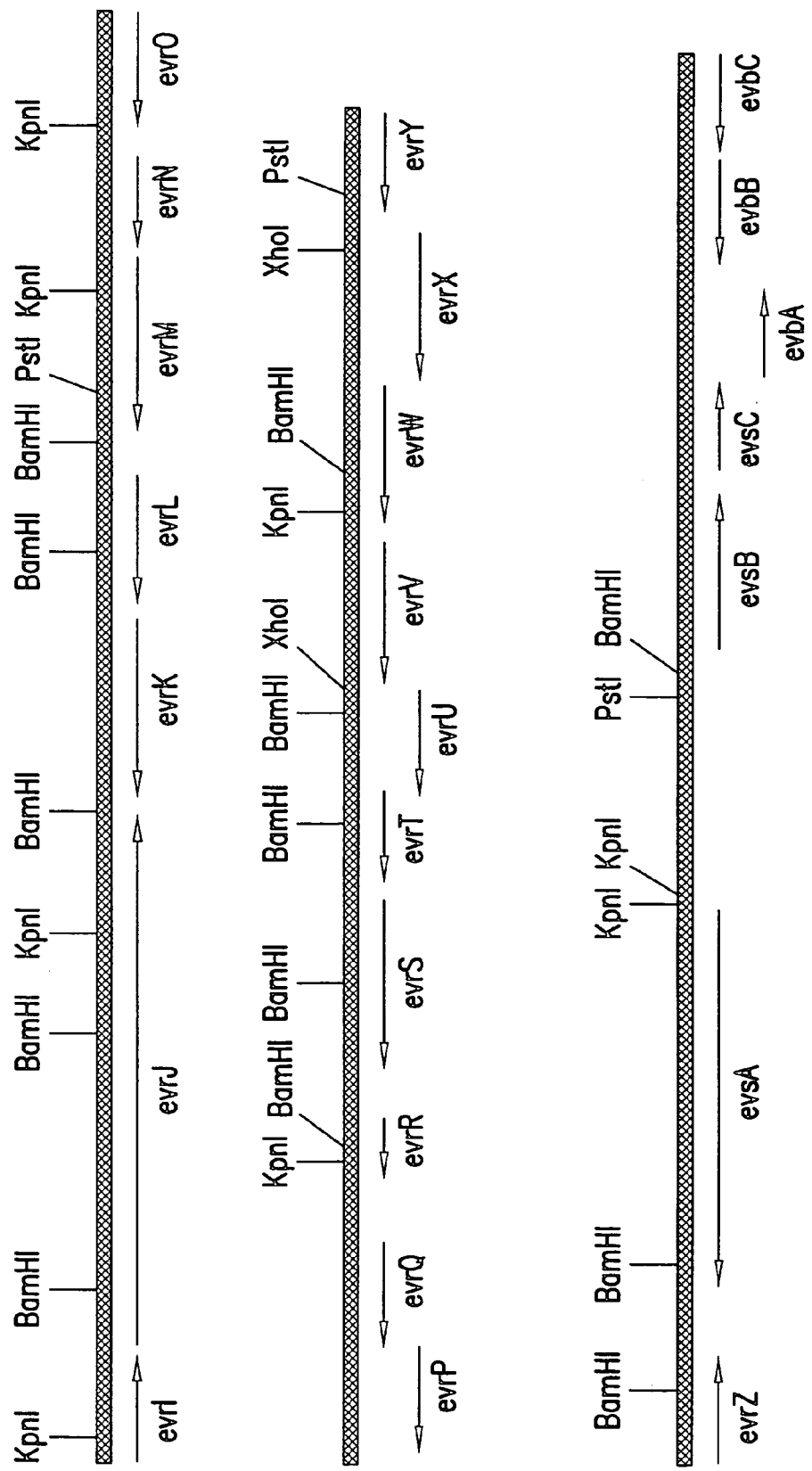
Figure 3C:
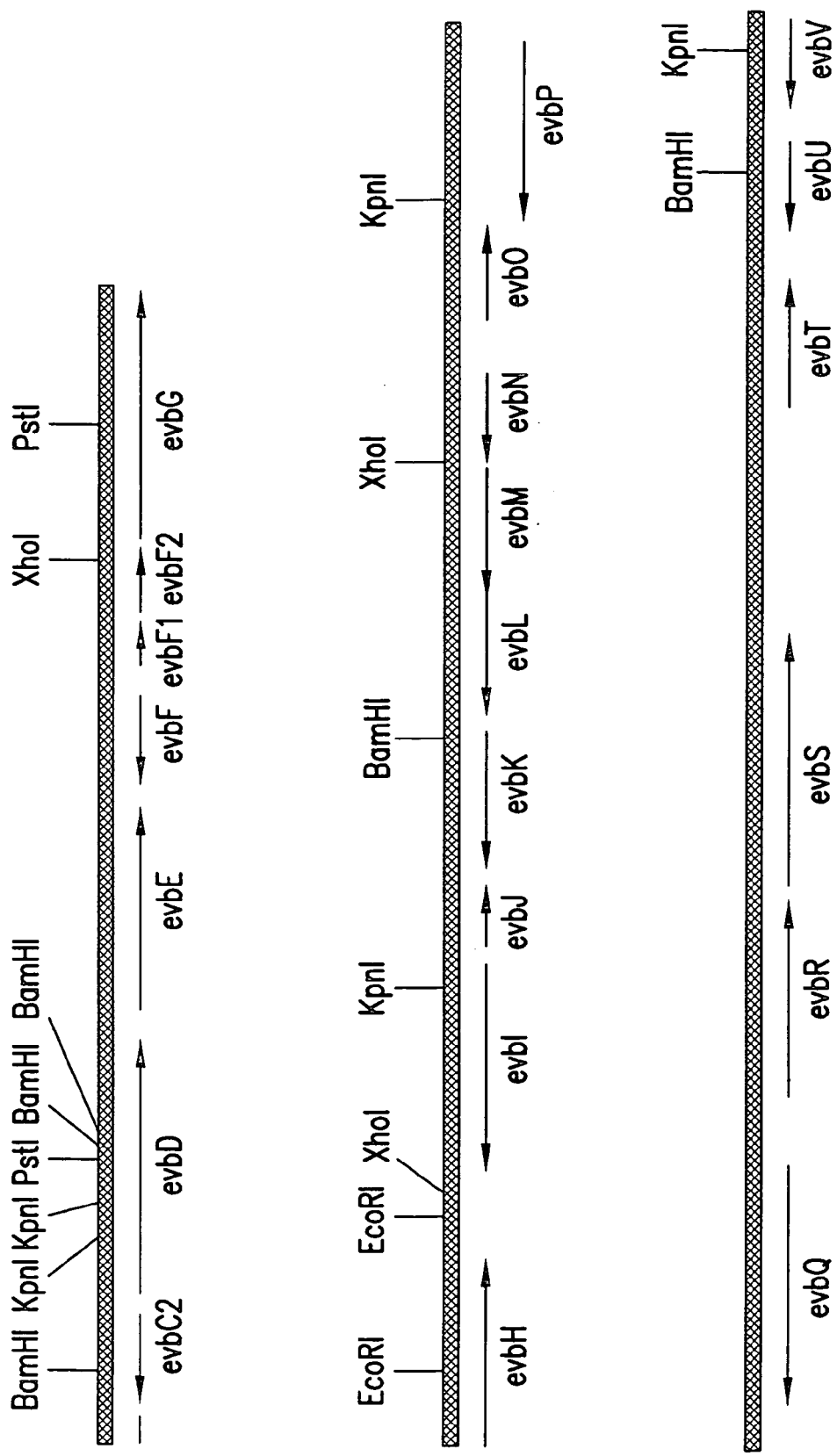
Figure 3D:
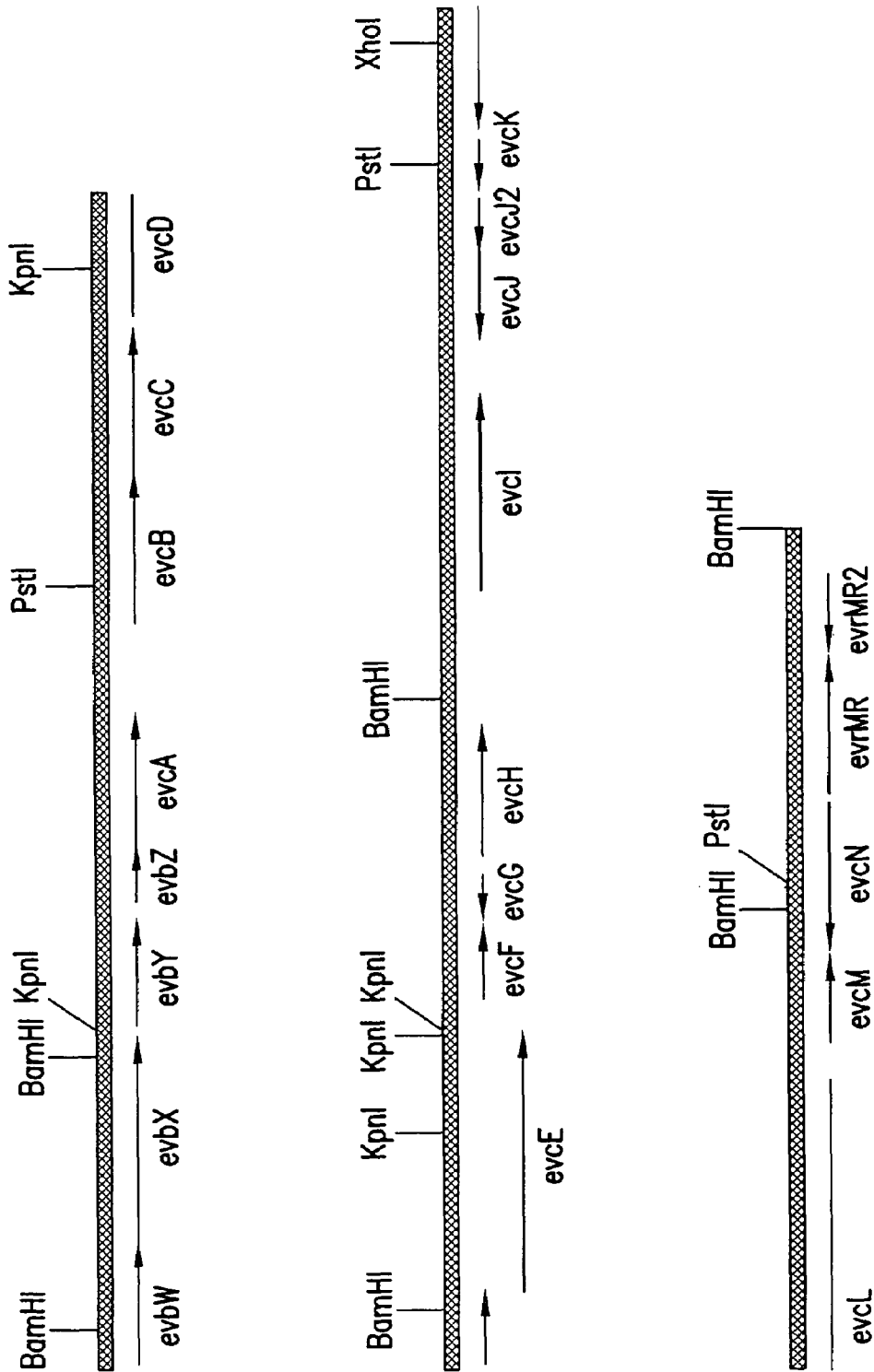

Preliminary sequences were also obtained for the cosmids pSPRX272 and pSPRX256. Restriction maps for these two cosmids are shown in FIGS. 2B and 2C, respectively. These restriction maps are characteristic of these two isolated cosmid clones of the *M. carbonaceae* everninomicin biosynthetic pathway or flanking regions thereof.

In order to obtain the evrJ gene, the sequence can be obtained by subcloning and sequencing of the fragments bounded by the KpnI sites at position 1,25.9 kb, 29.6 kb, and 34.2 kb. The sequence can also be obtained by subcloning and sequencing of the fragments bounded by the BamHI sites at position 1, 24.5 kb, 27.0 kb, 28.8 kb and 30.5 kb. The resulting fragments should be ligated and cloned in an appropriate recombinant DNA vector. Clones containing the correct orientation of the fragment can be identified by restriction enzyme site mapping.

Example 2

Transformation of M. carbonacea with pSPRH830

Figure 6:
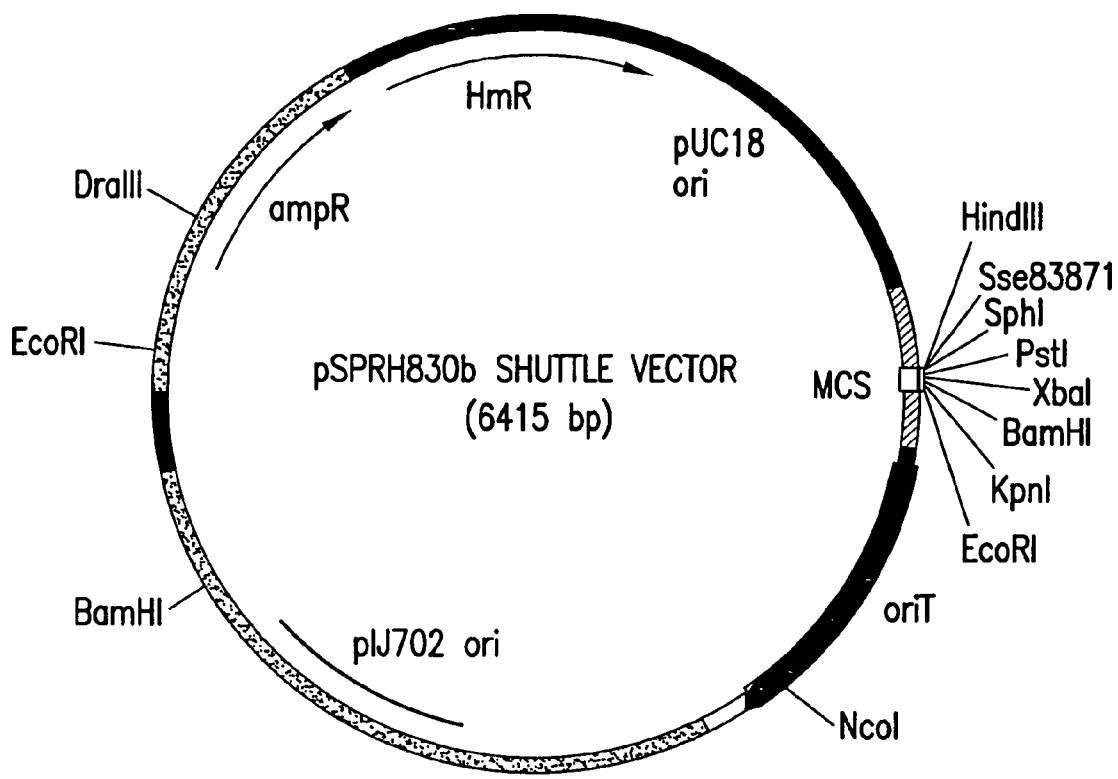

M. carbonacea was transformed with pSPRH830b (FIG. 6) by conjugation from E. coli S17-1 (Mazodier et al., Journal of Bacteriology, 1989, 6:3583-3585) to M. carbonacea. E. coli S17-1 containing pSPRH830b was grown overnight at 37° C. in LB supplemented with 100 μg/ml Ampicillin (Amp). The culture was inoculated into LB containing 100 μg/ml Amp at an 1:50 ratio and grown with shaking at 37° C. to an $OD_{600}$ of 0.4 to 0.5. Cells were harvested by centrifugation and washed three times with fresh LB lacking Amp. M. carbonacea was grown in TSB medium at 30° C. with shaking to stationary phase. E. coli S17-1 containing pSPRH830b prepared as described above was mixed with M. carbonacea in a total volume of 100 μl and plated on AS1 plates using a plastic hockey spreader. Plates were incubated for 15 hours at 29° C. and then overlaid with 50 μg/ml naladixic acid and 200 μg/ml Hygromycin for selection. Transconjugants appearing in 2-3 weeks were picked, homogenized and grown in TSB media with 50 μg/ml naladixic acid and 200 μg/ml hygromycin. Presence of pSPRH830b in M. carbonacea transformants was confirmed by PCR analysis and isolation of pSPRH830b from exconjugats.

The ability to transform M. carbonacea with pSPRH830b (on a multicopy plasmid) allows the introduction of second copies of genes contained in the everninomicin biosynthetic pathway or heterologous or mutated genes into M. carbonacea.

Example 3

Transformation of M. carbonacea with pSPRH840

Figure 7A:
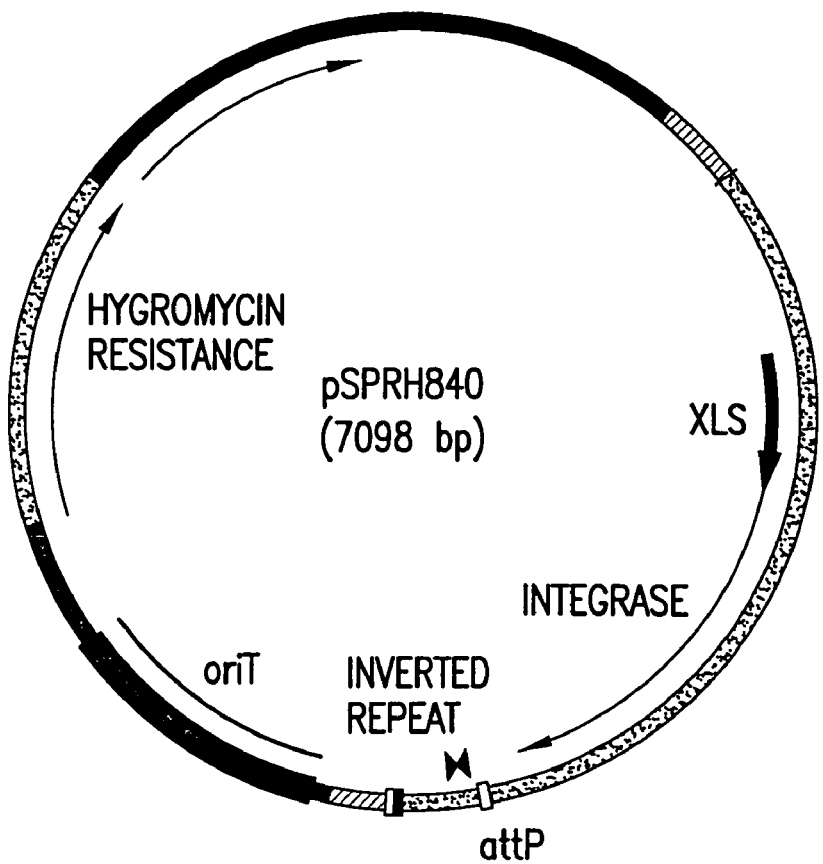
Figure 7B:
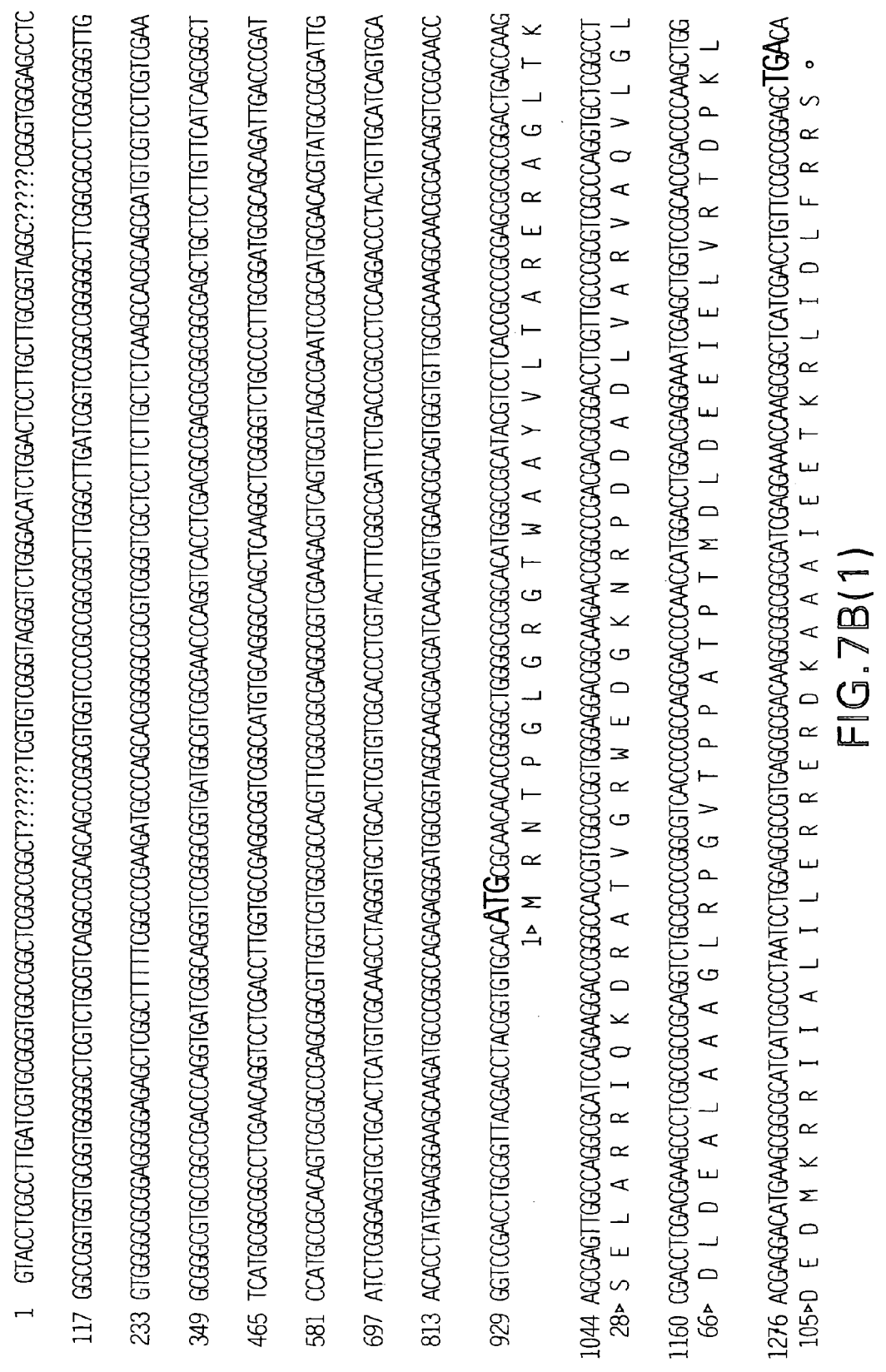

The pSPRH840 integrating vector (FIG. 7A) was constructed as follows. A 4.0 kb KpnII fragment from the pSPR150 cosmid containing the M. carbonacea pMLP1 intM gene was ligated with BamHI cleaved pBluescriptll (Stratagene) to yield pSPRH819. Sequence analysis of the 4.0 kb KpnI fragment from the cosmid revealed the presence of an integrase gene designated intM, an excisionase gene designated xis, and an integrase attachment site designated attP (FIG. 7B).

BLAST analysis of intM showed homology to other integrases in the NRRL database. Analysis of the predicted attP site showed homology to the attP sites found phage phiC31 and plasmid pSAM2.

Figure 8:
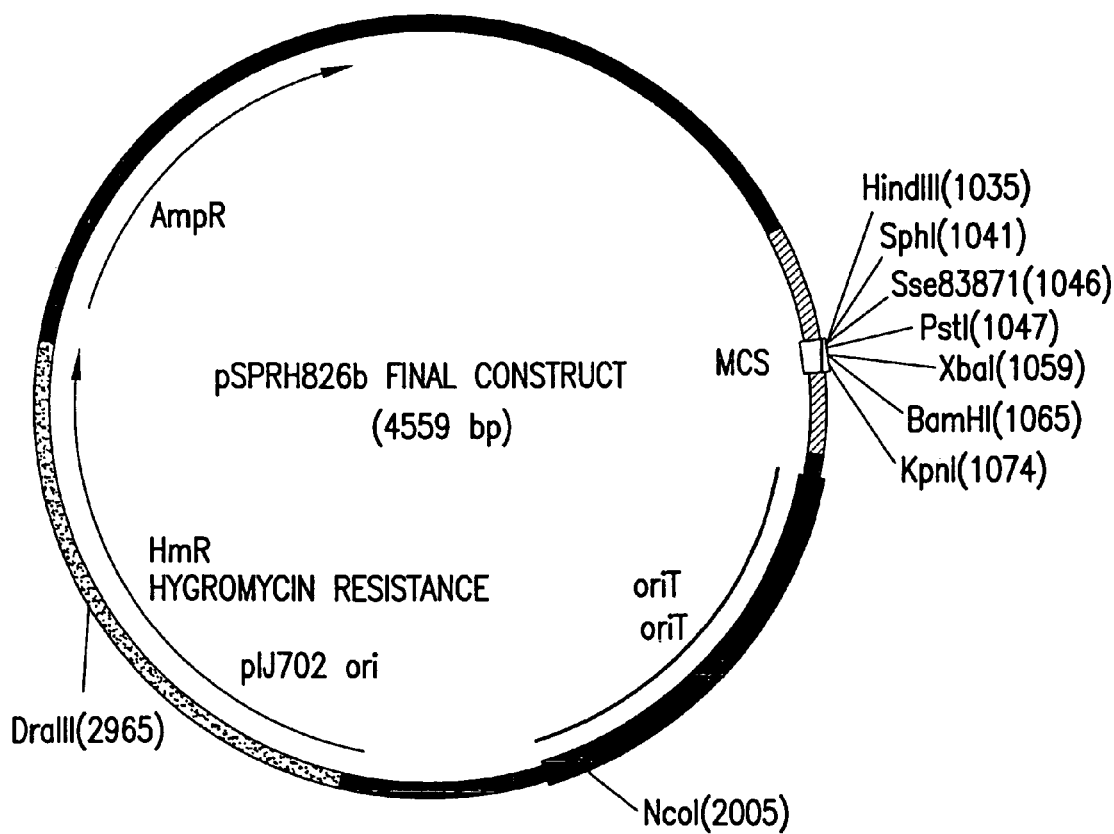

A 2.5 kb NruI to XhoI fragment from pSPR819 was treated with T4 polymerase to generate blunt DNA ends, alkaline phosphatase treated and ligated into the pCRTopo 2.1 vector (Invitrogen Corp, Carlsbad Calif.) to yield pSPRH853. A 2.6 kb KpnI to PstI fragment from pSPRH853 was ligated to KpnI and PstI digested pSPR826b (FIG. 8) to yield pSPRH840 (FIG. 7A). pSPRH840 was transformed into M. carbonacea SCC1413 and M. halophitica SCC760 as described in Example 2. Transconjugants appearing in two to three weeks were picked, homogenized, and grown in TSB medium supplimented with 50 μg/ml naladixic acid (Nac1) and 200 μg/ml Hygromycin. DNA was prepared from transconjugants, cleaved with BamHI, separated by gel electrophoresis, a Southern blot prepared, and probed with radiolabled pSPR826b. Southern hybridization analysis confirmed the presence of pSPR826b sequences integrated into the M. carbonacea and M. halophitica chromosomes. Regions including pSPRH840 and chromosomal flanking sequences were cloned by digesting chromosomal DNA with PstI or KpnI, ligating digested DNA and transforming E. coli XL10 (Stratagene, LaJolla, Calif.). E. coli transformants were isolated, plasmid DNA prepared and analyzed by digestion and gel electrophoresis. The attB/attP regions M. carbonacea and M. halophitica were each sequenced. Sequence analysis of this region confirmed that pSPRH840 had integrated into the M. carbonacea chromosome, specifically into a tRNA region (FIGS. 9A and 9B).

The ability to transform M. carbonacea with pSPRH840 allows the high frequency integration of second copies of genes contained in the everninomicin biosynthetic pathway or heterologous or mutated genes into M. carbonacea.

Example 4

Overexpression and Isolation of Proteins From the EV Region

The coding region, of evrF gene was amplified with PCR primers:

5' PR 657 CCC TCG AGA TGT CCA GCA AGA TCC TA (SEQ ID NO: 178);

3' PR 658 CGA ATT CTC AGG CAG ACT GCT CTG (SEQ ID NO: 179); and

5'PR-659: CCC TCG AGA ATG TCC AGC AAG ATC CTA (SEQ ID NO: 180);

3' PR 660: CGA ATT CAG ACT GCT CTG CCG CCG C (SEQ ID NO: 181);

using the Advantage-GC Genomic PCR kit and Advantage HF polymerase (Clontech, Palo Alto, Calif.) and a Perkin-Elmer 9600 PCR machine (Foster City, Calif.). The 1.5 kb PCR products were digested with XhoI and EcoRI and the fragments were ligated to XhoI and EcoRI digested pBADHisA (primer pair PR657/PR658 product) and pBADMycHisC (primer pair PR659/PR660 product) and transformed into E. coli Top10 (Stratagene, LaJolla, Calif.). Transformants were analyzed by plasmid isolation followed by digestion and gel electrophoresis analysis. Appropriate clones were also verified by sequence analysis. This yielded the evrF expression clones pSPRE59 (pBADHisA) and pSPRE19 (pBADMycHisC). Top10 cells containing either pSPRE59 and pSPRE19 were grown overnight at 37° C. with shaking in LB containing 50 ug/ml AMP. Overnight cultures were used to innoculate fresh LB containing 50 μg/ml and grown at 37° C. with shaking to an $OD_{600}$ of 0.4 to 0.5. L-arabinose was added to a final concentration of 0.02% and the culture was incubated for an additional 4hours. Cells were collected by centrifugation, resuspended in 100 μl Tris-Glycine buffer and boiled for five minutes. Whole cell protein lysate was loaded onto a SDS-PAGE gel, electrophoresed, and stained with coomassie blue to determine protein expression.

To isolate sufficient amounts of protein for raising antibodies, 100 ml of culture was processed as described above and the His-tagged EvrF protein was purified by Ni-NTA column chromatography using the Xpress Protein Purification System (Invitrogen, Carlsbad, Calif.). The recombinant EvrF protein was purified to over 90% homogeneity. This preparation was fractionated on SDS-PAGE gel, excised, and used to immunize New Zealand white rabbits to raise antibodies. Antisera were generated following standard protocol, i.e., priming with complete Freund's adjuvant, (CFA) and boosting with incomplete Freund's adjuvant (IFA).

Example 5

Everninomicin Pathway Expression of Putative Resistance Genes

Figure 10:
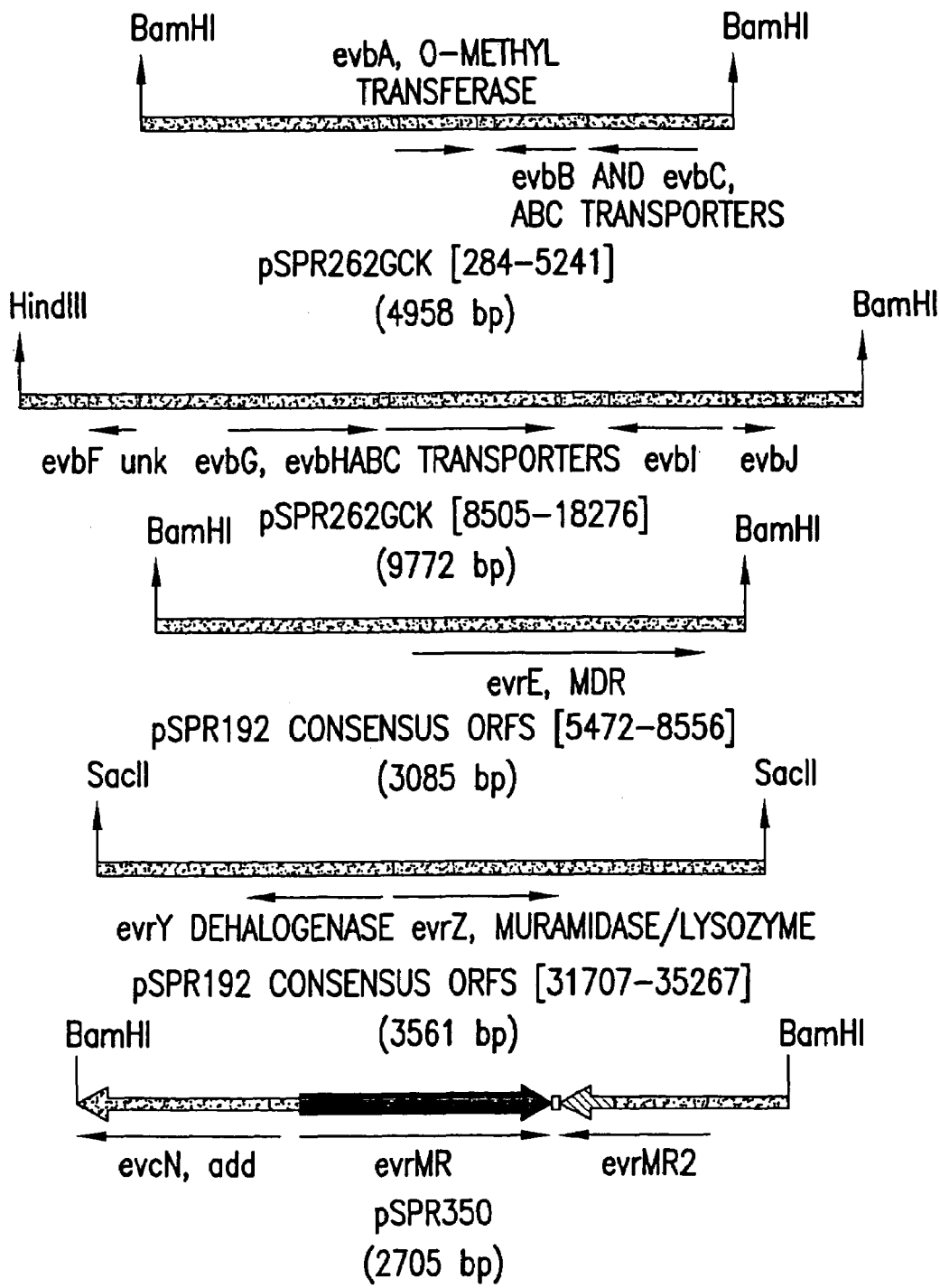

Putative everninomicin resistance genes are expressed in the actinomycete vector pSPRH830b. Clones are obtained using standard molecular biology procedures. Plasmids are transformed into Streptomyces lividans or Streptomyces griseofuscus by PEG protoplast transformation or other standard actinomycete transformation procedures. Transformants are tested for increased resistance levels to everninomicin. A schematic of pSPRH830 the specific fragments to be cloned into is attached and shown in FIG. 10.

The EV biosynthetic gene DNAs to be expressed by this recombinant vector are:
1) 4.9 kb BamHI fragment containing
   evrB, evrC—membrane pumps similar to mithramycin resistance.
2) 9.7 kb HindIII/BamHI fragment containing
   evbG, evbH—ABC transporter pumps, possible resistance mechanism.
3) 3.0 kb BamHI fragment containing
   evrE—MDR (Multiple drug resistance-type pump) transporter, possible resistance mechanism.
4) 3.56 kb SacII fragment containing
   evrY-dehalogenase, possible resistance mechanism
   evrZ-muramidase/lysozyme homology, possible resistance mechansim.
5) 2.7 kb BamHI fragment containing
   evrMR—23S rRNA methylase
6) A PCR fragment containing
   evcD and evcE—ABC transporters Example 6

Insertional Inactivation of EV Pathway Genes

To confirm involvement of evrJ, (orsellinic acid synthetase) evrF, (halogenase) and evrW (dTDP-glucose dehydratase) in EV biosynthesis these genes were disrupted in M carbonacea via homologous recombination using the conjugative suicide vector pSPRH900b. Internal fragments of evrJ, evrF, and evrW were cloned into pSPRH900b to yield pSPRX572, pSPRX570, and pSPRX589 respectively. Plasmids pSPRX572, pSPRX570, and pSPRX589 were inserted into the chromosome by conjugation from E. coli into M. carbonacea to yield strains 572X, 570X and 589X repectively. Southern analysis confirmed insertion into the correct chromosomal loci for each plasmid. 572X, 570X and 589X strains showed a loss of EV production as shown by fermentation and analysis by HPLC indicating these genes are essential for EV production.

Production and determination of EV production was determined as follows. A mycelia stock of M. carbonacea was inoculated into the seed medium SIM-1 (10 ml) and incubated at 28° C. and 300 rpm. The seed inoculum (5 ml) was then added to 4I+Co production medium (100 ml) and incubated at 28° C. and 300 rpm for 96 hours. A 10 ml aliquot of the fermentation broth was extracted with 20 ml of EtOAc, and the organic phase was evaporated to dryness. After resuspension in 2 ml of MeOH, 10 ml of the extract was subjected to HPLC analysis on a YMC-pack ODS-A C-18 column (3 mm, 150×4.6 mm, Waters Corporation, Milford, Mass.). The column was equilibrated with 3 mM tetramethyl ammonium hydroxide (pH to 7.2 with glacial acetic acid) with 70% (vol/vol) MeOH and developed with a 24-min linear gradient from 70 to 90% MeOH in the same 3 mM tetramethyl ammonium hydroxide buffer at a flow rate of 0.8 ml/min. EV was detected at 270 nm by UV-Vis detection using a Agilent Series1100 HPLC system (Agilent Technologies).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all sizes and all molecular weight or molecular mass values are approximate, and are provided for description.

Patents, patent applications, procedures, and publications cited throughout this application are incorporated herein by reference in their entireties.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07229813B2). An electronic copy of the "Sequence Listing" will also be available from the USPTO upon request and payment of the fee set forth in 37 CFR 1.19(b)(3).

We claim:

1. An isolated polypeptide comprising the amino acid sequence set forth in SEQ ID NO: 177.

2. The polypeptide of claim 1 fused to a heterologous polypeptide tag.

3. The polypeptide of claim 2 wherein the heterologous polypeptide tag is selected from the group consisting of a poly-histidine tag, a FLAG tag, a glutathione-S-transferase (GST) tag and a myc epitope tag.

4. A method for making the polypeptide of claim 1 comprising introducing a polynucleotide comprising the nucleotide sequence set forth in SEQ ID NO: 176 into a host cell and allowing expression of the polypeptide.

5. The method of claim 4 further comprising isolating the polypeptide from the host cell.

6. The isolated polypeptide of claim 1 consisting of the amino acid sequence set forth in SEQ ID NO: 177.

* * * * *